US012703703B2

(12) United States Patent
Deng et al.

(10) Patent No.: US 12,703,703 B2
(45) Date of Patent: Aug. 11, 2026

(54) FGFR AND MUTATION INHIBITOR THEREOF, PREPARATION METHOD THEREFOR AND USE THEREOF

(71) Applicant: Abbisko Therapeutics Co., Ltd., Shanghai (CN)

(72) Inventors: Haibing Deng, Shanghai (CN); Haiyan Ying, Shanghai (CN); Hongping Yu, Shanghai (CN); Zhui Chen, Shanghai (CN); Yaochang Xu, Shanghai (CN)

(73) Assignee: ABBISKO THERAPEUTICS CO., LTD., Shanghai (CN)

( * ) Notice: Subject to any disclaimer, the term of this patent is extended or adjusted under 35 U.S.C. 154(b) by 742 days.

(21) Appl. No.: 18/014,095

(22) PCT Filed: Aug. 11, 2021

(86) PCT No.: PCT/CN2021/112121
§ 371 (c)(1),
(2) Date: Dec. 30, 2022

(87) PCT Pub. No.: WO2022/033532
PCT Pub. Date: Feb. 17, 2022

(65) Prior Publication Data

US 2023/0303575 A1 Sep. 28, 2023

(30) Foreign Application Priority Data

Aug. 13, 2020 (CN) ......................... 202010811490.9

(51) Int. Cl.
*C07D 487/04* (2006.01)
*A61P 35/00* (2006.01)
*C07D 519/00* (2006.01)

(52) U.S. Cl.
CPC ............ *C07D 487/04* (2013.01); *A61P 35/00* (2018.01); *C07D 519/00* (2013.01)

(58) Field of Classification Search
CPC ...... C07D 487/04; C07D 519/00; A61P 35/00
See application file for complete search history.

(56) References Cited

U.S. PATENT DOCUMENTS

2016/0136168 A1 5/2016 Sootome
2016/0193210 A1 7/2016 Ochiiwa et al.
2017/0304313 A1 10/2017 Porter et al.

FOREIGN PATENT DOCUMENTS

CN 103958512 A 7/2014
CN 105461720 A 4/2016
CN 107344940 A 11/2017
CN 109776544 A * 11/2017 ........... C07D 487/04
WO 2007087395 A2 8/2007
WO 2015008844 A1 1/2015
WO 2016055916 A1 4/2016
WO 2021247971 A1 12/2021

OTHER PUBLICATIONS

International Search Report issued Nov. 15, 2021 in PCT/CN2021/112121.
Examination Report issued Nov. 23, 2023 in IN Application No. 202237076353.
Gangjee et al., "Synthesis of 5,7-disubstituted-4-methyl-7H-pyrrolo[2,3-d]pyrimidin-2-amines as microtubule inhibitors," Bioorganic & Medicinal Chemistry, vol. 21, pp. 1180-1189 (2013).
Office Action issued Dec. 22, 2023 in JP Application No. 2022-579114 (with translation).
Extended European Search Report issued Feb. 12, 2024 in EP Application No. 21855583.

* cited by examiner

*Primary Examiner* — Erich A Leeser
(74) *Attorney, Agent, or Firm* — Panitch Schwarze Belisario & Nadel LLP

(57) ABSTRACT

Provided are an FGFR and a mutation inhibitor thereof, and a preparation method therefor and the use thereof. In particular, provided are an FGFR having a structure of formula (I) and a mutation inhibitor thereof, a preparation method therefor, a pharmaceutical composition containing same, the use thereof as an FGFR and a mutation inhibitor thereof and the use thereof in the preparation of a drug for treating and/or preventing tumors or cancers mediated at least in part by means of an FGFR kinase and for treating a tumor patient having resistance to an FGFR inhibitor, and in particular, the use thereof in the preparation of a drug for treating and/or preventing a tumor patient with mutations at V561, V565, N550, N540, V555, E566, K660 and/or V550 of an FGFR signaling pathway. Each substituent of formula (I) has the same definition as in the description.

(I)

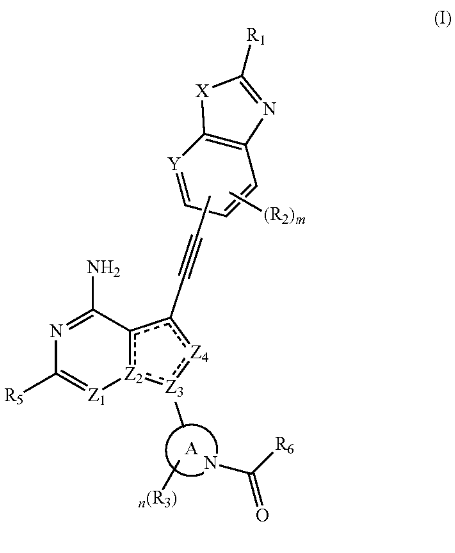

19 Claims, No Drawings

FGFR AND MUTATION INHIBITOR THEREOF, PREPARATION METHOD THEREFOR AND USE THEREOF

CROSS-REFERENCE TO RELATED APPLICATIONS

This application is a Section 371 of International Application No. PCT/CN2021/112121, filed Aug. 11, 2021, which was published in the Chinese language on Feb. 17, 2022 under International Publication No. WO 2022/033532 A1, which claims priority under 35 U.S.C. § 119(b) to Chinese Application No. 202010811490.9, filed Aug. 13, 2020, the disclosures of which are incorporated herein by reference in their entireties.

TECHNICAL FIELD

The present invention belongs to the field of pharmaceutical synthesis, and particularly relates to an FGFR and mutation inhibitor thereof, preparation method therefor and use thereof.

BACKGROUND

Fibroblast growth factor receptors (FGFRs) are tyrosine kinase receptors that bind to fibroblast growth factor ligands. Currently, 4 types of FGFRs have been found to be capable of binding to ligands. Fibroblast growth factor (FGF) signal pathways are thought to play important roles in many processes, such as embryogenesis, tissue differentiation, wound healing and metabolic regulation, and are also thought to be closely related to the characteristics of many tumors. When an FGF binds to its receptor, the receptor dimerizes and phosphorylates, stimulates activation of protein kinase activity and facilitates activation of a range of intracellular signal transduction pathways, including Ras-MAPK, AKT-PI3K and phosphatase C which are important signal pathways for cell growth, proliferation and survival.

Genetic changes in FGFR family members are often associated with tumor growth, metastasis, angiogenesis and survival. Many FGFR inhibitors have shown, in clinical trials, clinical responses in patients with FGFR abnormalities, and recently there are also FGFR inhibitors approved for marketing. However, in clinical trials, it was found that there was rapid emergence of acquired resistance to FGFR inhibitors, resulting in a relatively short progression-free survival. Mutations that affect FGFR amino acids may result in resistance to or reduce the activity of FGFR inhibitors. The generation of secondary FGFR kinase domain mutation under the action of FGFR inhibitor is an important mechanism for acquiring the resistance to FGFR inhibition. Corresponding FGFR point mutations are also present in tumors. The gatekeeper mutation is reported to be one of the major mechanisms for resistance to tyrosine kinases, and FGFR-resistant mutations have been reported in in vitro cell system and clinical trials as well. The gatekeeper mutations include FGFR3V555M, FGFR2V565F/V565I/V565L and the like. Recent studies have reported that the FGFR2V565F gatekeeper mutation was found in three out of the BGJ398-treated patients with cholangiocarcinoma, two of which also had other mutations in other FGFR2 kinase regions. Therefore, in order to address the problem that acquired resistance is present in treatment with the first-generation FGFR inhibitors in clinic application, there is an urgent need for a new-generation FGFR inhibitors that have more durable activity in tumors with gene mutations in the FGFR signal pathway. However, such second-generation FGFR inhibitors need to not only maintain the inhibitory activity against FGFRs, but also maintain the same level of activity against gatekeeper mutations against which the first-generation FGFR inhibitors have reduced activity.

SUMMARY

After an extensive and intensive research, the inventors of the present invention have developed, for the first time, an FGFR and mutation inhibitor thereof, preparation method therefor and use thereof. The series of compounds of the present invention have good activity against mutant FGFRs, particularly against FGFRs with gatekeeper mutations, and particularly against FGFR3 V555M, FGFR2 V565I, FGFR2 V565F, FGFR2 V565L, and non-gatekeeper mutation FGFR2 N550K, and new-generation FGFR inhibitors are expected to be developed.

The first aspect of the present invention provides a compound of formula (I), a stereoisomer or pharmaceutically acceptable salt thereof:

(I)

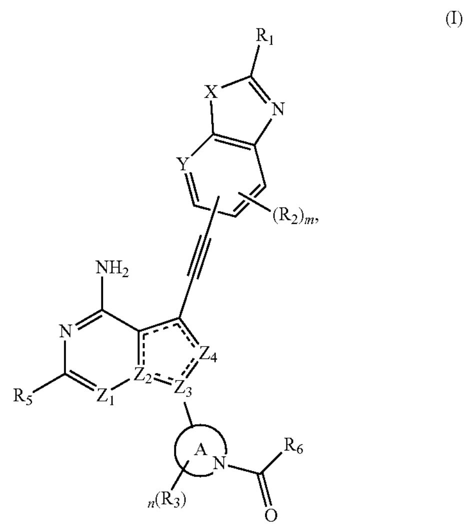

wherein, "---" is a double bond or a single bond;

X is O or S; Y is $CR_4$ or N;

$Z_1$ and $Z_4$ are each independently N or $CR_7$;

$Z_2$ and $Z_3$ are each independently N or C;

ring A is 3-12 membered nitrogen-containing heterocyclyl, wherein, the nitrogen atom is connected to carbonyl;

$R_1$ is selected from the group consisting of hydrogen, deuterium, halogen, cyano, nitro, azido, $C_{1-10}$ alkyl, $C_{2-10}$ alkenyl, $C_{2-10}$ alkynyl, $C_{3-12}$ cycloalkyl, 3-12 membered heterocyclyl, $C_{5-10}$ aryl, 5-10 membered heteroaryl, —$C_{0-8}$ alkyl-$SF_5$, —$C_{0-8}$ alkyl-$S(O)_rR_8$, —$C_{0-8}$ alkyl-O—$R_9$, —$C_{0-8}$ alkyl-C(O)$OR_9$, —$C_{0-8}$ alkyl-C(O)$R_{10}$, —$C_{0-8}$ alkyl-O—C(O)$R_{10}$, —$C_{0-8}$ alkyl-$NR_{11}R_{12}$, —$C_{0-8}$ alkyl-C(=$NR_{11}$)$R_{10}$, —$C_{0-8}$ alkyl-N($R_{11}$)—C(=$NR_{12}$)$R_{10}$, —$C_{0-8}$ alkyl-C(O)$NR_{11}R_{12}$ and —$C_{0-8}$ alkyl-N($R_{11}$)—C(O)$R_{10}$, the above groups are optionally further substituted with one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{5-10}$ aryl, 5-10 membered heteroaryl, =O, $-C_{0-8}$ alkyl-$SF_5$, $-C_{0-8}$ alkyl-$S(O)_rR_8$, $-C_{0-8}$ alkyl-O-$R_9$, $-C_{0-8}$ alkyl-C(O)$OR_9$, $-C_{0-8}$ alkyl-C(O)$R_{10}$, $-C_{0-8}$ alkyl-O-C(O)$R_{10}$, $-C_{0-8}$ alkyl-$NR_{11}R_{12}$, $-C_{0-8}$ alkyl-C(=$NR_{11}$)$R_{10}$, $-C_{0-8}$ alkyl-N($R_{11}$)-C(=$NR_{12}$)$R_{10}$, $-C_{0-8}$ alkyl-C(O)$NR_{11}R_{12}$ and $-C_{0-8}$ alkyl-N($R_{11}$)-C(O)$R_{10}$;

$R_2$, $R_3$ and $R_4$ are each independently selected from the group consisting of hydrogen, deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{5-10}$ aryl, 5-10 membered heteroaryl, $-C_{0-8}$ alkyl-$SF_5$, $-C_{0-8}$ alkyl-$S(O)_rR_8$, $-C_{0-8}$ alkyl-O-$R_9$, $-C_{0-8}$ alkyl-C(O)$OR_9$, $-C_{0-8}$ alkyl-C(O)$R_{10}$, $-C_{0-8}$ alkyl-O-C(O)$R_{10}$, $-C_{0-8}$ alkyl-$NR_{11}R_{12}$, $-C_{0-8}$ alkyl-C(=$NR_{11}$)$R_{10}$, $-C_{0-8}$ alkyl-N($R_{11}$)-C(=$NR_{12}$)$R_{10}$, $-C_{0-8}$ alkyl-C(O)$NR_{11}R_{12}$ and $-C_{0-8}$ alkyl-N($R_{11}$)-C(O)$R_{10}$;

$R_5$ and $R_7$ are each independently selected from the group consisting of hydrogen, deuterium, halogen, cyano, nitro, azido, $C_{1-10}$ alkyl, $C_{2-10}$ alkenyl, $C_{2-10}$ alkynyl, $C_{3-12}$ cycloalkyl, 3-12 membered heterocyclyl, $C_{3-10}$ aryl, 5-10 membered heteroaryl, $-C_{0-8}$ alkyl-$SF_5$, $-C_{0-8}$ alkyl-$S(O)_rR_8$, $-C_{0-8}$ alkyl-O-$R_9$, $-C_{0-8}$ alkyl-C(O)$OR_9$, $-C_{0-8}$ alkyl-C(O)$R_{10}$, $-C_{0-8}$ alkyl-O-C(O)$R_{10}$, $-C_{0-8}$ alkyl-$NR_{11}R_{12}$, $-C_{0-8}$ alkyl-C(=$NR_{11}$)$R_{10}$, $-C_{0-8}$ alkyl-N($R_{11}$)-C(=$NR_{12}$)$R_{10}$, $-C_{0-8}$ alkyl-C(O)$NR_{11}R_{12}$ and $-C_{0-8}$ alkyl-N($R_{11}$)-C(O)$R_{10}$, the above groups are optionally further substituted with one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{1-10}$ aryl, 5-10 membered heteroaryl, =O, $-C_{0-8}$ alkyl-$SF_5$, $-C_{0-8}$ alkyl-$S(O)_rR_8$, $-C_{0-8}$ alkyl-O-$R_9$, $-C_{0-8}$ alkyl-C(O)$OR_9$, $-C_{0-8}$ alkyl-C(O)$R_{10}$, $-C_{0-8}$ alkyl-O-C(O)$R_{10}$, $-C_{0-8}$ alkyl-$NR_{11}R_{12}$, $-C_{0-8}$ alkyl-C(=$NR_{11}$)$R_{10}$, $-C_{0-8}$ alkyl-N($R_{11}$)-C(=$NR_{12}$)$R_{10}$, $-C_{0-8}$ alkyl-C(O)$NR_{11}R_{12}$ and $-C_{0-8}$ alkyl-N($R_{11}$)-C(O)$R_{10}$;

$R_6$ is selected from the group consisting of $C_{1-10}$ alkyl, $C_{2-10}$ alkenyl, $C_{2-10}$ alkynyl, $C_{3-12}$ cycloalkyl, 3-12 membered heterocyclyl, -C(O)$R_{10}$, $-NR_{11}R_{12}$, -C(=$NR_{11}$)$R_{10}$, -N($R_{11}$)-C(=$NR_{12}$)$R_{10}$, -C(O)$NR_{11}R_{12}$ and -N($R_{11}$)-C(O)$R_{10}$, the above groups are optionally further substituted with one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{5-10}$ aryl, 5-10 membered heteroaryl, =O, $-C_{0-8}$ alkyl-$SF_5$, $-C_{0-8}$ alkyl-$S(O)_rR_8$, $-C_{0-8}$ alkyl-O-$R_9$, $-C_{0-8}$ alkyl-C(O)$OR_9$, $-C_{0-8}$ alkyl-C(O)$R_{10}$, $-C_{0-8}$ alkyl-O-C(O)$R_{10}$, $-C_{0-8}$ alkyl-$NR_{11}R_{12}$, $-C_{0-8}$ alkyl-C(=$NR_{11}$)$R_{10}$, $-C_{0-8}$ alkyl-N($R_{11}$)-C(=$NR_{12}$)$R_{10}$, $-C_{0-8}$ alkyl-C(O)$NR_{11}R_{12}$ and $-C_{0-8}$ alkyl-N($R_{11}$)-C(O)$R_{10}$;

each $R_8$ is independently selected from the group consisting of hydrogen, deuterium, hydroxy, $C_{1-10}$ alkyl, $C_{2-10}$ alkenyl, $C_{3-12}$ cycloalkyl, 3-12 membered heterocyclyl, $C_{5-10}$ aryl, 5-10 membered heteroaryl and $-NR_{11}R_{12}$, the above groups are optionally further substituted with one or more substituents selected from the group consisting of deuterium, halogen, hydroxy, oxo, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{5-10}$ aryl, $C_{5-10}$ aryloxy, 5-10 membered heteroaryl, 5-10 membered heteroaryloxy and $-NR_{11}R_{12}$;

each $R_9$ is independently selected from the group consisting of hydrogen, deuterium, $C_{1-10}$ alkyl, $C_{2-10}$ alkenyl, $C_{3-12}$ cycloalkyl, 3-12 membered heterocyclyl, $C_{5-10}$ aryl and 5-10 membered heteroaryl, the above groups are optionally further substituted with one or more substituents selected from the group consisting of deuterium, halogen, hydroxy, oxo, cyano, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{5-10}$ aryl, $C_{5-10}$ aryloxy, 5-10 membered heteroaryl, 5-10 membered heteroaryloxy and $-NR_{11}R_{12}$;

each $R_{10}$ is independently selected from the group consisting of hydrogen, deuterium, hydroxy, $C_{1-10}$ alkyl, $C_{1-10}$ alkoxy, $C_{2-10}$ alkenyl, $C_{2-10}$ alkynyl, $C_{3-12}$ cycloalkyl, $C_{3-12}$ cycloalkyloxy, 3-12 membered heterocyclyl, 3-12 membered heterocyclyloxy, $C_{5-10}$ aryl, $C_{5-10}$ aryloxy, 5-10 membered heteroaryl, 5-10 membered heteroaryloxy and $-NR_{11}R_{12}$, the above groups are optionally further substituted with one or more substituents selected from the group consisting of deuterium, halogen, hydroxy, cyano, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{5-10}$ aryl, $C_{5-10}$ aryloxy, 5-10 membered heteroaryl, 5-10 membered heteroaryloxy and $-NR_{11}R_{12}$;

each of $R_{11}$ and $R_{12}$ is independently selected from the group consisting of hydrogen, deuterium, hydroxy, $C_{1-10}$ alkoxy, $C_{1-10}$ alkyl, $C_{2-10}$ alkenyl, $C_{2-10}$ alkynyl, $C_{3-12}$ cycloalkyl, 3-12 membered heterocyclyl, $C_{5-10}$ aryl, 5-10 membered heteroaryl, sulfinyl, sulfonyl, methylsulfonyl, isopropylsulfonyl, cyclopropylsulfonyl, p-toluenesulfonyl, aminosulfonyl, dimethylaminosulfonyl, amino, monoalkylamino, dialkylamino and $C_{1-10}$ alkanoyl, the above groups are optionally further substituted with one or more substituents selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-10}$ alkanoyl;

or, $R_{11}$ and $R_{12}$, together with a nitrogen atom directly connected thereto, form 4-10 membered heterocyclyl, the above group is optionally further substituted with one or more substituents selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-10}$ alkanoyl;

m is 0, 1 or 2;

n is 0, 1, 2, 3 or 4;

each r is independently 0, 1 or 2.

As a preferred embodiment, in the compound of formula (I), the stereoisomer or pharmaceutically acceptable salt thereof, $R_5$ and $R_7$ are each independently selected from the group consisting of hydrogen, deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{5-8}$ aryl, 5-8 membered heteroaryl, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_9$, —$C_{0-4}$ alkyl-C(O)$R_{10}$, —$C_{0-4}$ alkyl-O—C(O)$R_{10}$, —$C_{0-4}$ alkyl-$NR_{11}R_{12}$, —$C_{0-4}$ alkyl-C(=$NR_{11}$)$R_{10}$, —$C_{0-4}$ alkyl-N($R_{11}$)—C(=$NR_{12}$)$R_{10}$, —$C_{0-4}$ alkyl-C(O)$NR_{11}R_{12}$ and —$C_{0-4}$ alkyl-N($R_{11}$)—C(O)$R_{10}$;

wherein, $R_8$, $R_9$, $R_{10}$, $R_{11}$, $R_{12}$ and r are defined as those in the compound of formula (I).

As a preferred embodiment, in the compound of formula (I), the stereoisomer or pharmaceutically acceptable salt thereof, $R_2$, $R_3$ and $R_4$ are each independently selected from the group consisting of hydrogen, deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{5-8}$ aryl, 5-8 membered heteroaryl, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_9$, —$C_{0-4}$ alkyl-C(O)$R_{10}$, —$C_{0-4}$ alkyl-O—C(O)$R_{10}$, —$C_{0-4}$ alkyl-$NR_{11}R_{12}$, —$C_{0-4}$ alkyl-C(=$NR_{11}$)$R_{10}$, —$C_{0-4}$ alkyl-N($R_{11}$)—C(=$NR_{12}$)$R_{10}$, —$C_{0-4}$ alkyl-C(O)$NR_{11}R_{12}$ and —$C_{0-4}$ alkyl-N($R_{11}$)—C(O)$R_{10}$;

wherein, $R_8$, $R_9$, $R_{10}$, $R_{11}$, $R_{12}$ and r are defined as those in the compound of formula (I).

As a preferred embodiment, in the compound of formula (I), the stereoisomer or pharmaceutically acceptable salt thereof, $R_6$ is selected from the group consisting of $C_{1-4}$ alkyl, $C_{2-4}$ alkenyl, $C_{2-4}$ alkynyl, $C_{3-6}$ cycloalkyl, 3-6 membered heterocyclyl, —C(O)$R_{10}$, —$NR_{11}R_{12}$, —C(=$NR_{11}$)$R_{10}$, —N($R_{11}$)—C(=$NR_{12}$)$R_{10}$, —C(O)$NR_{11}R_{12}$ and —N($R_{11}$)—C(O)$R_{10}$, the above groups are optionally further substituted with one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{5-8}$ aryl, 5-8 membered heteroaryl, =O, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_9$, —$C_{0-4}$ alkyl-C(O)$R_{10}$, —$C_{0-4}$ alkyl-O—C(O)$R_{10}$, —$C_{0-4}$ alkyl-$NR_{11}R_{12}$, —$C_{0-4}$ alkyl-C(=$NR_{11}$)$R_{10}$, —$C_{0-4}$ alkyl-N($R_{11}$)—C(=$NR_{12}$)$R_{10}$, —$C_{0-4}$ alkyl-C(O)$NR_{11}R_{12}$ and —$C_{0-4}$ alkyl-N($R_{11}$)—C(O)$R_{10}$;

wherein, $R_8$, $R_9$, $R_{10}$, $R_{11}$, $R_{12}$ and r are defined as those in the compound of formula (I).

As a preferred embodiment, in the compound of formula (I), the stereoisomer or pharmaceutically acceptable salt thereof, $R_1$ is selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, $C_{5-8}$ aryl, 5-8 membered heteroaryl, —$C_{0-4}$ alkyl-$SF_5$, —$C_{0-4}$ alkyl-S(O)$R_4$, —$C_{0-4}$ alkyl-O—$R_9$, —$C_{0-4}$ alkyl-C(O)$OR_9$, —$C_{0-4}$ alkyl-C(O)$R_{10}$, —$C_{0-4}$ alkyl-O—C(O)$R_{10}$, —$C_{0-4}$ alkyl-$NR_{11}R_{12}$, —$C_{0-4}$ alkyl-C(=$NR_{11}$)$R_{10}$, —$C_{0-4}$ alkyl-N($R_{11}$)—C(=$NR_{12}$)$R_{10}$, —$C_{0-4}$ alkyl-C(O)$NR_{11}R_{12}$ and —$C_{0-4}$ alkyl-N($R_{11}$)—C(O)$R_{10}$, the above groups are optionally further substituted with one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{5-8}$ aryl, 5-8 membered heteroaryl, =O, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_9$, —$C_{0-4}$ alkyl-C(O)$R_{10}$, —$C_{0-4}$ alkyl-O—C(O)$R_{10}$, —$C_{0-4}$ alkyl-$NR_{11}R_{12}$, —$C_{0-4}$ alkyl-C(=$NR_{11}$)$R_{10}$, —$C_{0-4}$ alkyl-N($R_{11}$)—C(=$NR_{12}$)$R_{10}$, —$C_{0-4}$ alkyl-C(O)$NR_{11}R_{12}$ and —$C_{0-4}$ alkyl-N($R_{11}$)—C(O)$R_{10}$;

wherein, $R_8$, $R_9$, $R_{10}$, $R_{11}$, $R_{12}$ and r are defined as those in the compound of formula (I).

As a more further preferred embodiment, in the compound of formula (I), the stereoisomer or pharmaceutically acceptable salt thereof, the compound of formula (I) is a compound having formula (II):

(II)

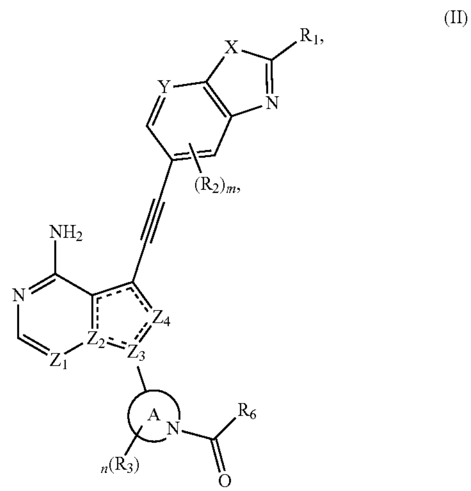

wherein, "---" is a double bond or a single bond;

X is O or S; Y is $CR_4$ or N;

$Z_1$ and $Z_4$ are each independently N or $CR_7$;

$Z_2$ and $Z_3$ are each independently N or C;

ring A is 3-8 membered nitrogen-containing heterocyclyl, wherein, the nitrogen atom is connected to carbonyl;

$R_1$ is selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, —$SF_5$, —$S(O)_rR_8$, —O—$R_9$, —C(O)$OR_9$, —C(O)$R_{10}$, —O—C(O)$R_{10}$, —$NR_{11}R_{12}$, —C(=$NR_{11}$)$R_{10}$, —N(Ru)—C(=$NR_{12}$)$R_{10}$, —C(O)$NR_{11}R_{12}$ and —N($R_{11}$)—C(O)$R_{10}$, the above groups are optionally further substituted with one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{5-8}$ aryl, 5-8 membered heteroaryl, =O, —$SF_5$, —$S(O)_rR_8$, —O—$R_9$, —C(O)$OR_9$, —C(O)$R_{10}$, —O—C(O)$R_{10}$, —$NR_{11}R_{12}$, —C(=$NR_{11}$)$R_{10}$, —N($R_{11}$)—C(=$NR_{12}$)$R_{10}$, —C(O)$NR_{11}R_{12}$ and —N($R_{11}$)—C(O)$R_{10}$;

each $R_2$ is independently selected from the group consisting of hydrogen, deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, —$SF_5$, —$S(O)_rR_8$, —O—$R_9$, —C(O)$OR_9$, —C(O)$R_{10}$, —O—C(O)$R_{10}$, —$NR_{11}R_{12}$, —C(=$NR_{11}$)$R_{10}$, —N($R_{11}$)—C(=$NR_{12}$)$R_{10}$, —C(O)$NR_{11}R_{12}$ and —N($R_{11}$)—C(O)$R_{10}$;

each $R_3$ is independently selected from the group consisting of hydrogen, deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $-SF_5$, $-S(O)_rR_8$, $-CH_2-O-R_9$, $-C(O)OR_9$, $-C(O)R_{10}$, $-O-C(O)R_{10}$, $-NR_{11}R_{12}$, $-C(=NR_{11})R_{10}$, $-N(R_{11})-C(=NR_{12})R_{10}$, $-C(O)NR_{11}R_{12}$ and $-N(R_{11})-C(O)R_{10}$;

$R_4$ is selected from the group consisting of hydrogen, deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $-SF_5$, $-S(O)_rR_8$, $-O-R_9$, $-C(O)OR_9$, $-C(O)R_{10}$, $-O-C(O)R_{10}$, $-NR_{11}R_{12}$, $-C(=NR_{11})R_{10}$, $-N(R_{11})-C(=NR_{12})R_{10}$, $-C(O)NR_{11}R_{12}$, and $-N(R_{11})-C(O)R_{10}$;

$R_6$ is selected from the group consisting of $C_{1-4}$ alkyl, $C_{2-4}$ alkenyl, $C_{2-4}$ alkynyl, $C_{3-6}$ cycloalkyl, 3-6 membered heterocyclyl, $-C(O)R_{10}$, $-NR_{11}R_{12}$, $-C(=NR_{11})R_{10}$ and $-N(R_{11})-C(=NR_{12})R_{10}$, the above groups are optionally further substituted with one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $=O$, $-SF_5$, $-S(O)NRs$, $-O-R_9$, $-C(O)OR_9$, $-C(O)R_{10}$, $-O-C(O)R_{10}$, $-CH_2-NR_{11}R_{12}$, $-C(=NR_{11})R_{10}$, $-N(R_{11})-C(=NR_{12})R_{10}$, $-C(O)NR_{11}R_{12}$ and $-N(R_{11})-C(O)R_{10}$;

each $R_7$ is independently selected from the group consisting of hydrogen, deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $-SF_5$, $-S(O)_rR_8$, $-O-R_9$, $-C(O)OR_9$, $-C(O)R_{10}$, $-O-C(O)R_{10}$, $-NR_{11}R_{12}$, $-C(=NR_{11})R_{10}$, $-N(R_{11})-C(=NR_{12})R_{10}$, $-C(O)NR_{11}R_{12}$ and $-N(R_{11})-C(O)R_{10}$;

wherein, $R_8$, $R_9$, $R_{10}$, $R_{11}$, $R_{12}$, m, n and r are defined as those in the compound of formula (I).

As a more further preferred embodiment, in the compound of formula (I), the stereoisomer or pharmaceutically acceptable salt thereof, the compound of formula (I) is a compound having formula (IIIa) or formula (IIIb):

(IIIa)

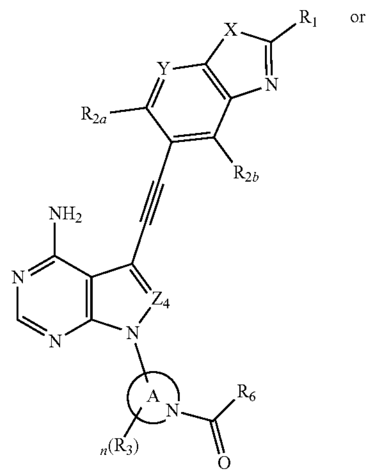

or

-continued (IIIb)

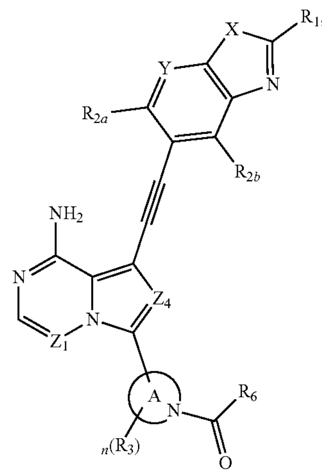

wherein, each X is independently O or S; each Y is independently CH or N;

in the compound of formula (IIIb), $Z_1$ is N or $CR_7$;

each $Z_4$ is independently N or $CR_7$;

each ring A is independently 4-6 membered nitrogen-containing heterocyclyl, wherein, the nitrogen atom is connected to carbonyl;

each $R_1$ is independently selected from the group consisting of hydrogen, deuterium, halogen, cyano, $C_{1-4}$ alkyl, $C_{3-6}$ cycloalkyl, 3-6 membered heterocyclyl, $-SF_5$, $-O-R_9$, $-C(O)OR_9$, $-C(O)R_{10}$, $-O-C(O)R_{10}$ and $-NR_{11}R_{12}$, the above groups are optionally further substituted with one or more substituents selected from the group consisting of deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, $=O$, $-SF_5$, $-O-R_9$, $-C(O)OR_9$, $-C(O)R_{10}$, $-O-C(O)R_{10}$ and $-NR_{11}R_{12}$;

each of $R_{2a}$ and $R_{2b}$ is independently selected from the group consisting of hydrogen, deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, $-SF_5$, $-O-R_9$, $-C(O)OR_9$, $-C(O)R_{10}$, $-O-C(O)R_{10}$ and $-NR_{11}R_{12}$;

each $R_3$ is independently selected from the group consisting of hydrogen, deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, $-SF_5$, $-CH_2-O-R_9$, $-C(O)OR_9$, $-C(O)R_{10}$, $-O-C(O)R_{10}$ and $-NR_{11}R_{12}$;

each $R_6$ is independently vinyl, the above group is optionally further substituted with one or more substituents selected from the group consisting of deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, $=O$, $-SF_5$, $-O-R_9$, $-C(O)OR_9$, $-C(O)R_{10}$, $-O-C(O)R_{10}$ and $-CH_2-NR_{11}R_{12}$;

each $R_7$ is independently selected from the group consisting of hydrogen, deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, $-SF_5$, $-O-R_9$, $-C(O)OR_9$, $-C(O)R_{10}$, $-O-C(O)R_{10}$ and $-NR_{11}R_{12}$;

wherein, $R_9$, $R_{10}$, $R_{11}$, $R_{12}$ and n are defined as those in the compound of formula (I).

As a still more further preferred embodiment, in the compound of formula (I), the stereoisomer or pharmaceutically acceptable salt thereof, ring A, together with $—(R_3)_n$, forms the following structure:

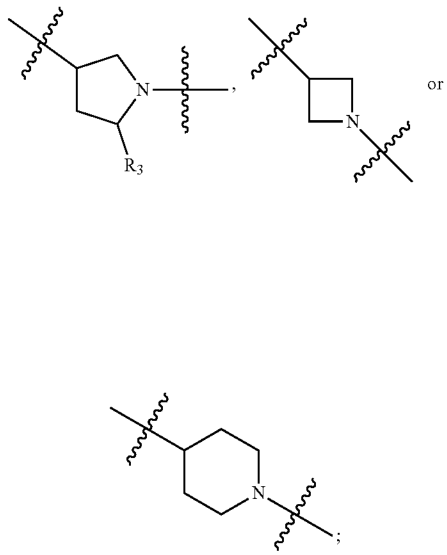

$R_3$ is selected from the group consisting of hydrogen, deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, $—SF_5$, $—CH_2—O—R_9$, $—C(O)OR_9$, $—C(O)R_{10}$, $—O—C(O)R_{10}$ and $—NR_{11}R_{12}$;

wherein, $R_9$, $R_{10}$, $R_{11}$, and $R_{12}$ are defined as those in the compound of formula (I).

As a more further preferred embodiment, in the compound of formula (I), the stereoisomer or pharmaceutically acceptable salt thereof, the compound of formula (I) is a compound having formula ($IVa_1$) or formula ($IVa_2$):

($IVa_1$)

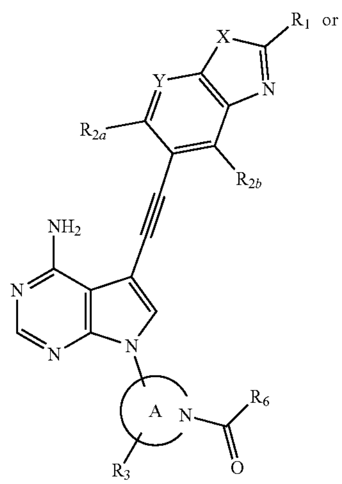

or

-continued ($IVa_2$)

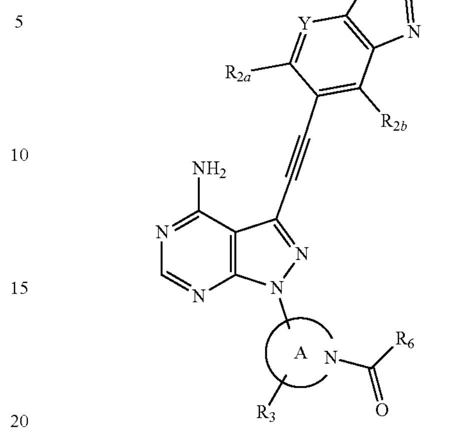

wherein, each X is independently O or S; each Y is independently CH or N;

ring A, together with $—R_3$, forms the following structure:

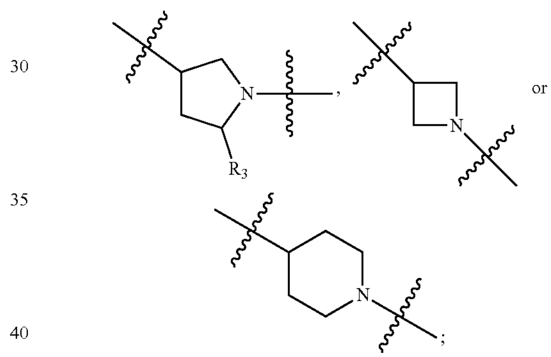

$R_3$ is selected from the group consisting of hydrogen, deuterium, halogen, $C_{1-4}$ alkyl, $C_{1-4}$ haloalkyl, $C_{1-4}$ deuterioalkyl and $—CH_2—O—R_9$;

each $R_1$ is independently selected from the group consisting of hydrogen, deuterium, fluorine, chlorine, cyano, $C_{1-4}$ alkyl, $C_{3-6}$ cycloalkyl, 3-6 membered heterocyclyl, $—SF_5$, $—O—R_9$, $—C(O)OR_9$, $—C(O)R_{10}$, $—O—C(O)R_{10}$ and $—NR_{11}R_{12}$, the above groups are optionally further substituted with one or more substituents selected from the group consisting of deuterium, fluorine, chlorine, cyano, $C_{1-4}$ alkyl, $C_{1-4}$ haloalkyl, $C_{1-4}$ deuterioalkyl, $C_{3-6}$ cycloalkyl, 3-6 membered heterocyclyl, $=O$, $—SF_5$, $—O—R_9$, $—C(O)OR_9$, $—C(O)R_{10}$, $—O—C(O)R_{10}$ and $—NR_{11}R_{12}$;

each of $R_{2a}$ and $R_{2b}$ is independently selected from the group consisting of hydrogen, deuterium, fluorine, chlorine, cyano, $C_{1-4}$ alkyl, $C_{1-4}$ haloalkyl, $C_{1-4}$ deuterioalkyl, $C_{3-6}$ cycloalkyl, $—SF_5$, $—O—R_9$, $—C(O)OR_9$, $—C(O)R_{10}$, $—O—C(O)R_{10}$ and $—NR_{11}R_{12}$;

each $R_6$ is independently vinyl, the above group is optionally further substituted with one or more substituents selected from the group consisting of deuterium, fluorine, cyano, methyl, ethyl, n-propyl and $—CH_2—NR_{11}R_{12}$;

wherein, $R_9$, $R_{10}$, $R_{11}$ and $R_{12}$ are defined as those in the compound of formula (I).

As a more further preferred embodiment, in the compound of formula (I), the stereoisomer or pharmaceutically acceptable salt thereof, the compound of formula (I) is a compound having formula ($IVb_1$) or formula ($IVb_2$):

($IVa_1$)

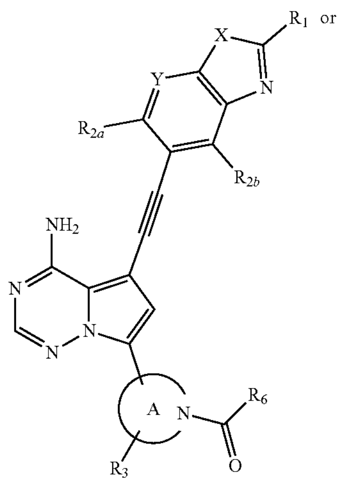

or ($IVa_2$)

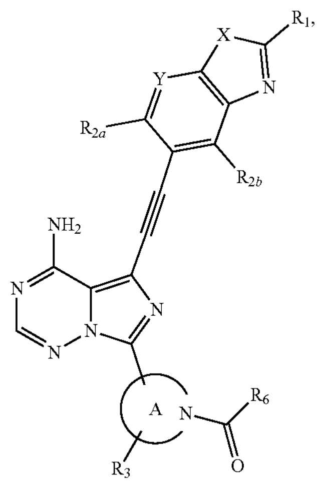

wherein, each X is independently O or S; each Y is independently CH or N;

ring A, together with —$R_3$, forms the following structure:

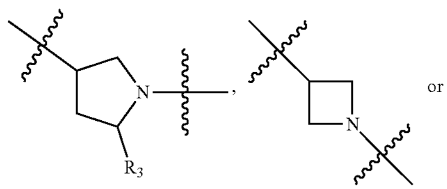

-continued

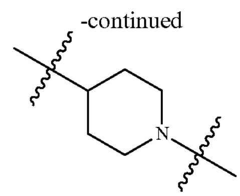

$R_3$ is selected from the group consisting of hydrogen, deuterium, halogen, $C_{1-4}$ alkyl, $C_{1-4}$ haloalkyl, $C_{1-4}$ deuterioalkyl and —$CH_2$—O—$R_9$;

each $R_1$ is independently selected from the group consisting of hydrogen, deuterium, fluorine, chlorine, cyano, $C_{1-4}$ alkyl, $C_{3-6}$ cycloalkyl, 3-6 membered heterocyclyl, —$SF_5$, —O—$R_9$, —C(O)$OR_9$, —C(O)$R_{10}$, —O—C(O)$R_{10}$ and —$NR_{11}R_{12}$, the above groups are optionally further substituted with one or more substituents selected from the group consisting of deuterium, fluorine, chlorine, cyano, $C_{1-4}$ alkyl, $C_{1-4}$ haloalkyl, $C_{1-4}$ deuterioalkyl, $C_{3-6}$ cycloalkyl, 3-6 membered heterocyclyl, =O, —$SF_5$, —O—$R_9$, —C(O)$OR_9$, —C(O)$R_{10}$, —O—C(O)$R_{10}$ and —$NR_{11}R_{12}$;

each of $R_{2a}$ and $R_{2b}$ is independently selected from the group consisting of hydrogen, deuterium, fluorine, chlorine, cyano, $C_{1-4}$ alkyl, $C_{1-4}$ haloalkyl, $C_{1-4}$ deuterioalkyl, $C_{3-6}$ cycloalkyl, —$SF_5$, —O—$R_9$, —C(O)$OR_9$, —C(O)$R_{10}$, —O—C(O)$R_{10}$ and —$NR_{11}R_{12}$;

each $R_6$ is independently vinyl, the above group is optionally further substituted with one or more substituents selected from the group consisting of deuterium, fluorine, cyano, methyl, ethyl, n-propyl and —$CH_2$—$NR_{11}R_{12}$;

wherein, $R_9$, $R_{10}$, $R_{11}$ and $R_{12}$ are defined as those in the compound of formula (I).

As a preferred embodiment, in the compound of formula (I), the stereoisomer or pharmaceutically acceptable salt thereof, each $R_8$ is independently selected from the group consisting of hydrogen, deuterium, hydroxy, $C_{1-4}$ alkyl, $C_{2-4}$ alkenyl, $C_{3-6}$ cycloalkyl, 3-6 membered heterocyclyl, $C_{5-8}$ aryl, 5-8 membered heteroaryl and —$NR_{11}R_{12}$, the above groups are optionally further substituted with one or more substituents selected from the group consisting of deuterium, halogen, hydroxy, oxo, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy and —$NR_{11}R_{12}$;

each $R_9$ is independently selected from the group consisting of hydrogen, deuterium, $C_{1-4}$ alkyl, $C_{2-4}$ alkenyl, $C_{3-6}$ cycloalkyl, 3-6 membered heterocyclyl, $C_{5-8}$ aryl and 5-8 membered heteroaryl, the above groups are optionally further substituted with one or more substituents selected from the group consisting of deuterium, halogen, hydroxy, oxo, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy and —$NR_{11}R_{12}$;

each $R_{10}$ is independently selected from the group consisting of hydrogen, deuterium, hydroxy, $C_{1-4}$ alkyl, $C_{1-4}$ alkoxy, $C_{2-4}$ alkenyl, $C_{2-4}$ alkynyl, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy and —$NR_{11}R_{12}$, the above groups are optionally further substituted with one or more substituents selected from the group consisting of deuterium, halogen, hydroxy, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy and $—NR_{11}R_{12}$;

each of $R_{11}$ and $R_{12}$ is independently selected from the group consisting of hydrogen, deuterium, hydroxy, $C_{1-4}$ alkoxy, $C_{1-4}$ alkyl, $C_{2-4}$ alkenyl, $C_{2-4}$ alkynyl, $C_{3-6}$ cycloalkyl, 3-6 membered heterocyclyl, $C_{5-8}$ aryl, 5-8 membered heteroaryl, sulfinyl, sulfonyl, methylsulfonyl, isopropylsulfonyl, cyclopropylsulfonyl, p-toluenesulfonyl, aminosulfonyl, dimethylaminosulfonyl, amino, monoalkylamino, dialkylamino and $C_{1-4}$ alkanoyl, the above groups are optionally further substituted with one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy, amino, monoalkylamino, dialkylamino and $C_{1-4}$ alkanoyl;

or, $R_{11}$ and $R_{12}$, together with a nitrogen atom directly connected thereto, form 4-6 membered heterocyclyl, the above group is optionally further substituted with one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy, amino, monoalkylamino, dialkylamino and $C_{1-4}$ alkanoyl.

As the most preferred embodiment, the compound of formula (I), the stereoisomer or pharmaceutically acceptable salt thereof include, but are not limited to, the following compounds:

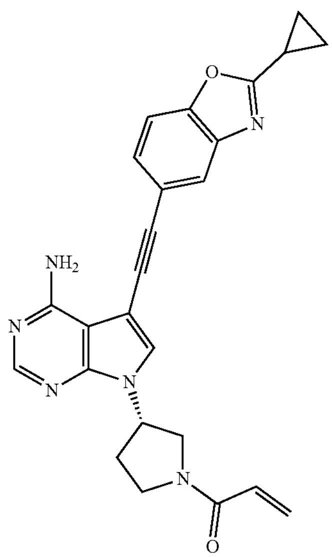

-continued

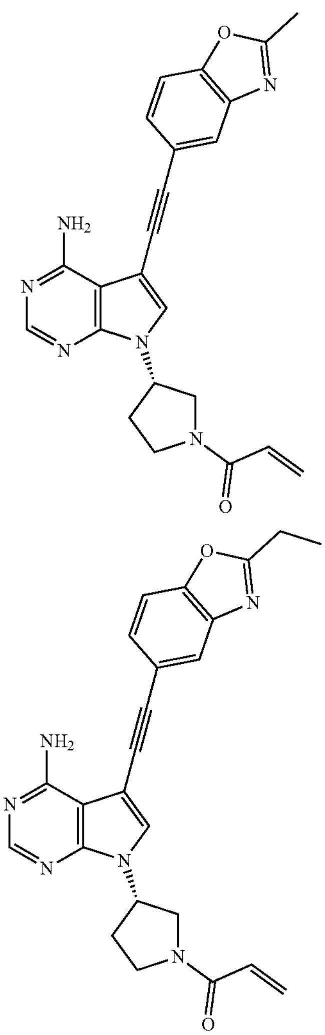

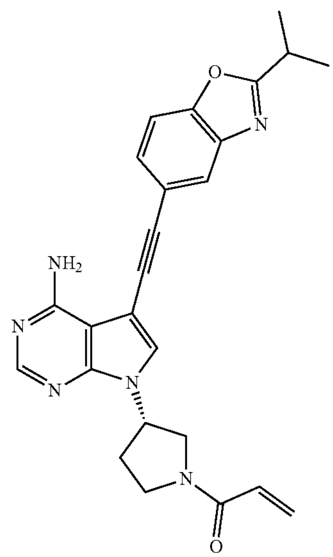

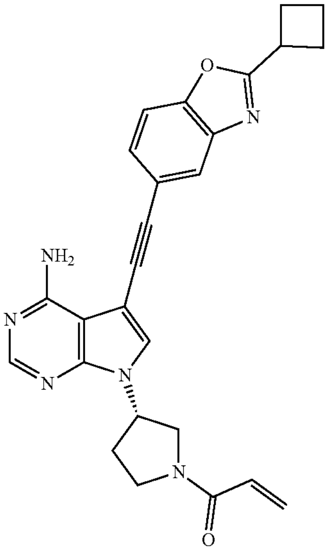
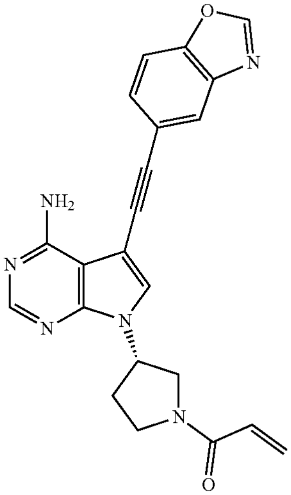
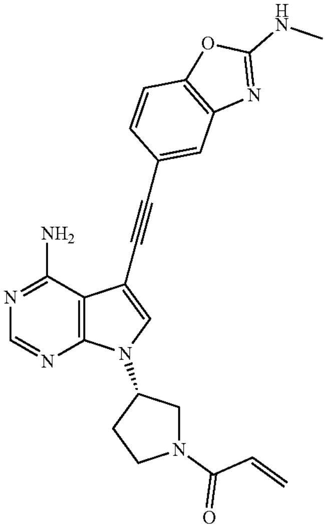
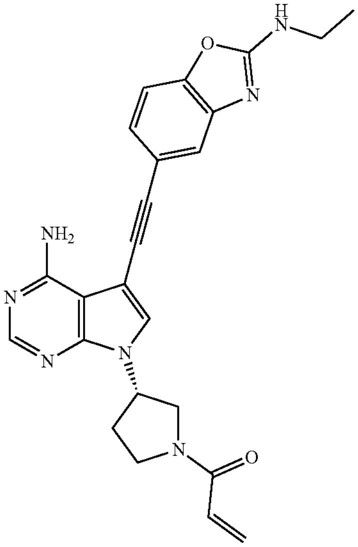
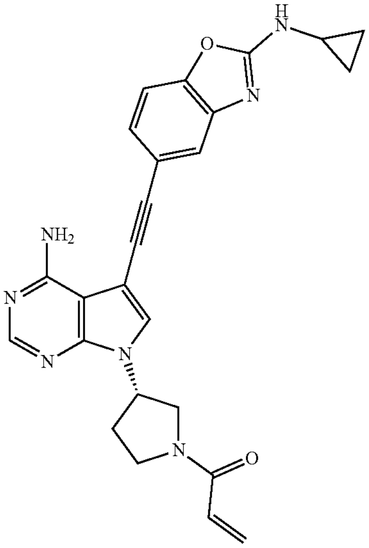
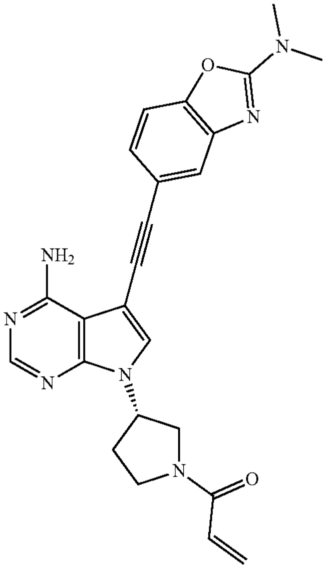

-continued
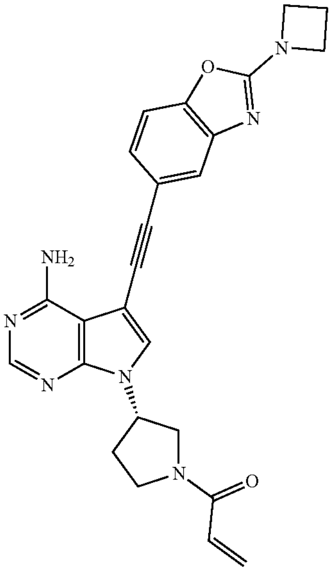
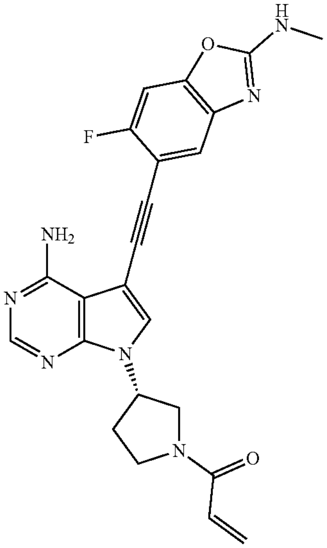
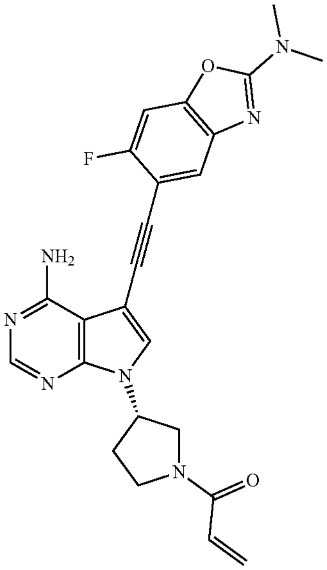
-continued
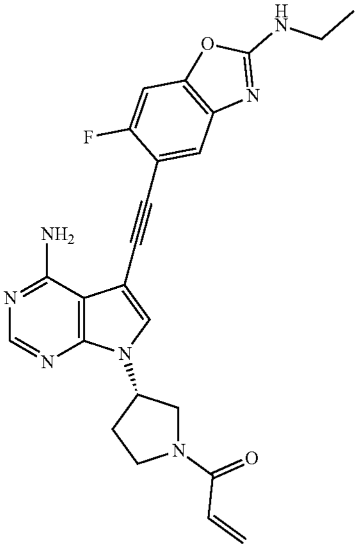
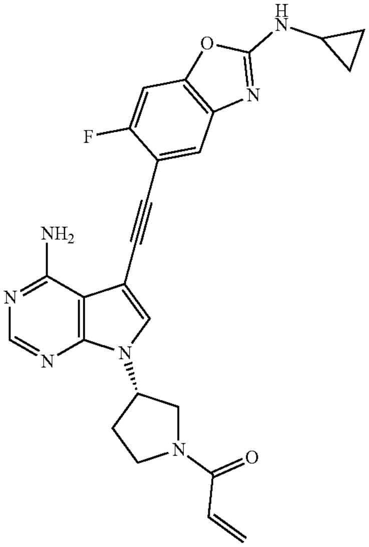
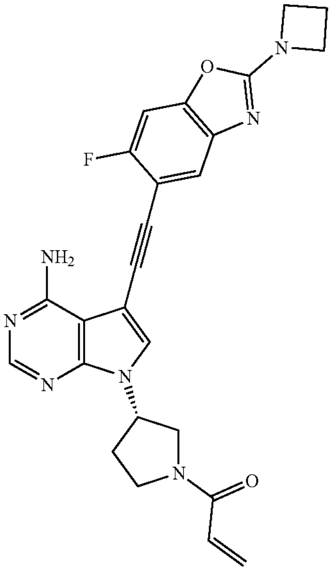

-continued
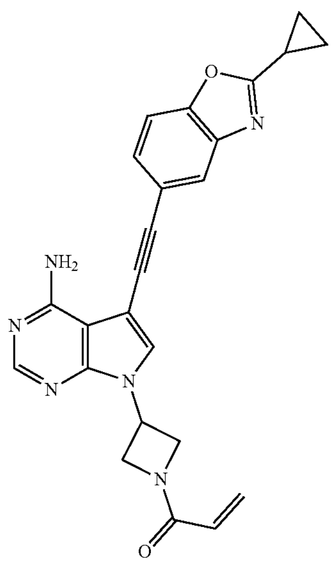
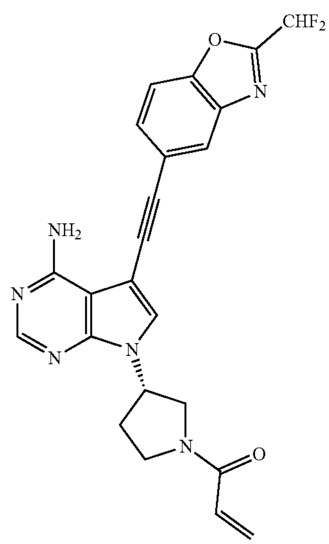
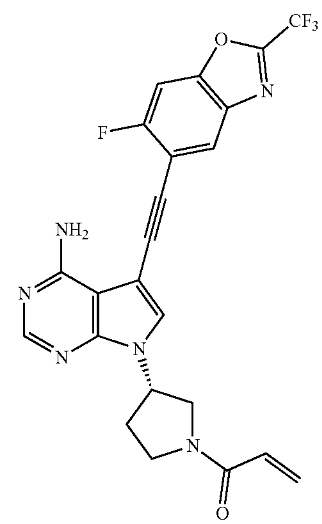
-continued
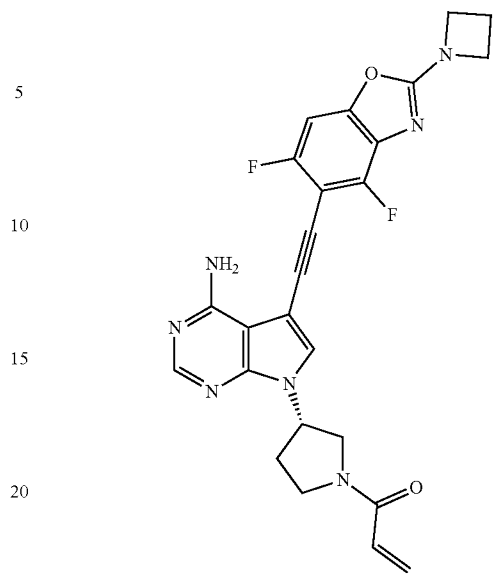
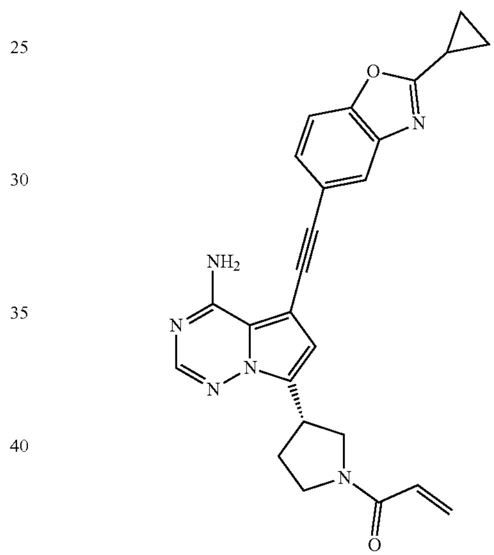
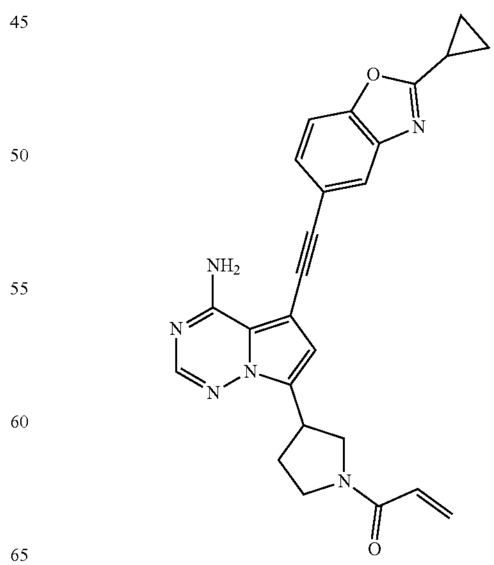

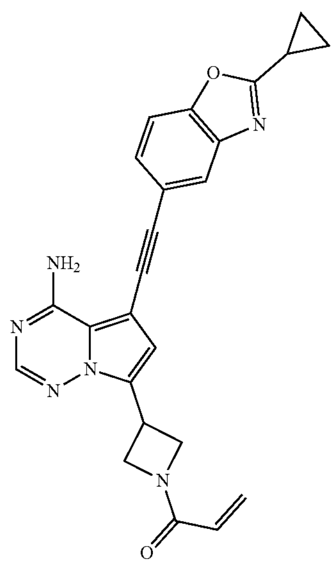
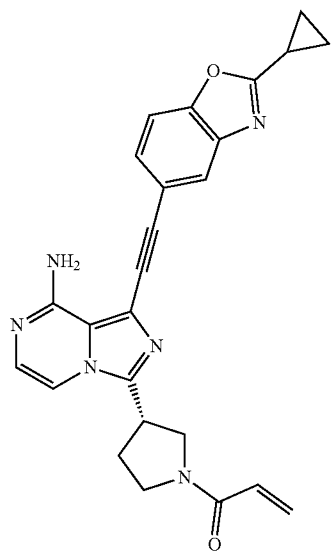
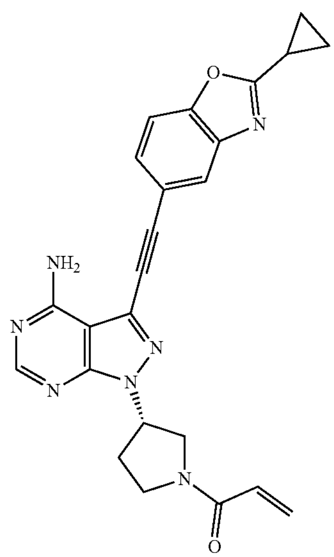
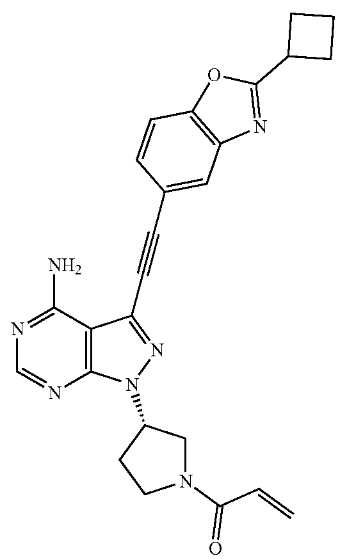
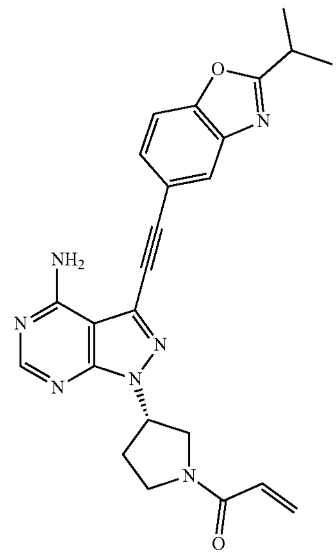
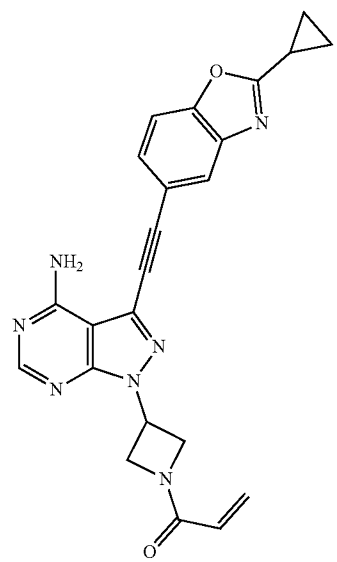

-continued
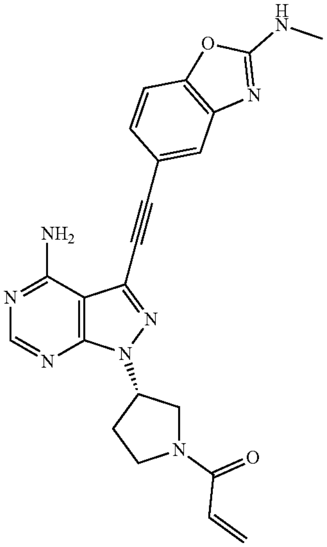
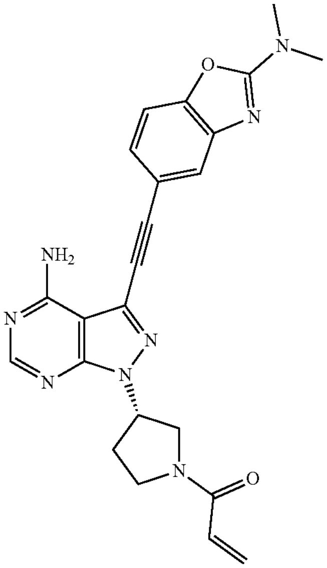
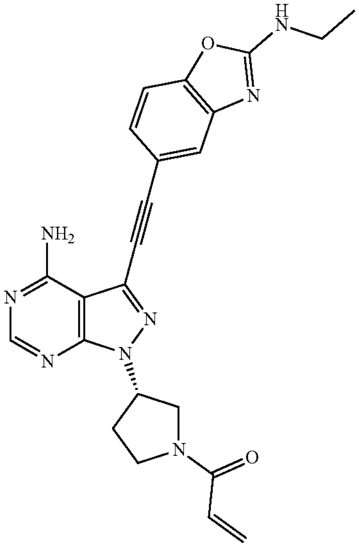
-continued
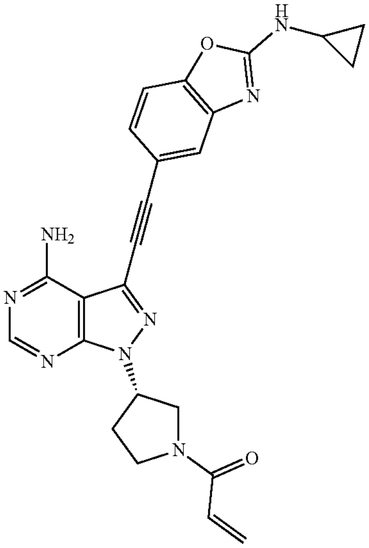
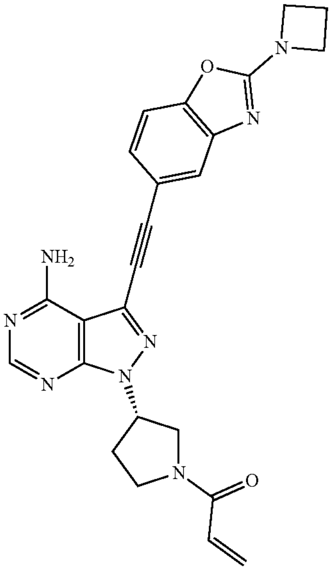
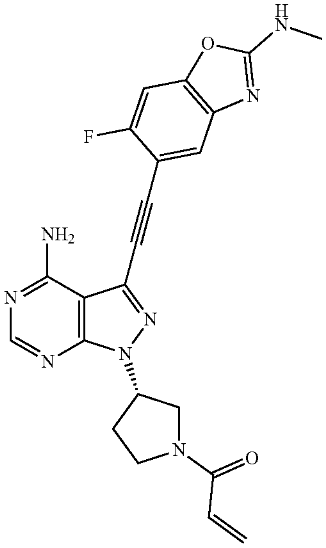

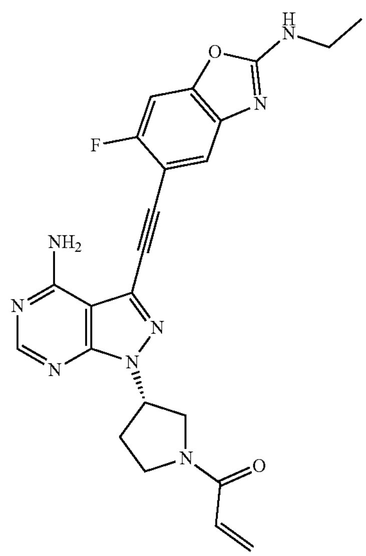
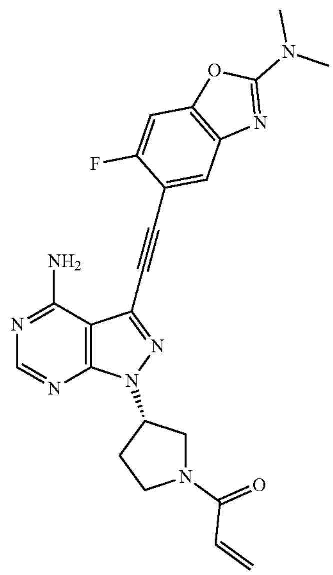
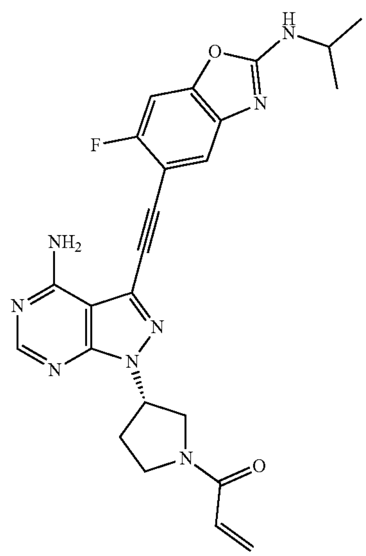
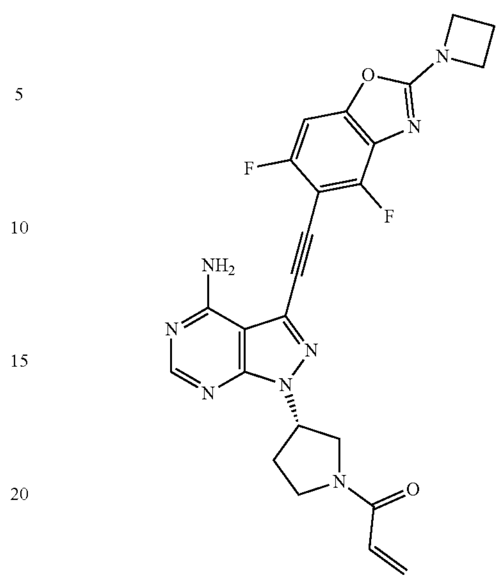
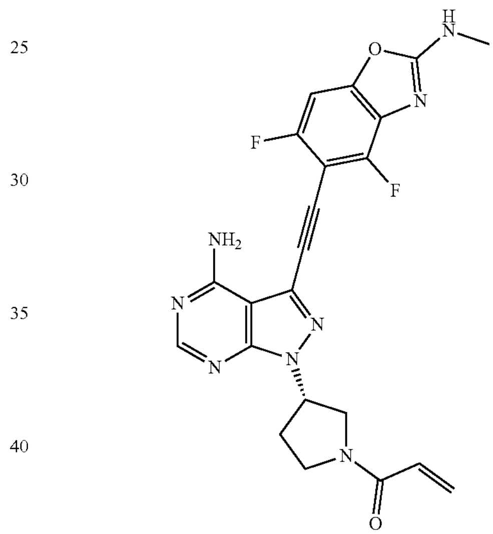
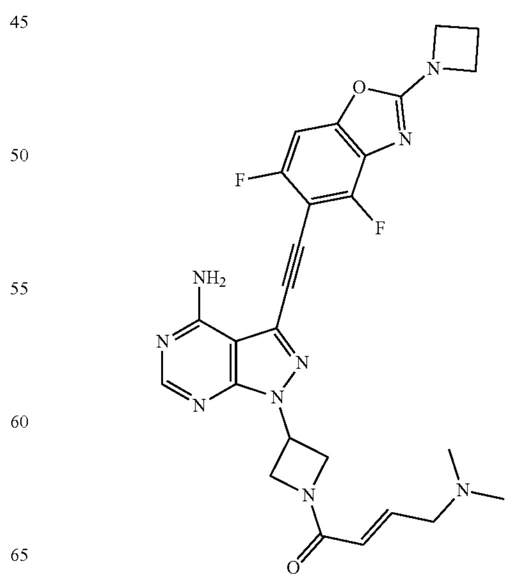

-continued
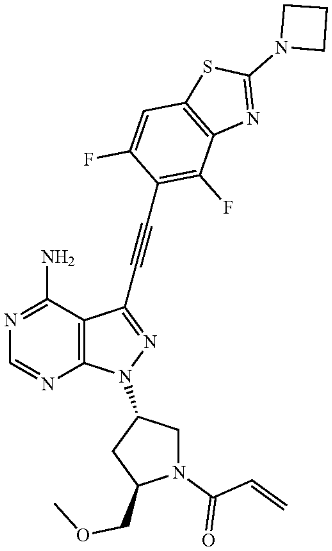
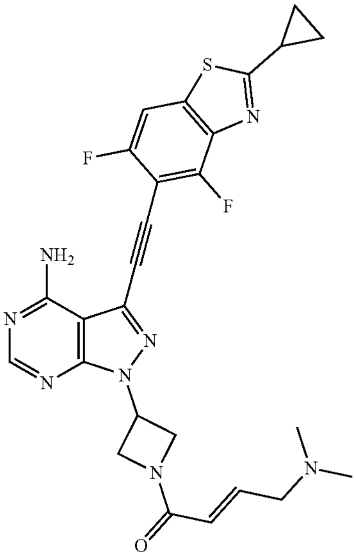
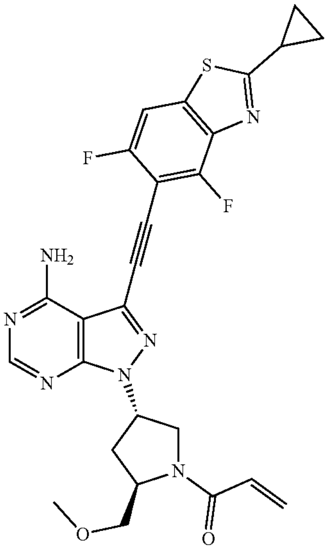
-continued
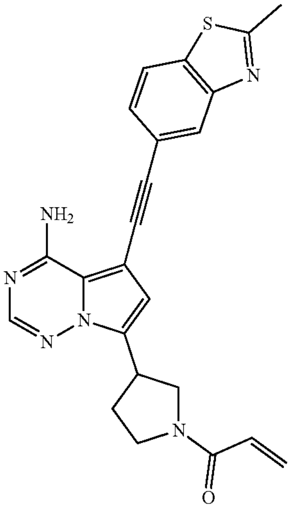
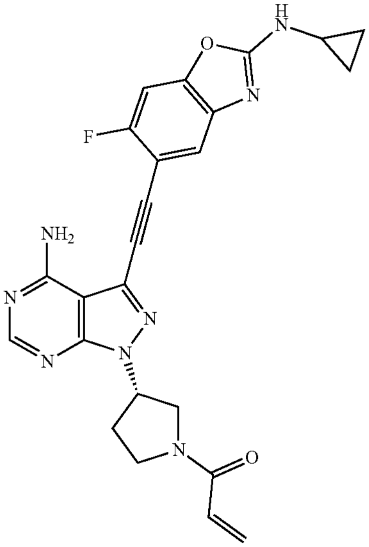
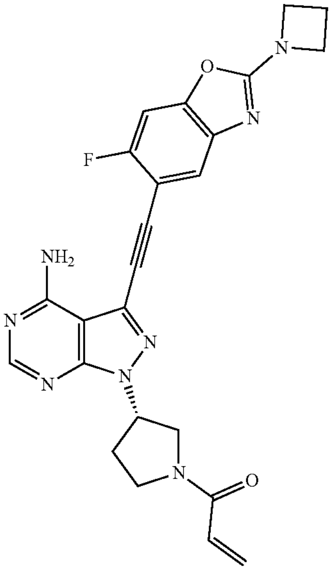

-continued
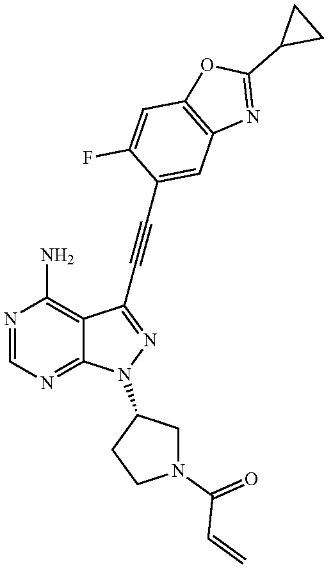
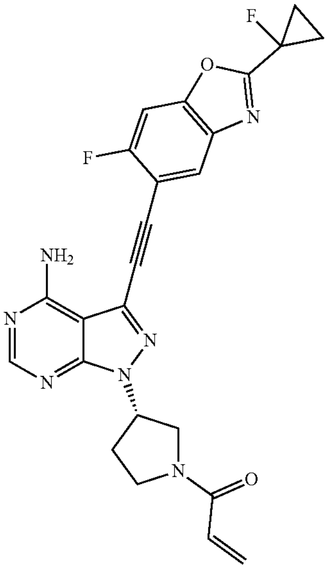
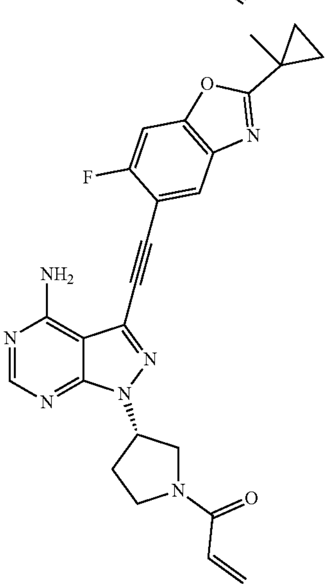
-continued
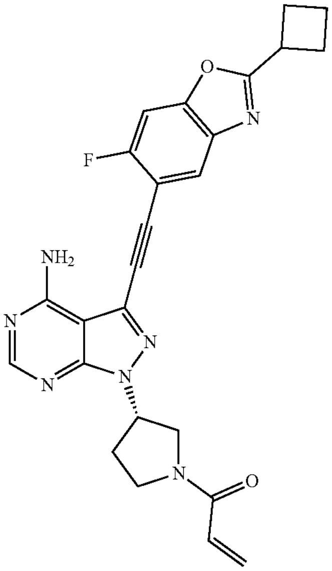
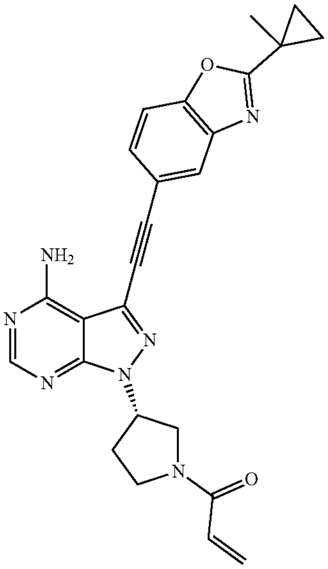
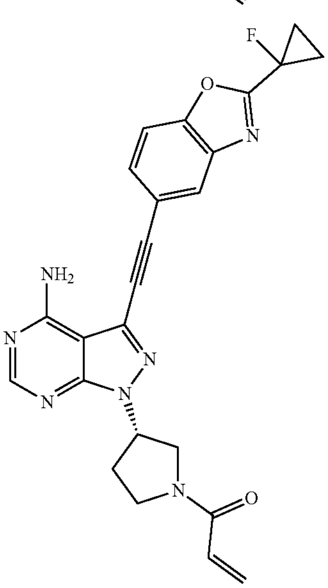

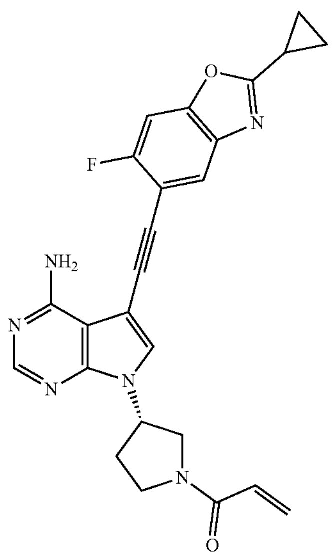
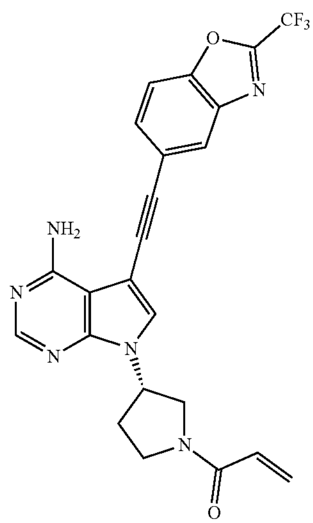
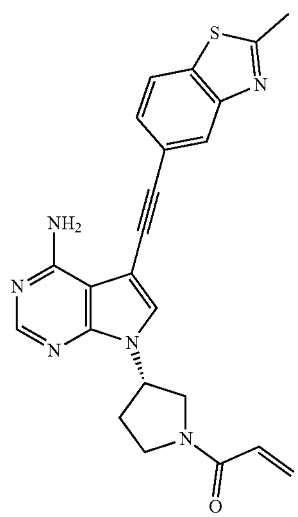
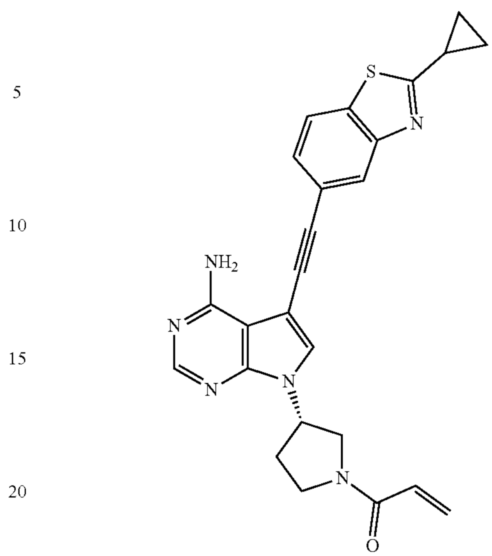
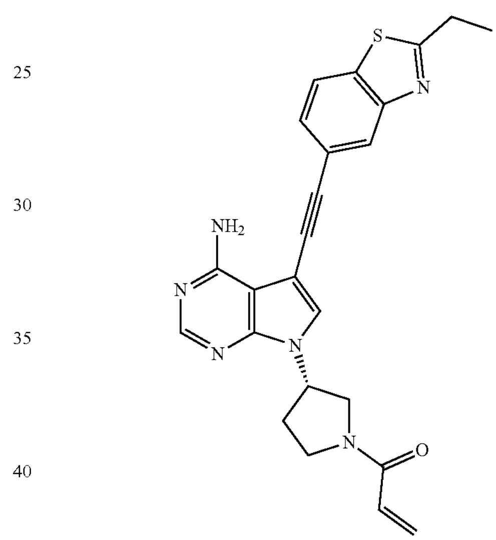
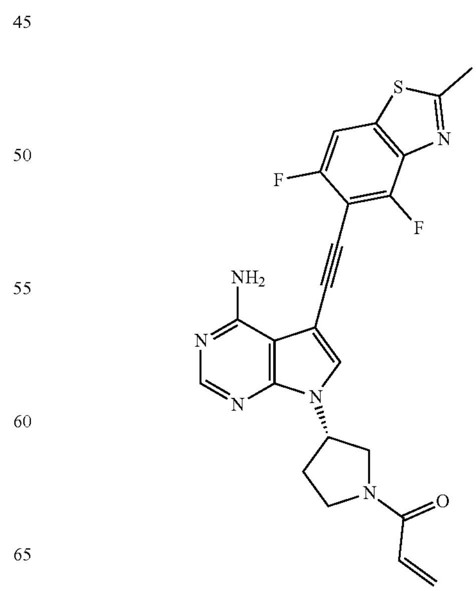

-continued
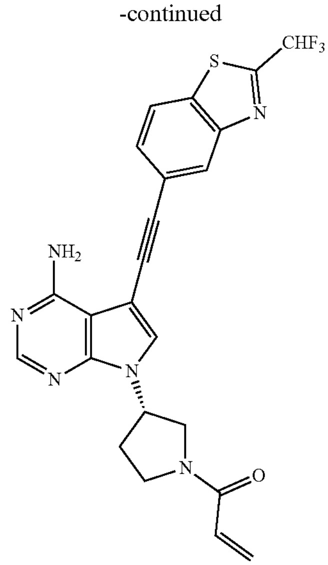
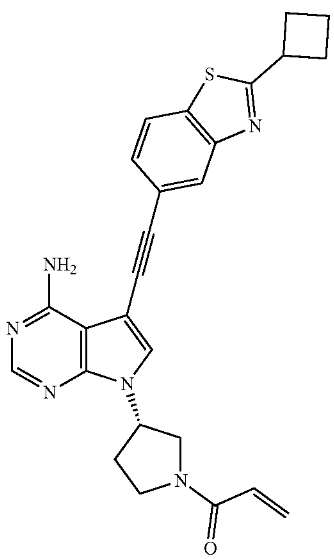
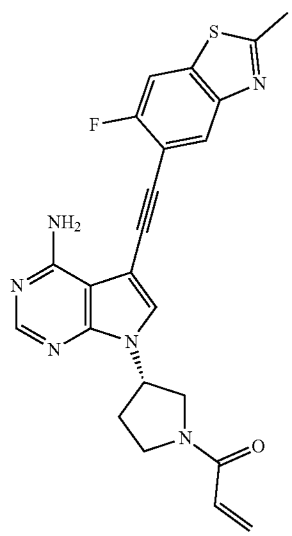
-continued
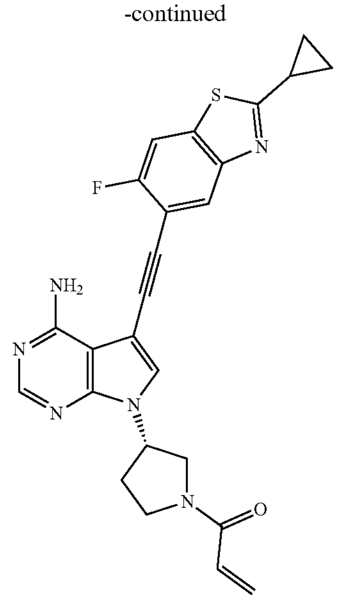
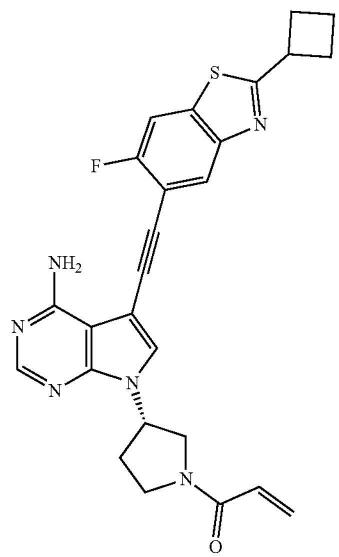
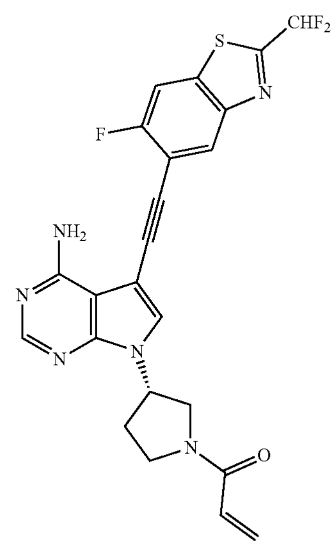

-continued
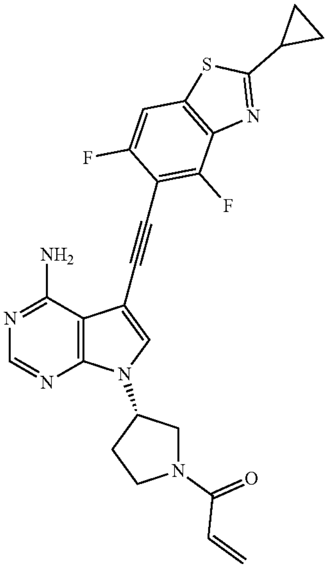
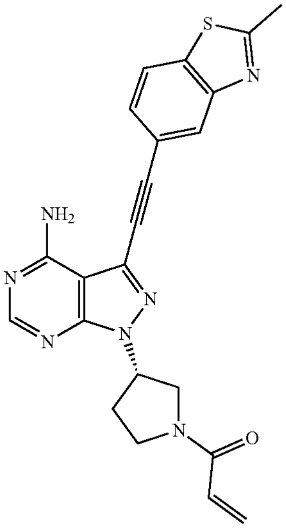
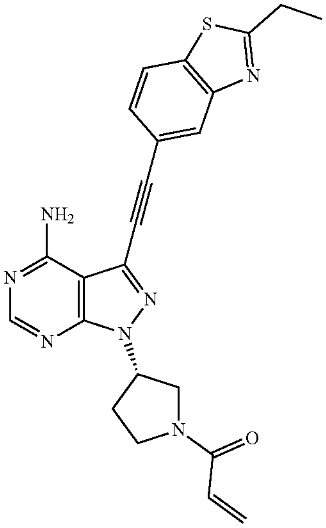
-continued
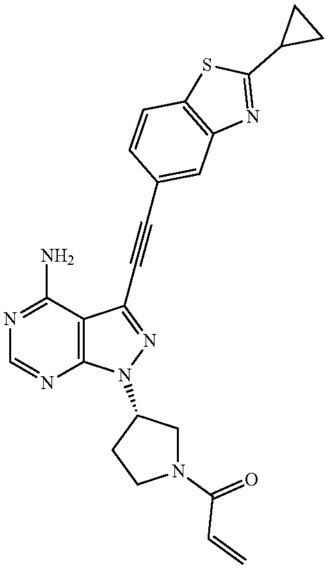
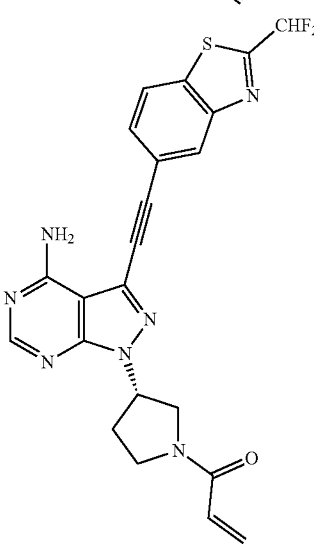
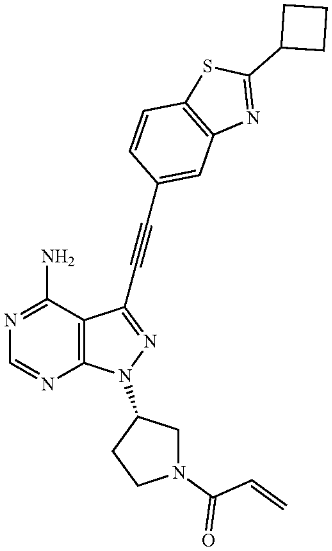

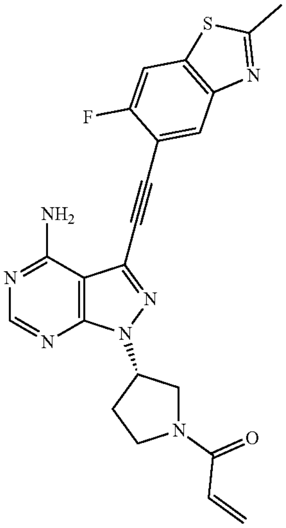
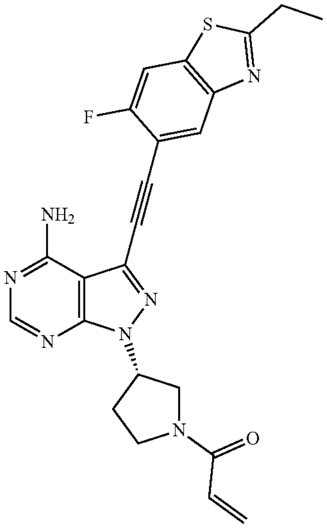
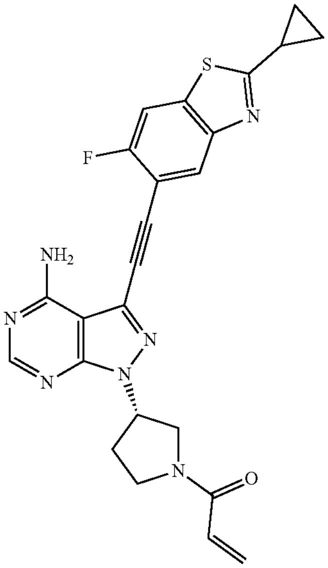
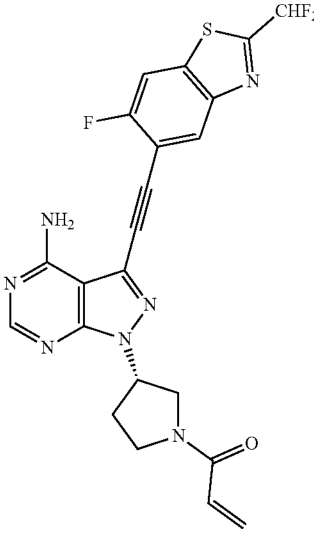
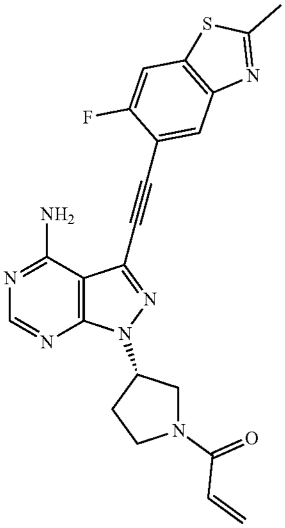
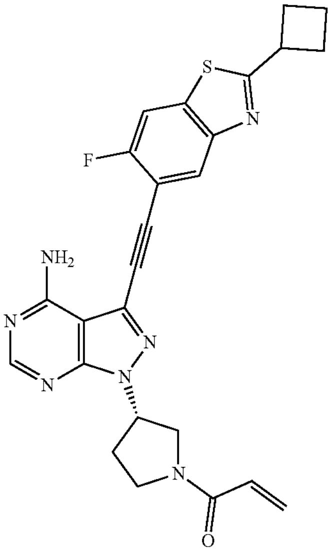
and

-continued
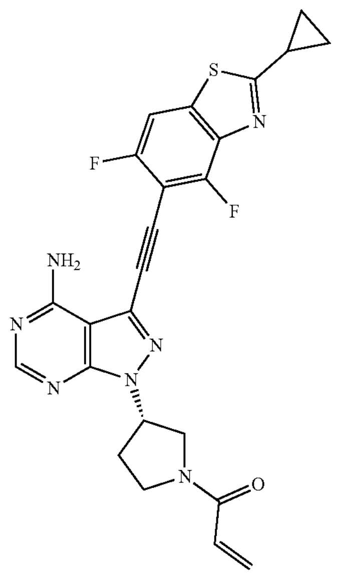
The second aspect of the present invention provides a method for preparing the compound of formula (I), the stereoisomer or pharmaceutically acceptable salt thereof, which comprises the following steps:
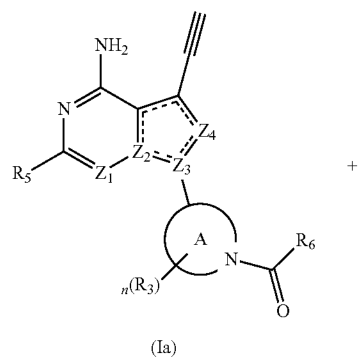
(Ia)
+
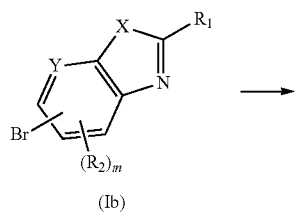
(Ib)
-continued
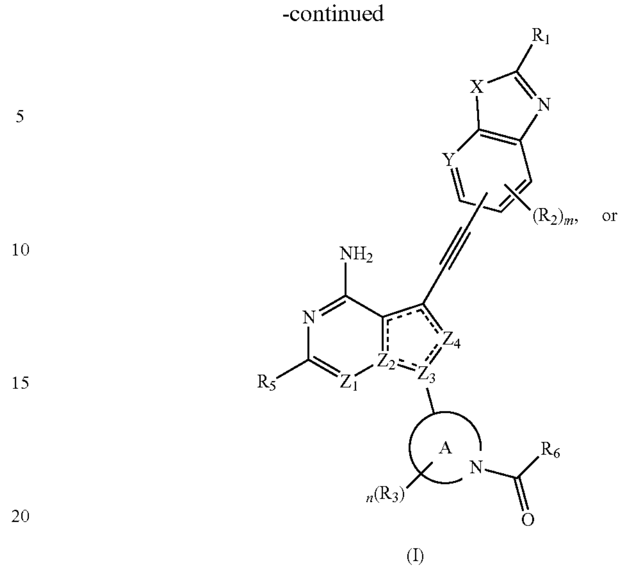
or
(I)
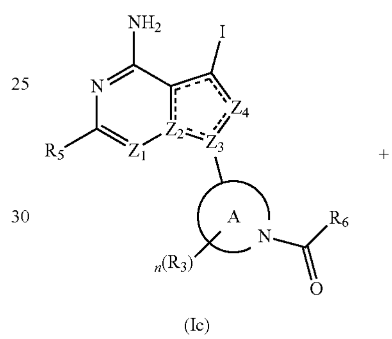
(Ic)
+
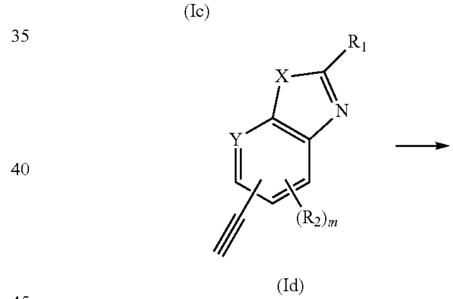
(Id)
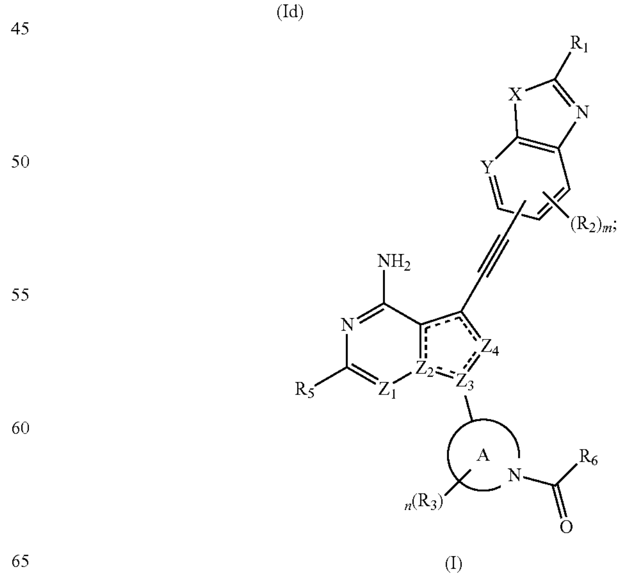
(I)

wherein, ring A, X, Y, $Z_1$, $Z_2$, $Z_3$, $Z_4$, $R_1$, $R_2$, $R_3$, $R_5$, $R_6$, m and n are defined as those in the compound of formula (I).

The third aspect of the present invention provides a pharmaceutical composition, which comprises the compound of formula (I), the stereoisomer or pharmaceutically acceptable salt thereof, and a pharmaceutically acceptable carrier.

The present invention also relates to a use of the compound of formula (I), the stereoisomer or pharmaceutically acceptable salt thereof in preparing a medicament for treating a tumor patient resistant to an FGFR inhibitor.

As a preferred embodiment, the tumor patient is one having mutations at FGFR V561, V565, N550, N540, V555, E566, K660 and/or V550.

As a more further preferred embodiment, the tumor patient is one having FGFR2 V565F, V565I, V565L, V565M, N550K, N550H, E566A, E566G, K660M and/or K660Q mutations.

As a still more further preferred embodiment, the tumor patient is one having FGFR3 V555M/L and/or N540K mutations.

The present invention also relates to the compound of formula (I), the stereoisomer or pharmaceutically acceptable salt thereof for use in preventing or treating an FGFR kinase-mediated disease state or condition.

The present invention also relates to the compound of formula (I), the stereoisomer or pharmaceutically acceptable salt thereof for use in preventing or treating an FGFR kinase-mediated tumor or cancer.

As a preferred embodiment, the tumor or cancer is bladder cancer, breast cancer, cervical cancer, colorectal cancer, endometrial cancer, gastric cancer, head and neck cancer, renal carcinoma, liver cancer, lung cancer, ovarian cancer, prostate cancer, esophageal cancer, gallbladder cancer, pancreatic cancer, thyroid cancer, skin cancer, leukemia, multiple myeloma, chronic lymphocytic lymphoma, adult T-cell leukemia, B-cell lymphoma, acute myelocytic leukemia, Hodgkin lymphoma or non-Hodgkin lymphoma, Waldenstrom macroglobulinemia, hairy cell lymphoma, cell lymphoma, Burkitt lymphoma, glioblastoma, melanoma or rhabdomyosarcoma.

The present invention also relates to a use of the compound of formula (I), the stereoisomer or pharmaceutically acceptable salt thereof in preparing a medicament for treating myeloproliferative disease, skeleton or cartilage cell disorder or hypophosphatemia.

In the present invention, the myeloproliferative disease is erythrocytosis, primary thrombocytosis or primary myelofibrosis; the skeleton or cartilage cell disorder is dysplasia, achondroplasia, dwarfism, thanatophoric dysplasia (TD), Alpert's syndrome, Crouzon syndrome, Jackson-Weiss syndrome, Beare-Stevenson cutis gyrata syndrome. Pfeiffer syndrome or cranial muscular atrophy syndrome; the hypophosphatemia is X-linked hypophosphatemic rickets, autosomal recessive hypophosphatemic rickets, autosomal dominant hypophosphatemic rickets or tumor-induced osteomalacia.

The present invention also relates to the compound of formula (I), the stereoisomer or pharmaceutically acceptable salt thereof or the pharmaceutical composition above for use in treating diseases associated with aberrant expression and mutation of FGFR2 and/or FGFR3 receptor or aberrant expression and activity of a corresponding ligand as a selective FGFR2 and/or FGFR3 inhibitor.

The present invention also relates to a method of treating a tumor patient resistant to an FGFR inhibitor, which comprises administering to a patient in need thereof the compound of formula (I), the stereoisomer or pharmaceutically acceptable salt thereof.

The present invention also relates to a method of treating a tumor patient having FGFR2 V565F, V565I, V565L, V565M, N550K, N550H, E566A, E566G, K660M and/or K660Q mutations, which comprises administering to a patient in need thereof the compound of formula (I), the stereoisomer or pharmaceutically acceptable salt thereof.

DETAILED DESCRIPTION OF THE INVENTION

After an extensive and intensive research, the inventors of the present invention have developed, for the first time, an FGFR and mutation inhibitor thereof, preparation method therefor and use thereof. The series of compounds of the present invention have good activity against mutant FGFRs, particularly against FGFRs with gatekeeper mutations, and particularly against FGFR3 V555M, FGFR2 V565I, FGFR2 V565F, FGFR2 V565L and FGFR2 N550K mutations.

Detailed description: unless otherwise stated or specified, the following terms used in the specification and claims have the following meanings.

"Alkyl" refers to linear or branched saturated aliphatic alkyl groups, preferably linear or branched alkyl groups containing 1 to 10, 1 to 6 or 1 to 4 carbon atoms, including but not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl or various branched isomers thereof, and the like. "$C_{1-10}$ alkyl" refers to linear alkyl and branched alkyl containing 1 to 10 carbon atoms, "$C_{1-4}$ alkyl" refers to linear alkyl and branched alkyl containing 1 to 4 carbon atoms, "$C_{0-8}$ alkyl" refers to linear alkyl and branched alkyl containing 0 to 8 carbon atoms, and "$C_{0-4}$ alkyl" refers to linear alkyl and branched alkyl containing 0 to 4 carbon atoms.

Alkyl may be optionally substituted or unsubstituted, and when it is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{5-10}$ aryl, 5-10 membered heteroaryl, $=O$, $-C_{0-8}$ alkyl-$SF_5$, $-C_{0-8}$ alkyl-$S(O)_rR_8$, $-C_{0-8}$ alkyl-$O-R_9$, $-C_{0-8}$ alkyl-$C(O)OR_9$, $-C_{0-8}$ alkyl-$C(O)R_{10}$, $-C_{0-8}$ alkyl-$O-C(O)R_{10}$, $-C_{0-8}$ alkyl-$NR_{11}R_{12}$, $-C_{0-8}$ alkyl-$C(=NR_{11})R_{10}$, $-C_{0-8}$ alkyl-$N(R_{11})-C(=NR_{12})R_{10}$, $-C_{0-8}$ alkyl-$C(O)NR_{11}R_{12}$ and $-C_{0-8}$ alkyl-$N(R_{11})-C(O)R_{10}$.

"Cycloalkyl" or "carbocycle" refers to a monocyclic or polycyclic hydrocarbon substituent that is saturated or partially unsaturated. The partially unsaturated cyclic hydrocarbon means that the cyclic hydrocarbon may contain one or more (preferably 1, 2 or 3) double bonds, but none of the rings has a fully conjugated π-electron system; cycloalkyl is classified into monocyclic cycloalkyl and polycyclic cycloalkyl, and is preferably cycloalkyl containing 3 to 12, 3 to 8, or 3 to 6 carbon atoms. For example, "$C_{3-12}$ cycloalkyl" refers to cycloalkyl containing 3 to 12 carbon atoms, and "$C_{3-6}$ cycloalkyl" refers to cycloalkyl containing 3 to 6 carbon atoms.

Monocyclic cycloalkyl includes, but is not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like;

polycyclic cycloalkyl includes spirocycloalkyl, fused cycloalkyl and bridged cycloalkyl. "Spirocycloalkyl" refers to a polycyclic group in which a carbon atom (called a spiro-atom) is shared among monocyclic rings, wherein those rings may contain one or more (preferably, 1, 2 or 3) double bonds, but none of them has a fully conjugated n-electron system. According to the number of the spiro-atoms shared among the rings, the spirocycloalkyl may be monospirocycloalkyl, bispirocycloalkyl or polyspirocycloalkyl, including but not limited to:

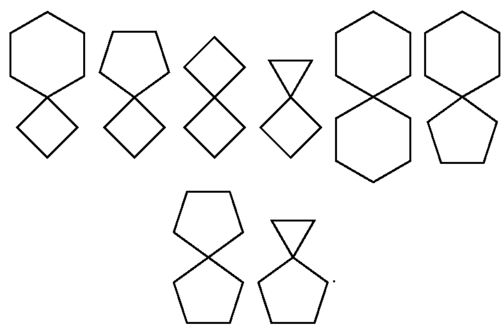

"Fused cycloalkyl" refers to an all-carbon polycyclic group in which each ring shares a pair of adjacent carbon atoms with the other rings in the system, wherein one or more of the rings may contain one or more (preferably, 1, 2 or 3) double bonds, but none of them has a fully conjugated π-electron system. According to the number of formed rings, the fused cycloalkyl may be bicyclic, tricyclic, tetracyclic or polycyclic, including but not limited to:

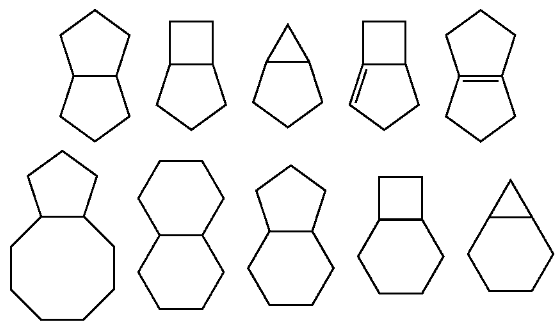

"Bridged cycloalkyl" refers to an all-carbon polycyclic group in which any two rings share two carbon atoms that are not directly connected to each other, wherein these rings may contain one or more (preferably, 1, 2 or 3) double bonds, but none of them has a fully conjugated π-electron system. According to the number of formed rings, the bridged cycloalkyl may be bicyclic, tricyclic, tetracyclic or polycyclic, including but not limited to:

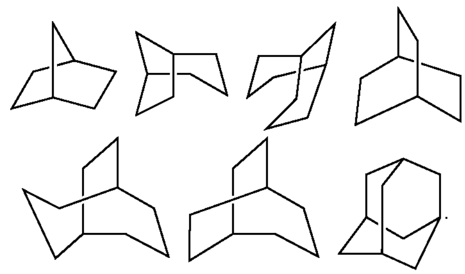

The cycloalkyl ring can be fused to an aryl, heteroaryl or heterocycloalkyl ring, wherein the ring attached to the parent structure is cycloalkyl, which includes, but is not limited to, indanyl, tetrahydronaphthyl, benzocycloheptyl, and the like.

Cycloalkyl may be optionally substituted or unsubstituted, and when it is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{5-10}$ aryl, 5-10 membered heteroaryl, =O, —$C_{0-8}$ alkyl-$SF_5$, —$C_{0-8}$ alkyl-$S(O)_rR_8$, —$C_{0-8}$ alkyl-O—$R_9$, —$C_{0-8}$ alkyl-C(O)$OR_9$, —$C_{0-8}$ alkyl-C(O)$R_{10}$, —$C_{0-8}$ alkyl-O—C(O)$R_{10}$, —$C_{0-8}$ alkyl-$NR_{11}R_{12}$, —$C_{0-8}$ alkyl-C(=$NR_{11}$)$R_{10}$, —$C_{0-8}$ alkyl-N($R_{11}$)—C(=$NR_{12}$)$R_{10}$, —$C_{0-8}$ alkyl-C(O)$NR_{11}R_{12}$ and —$C_{0-8}$ alkyl-N($R_{11}$)—C(O)$R_{10}$.

"Heterocyclyl" or "heterocycle" refers to a monocyclic or polycyclic cyclic hydrocarbon substituent that is saturated or partially unsaturated. The partially unsaturated cyclic hydrocarbon means that the cyclic hydrocarbon may contain one or more (preferably 1, 2 or 3) double bonds, but none of the rings has a fully conjugated π-electron system; in heterocyclyl, one or more (preferably 1, 2, 3 or 4) ring atoms are heteroatoms selected from the group consisting of nitrogen, oxygen, S(O)(=NH) and $S(O)_r$ (where r is an integer of 0, 1 or 2), excluding ring moiety of —O—O—, —O—S— or —S—S—, and the remaining ring atoms are carbon atoms. Preferably, heterocyclyl is one containing 3 to 12, 3 to 8, or 3 to 6 ring atoms; for example, "3-6 membered heterocyclyl" refers to a cyclic group containing 3 to 6 ring atoms, "4-6 membered heterocyclyl" refers to a cyclic group containing 4 to 6 ring atoms, "4-10 membered heterocyclyl" refers to a cyclic group containing 4 to 10 ring atoms, and "3-12 membered heterocyclyl" refers to a cyclic group containing 3 to 12 ring atoms.

Monocyclic heterocyclyl includes, but is not limited to, pyrrolidinyl, piperidinyl, piperazinyl, morpholinyl, thiomorpholinyl, homopiperazinyl, and the like.

Polycyclic heterocyclyl includes spiroheterocyclyl, fused heterocyclyl and bridged heterocyclyl. "Spiroheterocyclyl" refers to a polycyclic heterocyclyl group in which an atom (called a spiro-atom) is shared among monocyclic rings, wherein one or more (preferably 1, 2, 3 or 4) ring atoms are heteroatoms selected from the group consisting of nitrogen, oxygen, S(O)(=NH) and $S(O)_r$ (wherein r is an integer of 0, 1 or 2), and the remaining ring atoms are carbon atoms. These rings may contain one or more (preferably, 1, 2 or 3) double bonds, but none of them has a fully conjugated n-electron system. According to the number of spiro-atoms shared among the rings, the spiroheterocyclyl may be monospiroheterocyclyl, bispiroheterocyclyl or polyspiroheterocyclyl, including but not limited to:

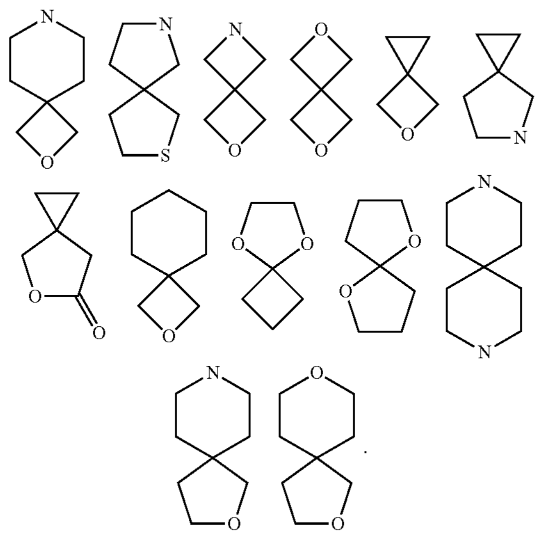

"Fused heterocyclyl" refers to a polycyclic heterocyclyl group in which each ring shares a pair of adjacent atoms with the other rings in the system, wherein one or more (preferably, 1, 2, 3 or 4) of the rings may contain one or more (preferably, 1, 2 or 3) double bonds, but none of them has a fully conjugated π-electron system, wherein one or more (preferably, 1, 2, 3 or 4) ring atoms are heteroatoms selected from the group consisting of nitrogen, oxygen, S(O)(=NH) and $S(O)_r$ (wherein r is an integer of 0, 1 or 2), and the remaining ring atoms are carbon atoms. According to the number of formed rings, the fused heterocycloalkyl may be bicyclic, tricyclic, tetracyclic or polycyclic, including but not limited to:

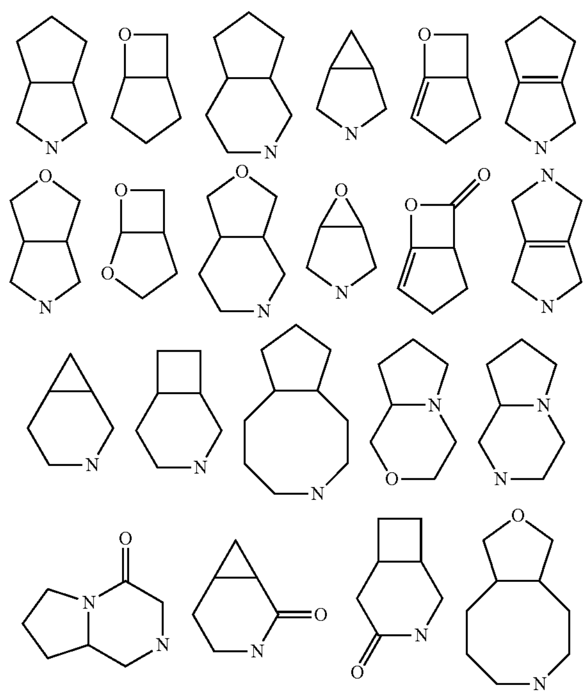

-continued

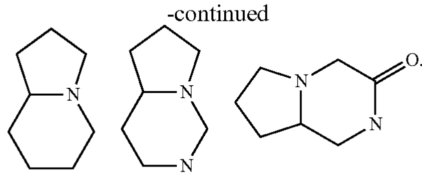

"Bridged heterocyclyl" refers to a polycyclic heterocyclyl group in which any two rings share two carbon atoms that are not directly connected to each other, wherein these rings may contain one or more (preferably, 1, 2 or 3) double bonds, but none of them has a fully conjugated i-electron system, wherein one or more (preferably, 1, 2, 3 or 4) ring atoms are heteroatoms selected from the group consisting of nitrogen, oxygen, S(O)(=NH) and $S(O)_r$ (wherein r is an integer of 0, 1 or 2), and the remaining ring atoms are carbon atoms. According to the number of formed rings, the bridged heterocyclyl may be bicyclic, tricyclic, tetracyclic or polycyclic, including but not limited to:

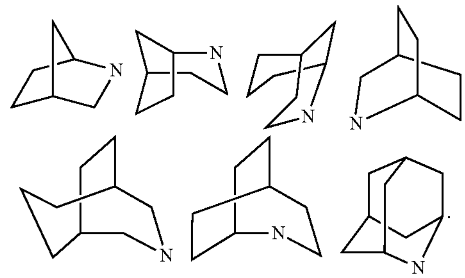

The heterocyclyl ring may be fused to an aryl, heteroaryl or cycloalkyl ring, wherein the ring attached to the parent structure is heterocyclyl, including but not limited to:

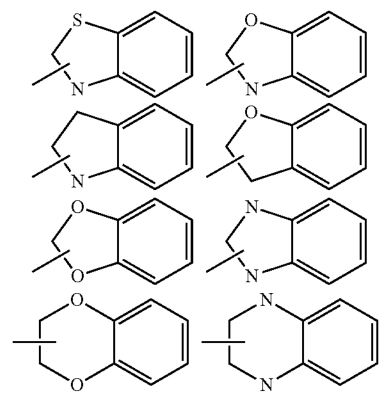

Heterocyclyl may be optionally substituted or unsubstituted, and when it is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{5-10}$ aryl, 5-10 membered heteroaryl, =O, —$C_{0-8}$ alkyl-$SF_5$, —$C_{0-8}$ alkyl-$S(O)_rR_8$, —$C_{0-8}$ alkyl-O—$R_9$, —$C_{0-8}$ alkyl-C(O)$OR_9$, —$C_{0-8}$ alkyl-C(O)$R_{10}$, —$C_{0-8}$ alkyl-O—C(O)$R_{10}$, —$C_{0-8}$ alkyl-$NR_{11}R_{12}$, —$C_{0-8}$ alkyl-C(=$NR_{11}$)$R_{10}$, —$C_{0-8}$ alkyl-N $(R_{11})$—C(=$NR_{12}$)$R_{10}$, —$C_{0-8}$ alkyl-C(O)$NR_{11}R_{12}$ and —$C_{0-8}$ alkyl-N($R_{11}$)—C(O)$R_{10}$.

"Aryl" or "aromatic ring" refers to an all-carbon monocyclic or fused-polycyclic group (i.e., rings that share a pair of adjacent carbon atoms) and a polycyclic group having a conjugated π-electron system (i.e., rings with adjacent pairs of carbon atoms), and is preferably all-carbon aryl containing 5 to 10 or 5 to 8 carbons atoms. For example, "$C_{5-10}$ aryl" refers to all-carbon aryl containing 5 to 10 carbon atoms, and "$C_{5-8}$ aryl" refers to all-carbon aryl containing 5 to 8 carbon atoms. It includes, but is not limited to, phenyl and naphthyl. The aryl ring can be fused to a heteroaryl, heterocyclyl or cycloalkyl ring, wherein the ring attached to the parent structure is the aryl ring, including but not limited to:

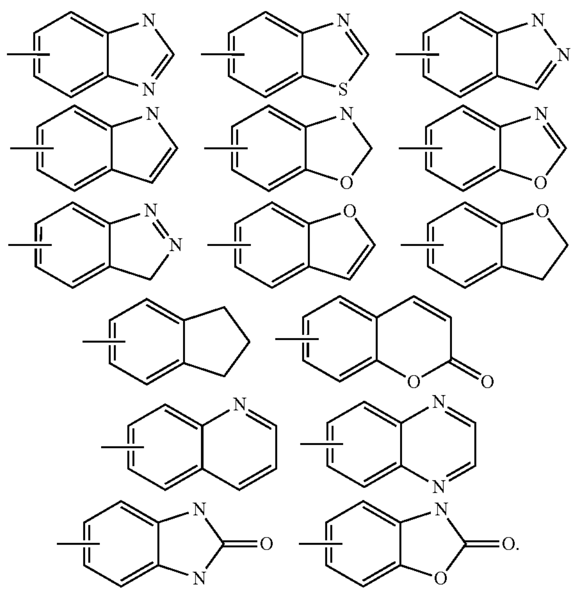

"Aryl" may be substituted or unsubstituted, and when it is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{5-10}$ aryl, 5-10 membered heteroaryl, =O, —$C_{0-4}$ alkyl-$SF_5$, —$C_{0-8}$ alkyl-S(O)$_r$$R_8$, —$C_{0-8}$ alkyl-O—$R_9$, —$C_{0-8}$ alkyl-C(O)O$R_9$, —$C_{0-8}$ alkyl-C(O)$R_{10}$, —$C_{0-8}$ alkyl-O—C(O)$R_{10}$, —$C_{0-8}$ alkyl-$NR_{11}R_{12}$, —$C_{0-8}$ alkyl-C(=$NR_{11}$)$R_{10}$, —$C_{0-8}$ alkyl-N($R_{11}$)—C(=$NR_{12}$)$R_{10}$, —$C_{0-8}$ alkyl-C(O)$NR_{11}R_{12}$ and —$C_{0-8}$ alkyl-N($R_{11}$)—C(O)$R_{10}$.

"Heteroaryl" refers to a heteroaromatic system containing one or more (preferably 1, 2, 3 or 4) heteroatoms including nitrogen, oxygen and S(O)$_r$ (wherein r is an integer of 0, 1 or 2), and is preferably a heteroaromatic system containing 5 to 10, 5 to 8 or 5 to 6 ring atoms. For example, "5-8 membered heteroaryl" refers to a heteroaromatic system containing 5 to 8 ring atoms, and "5-10 membered heteroaryl" refers to a heteroaromatic system containing 5 to 10 ring atoms. The heteroaryl includes, but is not limited to, furyl, thiophenyl, pyridyl, pyrrolyl, N-alkylpyrrolyl, pyrimidinyl, pyrazinyl, imidazolyl, tetrazolyl, etc. The heteroaryl ring can be fused to an aryl, heterocyclyl or cycloalkyl ring, wherein the ring attached to the parent structure is the heteroaryl ring, including but not limited to:

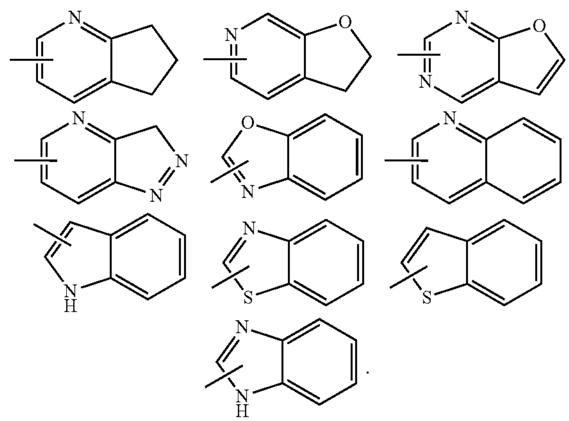

"Heteroaryl" may be optionally substituted or unsubstituted, and when it is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{5-10}$ aryl, 5-10 membered heteroaryl, =O, —$C_{0-8}$ alkyl-$SF_5$, —$C_{0-8}$ alkyl-S(O)$_r$$R_8$, —$C_{0-8}$ alkyl-O—$R_9$, —$C_{0-8}$ alkyl-C(O)O$R_9$, —$C_{0-8}$ alkyl-C(O)$R_{10}$, —$C_{0-8}$ alkyl-O—C(O)$R_{10}$, —$C_{0-8}$ alkyl-$NR_{11}R_{12}$, —$C_{0-8}$ alkyl-C(=$NR_{11}$)$R_{10}$, —$C_{0-8}$ alkyl-N($R_{11}$)—C(=$NR_{12}$)$R_{10}$, —$C_{0-8}$ alkyl-C(O)$NR_{11}R_{12}$ and —$C_{0-8}$ alkyl-N($R_{11}$)—C(O)$R_{10}$.

"Alkenyl" refers to alkyl defined as above consisting of at least two carbon atoms and at least one carbon-carbon double bond, and is preferably linear or branched alkenyl containing 2 to 10 or 2 to 4 carbon atoms. For example, "$C_{2-10}$ alkenyl" refers to linear or branched alkenyl containing 2 to 10 carbon atoms, and "$C_{2-4}$ alkenyl" refers to linear or branched alkenyl containing 2 to 4 carbon atoms. The alkenyl includes, but is not limited to, vinyl, 1-propenyl, 2-propenyl, 1-, 2- or 3-butenyl, and the like.

"Alkenyl" may be substituted or unsubstituted, and when it is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{5-10}$ aryl, 5-10 membered heteroaryl, =O, —$C_{0-8}$ alkyl-$SF_5$, —$C_{0-8}$ alkyl-S(O)$_r$$R_8$, —$C_{0-8}$ alkyl-O—$R_9$, —$C_{0-8}$ alkyl-C(O)O$R_9$, —$C_{0-8}$ alkyl-C(O)$R_{10}$, —$C_{0-8}$ alkyl-O—C(O)$R_{10}$, —$C_{0-8}$ alkyl-$NR_{11}R_{12}$, —$C_{0-8}$ alkyl-C(=$NR_{11}$)$R_{10}$, —$C_{0-8}$ alkyl-N($R_{11}$)—C(=$NR_{12}$)$R_{10}$, —$C_{0-8}$ alkyl-C(O)$NR_{11}R_{12}$ and —$C_{0-8}$ alkyl-N($R_{11}$)—C(O)$R_{10}$.

"Alkynyl" refers to alkyl defined as above consisting of at least two carbon atoms and at least one carbon-carbon triple bond, and is preferably linear or branched alkynyl containing 2 to 10 or 2 to 4 carbon atoms. For example, "$C_{2-10}$ alkynyl" refers to linear or branched alkynyl containing 2 to 10 carbon atoms, and "$C_{2-4}$ alkynyl" refers to linear or branched alkynyl containing 2 to 4 carbon atoms. The alkynyl includes, but is not limited to, ethynyl, 1-propynyl, 2-propynyl, 1-, 2- or 3-butynyl, and the like.

"Alkynyl" may be substituted or unsubstituted, and when it is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{5-10}$ aryl, 5-10 membered heteroaryl, =O, —$C_{0-8}$ alkyl-$SF_5$, —$C_{0-8}$ alkyl-$S(O)_rR_8$, —$C_{0-8}$ alkyl-O—$R_9$, —$C_{0-8}$ alkyl-C(O)$OR_9$, —$C_{0-8}$ alkyl-C(O)$R_{10}$, —$C_{0-8}$ alkyl-O—C(O)$R_{10}$, —$C_{0-8}$ alkyl-$NR_{11}R_{12}$, —$C_{0-8}$ alkyl-C(=$NR_{11}$)$R_{10}$, —$C_{0-8}$ alkyl-N($R_{11}$)—C(=$NR_{11}$)$R_{10}$, —$C_{0-8}$ alkyl-C(O)$NR_{11}R_{12}$ and —$C_{0-8}$ alkyl-N($R_{11}$)—C(O)$R_{10}$.

"Alkoxy" refers to —O-alkyl, wherein the alkyl is defined as above. For example, "$C_{1-10}$ alkoxy" refers to alkoxy containing 1 to 10 carbon atoms, and "$C_{1-4}$ alkoxy" refers to alkoxy containing 1 to 4 carbon atoms. The alkoxy includes, but is not limited to, methoxy, ethoxy, propoxy, butoxy and the like.

"Alkoxy" may be optionally substituted or unsubstituted, and when it is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{5-10}$ aryl, 5-10 membered heteroaryl, =O, —$C_{0-8}$ alkyl-$SF_5$, —$C_{0-8}$ alkyl-$S(O)_rR_8$, —$C_{0-8}$ alkyl-O—$R_9$, —$C_{0-8}$ alkyl-C(O)$OR_9$, —$C_{0-8}$ alkyl-C(O)$R_{10}$, —$C_{0-8}$ alkyl-O—C(O)$R_{10}$, —$C_{0-8}$ alkyl-$NR_{11}R_{12}$, —$C_{0-8}$ alkyl-C(=$NR_{11}$)$R_{10}$, —$C_{0-8}$ alkyl-N($R_{11}$)—C(=$NR_{12}$)$R_{10}$, —$C_{0-8}$ alkyl-C(O)$NR_{11}R_{12}$ and —$C_{0-8}$ alkyl-N($R_1$)—C(O)$R_{10}$.

"Cycloalkyloxy" refers to —O-cycloalkyl, wherein the cycloalkyl is defined as above. For example, "$C_{3-12}$ cycloalkyloxy" refers to cycloalkyloxy containing 3 to 12 carbon atoms, and "$C_{3-6}$ cycloalkyloxy" refers to cycloalkyloxy containing 3 to 6 carbon atoms. The cycloalkyloxy includes, but is not limited to, cyclopropyloxy, cyclobutyloxy, cyclopentyloxy, cyclohexyloxy, etc.

"Cycloalkyloxy" may be optionally substituted or unsubstituted, and when it is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{5-10}$ aryl, 5-10 membered heteroaryl, =O, —$C_{0-8}$ alkyl-$SF_5$, —$C_{0-8}$ alkyl-$S(O)_rR_8$, —$C_{0-8}$ alkyl-O—$R_9$, —$C_{0-8}$ alkyl-C(O)$OR_9$, —$C_{0-8}$ alkyl-C(O)$R_{10}$, —$C_{0-8}$ alkyl-O—C(O)$R_{10}$, —$C_{0-8}$ alkyl-$NR_{11}R_{12}$, —$C_{0-8}$ alkyl-C(=$NR_{11}$)$R_{10}$, —$C_{0-8}$ alkyl-N($R_{11}$)—C(=$NR_{11}$)$R_{10}$, —$C_{0-8}$ alkyl-C(O)$NR_{11}R_{12}$ and —$C_{0-8}$ alkyl-N($R_{11}$)—C(O)$R_{10}$.

"Heterocyclyloxy" refers to —O-heterocyclyl, wherein heterocyclyl is defined as above, and heterocyclyloxy includes, but is not limited to, azacyclobutyloxy, oxacyclobutyloxy, azacyclopentyloxy, nitrogen, oxacyclohexyloxy, etc.

"Heterocyclyloxy" may be optionally substituted or unsubstituted, and when it is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{5-10}$ aryl, 5-10 membered heteroaryl, =O, —$C_{0-8}$ alkyl-$SF_5$, —$C_{0-8}$ alkyl-$S(O)_rR_8$, —$C_{0-8}$ alkyl-O—$R_9$, —$C_{0-8}$ alkyl-C(O)$OR_9$, —$C_{0-8}$ alkyl-C(O)$R_{10}$, —$C_{0-8}$ alkyl-O—C(O)$R_{10}$, —$C_{0-8}$ alkyl-$NR_{11}R_{12}$, —$C_{0-8}$ alkyl-C(=$NR_{11}$)$R_{10}$, —$C_{0-8}$ alkyl-N($R_{11}$)—C(=$NR_{12}$)$R_{10}$, —$C_{0-8}$ alkyl-C(O)$NR_{11}R_{12}$ and —$C_{0-8}$ alkyl-N($R_{11}$)—C(O)$R_{10}$.

"$C_{1-10}$ alkanoyl" refers to a monovalent atomic group which is obtained after hydroxy is removed from the $C_{1-10}$ alkyl acid, and is also generally referred to as "$C_{0-9}$—C(O)—", wherein "$C_{0-9}$" refers to $C_{0-9}$ alkyl. For example, "$C_1$—C(O)—" refers to acetyl; "$C_2$—C(O)—" refers to propionyl; and "$C_3$—C(O)—" refers to butyryl or isobutyryl.

"—$C_{0-8}$ alkyl-$S(O)_rR_8$" means that the sulfur atom in —$S(O)_rR_8$ is connected to $C_{0-8}$ alkyl, wherein $C_{0-8}$ alkyl is defined as above.

"—$C_{0-8}$ alkyl-O—$R_9$" means that the oxygen atom in —O—$R_9$ is connected to $C_{0-8}$ alkyl, wherein $C_{0-8}$ alkyl is defined as above.

"—$C_{0-8}$ alkyl-C(O)$OR_9$" means that the carbonyl in —C(O)$OR_9$ is connected to $C_{0-8}$ alkyl, wherein $C_{0-8}$ alkyl is defined as above.

"—$C_{0-8}$ alkyl-C(O)$R_{10}$" means that the carbonyl in —C(O)$R_{10}$ is connected to $C_{0-8}$ alkyl, wherein $C_0$ alkyl means that there is 0 carbon atoms, and $C_{1-8}$ alkyl is defined as above.

"—$C_{0-8}$—O—C(O)$R_{10}$" means that the oxygen atom in —O—C(O)$R_{10}$ is connected to $C_{0-8}$ alkyl, wherein $C_{0-8}$ alkyl is defined as above.

"—$C_{0-8}$—$NR_{11}R_{12}$" means that the nitrogen atom in —$NR_{11}R_{12}$ is connected to $C_{0-8}$ alkyl, wherein $C_{0-8}$ alkyl is defined as above.

"—$C_{0-8}$—C(=$NR_{11}$)$R_{10}$" means that the carbon atom in —C(=$NR_{11}$)$R_{10}$ is connected to $C_{0-8}$ alkyl, wherein $C_{0-8}$ alkyl is defined as above.

"—$C_{0-8}$—N($R_{11}$)—C(=$NR_{12}$)$R_{10}$" means that the nitrogen atom in —N($R_{11}$)—C(=$NR_2$)$R_{10}$ is connected to $C_{0-8}$ alkyl, wherein $C_{0-8}$ alkyl is defined as above.

"—$C_{0-8}$—C(O)$NR_{11}R_{12}$" means that the carbonyl in —C(O)$NR_{11}R_{12}$ is connected to $C_{0-8}$ alkyl, wherein $C_{0-8}$ alkyl is defined as above.

"—$C_{0-8}$—N($R_{11}$)—C(O)$R_{10}$" means that the nitrogen atom in —N($R_{11}$)—C(O)$R_{10}$ is connected to $C_{0-8}$ alkyl, wherein $C_{0-8}$ alkyl is defined as above.

"$C_{1-10}$ haloalkyl" refers to an alkyl group having 1 to 10 carbon atoms in which hydrogen atoms on the alkyl are optionally substituted with a fluorine, chlorine, bromine or iodine atom, and it includes, but is not limited to, difluoromethyl, dichloromethyl, dibromomethyl, trifluoromethyl, trichloromethyl, tribromomethyl, etc.

"$C_{1-10}$ haloalkoxy" refers to an alkoxy group having 1 to 10 carbon atoms in which hydrogen atoms on the alkyl are optionally substituted with a fluorine, chlorine, bromine or iodine atom, and it includes, but is not limited to, difluoromethoxy, dichloromethoxy, dibromomethoxy, trifluoromethoxy, trichloromethoxy, tribromomethoxy, and the like.

"$C_{1-10}$ deuterioalkyl" refers to an alkyl group having 1 to 10 carbon atoms in which hydrogen atoms on the alkyl are optionally substituted with a deuterium atom, and it includes, but is not limited to, monodeuteriomethyl, dideuteriomethyl, trideuteriomethyl and the like.

"Halogen" refers to fluorine, chlorine, bromine or iodine. "PE" refers to petroleum ether. "EtOAc" refers to ethyl acetate. "DCM" refers to dichloromethane.

"Optional" or "optionally" means that the event or circumstance subsequently described may, but not necessarily, occur, and that the description includes instances where the event or circumstance occurs or does not occur, that is, instances where substitution occurs or does not occur. For example, "heterocyclyl group optionally substituted with alkyl" means that alkyl may be, but not necessarily, present, and that the description includes instances where the heterocyclyl group is or is not substituted with alkyl.

The term "substituted" means that one or more hydrogen atoms in the group are each independently substituted by a corresponding number of substituents. It goes without saying that a substituent is only in its possible chemical position and consistent with chemical valence bond theory, and those skilled in the art will be able to determine (by experiments or theories) possible or impossible substitution without undue efforts. For example, it may be unstable when amino or hydroxy having free hydrogen is bound to a carbon atom having an unsaturated bond (such as olefin).

"Stereoisomers" refer to isomers produced by different spatial arrangements of atoms in molecules, and can be classified into cis-trans isomers and enantiomers, and also into enantiomers and diastereomers. Stereoisomers resulting from rotation of single bonds are referred to as conformational stereo-isomers and sometimes also as rotamers. Stereoisomers resulting from bond lengths, bond angles, intramolecular double bonds, rings and the like are referred to as configuration stereo-isomers, and the configuration stereo-isomers are classified into two categories. Among them, isomers resulting from the fact that a double bond or a single bond of a ring-forming carbon atom cannot rotate freely are referred to as geometric isomers and also as cis-trans isomers, and the isomers are classified into Z and E configurations. For example, cis-2-butene and trans-2-butene are a pair of geometric isomers, and stereoisomers having different optical rotation properties due to the absence of anti-axisymmetry in the molecule are referred to as optical isomers, and are classified into R and S configurations. In the present invention, the term "stereoisomer" is understood to include one or more of the above enantiomers, configuration isomers and conformational isomers, unless otherwise specified.

"Pharmaceutically acceptable salt" as used herein refers to pharmaceutically acceptable acid addition salts or base addition salts, including inorganic and organic acid salts, which may be prepared by methods known in the art.

"Pharmaceutical composition" refers to a mixture containing one or more of the compounds described herein or a physiologically/pharmaceutically acceptable salt or prodrug thereof, and other chemical components, for example physiologically/pharmaceutically acceptable carriers and excipients. The purpose of the pharmaceutical composition is to promote the administration to an organism, which facilitates the absorption of the active ingredient, thereby exerting biological activity.

The Present Invention is Further Explained in Detail Below with Reference to Examples, which are not Intended to Limit the Present Invention, and the Present Invention is not Merely Limited to the Contents of the Examples.

The compound structure of the present invention is determined by nuclear magnetic resonance (NMR) and/or liquid chromatography-mass spectrometry (LC-MS). The NMR chemical shift (S) is given in parts per million (ppm). The NMR determination is conducted by using a Bruker AVANCE-400 nuclear magnetic resonance apparatus, with hexadeuterodimethyl sulfoxide (DMSO-$d_6$), tetradeuteromethanol ($CD_3OD$), and deuterated chloroform ($CDCl_3$) as determination solvents, and tetramethylsilane (TMS) as an internal standard.

The LC-MS determination is conducted by using an Agilent 6120 mass spectrometer. The HPLC determination is conducted by using an Agilent 1200 DAD high pressure liquid chromatograph (Sunfire C18 150*4.6 mm chromatographic column) and a Waters 2695-2996 high pressure liquid chromatograph (Gimini C18 150*4.6 mm chromatographic column).

A Yantai Yellow Sea HSGF254 or Qingdao GF254 silica gel plate is used as a thin layer chromatography (TLC) silica gel plate. The specification of the silica gel plate for TLC is 0.15-0.20 mm, and that for product separation and purification of TLC is 0.4-0.5 mm. The Yantai Yellow Sea silica gel of 200-300 mesh is generally utilized as a carrier in column chromatography.

Starting materials in the Examples of the present invention are known and commercially available, or may be synthesized by using or according to methods known in the art.

Unless otherwise stated, all reactions of the present invention are carried out under a dry nitrogen or argon atmosphere with continuous magnetic stirring, wherein the solvent is a dry solvent, and the reaction temperature is in degree centigrade (° C.).

Preparation of Intermediates

Intermediate 1: Preparation of 2-cyclopropyl-5-ethynylbenzo[d]oxazole

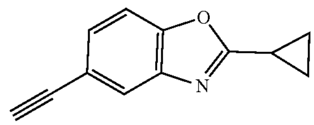

Step 1: Synthesis of N-(5-bromo-2-hydroxyphenyl)cyclopropanecarboxamide

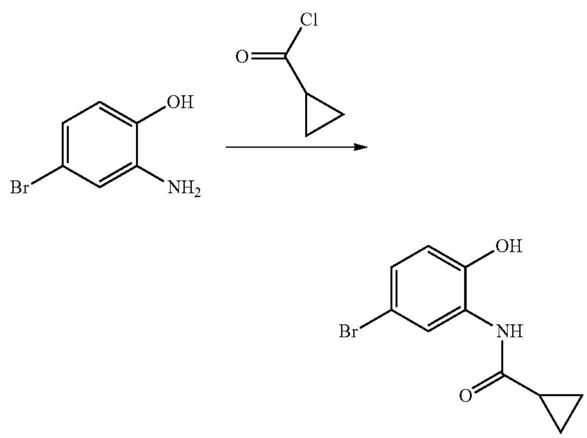

2-amino-4-bromophenol (2.0 g, 10.6 mmol) was dissolved in DCM (30 mL), and triethylamine (1.29 g, 12.8 mmol) and cyclopropylcarbonyl chloride (1.11 g, 10.6 mmol) were added successively at 0° C. The reaction mixture was stirred at 0° C. for 1 hr, diluted with aqueous sodium bicarbonate solution and extracted with DCM, and the organic phase was washed with saturated brine, dried over anhydrous sodium sulfate and concentrated. The residue was separated by the column chromatography to obtain N-(5-bromo-2-hydroxyphenyl)cyclopropanecarboxamide (1.34 g, yield: 49%). MS m/z (ESI): 256/258 $[M+H]^+$.

Step 2: Synthesis of 5-bromo-2-cyclopropylbenzo[d]oxazole

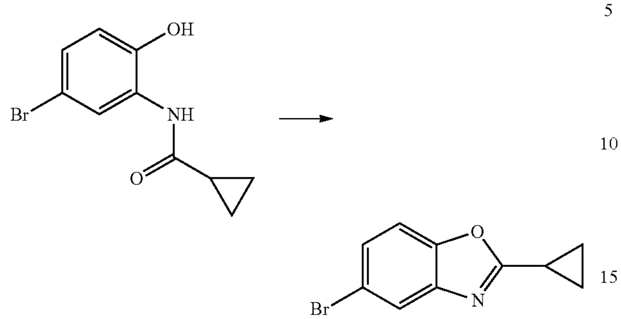

N-(5-bromo-2-hydroxyphenyl)cyclopropanecarboxamide (1.04 g, 4.06 mmol) was dissolved in acetonitrile (30 mL), and triphenylphosphine (4.26 g, 16.2 mmol) and carbon tetrachloride (1.25 g, 8.1 mmol) were added successively at room temperature. The reaction mixture was stirred at 60° C. for 1 hr, diluted with water and extracted with ethyl acetate, and the organic phase was washed with saturated brine, dried over anhydrous sodium sulfate and concentrated. The residue was separated by the column chromatography to obtain 5-bromo-2-cyclopropylbenzo[d]oxazole (548 mg, yield: 55%). MS m/z (ESI): 238/240 $[M+H]^+$.

Step 3: Synthesis of 2-cyclopropyl-5-((trimethylsilyl)ethynyl)benzo[d]oxazole

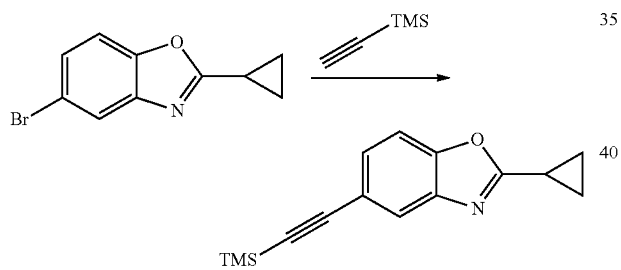

5-bromo-2-cyclopropylbenzo[d]oxazole (200 mg, 0.84 mmol) was added to DMF (3 mL), and triethylamine (1 mL), cuprous iodide (16 mg, 0.08 mmol), trimethylsilylacetylene (825 mg, 8.4 mmol) and tetrakis(triphenylphosphine)palladium (49 mg, 0.04 mmol) were added successively at room temperature. The reaction mixture was stirred at 80° C. for 16 hrs, diluted with water and extracted with ethyl acetate, and the organic phase was washed with saturated brine, dried over anhydrous sodium sulfate and concentrated. The residue was separated by the column chromatography to obtain 2-cyclopropyl-5-((trimethylsilyl)ethynyl)benzo[d]oxazole (204 mg, yield: 95%). MS m/z (ESI): 256 $[M+H]^+$.

Step 4: Synthesis of 2-cyclopropyl-5-ethynylbenzo[d]oxazole

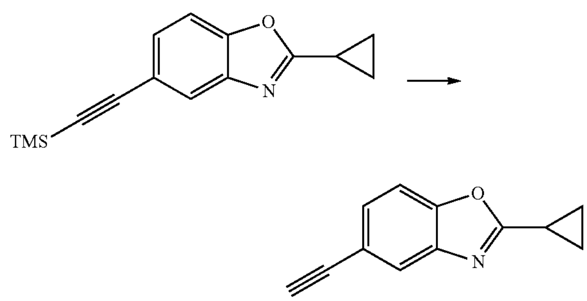 [SMILES: C[Si](C)(C)C#Cc1ccc2oc(C3CC3)nc2c1 ; C#Cc1ccc2oc(C3CC3)nc2c1]

2-cyclopropyl-5-((trimethylsilyl)ethynyl)benzo[d]oxazole (204 mg, 0.8 mmol) was added to methanol (8 mL), and potassium carbonate (1.1 g, 8 mmol) was added at room temperature. The reaction mixture was stirred at room temperature for 1 hr, diluted with water and extracted with ethyl acetate, and the organic phase was washed with saturated brine, dried over anhydrous sodium sulfate and concentrated. The residue was separated by the column chromatography to obtain 2-cyclopropyl-5-ethynylbenzo[d]oxazole (112 mg, yield: 76%). MS m/z (ESI): 184 $[M+H]^+$.

Intermediates 2-7 can be Prepared by Selecting Corresponding Raw Materials According to all or Part of the Synthesis Method of Intermediate 1:

| Intermediate No | Structural formula | Chemical name | $[M + H]^+$ |
|---|---|---|---|
| 2 | 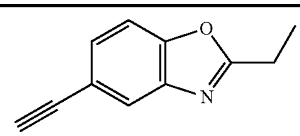 | 2-ethyl-5-ethynylbenzo[d]oxazole | 172 |
| 3 | 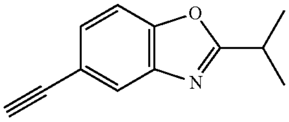 | 5-ethynyl-2-isopropylbenzo[d]oxazole | 186 |
| 4 | 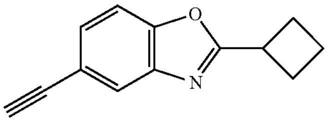 | 2-cyclobutyl-5-ethynylbenzo[d]oxazole | 198 |

-continued

| Intermediate No | Structural formula | Chemical name | [M + H]$^+$ |
|---|---|---|---|
| 5 | 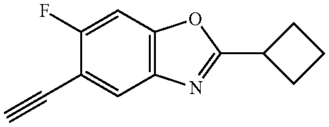 [SMILES: C#Cc1cc2nc(C3CCC3)oc2cc1F] | 2-cyclobutyl-5-ethynyl-6-fluorobenzo [d]oxazole | 216 |
| 6 | 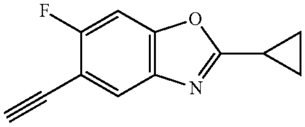 | 5-ethynyl-6-fluoro-2-cyclopropylbenzo [d]oxazole | 202 |
| 7 | 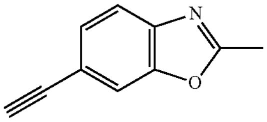 | 6-ethynyl-2-methylbenzo[d]oxazole | 158 |

Intermediate 8: Preparation of 5-bromo-2-(trifluoromethyl)benzo[d]oxazole

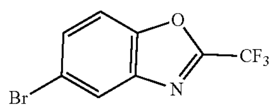 [SMILES: FC(F)(F)c1nc2cc(Br)ccc2o1]

Step 1: Synthesis of N-(5-bromo-2-hydroxyphenyl)-2,2,2-trifluoroacetamide

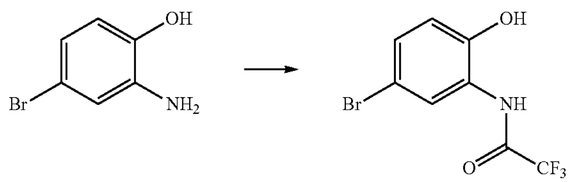 [SMILES: Nc1cc(Br)ccc1O ; O=C(Nc1cc(Br)ccc1O)C(F)(F)F]

2-amino-4-bromophenol (2.0 g, 10.6 mmol) was dissolved in DCM (30 mL), and triethylamine (1.29 g, 12.8 mmol) and trifluoroacetic anhydride (2.23 g, 10.6 mmol) were added successively at 0° C. The reaction mixture was stirred at room temperature for 1 hr, diluted with aqueous sodium bicarbonate solution and extracted with DCM, and the organic phase was washed with saturated brine, dried over anhydrous sodium sulfate and concentrated. The residue was separated by the column chromatography to obtain N-(5-bromo-2-hydroxyphenyl)-2,2,2-trifluoroacetamide (2.7 g, yield: 89%).

$^1$HNMR (400 MHz, DMSO-$d_6$): δ 10.6 (s, 1H), 10.3 (s, 1H), 7.55-7.54 (d, J=4 Hz, 1H), 7.33-7.30 (dd, J=4, 8 Hz, 1H), 6.92-6.91 (d, J=4 Hz, 1H).

Step 2: Synthesis of 5-bromo-2-(trifluoromethyl)benzo[d]oxazole

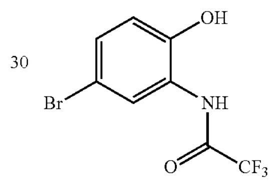

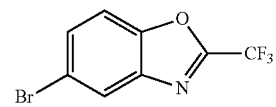

N-(5-bromo-2-hydroxyphenyl)-2,2,2-trifluoroacetamide (500 mg, 1.76 mmol) was dissolved in toluene (20 mL), and p-toluenesulfonic acid (303 mg, 1.76 mmol) was added. The reaction mixture was stirred at 120° C. for 24 hrs and then directly concentrated. The residue was separated by the column chromatography to obtain 5-bromo-2-(trifluoromethyl)benzo[d]oxazole (200 mg, yield: 43%).

$^1$HNMR (400 MHz, DMSO-$d_6$): δ 8.25-8.23 (d, J=8 Hz, 1H), 7.92-7.88 (dd, J=8.16 Hz, 1H), 7.79-7.77 (d, J=8 Hz, 1H).

Intermediate 9: Preparation of 5-ethynyl-N-methylbenzo[d]oxazol-2-amine

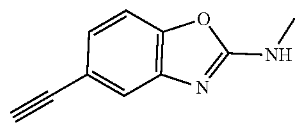

Step 1: Synthesis of 1-(5-bromo-2-hydroxyphenyl)-3-methylthiourea

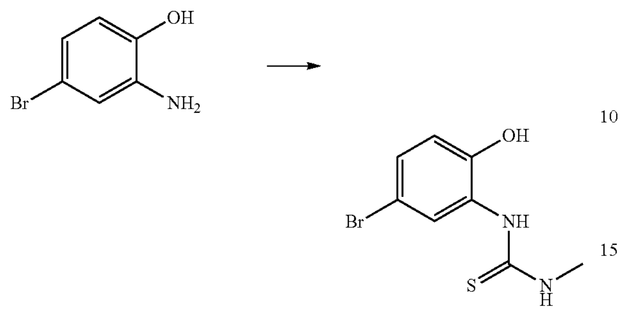

2-amino-4-bromophenol (1.0 g, 5.3 mmol) was added to tetrahydrofuran (20 mL), and isothiocyanatomethane (324 mg, 4.43 mmol) was added at 0° C. The reaction mixture was stirred at room temperature for 16 hrs, diluted with water and extracted with ethyl acetate, and the organic phase was washed with saturated brine, dried over anhydrous sodium sulfate and concentrated. The residue was separated by the column chromatography to obtain 1-(5-bromo-2-hydroxyphenyl)-3-methylthiourea (1.05 g, yield: 90%). MS m/z (ESI): 261/263 $[M+H]^+$.

Step 2: Synthesis of 5-bromo-N-methylbenzo[d]oxazol-2-amine

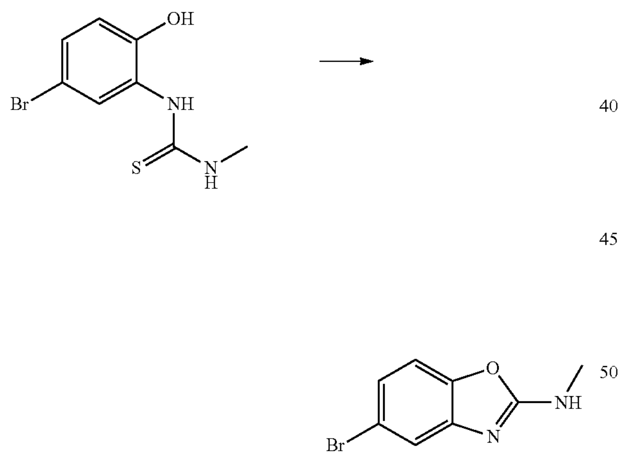

1-(5-bromo-2-hydroxyphenyl)-3-methylthiourea (970 mg, 3.71 mmol) was added to tetrahydrofuran (20 mL), and tetrabutylammonium iodide (14 mg, 0.04 mmol) and 30% hydrogen peroxide (841 mg, 7.42 mmol) were added successively at room temperature. The reaction mixture was stirred at room temperature for 1 hr, diluted with aqueous sodium sulfite and extracted with ethyl acetate, and the organic phase was washed with saturated brine, dried over anhydrous sodium sulfate and concentrated. The residue was separated by the column chromatography to obtain 5-bromo-N-methylbenzo[d]oxazol-2-amine (604 mg, yield: 72%). MS m/z (ESI): 227/229 $[M+H]^+$.

Step 3: Synthesis of N-methyl-5-((trimethylsilyl)ethynyl)benzo[d]oxazol-2-amine

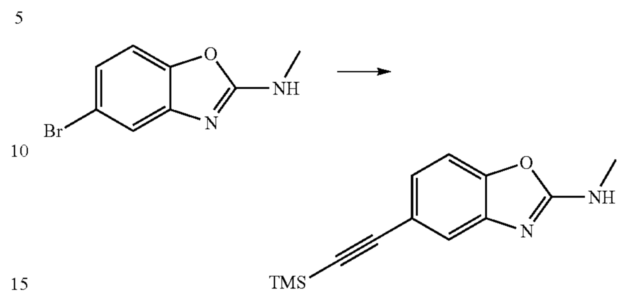

5-bromo-N-methylbenzo[d]oxazol-2-amine (600 mg, 2.64 mmol) was added to DMF (5 mL), and triethylamine (1.5 mL), cuprous iodide (50 mg, 0.26 mmol), trimethylsilylacetylene (2.6 g, 26.4 mmol) and tetrakis(triphenylphosphine)palladium (153 mg, 0.13 mmol) were added successively at room temperature. The reaction mixture was stirred at 100° C. for 16 hrs, diluted with water and extracted with ethyl acetate, and the organic phase was washed with saturated brine, dried over anhydrous sodium sulfate and concentrated. The residue was separated by the column chromatography to obtain N-methyl-5-((trimethylsilyl)ethynyl)benzo[d]oxazol-2-amine (230 mg, yield: 36%). MS m/z (ESI): 245 $[M+H]^+$.

Step 4: Synthesis of 5-ethynyl-N-methylbenzo[d]oxazol-2-amine

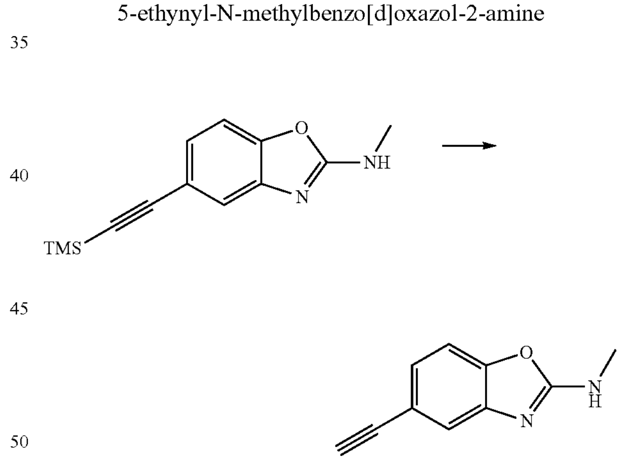

N-methyl-5-((trimethylsilyl)ethynyl)benzo[d]oxazol-2-amine (100 mg, 0.4 mmol) was added to methanol (8 mL), and potassium carbonate (566 mg, 4 mmol) was added at room temperature. The reaction mixture was stirred at room temperature for 1 hr, diluted with water and extracted with ethyl acetate, and the organic phase was washed with saturated brine, dried over anhydrous sodium sulfate and concentrated. The residue was separated by the column chromatography to obtain 5-ethynyl-N-methylbenzo[d]oxazol-2-amine (54 mg, yield: 77%). MS m/z (ESI): 173 $[M+H]^+$.

Intermediates 10-14 can be Prepared by Selecting Corresponding Raw Materials According to all or Part of the Synthesis Method of Intermediate 9:

| Intermediate No. | Structural formula | Chemical name | [M + H]+ |
|---|---|---|---|
| 10 | 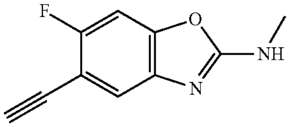 | 5-ethynyl-6-fluoro-N-methylbenzo [d]oxazol-2-amine | 191 |
| 11 | 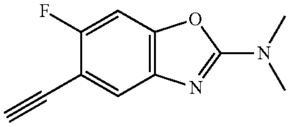 | 5-ethynyl-6-fluoro-N,N-dimethylbenzo [d]oxazol-2-amine | 205 |
| 12 | 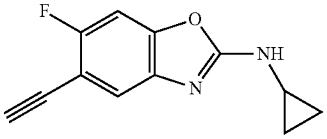 [SMILES: C#Cc1cc2nc(NC3CC3)oc2cc1F] | N-cyclopropyl-5-ethynyl-6-fluorobenzo [d]oxazol-2-amine | 217 |
| 13 | 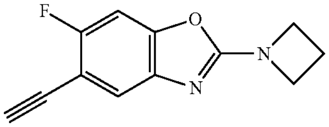 [SMILES: C#Cc1cc2nc(N3CCC3)oc2cc1F] | 2-(azetidin-1-yl)-5-ethynyl-6-fluorobenzo[d]oxazole | 217 |
| 14 | 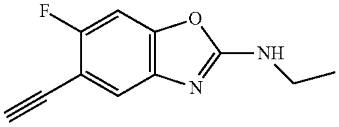 | N-ethyl-5-ethynyl-6-fluorobenzo [d]oxazol-2-amine | 205 |

Intermediate 15: Preparation of 2-cyclopropyl-5-ethynyl-6-fluorobenzo[d]thiazole

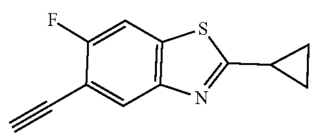

Step 1: Synthesis of N-(5-bromo-2,4-difluorophenyl)cyclopropanecarboxamide

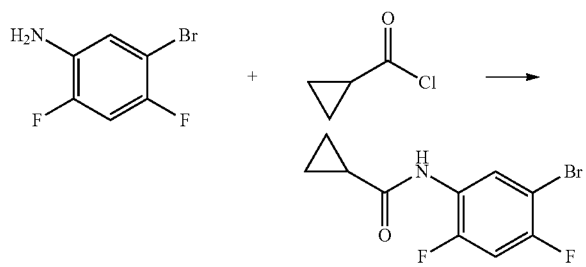

5-bromo-2,4-difluoroaniline (1.04 g, 5.0 mmol) was dissolved in dichloromethane (20 mL), and cyclopropylcarbonyl chloride (572 mg, 5.5 mmol) was added. The reaction mixture was stirred overnight at room temperature and then directly concentrated. The residue was separated by the column chromatography to obtain N-(5-bromo-2,4-difluorophenyl)cyclopropanecarboxamide (1.0 g, yield: 72%). MS m/z (ESI): 276/278[M+H]$^+$.

Step 2: Synthesis of N-(5-bromo-2,4-difluorophenyl)cyclopropanecarbothioamide

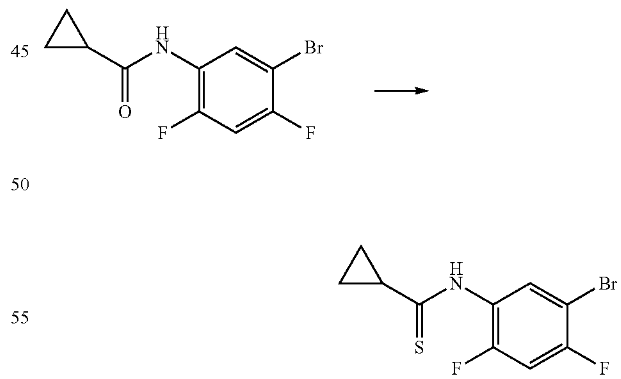

N-(5-bromo-2,4-difluorophenyl)cyclopropanecarboxamide (1.0 g, 3.6 mmol) and Lawesson's reagent (750 mg, 1.85 mmol) were dissolved in acetonitrile (25 mL), and then the reaction mixture was heated to 85° C. and stirred overnight. After the reaction was completed, the N-(5-bromo-2,4-difluorophenyl)cyclopropanecarbothioamide solution was used directly in the next step. MS m/z (ESI): 292/294[M+H]$^+$.

Step 3: Synthesis of 5-bromo-2-cyclopropyl-6-fluorobenzo thiazole

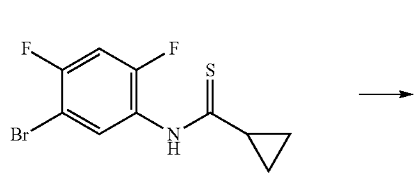

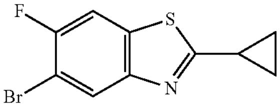

Sodium tert-butoxide (1.7 g, 18 mmol) was added to the cooled N-(5-bromo-2,4-difluorophenyl)cyclopropanecarbothioamide solution, and then the reaction mixture was heated to 50° C., stirred for 16 hrs and concentrated. The residue was separated by the column chromatography to obtain 5-bromo-2-cyclopropyl-6-fluorobenzo[d]thiazole (0.82 g, yield: 83%). MS m/z (ESI): 272/274 [M+H]$^+$.

Step 4: Synthesis of 2-cyclopropyl-5-ethynyl-6-fluorobenzo[d]thiazole

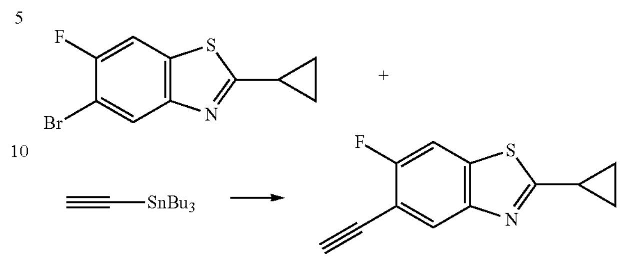

5-bromo-2-cyclopropyl-6-fluorobenzo[d]thiazole (0.82 g, 3.0 mmol) was dissolved in DMF (15 mL), and tributyl (ethynyl)stannane (1.9 g, 6.0 mmol) and tetrakis(triphenylphosphine)palladium (173 mg, 0.15 mmol) were added. The reaction mixture was stirred in a microwave reactor at 130° C. for 0.5 hrs and then concentrated. The residue was separated by the column chromatography to obtain 2-cyclopropyl-5-ethynyl-6-fluorobenzo[d]thiazole (0.16 g, yield: 25%). MS m/z (ESI): 218 [M+H]$^+$.

Intermediate 16-23 can be Prepared by Selecting Corresponding Raw Materials According to all or Part of the Synthesis Method of Intermediate 15:

| Intermediate No. | Structural formula | Chemical name | [M + H]$^+$ |
|---|---|---|---|
| 16 | 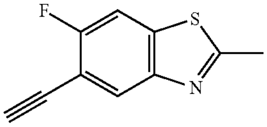 | 5-ethynyl-6-fluoro-2-methylbenzo[d]thiazole | 192 |
| 17 | 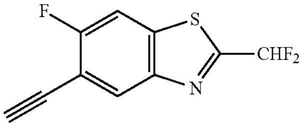 | 2-(difluoromethyl)-5-ethynyl-6-fluorobenzo[d]thiazole | 228 |
| 18 | 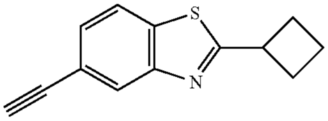 | 2-cyclobutyl-5-ethynylbenzo[d]thiazole | 214 |
| 19 | 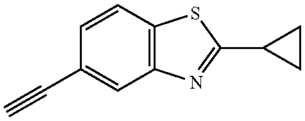 | 2-cyclopropyl-5-ethynylbenzo[d]thiazole | 200 |
| 20 | 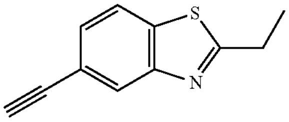 | 2-ethyl-5-ethynylbenzo[d]thiazole | 188 |
| 21 | 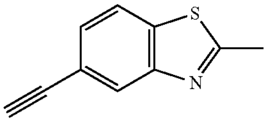 | 5-ethynyl-2-methylbenzo[d]thiazole | 174 |

-continued

| Intermediate No. | Structural formula | Chemical name | $[M+H]^+$ |
|---|---|---|---|
| 22 | 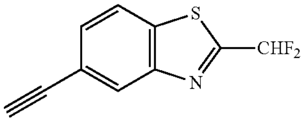 | 2-(difluoromethyl)-5-ethynylbenzo[d] thiazole | 210 |
| 23 | 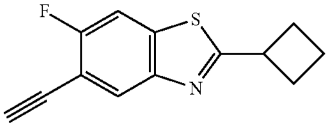 [SMILES: C#Cc1cc2nc(C3CCC3)sc2cc1F] | 2-cyclobutyl-5-ethynyl-6-fluorobenzo [d]thiazole | 232 |

Intermediate 24: Preparation of (S)-1-(3-(4-amino-5-iodo-7H-pyrrolo[2,3-d]pyrimidin-7-yl)pyrrolidin-1-yl)prop-2-en-1-one

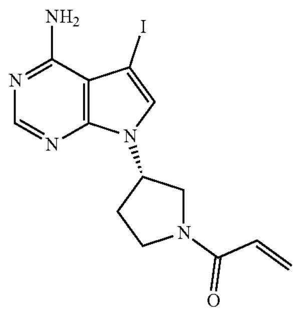 [SMILES: C=CC(=O)N1CC[C@H](n2cc(I)c3c(N)ncnc32)C1]

Step 1: Synthesis of tert-butyl(S)-3-(4-amino-5-iodo-7H-pyrrolo[2,3-a]pyrimidin-7-yl)pyrrolidine-1-carboxylate

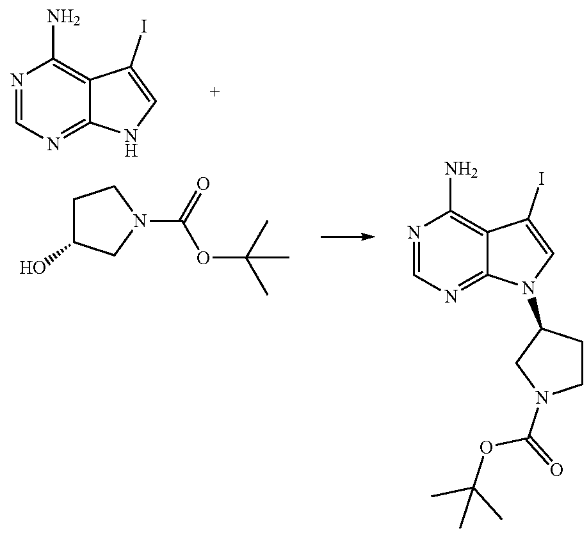

5-iodo-7H-pyrrolo[2,3-d]pyrimidin-4-amine (520 mg, 2 mmol), tert-butyl (R)-3-hydroxypyrrolidine-1-carboxylate (561 mg, 3 mmol) and triphenylphosphine (786 mg, 3 mmol) were dissolved in tetrahydrofuran (10 mL), and diisopropyl azodiformate (0.6 mL, 3 mmol) was added. The reaction mixture was stirred at room temperature for 16 hrs. After the reaction was completed, the reaction mixture was concentrated to dryness, and the residue was separated by the column chromatography to obtain tert-butyl (S)-3-(4-amino-5-iodo-7H-pyrrolo[2,3-d]pyrimidin-7-yl)pyrrolidine-1-carboxylate (300 mg, yield: 35%). MS m/z (ESI): 430 $[M+H]^+$.

Step 2: Synthesis of (S)-5-iodo-7-(pyrrolidin-3-yl)-7H-pyrrolo[2,3-d]pyrimidin-4-amine

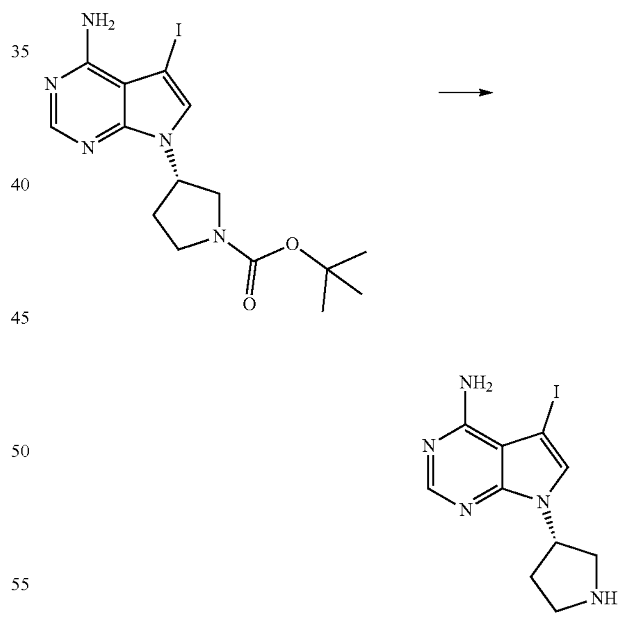

Tert-butyl (S)-3-(4-amino-5-iodo-7H-pyrrolo[2,3-d]pyrimidin-7-yl)pyrrolidine-1-carboxylate (300 mg, 0.69 mmol) was dissolved in dichloromethane (10 mL), and HCl/dioxane solution (5 mL) was added. The reaction mixture was stirred at room temperature for 4 hrs. After the reaction was completed, the reaction mixture was concentrated to dryness to obtain (S)-5-iodo-7-(pyrrolidin-3-yl)-7H-pyrrolo[2,3-d]pyrimidin-4-amine (230 mg, yield: 100%). MS m/z (ESI): 330 $[M+H]^+$.

Step 3: Synthesis of (S)-1-(3-(4-amino-5-iodo-7H-pyrrolo[2,3-d]pyrimidin-7-yl)pyrrolidin-1-yl)prop-2-en-1-one

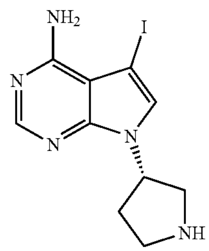
+
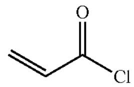
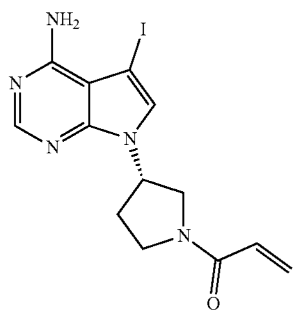

(S)-5-iodo-7-(pyrrolidin-3-yl)-7H-pyrrolo[2,3-d]pyrimidin-4-amine (230 mg, 0.70 mmol) was dissolved in tetrahydrofuran (4 mL) and saturated aqueous sodium bicarbonate solution (I mL), and then the mixture was cooled to 0° C. and acryloyl chloride (65 mg, 0.7 mmol) was added. The reaction mixture was stirred under an ice bath for 0.5 hrs. After the reaction was completed, the reaction mixture was separated by the reverse phase chromatography to obtain (S)-1-(3-(4-amino-5-iodo-7H-pyrrolo[2,3-d]pyrimidin-7-yl)pyrrolidin-1-yl)prop-2-en-1-one (50 mg, yield: 18%). MS m/z (ESI): 384 $[M+H]^+$.

Intermediate 25: Preparation of (S)-1-(3-(4-amino-3-iodo-1H-pyrazolo[3,4-d]pyrimidin-1-yl)pyrrolidin-1-yl)prop-2-en-1-one

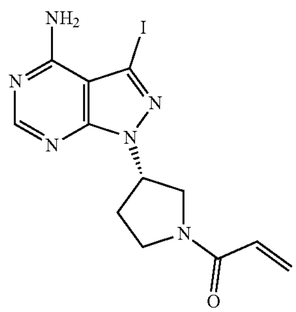 [SMILES: C=CC(=O)N1CC[C@H](n2nc(I)c3c(N)ncnc32)C1]

Step 1: Synthesis of tert-butyl (S)-3-(4-amino-3-iodo-1H-pyrazolo[3,4-d]pyrimidin-1-yl)pyrrolidine-1-carboxylate

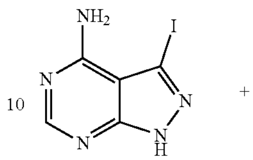
+
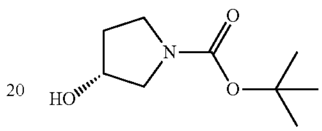
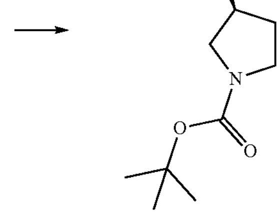

3-iodo-1H-pyrazolo[3,4-d]pyrimidin-4-amine (1000 mg, 3.82 mmol), tert-butyl (R)-3-hydroxypyrrolidine-1-carboxylate (1070 mg, 5.73 mmol) and triphenylphosphine (1500 mg, 5.73 mmol) were dissolved in tetrahydrofuran (100 mL), and diisopropyl azodiformate (1150 mL, 5.73 mmol) was added. The reaction mixture was stirred at room temperature for 16 hrs. After the reaction was completed, the reaction mixture was concentrated to dryness, and the residue was separated by the column chromatography to obtain tert-butyl (S)-3-(4-amino-3-iodo-1H-pyrazolo[3,4-d]pyrimidin-1-yl)pyrrolidine-1-carboxylate (1100 mg, yield: 67%). MS m/z (ESI): 431 [M+H].

Step 2: Synthesis of (S)-3-iodo-1-(pyrrolidin-3-yl)-1H-pyrazolo[3,4-d]pyrimidin-4-amine

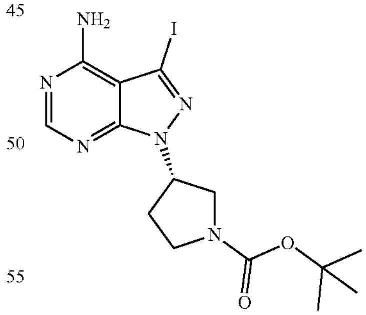
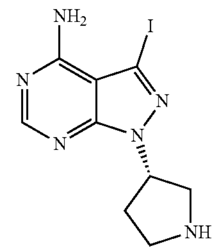

Tert-butyl (S)-3-(4-amino-3-iodo-1H-pyrazolo[3,4-d]pyrimidin-1-yl)pyrrolidine-1-carboxylate (2000 mg, 4.65 mmol) was dissolved in dichloromethane (50 mL), and HCl/dioxane solution (10 mL) was added. The reaction mixture was stirred at room temperature for 1 hr. After the reaction was completed, the reaction mixture was concentrated to dryness to obtain (S)-3-iodo-1-(pyrrolidin-3-yl)-1H-pyrazolo[3,4-d]pyrimidin-4-amine (1540 mg, yield: 100%). MS m/z (ESI): 331 $[M+H]^+$.

Step 3: Synthesis of (S)-1-(3-(4-amino-3-iodo-1H-pyrazolo[3,4-d]pyrimidin-1-yl)pyrrolidin-1-yl)prop-2-en-1-one

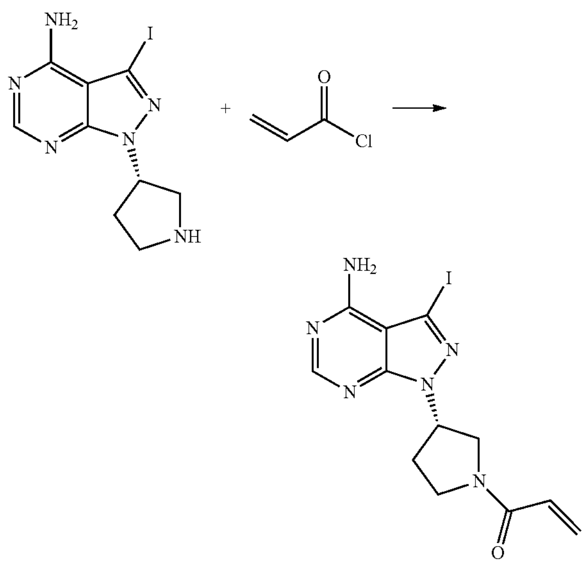

(S)-3-iodo-1-(pyrrolidin-3-yl)-1H-pyrazolo[3,4-d]pyrimidin-4-amine (1.54 mg, 4.65 mmol) was dissolved in tetrahydrofuran (20 mL) and saturated aqueous sodium bicarbonate solution (5 mL), and then the mixture was cooled to 0° C. and acryloyl chloride (473 mg, 5.11 mmol) was added. The reaction mixture was stirred under an ice bath for 1 hr. After the reaction was completed, the reaction mixture was separated by the reverse phase chromatography to obtain (S)-1-(3-(4-amino-3-iodo-1H-pyrazolo[3,4-d]pyrimidin-1-yl)pyrrolidin-1-yl)prop-2-en-1-one (500 mg, yield: 28%). MS m/z (ESI): 385 $[M+H]^+$.

Intermediate 26: Preparation of (S)-1-(3-(8-amino-1-iodoimidazo[1,5-a]pyrazin-3-yl)pyrrolidin-1-yl)prop-2-en-1-one

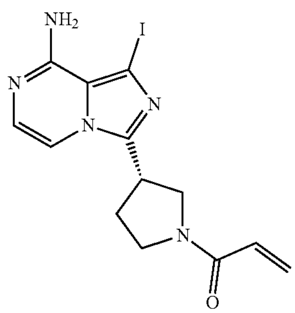 [SMILES: C=CC(=O)N1CC[C@H](c2nc(I)c3c(N)nccn23)C1]

Step 1: Synthesis of benzyl (S)-3-(((3-chloropyrazin-2-yl)methyl)carbamoyl)pyrrolidine-1-carboxylate

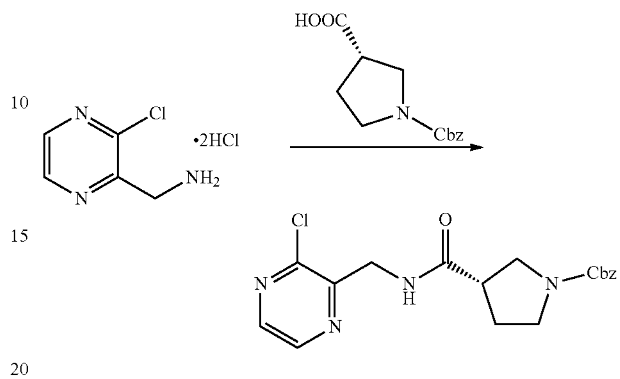

3-chloropyrazine-2-methanamine dihydrochloride (4.45 g, 20.55 mmol), (S)-1-((benzyloxy)carbonyl)pyrrolidine-3-carboxylic acid (5.12 g, 20.55 mmol), 2-(7-azabenzotriazol-1-yl)-N,N,N',N'-tetramethyluronium hexafluorophosphate (8.2 g, 21.57 mmol) and triethylamine (8.3 g, 82.20 mmol) were dissolved in anhydrous dichloromethane (100 mL), and the reaction mixture was stirred overnight at room temperature. Saturated sodium bicarbonate solution (50 mL) was added to quench the reaction, and the resulting reaction mixture was extracted three times with dichloromethane (50 mL). The organic phases were combined, washed with saturated brine (50 mL), dried over sodium sulfate, filtered and concentrated to obtain crude benzyl (S)-3-(((3-chloropyrazin-2-yl)methyl)carbamoyl)pyrrolidine-1-carboxylate (8 g, yield: 95%). MS m/z (ESI): 375 $[M+H]^+$.

Step 2: Synthesis of benzyl (S)-3-(8-chloroimidazo[1,5-a]pyrazin-3-yl)pyrrolidine-1-carboxylate

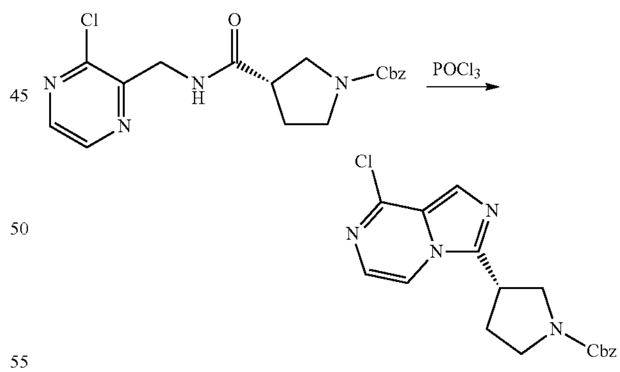

Benzyl (S)-3-(((3-chloropyrazin-2-yl)methyl)carbamoyl)pyrrolidine-1-carboxylate (8 g, 21.4 mmol) was dissolved in anhydrous acetonitrile (100 mL), and phosphorus oxychloride (16.4 g, 107.0 mmol) was added dropwise under an ice bath. The reaction mixture was slowly heated to 80° C. and stirred for 5 hrs. The reaction mixture was cooled down, then saturated aqueous sodium bicarbonate solution was added dropwise to quench the reaction (keeping the internal temperature at no more than 5° C.), and the resulting reaction mixture was extracted three times with ethyl acetate (60 mL). The organic phase was washed with saturated brine (50 mL), dried over sodium sulfate, filtered and concentrated, and the residue was separated by the column chromatography to obtain benzyl (S)-3-(8-chloroimidazo[1,5-a]pyrazin-3-yl)pyrrolidine-1-carboxylate (3.8 g, yield: 50%). MS m/z (ESI): 357 $[M+H]^+$.

Step 3: Synthesis of benzyl (S)-3-(8-chloro-1-iodo-imidazo[1,5-a]pyrazin-3-yl)pyrrolidine-1-carboxylate

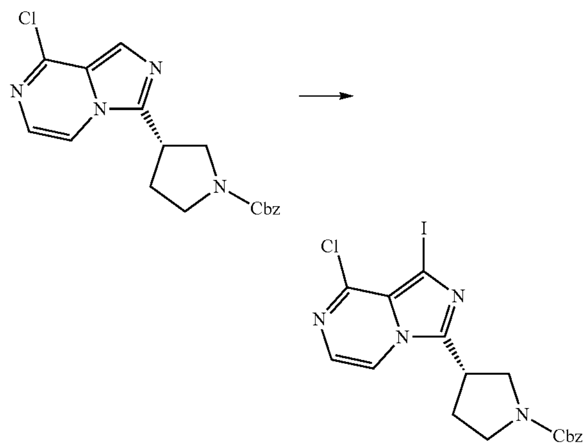

Benzyl (S)-3-(8-chloroimidazo[1,5-a]pyrazin-3-yl)pyrrolidine-1-carboxylate (0.65 g, 1.82 mmol) and N-iodosuccinimide (1.43 g, 6.37 mmol) were dissolved in DMF (10 mL), and the reaction mixture was stirred overnight at room temperature. Deionized water was then added, and the resulting reaction mixture was extracted twice with ethyl acetate. The organic phases were combined, washed with saturated brine (30 mL), dried over sodium sulfate, filtered and concentrated, and the residue was separated by the column chromatography to obtain benzyl (S)-3-(8-chloro-1-iodoimidazo[1,5-a]pyrazin-3-yl)pyrrolidine-1-carboxylate (0.76 g, yield: 86%). MS m/z (ESI): 483 $[M+H]^+$.

Step 4: Synthesis of benzyl (S)-3-(8-amino-1-iodo-imidazo[1,5-a]pyrazin-3-yl)pyrrolidine-1-carboxylate

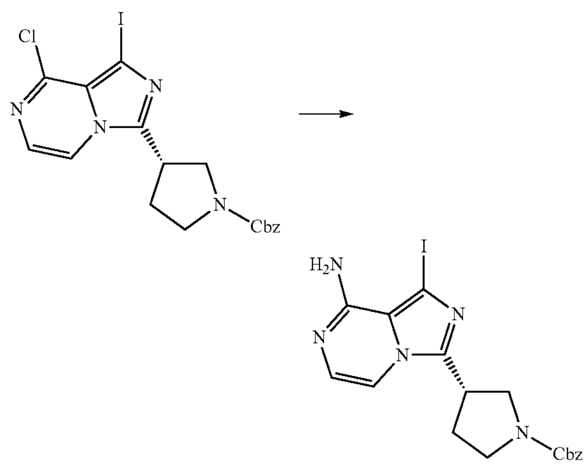

Benzyl (S)-3-(8-chloro-1-iodoimidazo[1,5-a]pyrazin-3-yl)pyrrolidine-1-carboxylate (0.76 g, 1.57 mmol) was dissolved in dioxane (10 mL), and then concentrated ammonia liquor (20 mL) was added to the sealed tube. The reaction mixture was heated to 80° C., stirred overnight and then concentrated. The residue was separated by the column chromatography to obtain benzyl (S)-3-(8-amino-1-iodoimidazo[1,5-a]pyrazin-3-yl)pyrrolidine-1-carboxylate (0.64 g, yield: 88%). MS m/z (ESI): 464 $[M+H]^+$.

Step 5: Synthesis of (S)-1-iodo-3-(pyrrolidin-3-yl)imidazo[1,5-a]pyrazin-8-amine

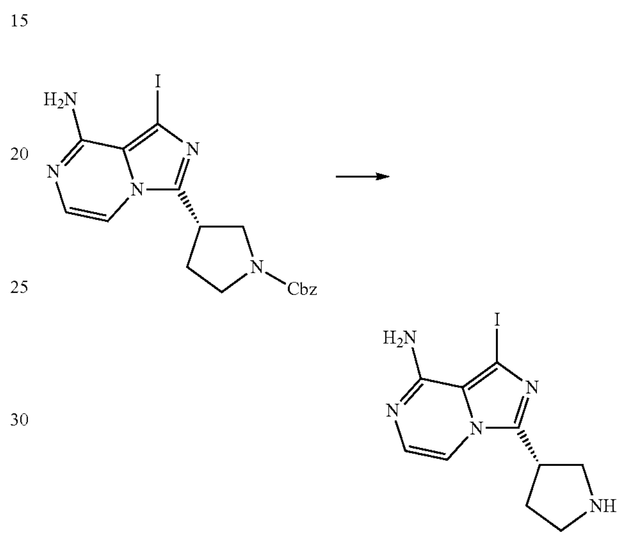

Benzyl (S)-3-(8-amino-1-iodoimidazo[1,5-a]pyrazin-3-yl)pyrrolidine-1-carboxylate (0.64 g, 1.38 mmol) was dissolved in dichloromethane (15 mL), and then the mixture was cooled to 0° C. and trimethylsilyl iodide (0.7 g, 2.76 mmol) was added dropwise. The reaction mixture was stirred at 0° C. for 2 hrs. Saturated aqueous sodium thiosulfate solution was then added to quench the reaction, and the resulting reaction mixture was extracted three times with dichloromethane. The organic phases were combined, dried over sodium sulfate, filtered and concentrated, and the residue was separated by the column chromatography to obtain (S)-1-iodo-3-(pyrrolidin-3-yl)imidazo[1,5-a]pyrazin-8-amine (95 mg, yield: 21%). MS m/z (ESI): 330 $[M+H]^+$.

Step 6: Synthesis of (S)-1-(3-(8-amino-1-iodoimidazo[1,5-a]pyrazin-3-yl)pyrrolidin-1-yl)prop-2-en-1-one

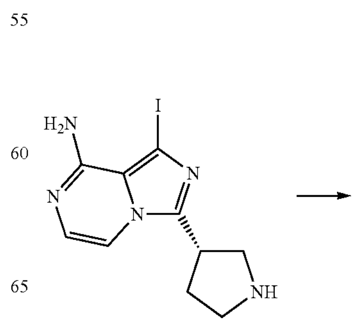

-continued

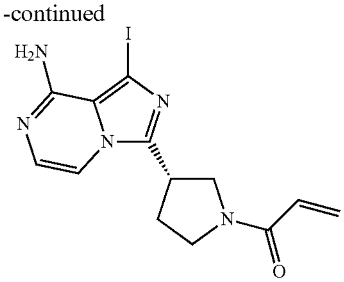

(S)-1-iodo-3-(pyrrolidin-3-yl)imidazo[1,5-a]pyrazin-8-amine (95 mg, 0.29 mmol) was dissolved in tetrahydrofuran (4 mL) and saturated aqueous sodium bicarbonate solution (2 mL), and acryloyl chloride (31 mg, 0.35 mmol) was added under an ice bath. The reaction mixture was reacted for 30 min under an ice bath and then directly separated by reverse phase chromatography, and the resulting aqueous phase was lyophilized to obtain (S)-1-(3-(8-amino-1-iodo-imidazo[1,5-a]pyrazin-3-yl)pyrrolidin-1-yl)prop-2-en-1-one (72 mg, yield: 65%). MS m/z (ESI): 384 [M+H]$^+$.

Intermediate 27: Preparation of 1-(3-(4-amino-5-iodopyrrolo[2,1-f][1,2,4]triazin-7-yl)pyrrolidin-1-yl) prop-2-en-1-one

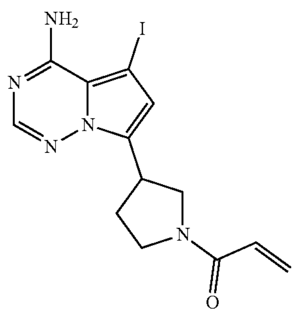 [SMILES: C=CC(=O)N1CCC(c2cc(I)c3c(N)ncnn23)C1]

Step 1: Synthesis of 7-iodopyrrolo[2,1-f][1,2,4] triazin-4-amine

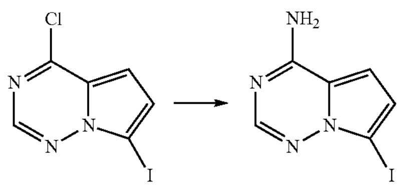 [SMILES: Clc1ncnn2c(I)ccc12 ; Nc1ncnn2c(I)ccc12]

4-chloro-7-iodopyrrolo[2,1-f][1,2,4]triazine (1 g, 3.58 mmol) was dissolved in isopropanol (10 mL), and then concentrated ammonia liquor (10 mL) was added to the sealed tube. The reaction mixture was heated to 70° C. and stirred for 3 hrs. After being cooled down, the reaction mixture was directly concentrated to obtain crude 7-iodopyrrolo[2,1-f][1,2,4]triazin-4-amine (1 g, yield: 100%). MS m/z (ESI): 261 [M+H]$^+$.

Step 2: Synthesis of tert-butyl 3-(4-aminopyrrolo[2,1-f][1,2,4]triazin-7-yl)-2,5-dihydro-1H-pyrrole-1-carboxylate

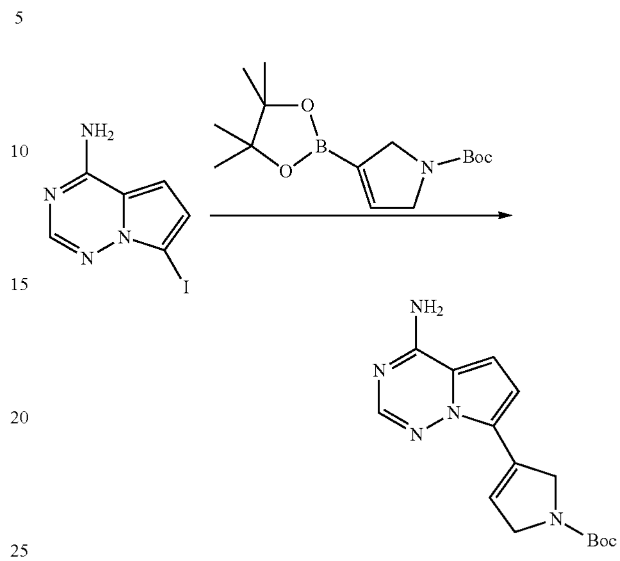

7-iodopyrrolo[2,1-f][1,2,4]triazin-4-amine (0.55 g, 2.11 mmol), tert-butyl 3-(4,4,5,5-tetramethyl-1,3,2-dioxaborolan-2-yl)-2,5-dihydro-1H-pyrrole-1-carboxylate (0.75 g, 2.54 mmol), [1,1'-bis(diphenylphosphino)ferrocene]palladium dichloride (172 mg, 0.21 mmol) and potassium carbonate (0.87 g, 6.33 mmol) were dissolved in dioxane (10 mL) and water (2 mL), and the reaction mixture was heated to 80° C., stirred overnight and then concentrated. The residue was separated by the column chromatography to obtain tert-butyl 3-(4-aminopyrrolo[2,1-f][1,2,4]triazin-7-yl)-2,5-dihydro-1H-pyrrole-1-carboxylate (0.5 g, yield: 79%). MS m/z (ESI): 302 [M+H]$^+$.

Step 3: Synthesis of tert-butyl 3-(4-aminopyrrolo[2,1-f][1,2,4]triazin-7-yl)pyrrolidine-1-carboxylate

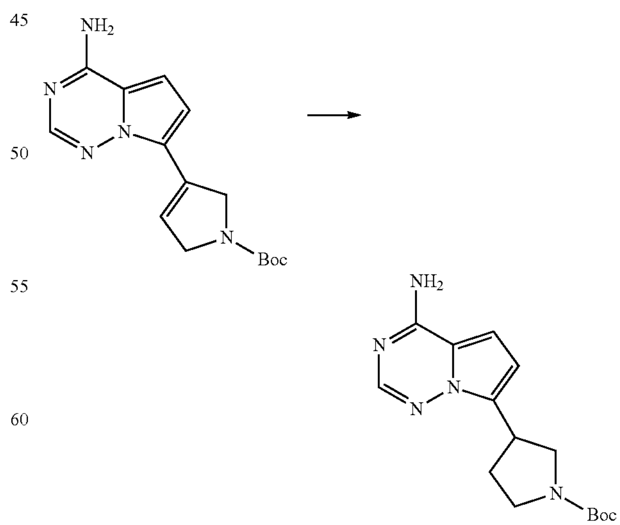

Tert-butyl 3-(4-aminopyrrolo[2,1-f][1,2,4]triazin-7-yl)-2,5-dihydro-1H-pyrrole-1-carboxylate (0.5 g, 1.66 mmol) was dissolved in methanol (10 mL), and 10% wet palladium on carbon (100 mg) was added. The reaction mixture was heated to 50° C. under hydrogen atmosphere, stirred overnight and then filtered, and the filtrate was concentrated. The residue was dried to obtain tert-butyl 3-(4-aminopyrrolo[2,1-f][1,2,4]triazin-7-yl)pyrrolidine-1-carboxylate (460 mg, yield: 91%). MS m/z (ESI): 304 [M+H]$^+$.

Step 4: Synthesis of tert-butyl 3-(4-amino-5-iodopyrrolo[2,1-f][1,2,4]triazin-7-yl)pyrrolidine-1-carboxylate

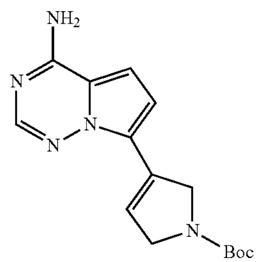

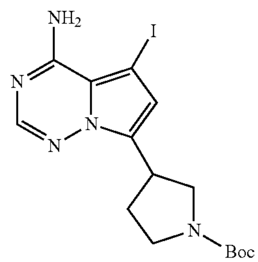

Tert-butyl 3-(4-aminopyrrolo[2,1-f][1,2,4]triazin-7-yl) pyrrolidine-1-carboxylate (0.46 g, 1.52 mmol) and N-iodosuccinimide (1.02 g, 4.55 mmol) were dissolved in N,N-dimethylformamide (5 mL), and the reaction mixture was stirred overnight at room temperature. Deionized water (50 mL) was added, and a large amount of solid was precipitated out. The mixture was filtered, and the filter cake was washed twice with acetone (10 mL) and dried to obtain tert-butyl 3-(4-amino-5-iodopyrrolo[2,1-f][1,2,4]triazin-7-yl)pyrrolidine-1-carboxylate (0.74 g, yield: 95%). MS m/z (ESI): 430 [M+H]$^+$.

Step 5: Synthesis of 5-iodo-7-(pyrrolidin-3-yl)pyrrolo[2,1-f][1,2,4]triazin-4-amine

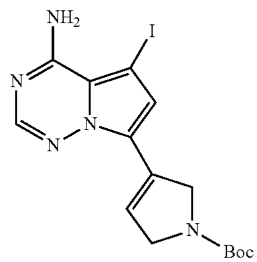

-continued

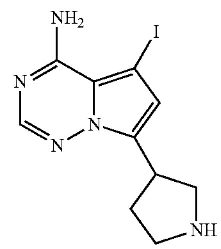

Tert-butyl 3-(4-amino-5-iodopyrrolo[2,1-f][1,2,4]triazin-7-yl)pyrrolidine-1-carboxylate (300 mg, 0.70 mmol) was dissolved in ethyl acetate (10 mL), and 4 N HCl/dioxane solution (1 mL) was added dropwise. The reaction mixture was stirred at room temperature for 4 hrs and then concentrated, and the residue was dried to obtain 5-iodo-7-(pyrrolidin-3-yl)pyrrolo[2,1-f][1,2,4]triazin-4-amine (300 mg, yield: 100%). MS m/z (ESI): 330 [M+H]$^+$.

Step 6: Synthesis of 1-(3-(4-amino-5-iodopyrrolo[2,1-f][1,2,4]triazin-7-yl)pyrrolidin-1-yl)prop-2-en-1-one

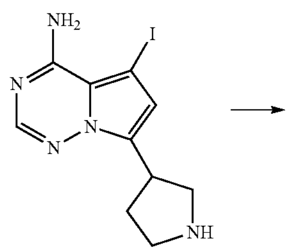

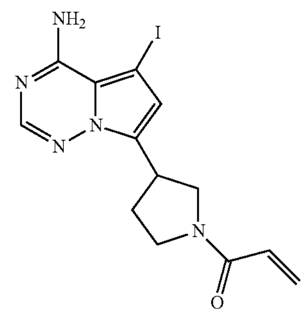

5-iodo-7-(pyrrolidin-3-yl)pyrrolo[2,1-f][1,2,4]triazin-4-amine (300 mg, 0.91 mmol) was dissolved in tetrahydrofuran (10 mL) and saturated sodium bicarbonate (5 mL), and then the mixture was cooled to 0° C. and acryloyl chloride (90 mg, 0.99 mmol) was added dropwise. The reaction mixture was stirred for 30 min and then directly separated by the reverse phase chromatography, and the resulting aqueous phase was lyophilized to obtain 1-(3-(4-amino-5-iodopyrrolo[2,1-f][1,2,4]triazin-7-yl)pyrrolidin-1-yl)prop-2-en-1-one (300 mg, yield: 85%). MS m/z (ESI): 384 [M+H]$^+$.

Intermediate 28: Preparation of 2-cyclopropyl-5-ethynyl-4,6-difluorobenzo[d]thiazole

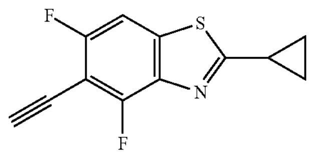 [SMILES: C#Cc1c(F)cc2sc(C3CC3)nc2c1F]

Step 1: Synthesis of N-(2,4-difluorophenyl)cyclopropanecarboxamide

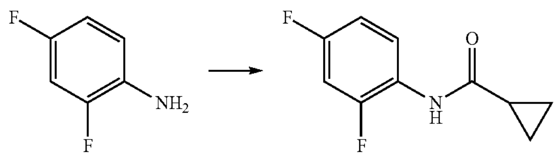 [SMILES: Nc1ccc(F)cc1F ; O=C(Nc1ccc(F)cc1F)C1CC1]

2,4-difluoroaniline (10 g, 77.45 mmol) was dissolved in dichloromethane (100 mL), and triethylamine (15.64 g, 154.9 mmol) was added. Cyclopropylcarbonyl chloride (8.1 g, 77.45 mmol) was added dropwise under an ice bath, and then the reaction mixture was stirred overnight at room temperature. The reaction mixture was then washed with an appropriate amount of saturated aqueous ammonium chloride solution and saturated brine, dried over anhydrous sodium sulfate and concentrated, and the residue was separated by the silica gel column chromatography to obtain N-(2,4-difluorophenyl)cyclopropanecarboxamide (10.1 g, yield: 66%). MS m/z (ESI): 196 $[M+H]^+$.

Step 2: Synthesis of N-(2,4-difluorophenyl)cyclopropanecarbothioamide

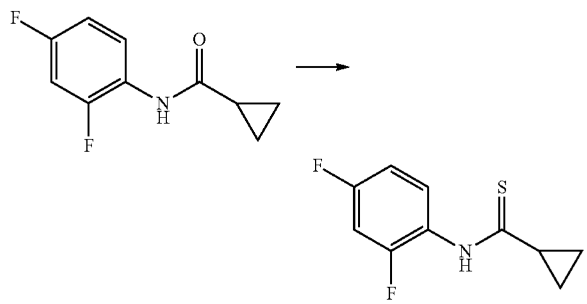

N-(2,4-difluorophenyl)cyclopropanecarboxamide (5 g, 25.36 mmol) was dissolved in xylene (80 mL), and Lawesson's reagent (7.18 g, 17.75 mmol) was added. The reaction mixture was heated to 120° C., stirred overnight, and then concentrated. The residue was directly separated by the silica gel column chromatography to obtain N-(2,4-difluorophenyl)cyclopropanecarbothioamide (4.1 g, yield: 75%). MS m/z (ESI): 212 $[M+H]^+$.

Step 3: Synthesis of 2-cyclopropyl-4,6-difluorobenzo[d]thiazole

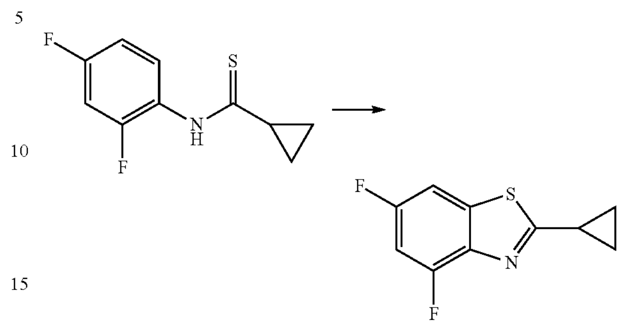

N-(2,4-difluorophenyl)cyclopropanecarbothioamide (1 g, 4.69 mmol) was dissolved in sodium hydroxide solution (1.69 g, 42.21 mmol), and then the solution was dissolved in ethanol (5 mL) and water (10 mL) (a mass concentration of about 30%). The resulting solution was added dropwise to aqueous potassium ferricyanide solution (6.18 g, 18.78 mmol, dissolved in 10 mL of water) preheated to 90° C., and the reaction mixture was stirred for 2 hrs and then the heating was stopped immediately. The reaction mixture was cooled down, adjusted to weakly acidic with concentrated hydrochloric acid and extracted with ethyl acetate. The resulting extract was washed with saturated brine and concentrated, and the residue was separated by the silica gel column chromatography to obtain 2-cyclopropyl-4,6-difluorobenzo[d]thiazole (500 mg, yield: 51%). MS m/z (ESI): 212 $[M+H]^+$.

Step 4: Synthesis of 2-cyclopropyl-4,6-difluorobenzo[d]thiazole-5-carbaldehyde

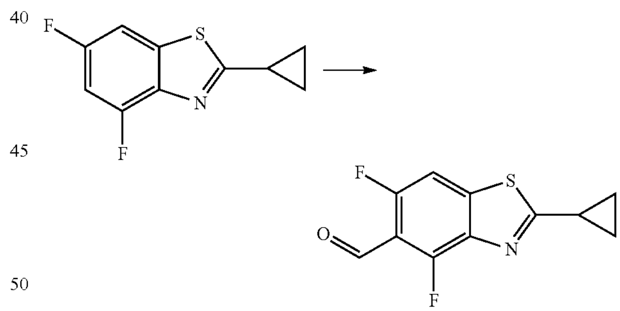

2-cyclopropyl-4,6-difluorobenzo[d]thiazole (980 mg, 4.64 mmol) was dissolved in tetrahydrofuran (15 mL), and then the mixture was cooled to −70° C. and lithium diisopropylamide (2.55 mL, 5.104 mmol, 2 M) was added dropwise. After maintaining at this temperature for 2 hrs, N,N-dimethylformamide (1.01 g, 13.92 mmol) was added, and then after maintaining at this temperature for 2 hrs, an appropriate amount of aqueous ammonium chloride solution was added to quench the reaction. The reaction mixture was warmed to room temperature and extracted with ethyl acetate, and the organic phase was dried over anhydrous sodium sulfate, filtered and concentrated. The residue was separated by the silica gel column chromatography to obtain 2-cyclopropyl-4,6-difluorobenzo[d]thiazole-5-carbaldehyde (675 mg, yield: 65%). MS m/z (ESI): 240 $[M+H]^+$.

Step 5: Synthesis of 2-cyclopropyl-5-ethynyl-4,6-difluorobenzo[d]thiazole

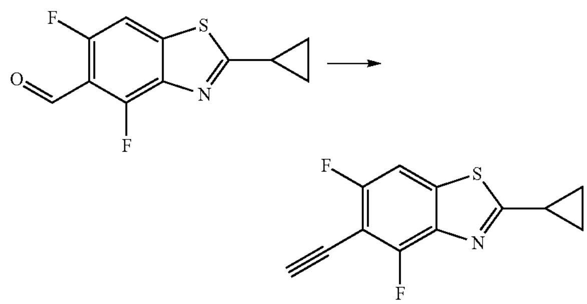

2-cyclopropyl-4,6-difluorobenzo[d]thiazole-5-carbaldehyde (122 mg, 0.51 mmol) was dissolved in methanol (10 mL), and potassium carbonate (211 mg, 1.53 mmol) and (1-diazo-2-oxopropyl)-phosphonic acid dimethyl ester (159 mg, 0.76 mmol) were added successively. The reaction mixture was stirred overnight at room temperature and then concentrated. The residue was separated by the silica gel column chromatography to obtain 2-cyclopropyl-5-ethynyl-4,6-difluorobenzo[d]thiazole (73 mg, yield: 61%). MS m/z (ESI): 236 $[M+H]^+$.

Intermediate 29 can be Prepared by Selecting Corresponding Raw Materials According to all or Part of the Synthesis Method of Intermediate 28:

| Intermediate No. | Structural formula | Chemical name | $[M + H]^+$ |
|---|---|---|---|
| 29 | 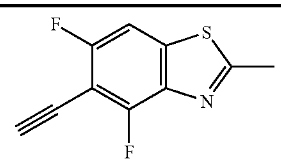 | 5-ethynyl-4,6-difluoro-2-methyl benzo[d]thiazole | 210 |

Intermediate 30: Preparation of 2-(azetidin-1-yl)-5-ethynyl-4,6-difluorobenzo[d]oxazole

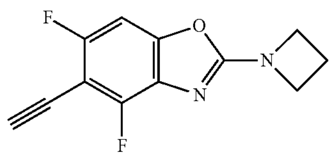 [SMILES: C#Cc1c(F)cc2oc(N3CCC3)nc2c1F]

Step 1: Synthesis of 2-amino-3,5-difluorophenol

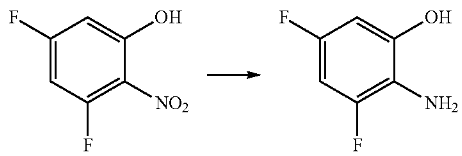 [SMILES: O=[N+]([O-])c1c(O)cc(F)cc1F ; Nc1c(O)cc(F)cc1F]

3,5-difluoro-2-nitrophenol (10 g, 57.11 mmol) was dissolved in methanol (100 mL), and palladium on carbon (1 g) was added. The reaction mixture was stirred overnight at room temperature and filtered, and the filtrate was concentrated to obtain 2-amino-3,5-difluorophenol (8.5 g, yield: 100%). MS m/z (ESI): 146 $[M+H]^+$.

Step 2: Synthesis of 4,6-difluorobenzo[d]oxazole-2-thiol

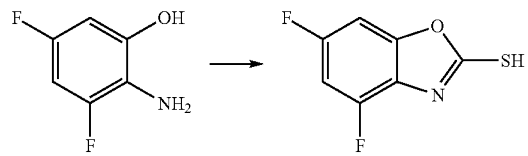 [SMILES: Nc1c(O)cc(F)cc1F ; Fc1cc(F)c2nc(S)oc2c1]

2-amino-3,5-difluorophenol (8.5 g, 58.62 mmol) was dissolved in ethanol (100 mL), and potassium O-ethyldisulfate (1.13 g, 70.34 mmol) was added. The reaction mixture was heated to 95° C. and reacted overnight. The reaction mixture was then cooled and filtered, and the filtrate was concentrated. The residue was separated by the silica gel column chromatography to obtain 4,6-difluorobenzo[d]oxazole-2-thiol (11 g, 95.31%). MS m/z (ESI): 188 $[M+H]^+$.

Step 3: Synthesis of 2-chloro-4,6-difluorobenzo[d]oxazole

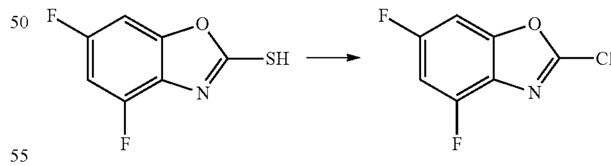

4,6-difluorobenzo[d]oxazole-2-thiol (4 g, 21.371 mmol) was dissolved in dichloromethane (50 mL), and oxalyl chloride (10.85 g, 85.48 mmol) and N,N-dimethylformamide (0.16 g, 2.14 mmol) were added. The reaction mixture was stirred at room temperature for 2 hrs and concentrated to obtain crude 2-chloro-4,6-difluorobenzo[d]oxazole (4.05 g, yield: 100%), which was used directly in the next step. MS m/z (ESI): 190 $[M+H]^+$.

Step 4: Synthesis of 2-(azetidin-1-yl)-4,6-difluorobenzo[d]oxazole

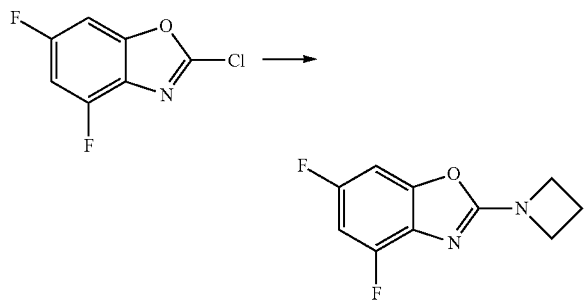

The crude 2-chloro-4,6-difluorobenzo[d]oxazole (4.05 g, 21.36 mmol) was dissolved in tetrahydrofuran (50 mL), and N,N-diisopropylethylamine (5.51 g, 42.72 mmol) and azetidine hydrochloride (2.40 g, 25.63 mmol) were added. The reaction mixture was stirred at room temperature for 2 hrs and then concentrated. Ethyl acetate was added to the residue, and the mixture was washed twice with saturated aqueous ammonium chloride solution and washed twice with saturated brine, dried over sodium sulfate and filtered. The filtrate was concentrated, and the residue was separated by the silica gel column chromatography to obtain 2-(azetidin-1-yl)-4,6-difluorobenzo[d]oxazole (3.2 g, yield: 72%). MS m/z (ESI): 211 $[M+H]^+$.

Step 5: Synthesis of 2-(azetidin-1-yl)-4,6-difluorobenzo[d]oxazole-5-carbaldehyde

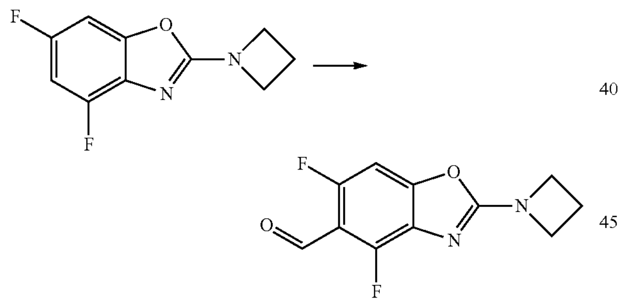

2-(azetidin-1-yl)-4,6-difluorobenzo[d]oxazole (3 g, 14.28 mmol) was dissolved in tetrahydrofuran (100 mL), and then the mixture was cooled to −70° C. and a solution of lithium diisopropylamide in tetrahydrofuran (10.7 mL, 21.41 mmol, 2 M) was added dropwise. The reaction mixture was stirred at low temperature for 1 hr, and then N,N-dimethylformamide (11.04 mL, 142.73 mmol) was added in one portion. Then the reaction mixture was stirred at low temperature for 2 hrs, and an appropriate amount of saturated aqueous ammonium chloride solution was added to quench the reaction. The reaction mixture was then warmed to room temperature and extracted twice with ethyl acetate. Ethyl acetate phases were combined, washed twice with saturated brine, dried over sodium sulfate and filtered, and the filtrate was concentrated. The residue was separated by the silica gel column chromatography to obtain 2-(azetidin-1-yl)-4,6-difluorobenzo[d]oxazole-5-carbaldehyde (0.8 g. yield: 24%). MS m/z (ESI): 239 $[M+H]^+$.

Step 6: Synthesis of 2-(azetidin-1-yl)-5-ethynyl-4,6-difluorobenzo oxazole

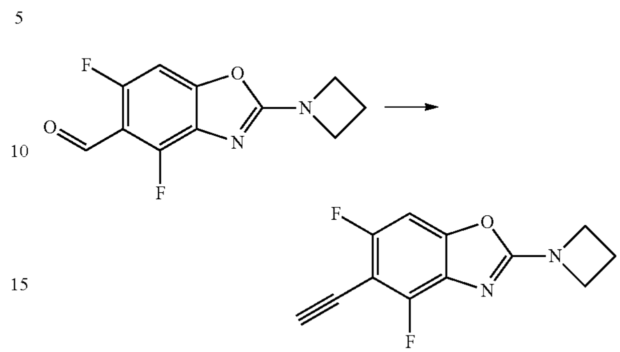

2-(azetidin-1-yl)-4,6-difluorobenzo[d]oxazole-5-carbaldehyde (0.8 g, 3.40 mmol) was dissolved in methanol (10 mL) and tetrahydrofuran (10 mL), and potassium carbonate (1.17 g, 8.5 mmol) and (1-diazo-2-oxopropyl)-phosphonic acid dimethyl ester (1.31 g, 6.801 mmol) were added. The reaction mixture was stirred at room temperature for 2 hrs and concentrated, and an appropriate amount of saturated aqueous ammonium chloride solution was added to quench the reaction. The reaction mixture was then warmed to room temperature and extracted twice with ethyl acetate. Ethyl acetate phases were combined, washed twice with saturated brine, dried over sodium sulfate and filtered, and the filtrate was concentrated. The residue was separated by the silica gel column chromatography to obtain 2-(azetidin-1-yl)-5-ethynyl-4,6-difluorobenzo[d]oxazole (0.75 g, yield: 94%). MS m/z (ESI): 235 $[M+H]^+$.

Intermediate 31: Preparation of 5-ethynyl-4,6-difluoro-N-methylbenzo[d]oxazol-2-amine

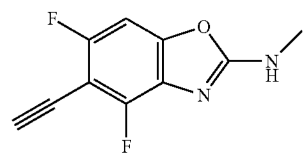

Step 1: Synthesis of 2-amino-3,5-difluorophenol

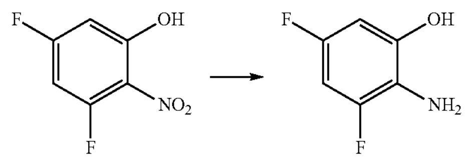 [SMILES: O=[N+]([O-])c1c(O)cc(F)cc1F ; Nc1c(O)cc(F)cc1F]

3,5-difluoro-2-nitrophenol (10 g, 57.11 mmol) was dissolved in methanol (100 mL), and palladium on carbon (1 g) was added. The reaction mixture was stirred overnight at room temperature and filtered, and the filtrate was concentrated to obtain 2-amino-3,5-difluorophenol (8.5 g. yield: 100%). MS m/z (ESI): 146 $[M+H]^+$.

Step 2: Synthesis of 4,6-difluorobenzo[d]oxazole-2-thiol

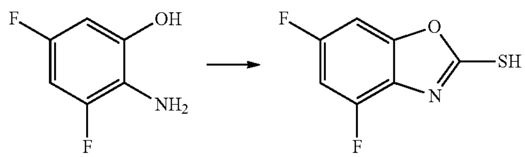 [SMILES: Nc1c(O)cc(F)cc1F ; Fc1cc(F)c2nc(S)oc2c1]

2-amino-3,5-difluorophenol (8.5 g, 58.62 mmol) was dissolved in ethanol (100 mL), and potassium O-ethyldisulfate (1.13 g, 70.34 mmol) was added. The reaction mixture was heated to 95° C. and reacted overnight. The reaction mixture was then cooled and filtered, and the filtrate was concentrated. The residue was separated by the silica gel column chromatography to obtain 4,6-difluorobenzo[d]oxazole-2-thiol (11 g, 95.31%). MS m/z (ESI): 188 $[M+H]^+$.

Step 3: Synthesis of 2-chloro-4,6-difluorobenzo[d]oxazole

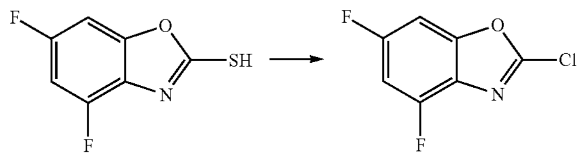 [SMILES: Fc1cc(F)c2nc(S)oc2c1 ; Fc1cc(F)c2nc(Cl)oc2c1]

4,6-difluorobenzo[d]oxazole-2-thiol (4 g, 21.37 mmol) was dissolved in dichloromethane (50 mL), and oxalyl chloride (10.85 g, 85.48 mmol) and N,N-dimethylformamide (0.16 g, 2.14 mmol) were added. The reaction mixture was stirred at room temperature for 2 hrs, and after the reaction was completed, the reaction mixture was directly concentrated to obtain crude 2-chloro-4,6-difluorobenzo[d]oxazole (4.05 g), which was used directly in the next step. MS m/z (ESI): 190 $[M+H]^+$.

Step 4: Synthesis of 4,6-difluoro-N-methylbenzo[d]oxazol-2-amine

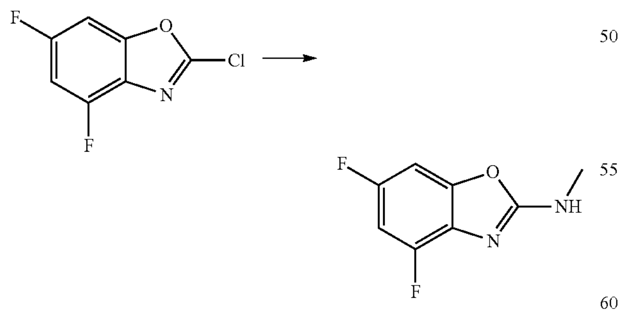

2-chloro-4,6-difluorobenzo[d]oxazole (1 g, 5.28 mmol) was dissolved in tetrahydrofuran (10 mL), and a solution of methylamine in ethanol (7.92 mL, 15.84 mmol) was added. The reaction mixture was stirred at room temperature for 2 hrs and then concentrated, and the residue was directly separated by the silica gel column chromatography to obtain 4,6-difluoro-N-methylbenzo[d]oxazol-2-amine (0.4 g, yield: 29%). MS m/z (ESI): 190 $[M+H]^+$.

Step 5: Synthesis of 4,6-difluoro-2-(methylamino)benzo[d]oxazole-5-carbaldehyde

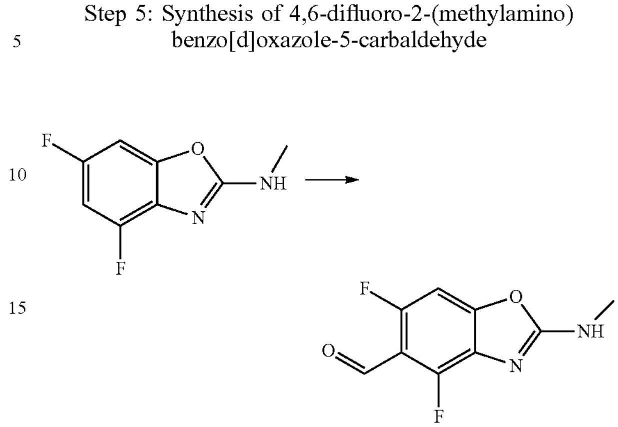

4,6-difluoro-N-methylbenzo[d]oxazol-2-amine (0.25 g, 1.36 mmol) was dissolved in tetrahydrofuran (25 mL), and then the mixture was cooled to −70° C. and a solution of lithium diisopropylamide in tetrahydrofuran (2.0 mL, 4.07 mmol, 2 M) was added dropwise. The reaction mixture was stirred at low temperature for 1 hr, and then N,N-dimethylformamide (2.1 mL, 27.15 mmol) was added in one portion. Then the reaction mixture was stirred at low temperature for 2 hrs, and an appropriate amount of saturated aqueous ammonium chloride solution was added to quench the reaction. The reaction mixture was then warmed to room temperature and extracted twice with ethyl acetate. Ethyl acetate phases were combined, washed twice with saturated brine, dried over sodium sulfate and filtered, and the filtrate was concentrated. The residue was separated by the silica gel column chromatography to obtain 4,6-difluoro-2-(methylamino)benzo[d]oxazole-5-carbaldehyde (0.12 g, yield: 41%). MS m/z (ESI): 213 $[M+H]^+$.

Step 6: Synthesis of 5-ethynyl-4,6-difluoro-N-methylbenzo[d]oxazol-2-amine

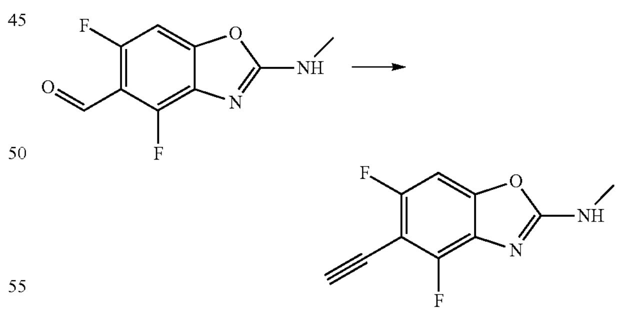

4,6-difluoro-2-(methylamino)benzo[d]oxazole-5-carbaldehyde (120 mg, 0.57 mmol) was dissolved in methanol (5 mL) and tetrahydrofuran (5 ML), and potassium carbonate (195 mg, 1.41 mmol) and (1-diazo-2-oxopropyl)-phosphonic acid dimethyl ester (217 mg, 1.13 mmol) were added. The reaction mixture was stirred at room temperature for 2 hrs and concentrated, and an appropriate amount of saturated aqueous ammonium chloride solution was added to quench the reaction. The reaction mixture was then warmed to room temperature and extracted twice with ethyl acetate. Ethyl acetate phases were combined, washed twice with saturated brine, dried over sodium sulfate and filtered, and the filtrate was concentrated. The residue was separated by the silica gel column chromatography to obtain 5-ethynyl-4,6-difluoro-N-methylbenzo[d]oxazol-2-amine (110 mg, yield: 91%). MS m/z (ESI): 209[M+H]$^+$.

Intermediate 32: Preparation of 1-((2R,4S)-4-(4-amino-3-iodo-1H-pyrazolo[3,4-d]pyrimidin- 1-yl)-2-(methoxymethyl)pyrrolidin-1-yl)prop-2-en-1-one

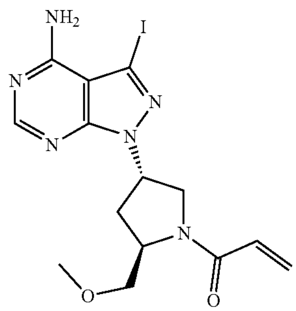 [SMILES: C=CC(=O)N1C[C@@H](n2nc(I)c3c(N)ncnc32)C[C@@H]1COC]

Step 1: Synthesis of 1-(tert-butyl) 2-methyl (2R,4R)-4-(benzyloxy)pyrrolidine-1,2-dicarboxylate

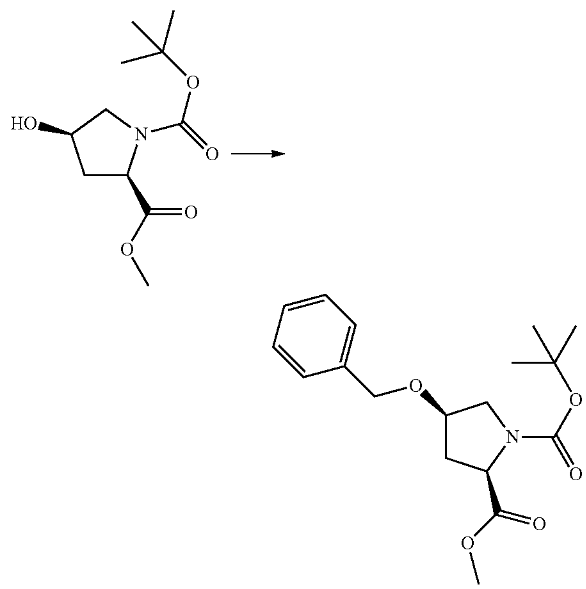

1-(tert-butyl) 2-methyl (2R,4R)-4-hydroxypyrrolidine-1,2-dicarboxylate (10 g, 40.77 mmol) was dissolved in N,N-dimethylformamide (120 mL), and then the mixture was placed in ice water and sodium hydride (1.63 g, 40.77 mmol) was added. The reaction mixture was stirred for 0.5 hrs, and then benzyl bromide (6.5 mL, 54.36 mmol) was added. The resulting reaction mixture was stirred overnight at room temperature. After the reaction was completed, diluted hydrochloric acid was added to quench the reaction, and the resulting mixture was extracted twice with an appropriate amount of ethyl acetate. The organic phases were combined, washed twice with saturated brine, dried over sodium sulfate and filtered, and the filtrate was concentrated. The residue was separated by the silica gel column chromatography to obtain 1-(tert-butyl) 2-methyl (2R,4R)-4-(benzyloxy)pyrrolidine-1,2-dicarboxylate (11.8 g, yield: 97%). MS m/z (ESI): 336[M+H]$^+$.

Step 2: Synthesis of tert-butyl (2R,4R)-4-(benzyloxy)-2-(hydroxymethyl)pyrrolidine-1-carboxylate

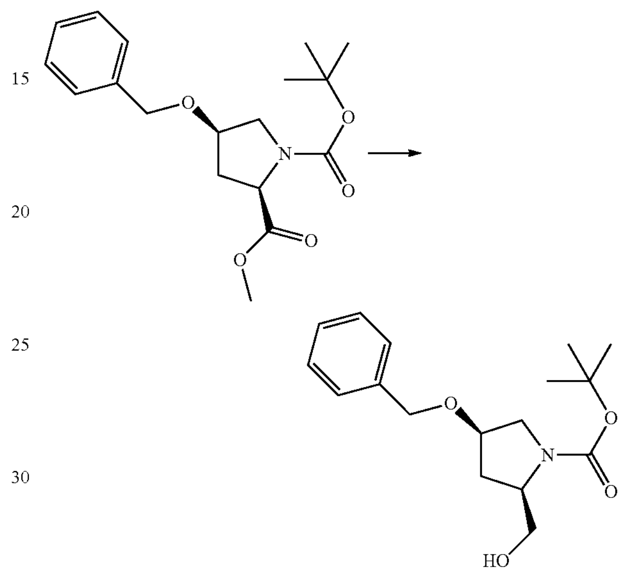

1-(tert-butyl) 2-methyl (2R,4R)-4-(benzyloxy)pyrrolidine-1,2-dicarboxylate (11.8 g, 26.39 mmol) was dissolved in tetrahydrofuran (150 mL), and lithium borohydride (0.86 g, 39.58 mmol) was added under an ice bath. The reaction mixture was stirred overnight at room temperature. Diluted hydrochloric acid was then added to quench the reaction, and the resulting mixture was extracted twice with an appropriate amount of ethyl acetate. The organic phases were combined, washed twice with saturated brine, dried over sodium sulfate and filtered, and the filtrate was concentrated. The residue was separated by the silica gel column chromatography to obtain tert-butyl (2R,4R)-4-(benzyloxy)-2-(hydroxymethyl)pyrrolidine-1-carboxylate (8 g, yield: 98%). MS m/z (ESI): 308[M+H]$^+$.

Step 3: Synthesis of tert-butyl (2R,4R)-4-(benzyloxy)-2-(methoxymethyl)pyrrolidine-1-carboxylate

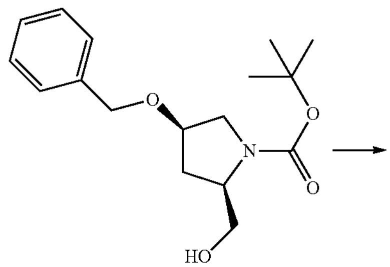

-continued

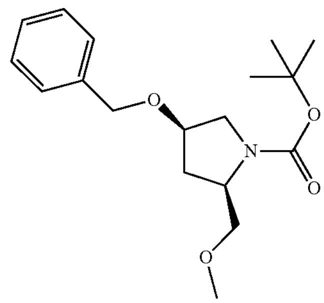

Tert-butyl (2R,4R)-4-(benzyloxy)-2-(hydroxymethyl) pyrrolidine-1-carboxylate (8.00 g, 26.03 mmol) was dissolved in N,N-dimethylformamide (120 mL), and then the mixture was placed in ice water and sodium hydride (3.12 g, 78.08 mmol) was added. The reaction mixture was stirred for 0.5 hrs, and then iodomethane (16.2 mL, 260.26 mmol) was added. The resulting reaction mixture was stirred overnight at room temperature. After the reaction was completed, diluted hydrochloric acid was added to quench the reaction, and the resulting mixture was extracted twice with an appropriate amount of ethyl acetate. The organic phases were combined, washed twice with saturated brine, dried over sodium sulfate and filtered, and the filtrate was concentrated. The residue was separated by the silica gel column chromatography to obtain tert-butyl (2R,4R)-4-(benzyloxy)-2-(methoxymethyl)pyrrolidine-1-carboxylate (8 g, yield: 95%). MS m/z (ESI): 322[M+H]$^+$.

Step 4: Synthesis of tert-butyl (2R,4R)-4-hydroxy-2-(methoxymethyl)pyrrolidine-1-carboxylate

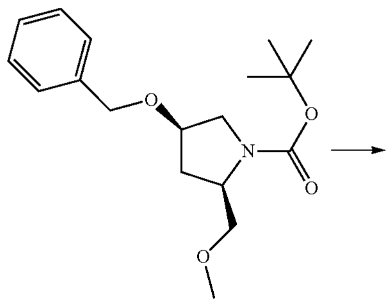

Teri-butyl (2R,4R)-4-(benzyloxy)-2-(methoxymethyl) pyrrolidine-1-carboxylate (1.0 g, 3.11 mmol) was dissolved in ethanol (20 mL), and 10% palladium on carbon (0.15 g) was added. The hydrogen was charged to replace three times by evacuation, and then the reaction mixture was stirred overnight at room temperature and filtered. The filtrate was concentrated to obtain tert-butyl (2R,4R)-4-hydroxy-2-(methoxymethyl)pyrrolidine-1-carboxylate (0.7 g, yield: 99%). MS m/z (ESI): 232[M+H]$^+$.

Step 5: Synthesis of tert-butyl (2R,4R)-2-(methoxymethyl)-4-((methylsulfonyl)oxy)pyrrolidine-1-carboxylate

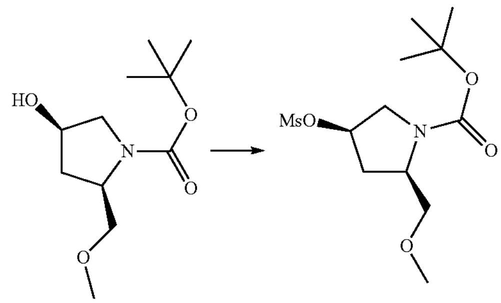 [SMILES: COC[C@H]1C[C@@H](O)CN1C(=O)OC(C)(C)C ; COC[C@H]1C[C@@H](OS(C)(=O)=O)CN1C(=O)OC(C)(C)C]

tert-butyl (2R,4R)-4-hydroxy-2-(methoxymethyl)pyrrolidine-1-carboxylate (300 mg, 1.30 mmol) was dissolved in dichloromethane (10 mL), and N,N-diisopropylethylamine (1 mL, 6.49 mmol) and methanesulfonyl chloride (0.3 mL, 3.89 mmol) were added. The reaction mixture was stirred overnight at room temperature and then concentrated to obtain tert-butyl (2R,4R)-2-(methoxymethyl)-4-((methylsulfonyl)oxy)pyrrolidine-1-carboxylate (355 mg, yield: 88%), and the crude product was used directly in the next step without further purification. MS m/z (ESI): 310[M+H]$^+$.

Step 6: Synthesis of tert-butyl (2R,4S)-4-(4-amino-3-iodo-1H-pyrazolo[3,4-d]pyrimidin-1-yl)-2-(methoxymethyl)pyrrolidine-1-carboxylate

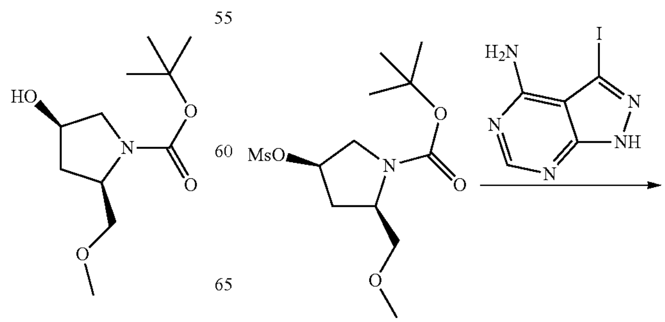

-continued

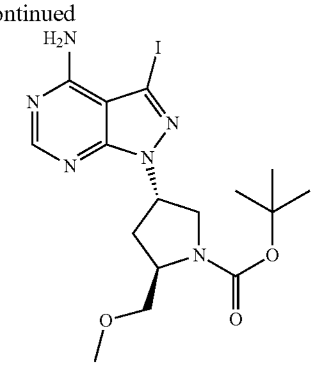

Tert-butyl (2R,4R)-2-(methoxymethyl)-4-((methylsulfonyl)oxy)pyrrolidine-1-carboxylate (355 mg, 1.15 mmol) and 3-iodo-1H-pyrazolo[3,4-d]pyrimidin-4-amine (300 mg, 1.15 mmol) were dissolved successively in N,N-dimethylformamide (15 mL), and then cesium carbonate (1.12 g, 3.45 mmol) was added. The reaction mixture was warmed to 80° C. and stirred overnight. After the reaction was completed, the reaction mixture was cooled to room temperature, an appropriate amount of saturated aqueous sodium bicarbonate solution was added, and the aqueous phase was extracted three times with an appropriate amount of ethyl acetate. The organic phases were combined, washed twice with saturated brine, dried over sodium sulfate and filtered, and the filtrate was concentrated. The residue was separated by the silica gel column chromatography to obtain tert-butyl (2R,4S)-4-(4-amino-3-iodo-1H-pyrazolo[3,4-d]pyrimidin-1-yl)-2-(methoxymethyl)pyrrolidine-1-carboxylate (456 mg, yield: 96%). MS m/z (ESI): 475[M+H]$^+$.

Step 7: Synthesis of 3-iodo-1-((3S,5R)-5-(methoxymethyl)pyrrolidin-3-yl)-1H-pyrazolo[3,4-d]pyrimidin-4-amine

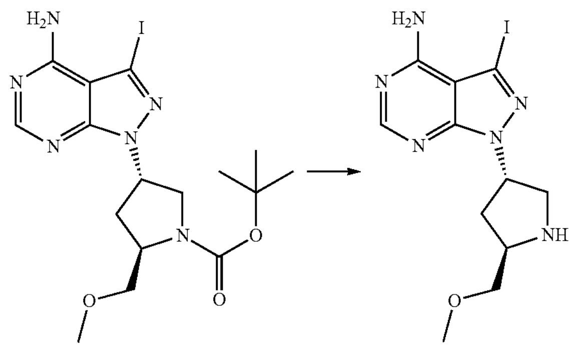 [SMILES: COC[C@H]1C[C@H](n2nc(I)c3c(N)ncnc32)CN1C(=O)OC(C)(C)C ; COC[C@H]1C[C@H](n2nc(I)c3c(N)ncnc32)CN1]

Tert-butyl (2R,4S)-4-(4-amino-3-iodo-1H-pyrazolo[3,4-d]pyrimidin-1-yl)-2-(methoxymethyl)pyrrolidine-1-carboxylate (456 mg, 0.96 mmol) was dissolved in tetrahydrofuran (10 mL), and a solution of hydrogen chloride in 1,4-dioxane (3.2 mL, 19.23 mmol) was added. The reaction mixture was stirred at room temperature for 3 hrs. After the reaction was completed, the reaction mixture was directly concentrated, and the residue was dried to obtain 3-iodo-1-((3S,5R)-5-(methoxymethyl)pyrrolidin-3-yl)-1H-pyrazolo[3,4-d]pyrimidin-4-amine (300 mg, yield: 69%). MS m/z (ESI): 375[M+H]$^+$.

Step 8: Synthesis of 1-((2R,4S)-4-(4-amino-3-iodo-1H-pyrazolo[3,4-d]pyrimidin-1-yl)-2-(methoxymethyl)pyrrolidin-1-yl)prop-2-en-1-one

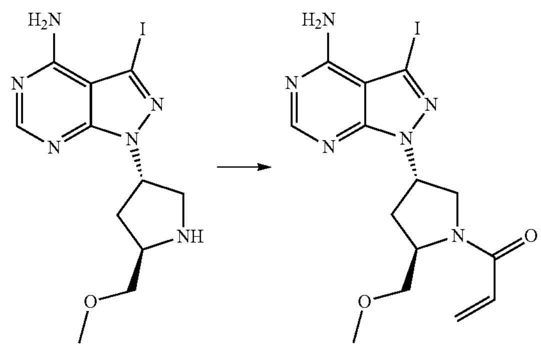 [SMILES: COC[C@H]1C[C@H](n2nc(I)c3c(N)ncnc32)CN1 ; C=CC(=O)N1C[C@@H](n2nc(I)c3c(N)ncnc32)C[C@@H]1COC]

3-iodo-1-((3S,5R)-5-(methoxymethyl)pyrrolidin-3-yl)-1H-pyrazolo[3,4-d]pyrimidin-4-amine (300 mg, 0.67 mmol) was dissolved in tetrahydrofuran (10 mL) and water (5 mL), and sodium bicarbonate (281.84 mg, 3.35 mmol). The reaction mixture was placed in an ice bath, and a solution of acryloyl chloride (0.07 mL, 0.87 mmol) in tetrahydrofuran (I mL) was added dropwise slowly. After the dropwise addition was completed, the reaction mixture was stirred for 10 min, an appropriate amount of saturated aqueous sodium bicarbonate solution was added to quench the reaction, and the resulting reaction mixture was extracted three times with ethyl acetate. The organic phases were combined, washed twice with saturated brine, dried over sodium sulfate, filtered, and the residue was separated by the silica gel column chromatography to obtain 1-((2R,4S)-4-(4-amino-3-iodo-1H-pyrazolo[3,4-d]pyrimidin-1-yl)-2-(methoxymethyl)pyrrolidin-1-yl)prop-2-en-1-one (180 mg, yield: 63%). MS m/z (ESI): 429[M+H]$^+$.

Intermediate 33: Preparation of tert-butyl 3-(4-amino-3-iodo-1H-pyrazolo[3,4-d]pyrimidin-1-yl azetidine-1-carboxylate

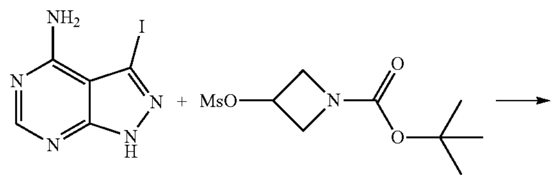

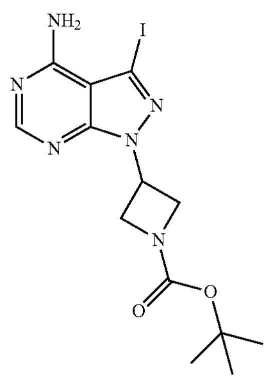

3-iodo-1H-pyrazolo[3,4-d]pyrimidine-4-amine (2500 mg, 10.16 mmol), tert-butyl 3-((methylsulfonyl)oxy)azetidine-1-carboxylate (2550 mg, 10.16 mmol) and cesium carbonate (4970 mg, 15.24 mmol) were dissolved in N,N-dimethylformamide (30 mL), and the reaction mixture was stirred at 80° C. for 16 hrs. After the reaction was completed, water (60 mL) was added, and the resulting reaction mixture was filtered to obtain tert-butyl 3-(4-amino-3-iodo-1H-pyrazolo[3,4-d]pyrimidin-1-yl)azetidine-1-carboxylate (2000 mg, yield: 47%). MS m/z (ESI): 417 [M+H]+.

II. Preparation of Specific Examples

Example 1: Preparation of (S)-1-(3-(4-amino-5-((2-cyclopropylbenzo[d]oxazol-5-yl)ethynyl)-7H-pyrrolo[2,3-d]pyrimidin-7-yl)pyrrolidin-1-yl)prop-2-en-1-one

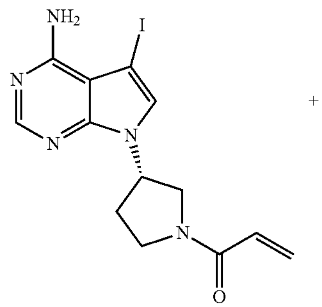

+

-continued

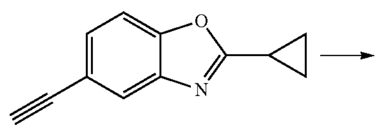

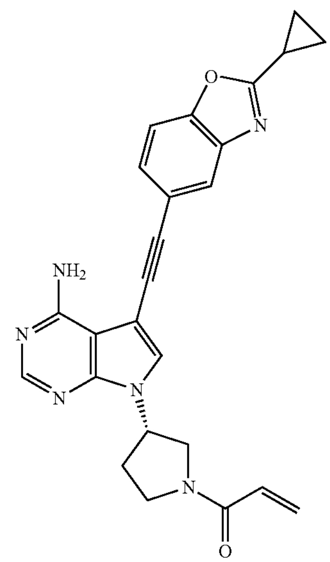

(S)-1-(3-(4-amino-5-iodo-7H-pyrrolo[2,3-d]pyrimidin-7-yl)pyrrolidin-1-yl)prop-2-en-1-one (40 mg, 0.1 mmol), 2-cyclopropyl-5-ethynylbenzo[d]oxazole (23 mg, 0.12 mmol), triethylamine (0.4 mL), cuprous iodide (2 mg, 0.01 mmol) and tetrakis(triphenylphosphine)palladium (12 mg, 0.01 mmol) were added to DMF (2 mL). The reaction mixture was stirred at 80° C. for 1 hr under nitrogen protection, and then directly separated by the reverse phase column chromatography and lyophilized to obtain (S)-1-(3-(4-amino-5-((2-cyclopropylbenzo[d]oxazol-5-yl)ethynyl)-7H-pyrrolo[2,3-d]pyrimidin-7-yl)pyrrolidin-1-yl)prop-2-en-1-one (29.5 mg, yield: 65%). MS m/z (ESI): 439 [M+H]+.

$^1$HNMR (400 MHz, DMSO-$d_6$): δ 8.11 (s, 1H), 7.78-7.77 (d, J=4 Hz, 1H), 7.69-7.65 (d, J=16 Hz, 1H), 7.61-7.59 (d, J=8 Hz, 1H), 7.46-7.44 (m, 1H), 6.85-6.48 (m, 3H), 6.14-6.07 (m, 1H), 5.67-5.59 (m, 1H), 5.31-5.18 (m, 1H), 4.06-3.79 (m, 2H), 3.71-3.43 (m, 2H), 2.38-2.19 (m, 3H), 1.17-1.07 (m, 4H).

Examples 2-75 can be Prepared by Selecting Corresponding Raw Materials According to all or Part of the Synthesis Method in Example 1.

| Example No. | Structural formula | Chemical name | [M + H]+ |
|---|---|---|---|
| 2 | 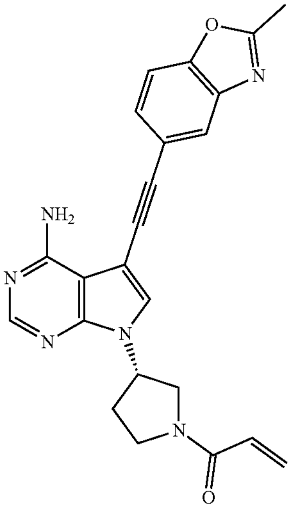 [SMILES: C=CC(=O)N1CC[C@H](n2cc(C#Cc3ccc4oc(C)nc4c3)c3c(N)ncnc32)C1] | (S)-1-(3-(4-amino-5-((2-methylbenzo[d]oxazol-5-yl)ethynyl)-7H-pyrrolo[2,3-d]pyrimidin-7-yl)pyrrolidin-1-yl)prop-2-en-1-one | 413 |
| 3 | 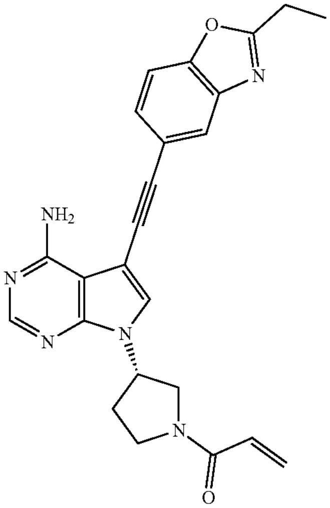 [SMILES: C=CC(=O)N1CC[C@H](n2cc(C#Cc3ccc4oc(CC)nc4c3)c3c(N)ncnc32)C1] | (S)-1-(3-(4-amino-5-((2-ethylbenzo[d]oxazol-5-yl)ethynyl)-7H-pyrrolo[2,3-d]pyrimidin-7-yl)pyrrolidin-1-yl)prop-2-en-1-one | 427 |
| 4 | 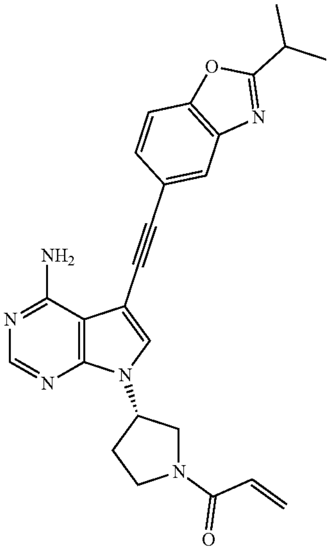 [SMILES: C=CC(=O)N1CC[C@H](n2cc(C#Cc3ccc4oc(C(C)C)nc4c3)c3c(N)ncnc32)C1] | (S)-1-(3-(4-amino-5-((2-isopropylbenzo[d]oxazol-5-yl)ethynyl)-7H-pyrrolo[2,3-d]pyrimidin-7-yl)pyrrolidin-1-yl)prop-2-en-1-one | 441 |

-continued
| Example No. | Structural formula | Chemical name | [M + H]+ |
|---|---|---|---|
| 5 | 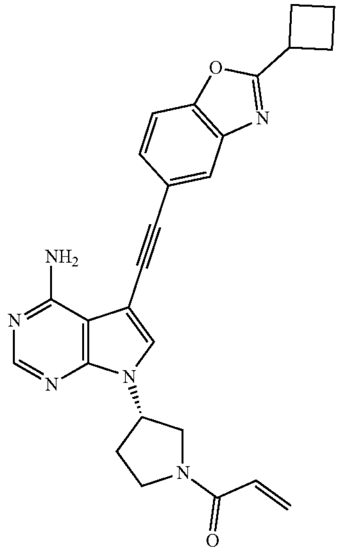 [SMILES: C=CC(=O)N1CC[C@H](n2cc(C#Cc3ccc4oc(C5CCC5)nc4c3)c3c(N)ncnc32)C1] | (S)-1-(3-(4-amino-5-((2-cyclobutylbenzo[d]oxazol-5-yl)ethynyl)-7H-pyrrolo[2,3-d]pyrimidin-7-yl)pyrrolidin-1-yl)prop-2-en-1-one | 453 |
| 6 | 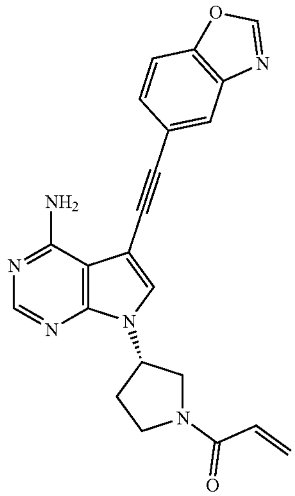 [SMILES: C=CC(=O)N1CC[C@H](n2cc(C#Cc3ccc4ocnc4c3)c3c(N)ncnc32)C1] | (S)-1-(3-(4-amino-5-(benzo[d]oxazol-5-ylethynyl)-7H-pyrrolo[2,3-d]pyrimidin-7-yl)pyrrolidin-1-yl)prop-2-en-1-one | 399 |
| 7 | 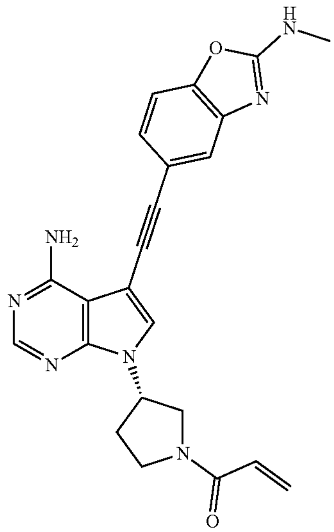 [SMILES: C=CC(=O)N1CC[C@H](n2cc(C#Cc3ccc4oc(NC)nc4c3)c3c(N)ncnc32)C1] | (S)-1-(3-(4-amino-5-((2-(methylamino)benzo[d]oxazol-5-yl)ethynyl)-7H-pyrrolo[2,3-d]pyrimidin-7-yl)pyrrolidin-1-yl)prop-2-en-1-one | 428 |

-continued
| Example No. | Structural formula | Chemical name | [M + H]+ |
|---|---|---|---|
| 8 | 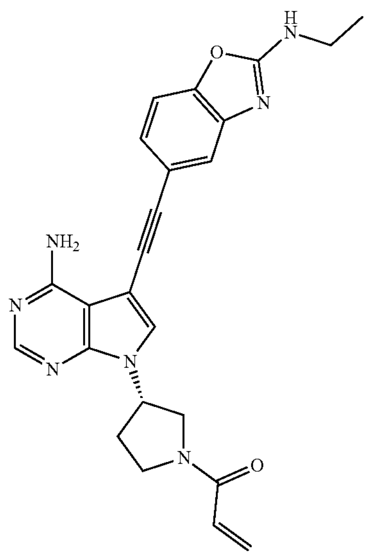 [SMILES: C=CC(=O)N1CC[C@H](n2cc(C#Cc3ccc4oc(NCC)nc4c3)c3c(N)ncnc32)C1] | (S)-1-(3-(4-amino-5-((2-(ethylamino)benzo[d]oxazol-5-yl)ethynyl)-7H-pyrrolo[2,3-d]pyrimidin-7-yl)pyrrolidin-1-yl)prop-2-en-1-one | 442 |
| 9 | 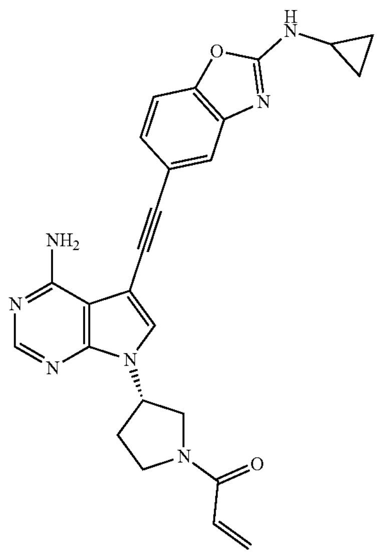 [SMILES: C=CC(=O)N1CC[C@H](n2cc(C#Cc3ccc4oc(NC5CC5)nc4c3)c3c(N)ncnc32)C1] | (S)-1-(3-(4-amino-5-((2-(cyclopropylamino)benzo[d]oxazol-5-yl)ethynyl)-7H-pyrrolo[2,3-d]pyrimidin-7-yl)pyrrolidin-1-yl)prop-2-en-1-one | 454 |

-continued
| Example No. | Structural formula | Chemical name | [M + H]+ |
|---|---|---|---|
| 10 | 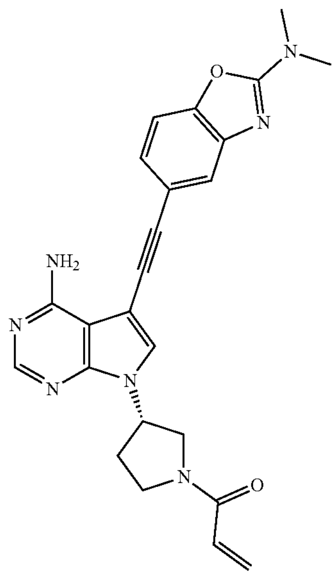 [SMILES: C=CC(=O)N1CC[C@H](n2cc(C#Cc3ccc4oc(N(C)C)nc4c3)c3c(N)ncnc32)C1] | (S)-1-(3-(4-amino-5-((2-(dimethylamino)benzo[d]oxazol-5-yl)ethynyl)-7H-pyrrolo[2,3-d]pyrimidin-7-yl)pyrrolidin-1-yl)prop-2-en-1-one | 442 |
| 11 | 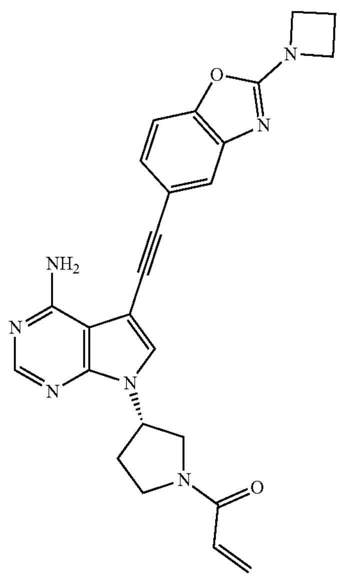 [SMILES: C=CC(=O)N1CC[C@H](n2cc(C#Cc3ccc4oc(N5CCC5)nc4c3)c3c(N)ncnc32)C1] | (S)-1-(3-(4-amino-5-((2-(azetidin-1-ylbenzo[d]oxazol-5-yl)ethynyl)-7H-pyrrolo[2,3-d]pyrimidin-7-yl)pyrrolidin-1-yl)prop-2-en-1-one | 454 |

-continued
| Example No. | Structural formula | Chemical name | [M + H]+ |
|---|---|---|---|
| 12 | 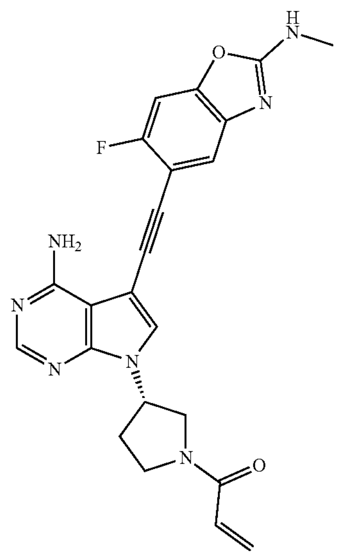 [SMILES: C=CC(=O)N1CC[C@H](n2cc(C#Cc3cc4nc(NC)oc4cc3F)c3c(N)ncnc32)C1] | (S)-1-(3-(4-amino-5-((6-fluoro-2-(methylamino)benzo[d]oxazol-5-yl)ethynyl)-7H-pyrrolo[2,3-d]pyrimidin-7-yl)pyrrolidin-1-yl)prop-2-en-1-one | 446 |
| 13 | 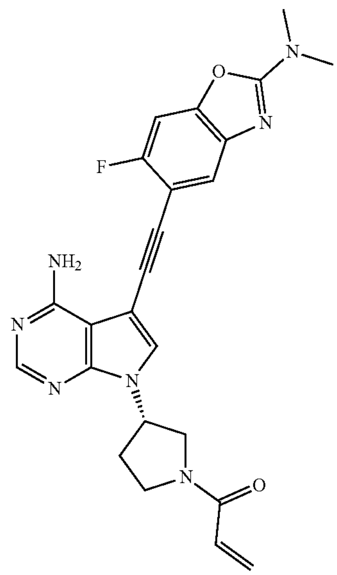 [SMILES: C=CC(=O)N1CC[C@H](n2cc(C#Cc3cc4nc(N(C)C)oc4cc3F)c3c(N)ncnc32)C1] | (S)-1-(3-(4-amino-5-((2-(dimethylamino)-6-fluoro-benzo[d]oxazol-5-yl)ethynyl)-7H-pyrrolo[2,3-d]pyrimidin-7-yl)pyrrolidin-1-yl)prop-2-en-1-one | 460 |

-continued
| Example No. | Structural formula | Chemical name | [M + H]+ |
|---|---|---|---|
| 14 | 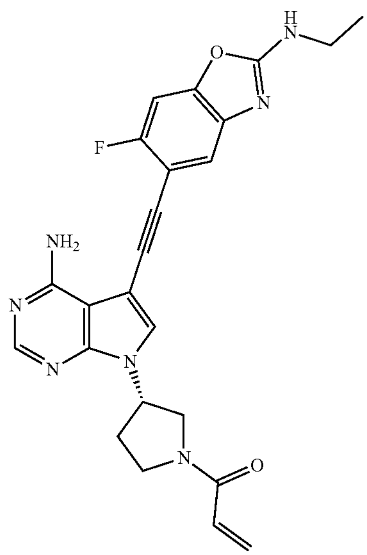 [SMILES: C=CC(=O)N1CC[C@H](n2cc(C#Cc3cc4nc(NCC)oc4cc3F)c3c(N)ncnc32)C1] | (S)-1-(3-(4-amino-5-((2-(ethylamino)-6-fluorobenzo[d]oxazol-5-yl)ethynyl)-7H-pyrrolo[2,3-d]pyrimidin-7-yl)pyrrolidin-1-yl)prop-2-en-1-one | 460 |
| 15 | 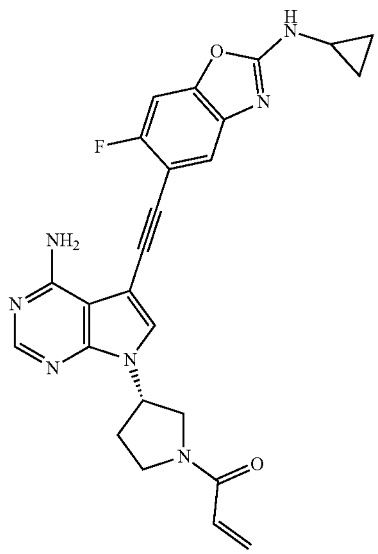 [SMILES: C=CC(=O)N1CC[C@H](n2cc(C#Cc3cc4nc(NC5CC5)oc4cc3F)c3c(N)ncnc32)C1] | (S)-1-(3-(4-amino-5-(2-(cyclopropylamino)-6-fluoro-benzo[d]oxazol-5-yl)ethynyl)-7H-pyrrolo[2,3-d]pyrimidin-7-yl)pyrrolidin-1-yl)prop-2-en-1-one | 472 |

-continued
| Example No. | Structural formula | Chemical name | [M + H]+ |
| --- | --- | --- | --- |
| 16 | 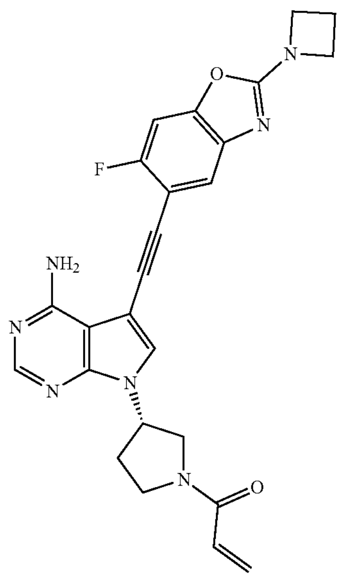 [SMILES: C=CC(=O)N1CC[C@H](n2cc(C#Cc3cc4nc(N5CCC5)oc4cc3F)c3c(N)ncnc32)C1] | (S)-1-(3-(4-amino-5-((2-(azetidin-1-yl)-6-fluorobenzo[d]oxazol-5-yl)ethynyl)-7H-pyrrolo[2,3-d]pyrimidin-7-yl)pyrrolidin-1-yl)prop-2-en-1-one | 472 |
| 17 | 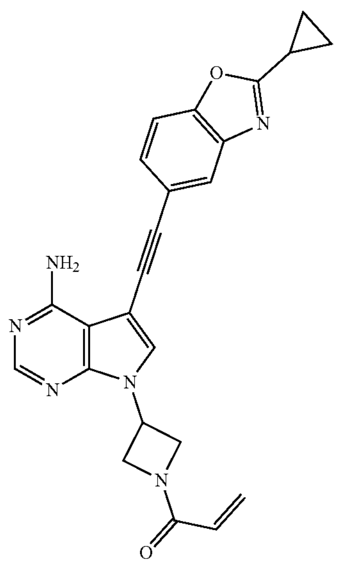 [SMILES: C=CC(=O)N1CC(n2cc(C#Cc3ccc4oc(C5CC5)nc4c3)c3c(N)ncnc32)C1] | 1-(3-(4-amino-5-((2-cyclopropylbenzo[d]oxazol-5-yl)ethynyl)-7H-pyrrolo[2,3-d]pyrimidin-7-yl)azetidin-1-yl)prop-2-en-1-one | 425 |

-continued
| Example No. | Structural formula | Chemical name | [M + H]$^+$ |
|---|---|---|---|
| 18 | 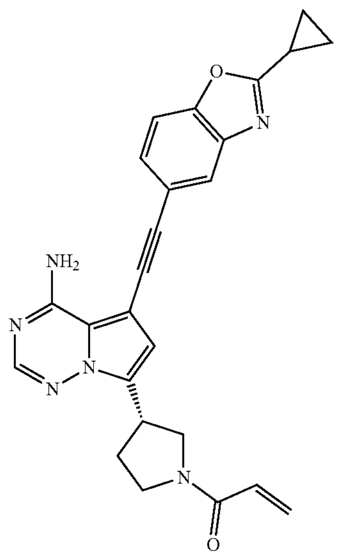 | (S)-1-(3-(4-amino-5-((2-cyclopropylbenzo[d]oxazol-5-yl)ethynyl)pyrrolo[2,1-f][1,2,4]triazin-7-yl)pyrrolidin-1-yl)prop-2-en-1-one | 439 |
| 19 | 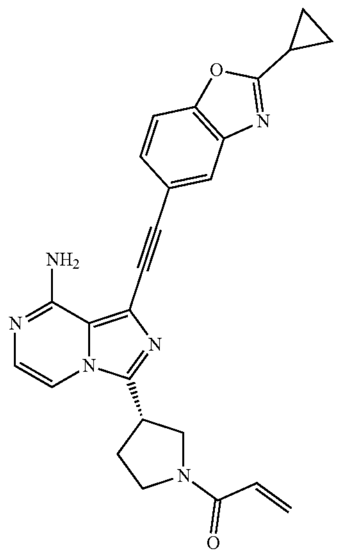 [SMILES: C=CC(=O)N1CC[C@H](c2nc(C#Cc3ccc4oc(C5CC5)nc4c3)c3c(N)nccn23)C1] | (S)-1-(3-(8-amino-1-((2-cyclopropylbenzo[d]oxazol-5-yl)ethynyl)imidazo[1,5-a]pyrazin-3-yl)pyrrolidin-1-yl)prop-2-en-1-one | 439 |

-continued
| Example No. | Structural formula | Chemical name | [M + H]+ |
|---|---|---|---|
| 20 | 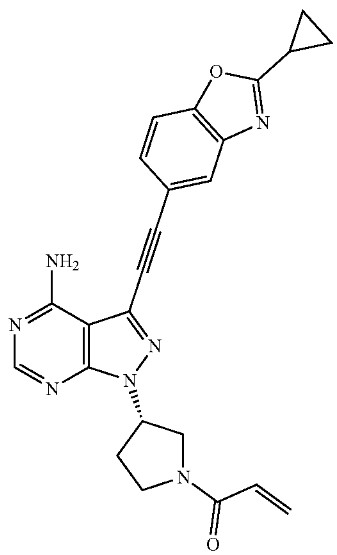 [SMILES: C=CC(=O)N1CC[C@H](n2nc(C#Cc3ccc4oc(C5CC5)nc4c3)c3c(N)ncnc32)C1] | (S)-1-(3-(4-amino-3-((2-cyclopropylbenzo[d]oxazol-5-yl)ethynyl)-1H-pyrazolo[3,4-d]pyrimidin-1-yl)pyrrolidin-1-yl)prop-2-en-1-one | 440 |
| 21 | 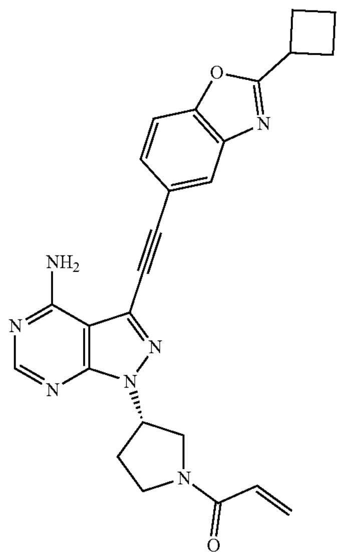 [SMILES: C=CC(=O)N1CC[C@H](n2nc(C#Cc3ccc4oc(C5CCC5)nc4c3)c3c(N)ncnc32)C1] | (S)-1-(3-(4-amino-3-((2-cyclobutylbenzo[d]oxazol-5-yl)ethynyl)-1H-pyrazolo[3,4-d]pyrimidin-1-yl)pyrrolidin-1-yl)prop-2-en-1-one | 454 |

-continued
| Example No. | Structural formula | Chemical name | [M + H]+ |
|---|---|---|---|
| 22 | 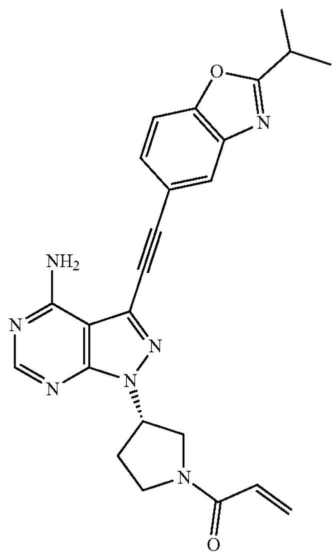 [SMILES: C=CC(=O)N1CC[C@H](n2nc(C#Cc3ccc4oc(C(C)C)nc4c3)c3c(N)ncnc32)C1] | (S)-1-(3-(4-amino-3-((2-isopropylbenzo[d]oxazol-5-yl)ethynyl)-1H-pyrazolo[3,4-d]pyrimidin-1-yl)pyrrolidin-1-yl)prop-2-en-1-one | 442 |
| 23 | 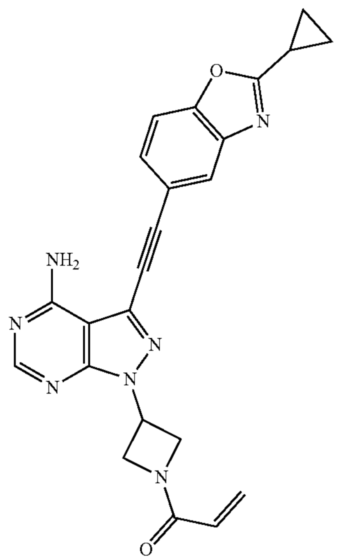 [SMILES: C=CC(=O)N1CC(n2nc(C#Cc3ccc4oc(C5CC5)nc4c3)c3c(N)ncnc32)C1] | 1-(3-(4-amino-3-((2-cyclopropylbenzo[d]oxazol-5-yl)ethynyl)-1H-pyrazolo[3,4-d]pyrimidin-1-yl)azetidin-1-yl)prop-2-en-1-one | 426 |

-continued
| Example No. | Structural formula | Chemical name | [M + H]+ |
|---|---|---|---|
| 24 | 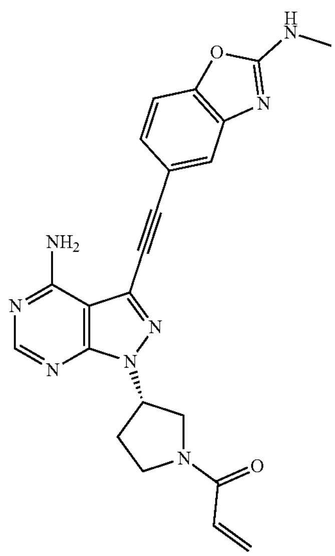 [SMILES: C=CC(=O)N1CC[C@H](n2nc(C#Cc3ccc4oc(NC)nc4c3)c3c(N)ncnc32)C1] | (S)-1-(3-(4-amino-3-((2-(methylamino)benzo[d]oxazol-5-yl)ethynyl)-1H-pyrazolo[3,4-d]pyrimidin-1-yl)pyrrolidin-1-yl)prop-2-en-1-one | 429 |
| 25 | 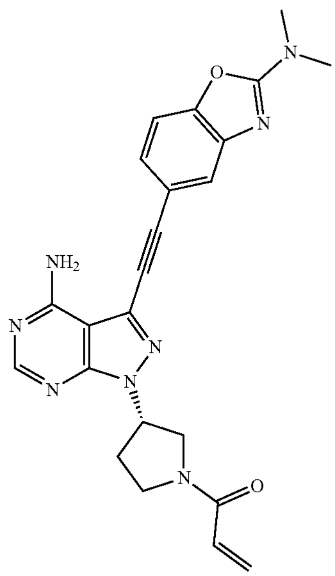 [SMILES: C=CC(=O)N1CC[C@H](n2nc(C#Cc3ccc4oc(N(C)C)nc4c3)c3c(N)ncnc32)C1] | (S)-1-(3-(4-amino-3-((2-(dimethylamino)benzo[d]oxazol-5-yl)ethynyl)-1H-pyrazolo[3,4-d]pyrimidin-1-yl)pyrrolidin-1-yl)prop-2-en-1-one | 443 |

-continued
| Example No. | Structural formula | Chemical name | [M + H]+ |
|---|---|---|---|
| 26 | 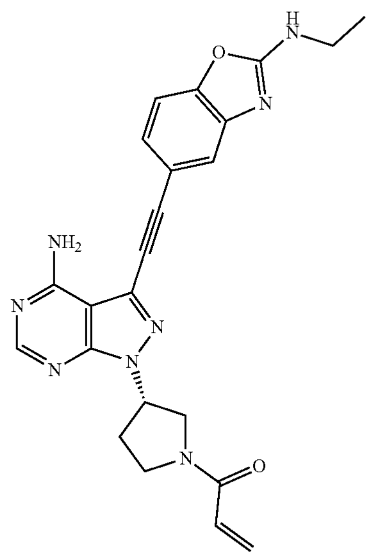 [SMILES: C=CC(=O)N1CC[C@H](n2nc(C#Cc3ccc4oc(NCC)nc4c3)c3c(N)ncnc32)C1] | (S)-1-(3-(4-amino-3-((2-(ethylamino)benzo[d]oxazol-5-yl)ethynyl)-1H-pyrazolo[3,4-d]pyrimidin-1-yl)pyrrolidin-1-yl)prop-2-en-1-one | 443 |
| 27 | 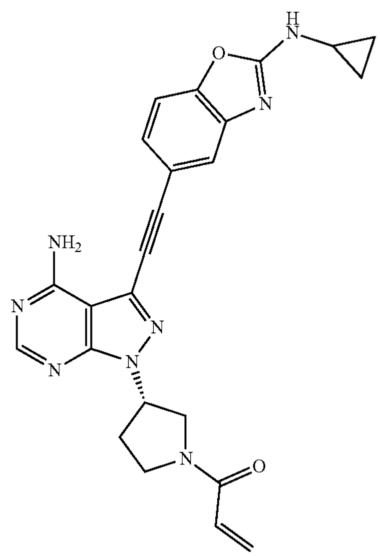 [SMILES: C=CC(=O)N1CC[C@H](n2nc(C#Cc3ccc4oc(NC5CC5)nc4c3)c3c(N)ncnc32)C1] | (S)-1-(3-(4-amino-3-((2-(cyclopropylamino)benzo[d]oxazol-5-yl)ethynyl)-1H-pyrazolo[3,4-d]pyrimidin-1-yl)pyrrolidin-1-yl)prop-2-en-1-one | 455 |

-continued
| Example No. | Structural formula | Chemical name | [M + H]+ |
|---|---|---|---|
| 28 | 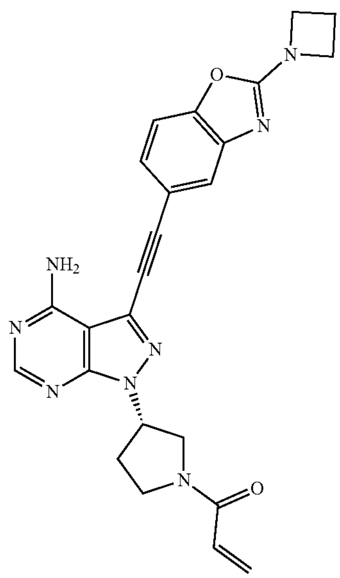 [SMILES: C=CC(=O)N1CC[C@H](n2nc(C#Cc3ccc4oc(N5CCC5)nc4c3)c3c(N)ncnc32)C1] | (S)-1-(3-(4-amino-3-((2-(azetidin-1-ylbenzo[d]oxazol-5-yl)ethynyl)-1H-pyrazolo[3,4-d]pyrimidin-1-yl)pyrrolidin-1-yl)prop-2-en-1-one | 455 |
| 29 | 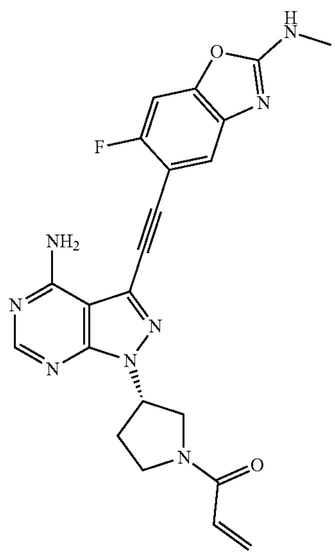 [SMILES: C=CC(=O)N1CC[C@H](n2nc(C#Cc3cc4nc(NC)oc4cc3F)c3c(N)ncnc32)C1] | (S)-1-(3-(4-amino-3-((6-fluoro-2-(methylamino)benzo[d]oxazol-5-yl)ethynyl)-1H-pyrazolo[3,4-d]pyrimidin-1-yl)pyrrolidin-1-yl)prop-2-en-1-one | 447 |

-continued
| Example No. | Structural formula | Chemical name | [M + H]+ |
|---|---|---|---|
| 30 | 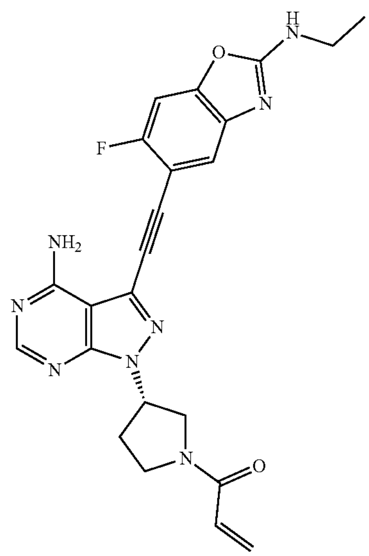 [SMILES: C=CC(=O)N1CC[C@H](n2nc(C#Cc3cc4nc(NCC)oc4cc3F)c3c(N)ncnc32)C1] | (S)-1-(3-(4-amino-3-((2-(ethylamino)-6-fluorobenzo[d]oxazol-5-yl)ethynyl)-1H-pyrazolo[3,4-d]pyrimidin-1-yl)pyrrolidin-1-yl)prop-2-en-1-one | 461 |
| 31 | 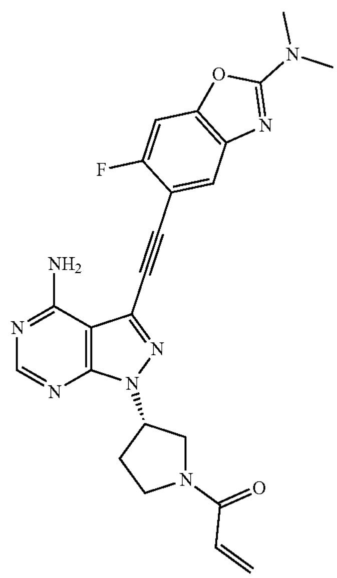 [SMILES: C=CC(=O)N1CC[C@H](n2nc(C#Cc3cc4nc(N(C)C)oc4cc3F)c3c(N)ncnc32)C1] | (S)-1-(3-(4-amino-3-((2-(dimethylamino)-6-fluoro-benzo[d]oxazol-5-yl)ethynyl)-1H-pyrazolo[3,4-d]pyrimidin-1-yl)pyrrolidin-1-yl)prop-2-en-1-one | 461 |

-continued
| Example No. | Structural formula | Chemical name | [M + H]$^+$ |
|---|---|---|---|
| 32 | 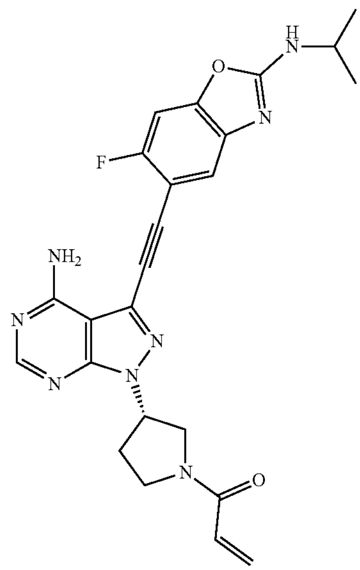 [SMILES: C=CC(=O)N1CC[C@H](n2nc(C#Cc3cc4nc(NC(C)C)oc4cc3F)c3c(N)ncnc32)C1] | (S)-1-(3-(4-amino-3-((2-(isopropylamino)-6-fluoro-benzo[d]oxazol-5-yl)ethynyl)-1H-pyrazolo[3,4-d]pyrimidin-1-yl)pyrrolidin-1-yl)prop-2-en-1-one | 473 |
| 33 | 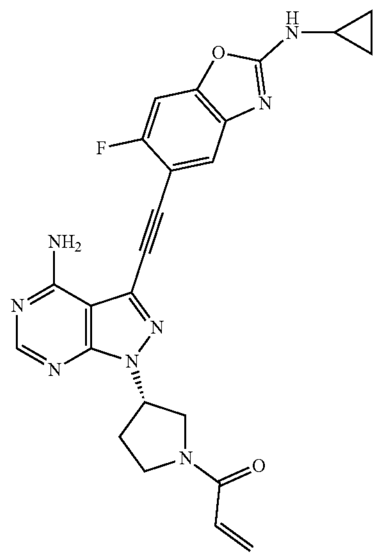 [SMILES: C=CC(=O)N1CC[C@H](n2nc(C#Cc3cc4nc(NC5CC5)oc4cc3F)c3c(N)ncnc32)C1] | (S)-1-(3-(4-amino-3-((2-(cyclopropylamino)-6-fluorobenzo[d]oxazol-5-yl)ethynyl)-1H-pyrazolo[3,4-d]pyrimidin-1-yl)pyrrolidin-1-yl)prop-2-en-1-one | 473 |

-continued
| Example No. | Structural formula | Chemical name | [M + H]+ |
|---|---|---|---|
| 34 | 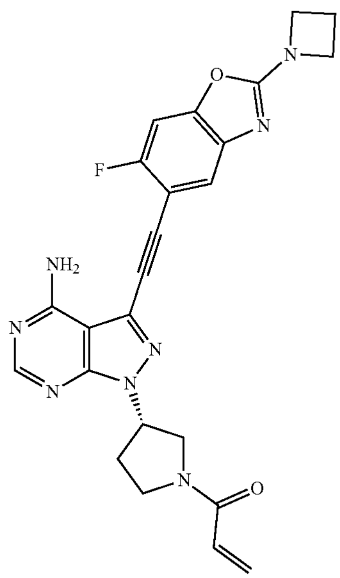 [SMILES: C=CC(=O)N1CC[C@H](n2nc(C#Cc3cc4nc(N5CCC5)oc4cc3F)c3c(N)ncnc32)C1] | (S)-1-(3-(4-amino-3-((2-(azetidin-1-yl)-6-fluorobenzo[d]oxazol-5-yl)ethynyl)-1H-pyrazolo[3,4-d]pyrimidin-1-yl)pyrrolidin-1-yl)prop-2-en-1-one | 473 |
| 35 | 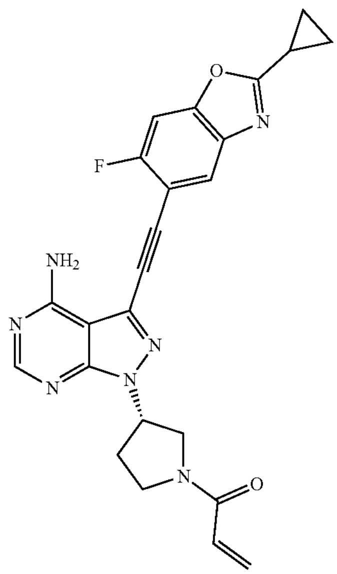 [SMILES: C=CC(=O)N1CC[C@H](n2nc(C#Cc3cc4nc(C5CC5)oc4cc3F)c3c(N)ncnc32)C1] | (S)-1-(3-(4-amino-3-((2-cyclopropyl-6-fluorobenzo[d]oxazol-5-yl)ethynyl)-1H-pyrazolo[3,4-d]pyrimidin-1-yl)pyrrolidin-1-yl)prop-2-en-1-one | 458 |

-continued
| Example No. | Structural formula | Chemical name | [M + H]+ |
|---|---|---|---|
| 36 | 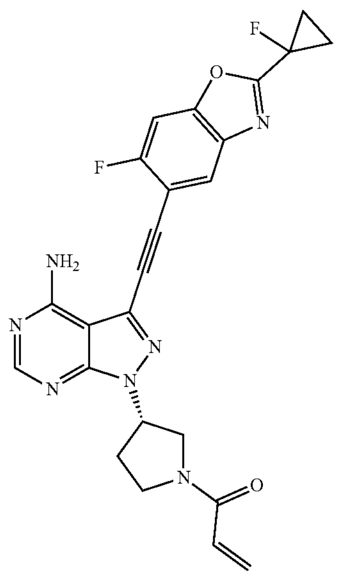 [SMILES: C=CC(=O)N1CC[C@H](n2nc(C#Cc3cc4nc(C5(F)CC5)oc4cc3F)c3c(N)ncnc32)C1] | (S)-1-(3-(4-amino-3-((6-fluoro-2-(1-fluorocyclopropyl) benzo[d]oxazol-5-yl) ethynyl)-1H-pyrazolo[3,4-n-1-yl)prop-2-en-1-one | 476 |
| 37 | 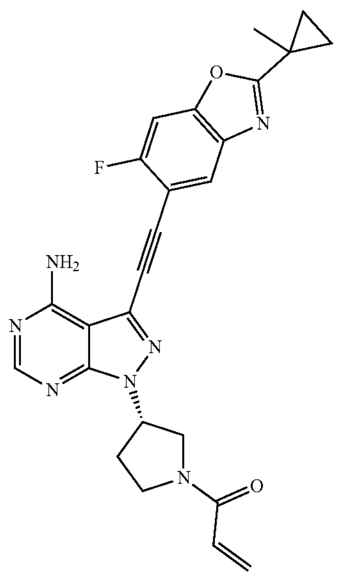 [SMILES: C=CC(=O)N1CC[C@H](n2nc(C#Cc3cc4nc(C5(C)CC5)oc4cc3F)c3c(N)ncnc32)C1] | (S)-1-(3-(4-amino-3-((6-fluoro-2-(1-methylcyclopropyl) benzo[d]oxazol-5-yl) ethynyl)-1H-pyrazolo[3,4-d]pyrimidin-1-yl)pyrrolidin-1-yl)prop-2-en-1-one | 472 |

-continued
| Example No. | Structural formula | Chemical name | [M + H]+ |
|---|---|---|---|
| 38 | 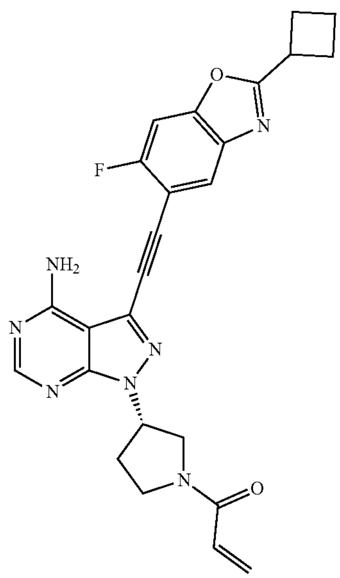 [SMILES: C=CC(=O)N1CC[C@H](n2nc(C#Cc3cc4nc(C5CCC5)oc4cc3F)c3c(N)ncnc32)C1] | (S)-1-(3-(4-amino-3-((2-cyclobutyl-6-fluorobenzo[d]oxazol-5-yl)ethynyl)-1H-pyrazolo[3,4-d]pyrimidin-1-yl)pyrrolidin-1-yl)prop-2-en-1-one | 472 |
| 39 | 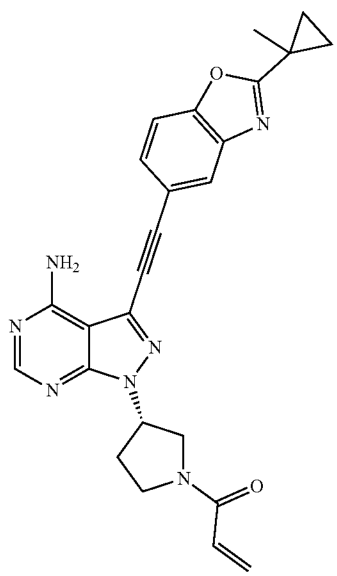 [SMILES: C=CC(=O)N1CC[C@H](n2nc(C#Cc3ccc4oc(C5(C)CC5)nc4c3)c3c(N)ncnc32)C1] | (S)-1-(3-(4-amino-3-((2-(1-methylcyclopropyl)benzo[d]oxazol-5-yl)ethynyl)-1H-pyrazolo[3,4-d]pyrimidin-1-yl)pyrrolidin-1-yl)prop-2-en-1-one | 454 |

-continued
| Example No. | Structural formula | Chemical name | [M + H]+ |
|---|---|---|---|
| 40 | 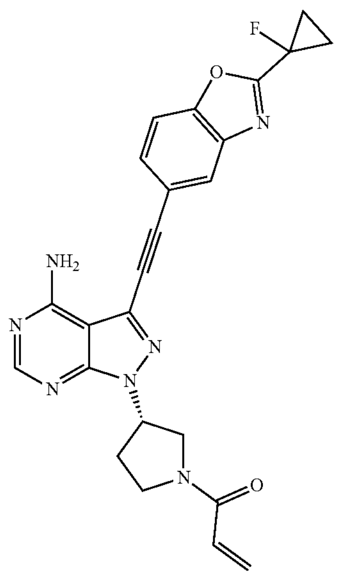 [SMILES: C=CC(=O)N1CC[C@H](n2nc(C#Cc3ccc4oc(C5(F)CC5)nc4c3)c3c(N)ncnc32)C1] | (S)-1-(3-(4-amino-3-((2-(1-fluorocyclopropyl)benzo[d]oxazol-5-yl)ethynyl)-1H-pyrazolo[3,4-d]pyrimidin-1-yl)pyrrolidin-1-yl)prop-2-en-1-one | 458 |
| 41 | 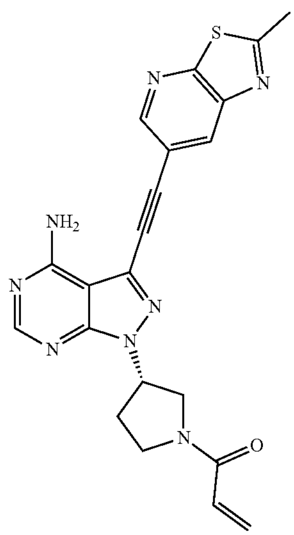 [SMILES: C=CC(=O)N1CC[C@H](n2nc(C#Cc3cnc4sc(C)nc4c3)c3c(N)ncnc32)C1] | (S)-1-(3-(4-amino-3-((2-methylthiazolo[5,4-6]pyridin-6-yl)ethynyl)-1H-pyrazolo[3,4-d]pyrimidin-1-yl)pyrrolidin-1-yl)prop-2-en-1-one | 431 |

-continued
| Example No. | Structural formula | Chemical name | [M + H]+ |
|---|---|---|---|
| 42 | 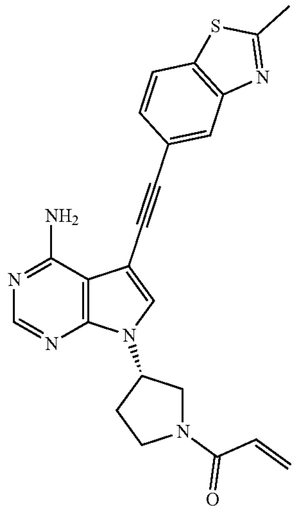 [SMILES: C=CC(=O)N1CC[C@H](n2cc(C#Cc3ccc4sc(C)nc4c3)c3c(N)ncnc32)C1] | (S)-1-(3-(4-amino-5-((2-methylbenzo[d]thiazol-5-yl)ethynyl)-7H-pyrrolo[2,3-d]pyrimidin-7-yl)pyrrolidin-1-yl)prop-2-en-1-one | 429 |
| 43 | 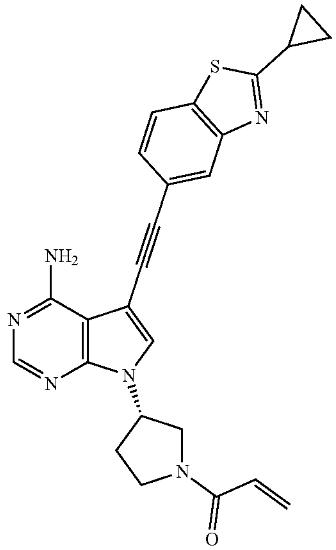 [SMILES: C=CC(=O)N1CC[C@H](n2cc(C#Cc3ccc4sc(C5CC5)nc4c3)c3c(N)ncnc32)C1] | (S)-1-(3-(4-amino-5-((2-cyclopropylbenzo[d]thiazol-5-yl)ethynyl)-7H-pyrrolo[2,3-d]pyrimidin-7-yl)pyrrolidin-1-yl)prop-2-en-1-one | 455 |
| 44 | 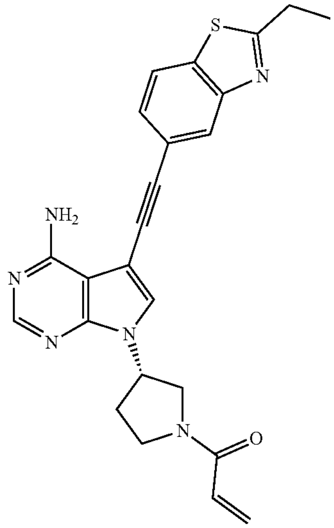 [SMILES: C=CC(=O)N1CC[C@H](n2cc(C#Cc3ccc4sc(CC)nc4c3)c3c(N)ncnc32)C1] | (S)-1-(3-(4-amino-5-((2-ethylbenzo[d]thiazol-5-yl)ethynyl)-7H-pyrrolo[2,3-d]pyrimidin-7-yl)pyrrolidin-1-yl)prop-2-en-1-one | 443 |

-continued
| Example No. | Structural formula | Chemical name | [M + H]+ |
|---|---|---|---|
| 45 | 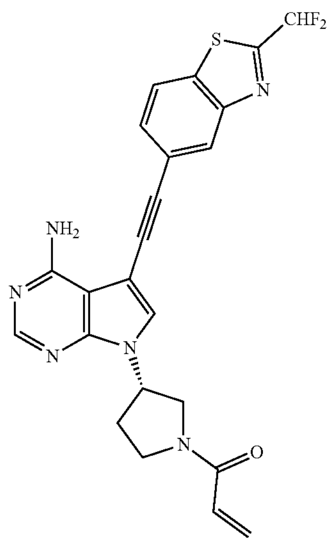 [SMILES: C=CC(=O)N1CC[C@H](n2cc(C#Cc3ccc4sc(C(F)F)nc4c3)c3c(N)ncnc32)C1] | (S)-1-(3-(4-amino-5-((2-(difluoromethyl)benzo[d]thiazol-5-yl)ethynyl)-7H-pyrrolo[2,3-d]pyrimidin-7-yl)pyrrolidin-1-yl)prop-2-en-1-one | 465 |
| 46 | 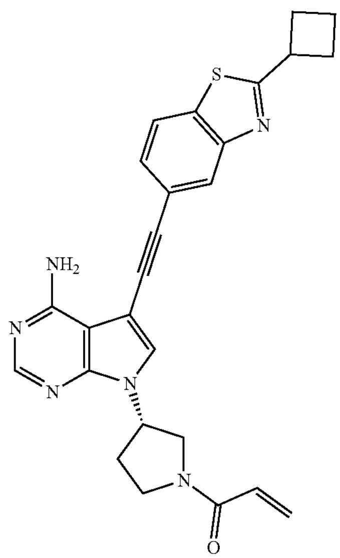 [SMILES: C=CC(=O)N1CC[C@H](n2cc(C#Cc3ccc4sc(C5CCC5)nc4c3)c3c(N)ncnc32)C1] | (S)-1-(3-(4-amino-5-((2-cyclobutylbenzo[d]thiazol-5-yl)ethynyl)-7H-pyrrolo[2,3-d]pyrimidin-7-yl)pyrrolidin-1-yl)prop-2-en-1-one | 469 |

-continued
| Example No. | Structural formula | Chemical name | [M + H]+ |
|---|---|---|---|
| 47 | 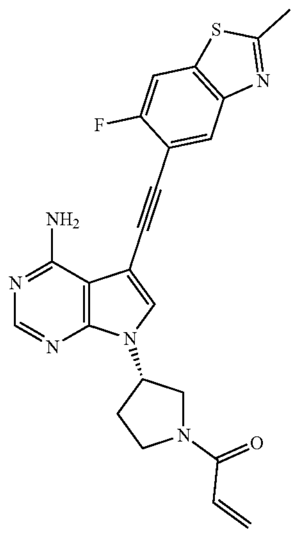 [SMILES: C=CC(=O)N1CC[C@H](n2cc(C#Cc3cc4nc(C)sc4cc3F)c3c(N)ncnc32)C1] | (S)-1-(3-(4-amino-5-((6-fluoro-2-methylbenzo[d] thiazol-5-yl)ethynyl)-7H-pyrrolo[2,3-d]pyrimidin-7-yl) pyrrolidin-1-yl)prop-2-en-1-one | 447 |
| 48 | 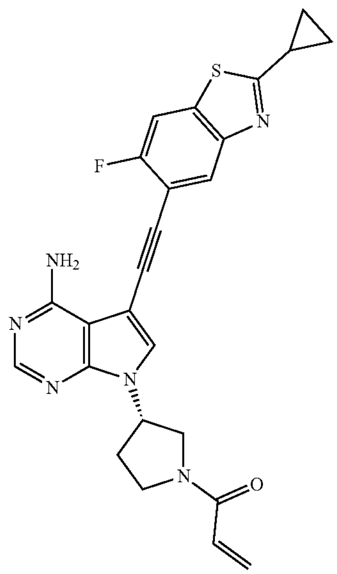 [SMILES: C=CC(=O)N1CC[C@H](n2cc(C#Cc3cc4nc(C5CC5)sc4cc3F)c3c(N)ncnc32)C1] | (S)-1-(3-(4-amino-5-((2-cyclopropyl-6-fluorobenzo [d]thiazol-5-yl)ethynyl)-7H-pyrrolo[2,3-d]pyrimidin-7-yl)pyrrolidin-1-yl)prop-2-en-1-one | 473 |

-continued
| Example No. | Structural formula | Chemical name | [M + H]+ |
|---|---|---|---|
| 49 | 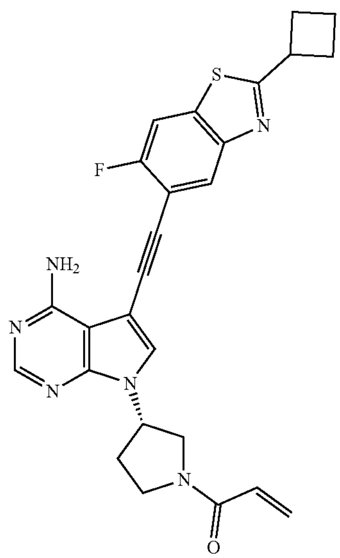 [SMILES: C=CC(=O)N1CC[C@H](n2cc(C#Cc3cc4nc(C5CCC5)sc4cc3F)c3c(N)ncnc32)C1] | (S)-1-(3-(4-amino-5-((2-cyclobutyl-6-fluorobenzo[d]thiazol-5-yl)ethynyl)-7H-pyrrolo[2,3-d]pyrimidin-7-yl)pyrrolidin-1-yl)prop-2-en-1-one | 487 |
| 50 | 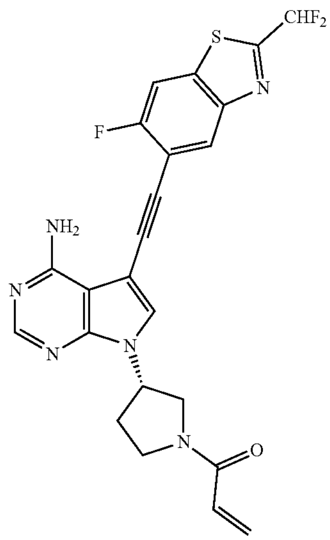 [SMILES: C=CC(=O)N1CC[C@H](n2cc(C#Cc3cc4nc(C(F)F)sc4cc3F)c3c(N)ncnc32)C1] | (S)-1-(3-(4-amino-5-((2-(difluoromethyl)-6-fluoro-benzo[d]thiazol-5-yl)ethynyl)-7H-pyrrolo[2,3-d]pyrimidin-7-yl)pyrrolidin-1-yl)prop-2-en-1-one | 483 |

-continued
| Example No. | Structural formula | Chemical name | [M + H]+ |
|---|---|---|---|
| 51 | 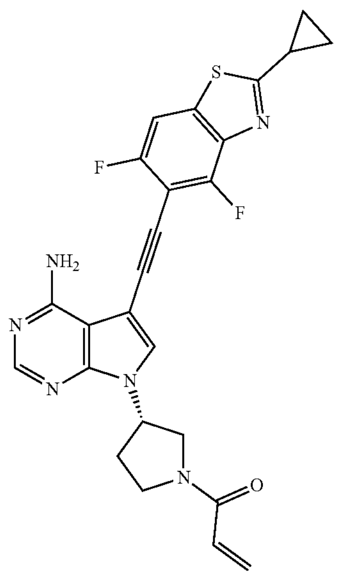 [SMILES: C=CC(=O)N1CC[C@H](n2cc(C#Cc3c(F)cc4sc(C5CC5)nc4c3F)c3c(N)ncnc32)C1] | (S)-1-(3-(4-amino-5-((2-cyclopropyl-4,6-difluoro-benzo[d]thiazol-5-yl)ethynyl)-7H-pyrrolo[2,3-d]pyrimidin-7-yl)pyrrolidin-1-yl)prop-2-en-1-one | 490 |
| 52 | 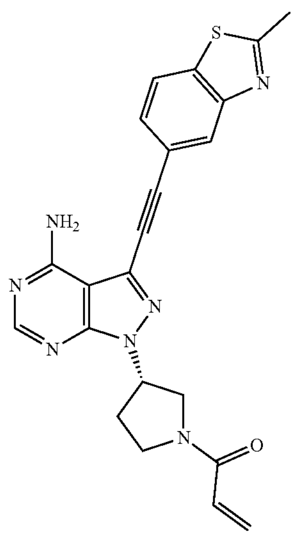 [SMILES: C=CC(=O)N1CC[C@H](n2nc(C#Cc3ccc4sc(C)nc4c3)c3c(N)ncnc32)C1] | (S)-1-(3-(4-amino-3-((2-methylbenzo[d]thiazol-5-yl)ethynyl)-1H-pyrazolo[3,4-d]pyrimidin-1-yl)pyrrolidin-1-yl)prop-2-en-1-one | 430 |

-continued
| Example No. | Structural formula | Chemical name | [M + H]$^+$ |
|---|---|---|---|
| 53 | 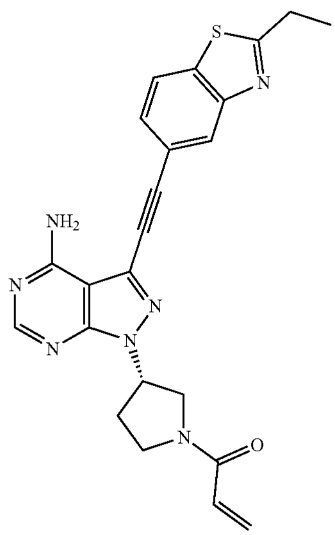 [SMILES: C=CC(=O)N1CC[C@H](n2nc(C#Cc3ccc4sc(CC)nc4c3)c3c(N)ncnc32)C1] | (S)-1-(3-(4-amino-3-((2-ethylbenzo[d]thiazol-5-yl) ethynyl)-1H-pyrazolo[3,4-d] pyrimidin-1-yl)pyrrolidin-1-yl)prop-2-en-1-one | 444 |
| 54 | 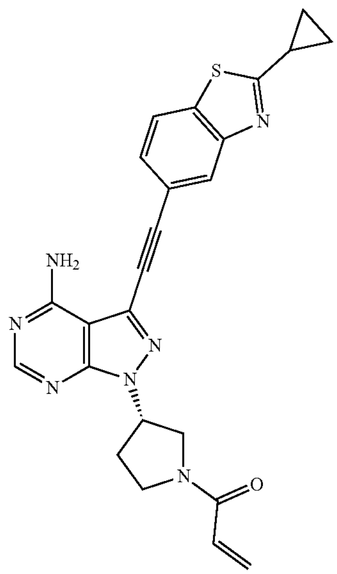 [SMILES: C=CC(=O)N1CC[C@H](n2nc(C#Cc3ccc4sc(C5CC5)nc4c3)c3c(N)ncnc32)C1] | (S)-1-(3-(4-amino-3-((2-cyclopropylbenzo[d]thiazol-5-yl)ethynyl)-1H-pyrazolo [3,4-d]pyrimidin-1-yl) pyrrolidin-1-yl)prop-2-en-1-one | 456 |

-continued
| Example No. | Structural formula | Chemical name | [M + H]+ |
|---|---|---|---|
| 55 | 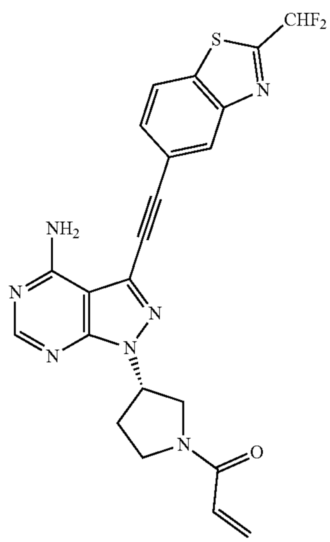 [SMILES: C=CC(=O)N1CC[C@H](n2nc(C#Cc3ccc4sc(C(F)F)nc4c3)c3c(N)ncnc32)C1] | (S)-1-(3-(4-amino-3-((2-(difluoromethyl)benzo[d]thiazol-5-yl)ethynyl)-1H-pyrazolo[3,4-d]pyrimidin-1-yl)pyrrolidin-1-yl)prop-2-en-1-one | 466 |
| 56 | 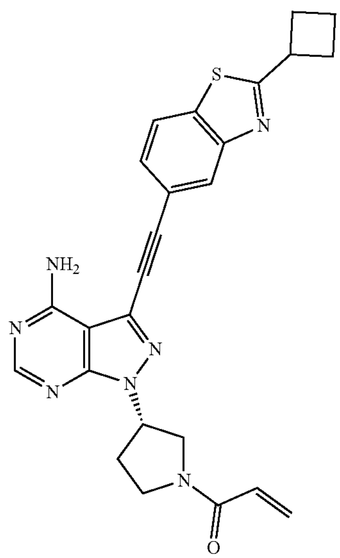 [SMILES: C=CC(=O)N1CC[C@H](n2nc(C#Cc3ccc4sc(C5CCC5)nc4c3)c3c(N)ncnc32)C1] | (S)-1-(3-(4-amino-3-((2-cyclobutylbenzo[d]thiazol-5-yl)ethynyl)-1H-pyrazolo[3,4-d]pyrimidin-1-yl)pyrrolidin-1-yl)prop-2-en-1-one | 470 |

-continued
| Example No. | Structural formula | Chemical name | [M + H]$^+$ |
|---|---|---|---|
| 57 | 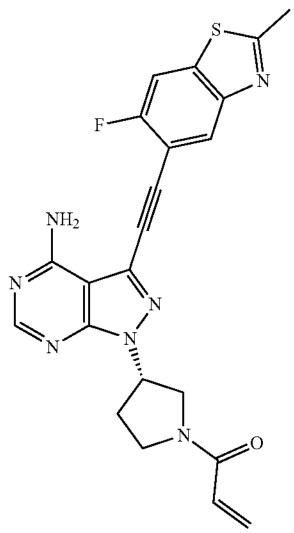 [SMILES: C=CC(=O)N1CC[C@H](n2nc(C#Cc3cc4nc(C)sc4cc3F)c3c(N)ncnc32)C1] | (S)-1-(3-(4-amino-3-((6-fluoro-2-methylbenzo[d]thiazol-5-yl)ethynyl)-1H-pyrazolo[3,4-d]pyrimidin-1-yl)pyrrolidin-1-yl)prop-2-en-1-one | 448 |
| 58 | 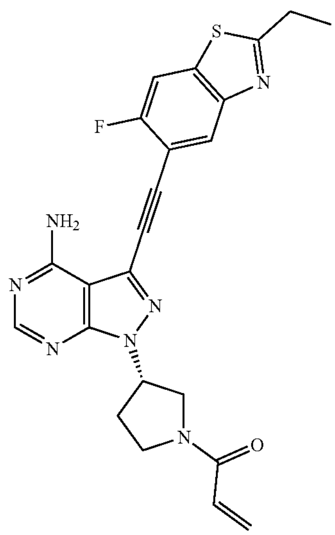 [SMILES: C=CC(=O)N1CC[C@H](n2nc(C#Cc3cc4nc(CC)sc4cc3F)c3c(N)ncnc32)C1] | (S)-1-(3-(4-amino-3-((2-ethyl-6-fluorobenzo[d]thiazol-5-yl)ethynyl)-1H-pyrazolo[3,4-d]pyrimidin-1-yl)pyrrolidin-1-yl)prop-2-en-1-one | 462 |

-continued
| Example No. | Structural formula | Chemical name | [M + H]+ |
|---|---|---|---|
| 59 | 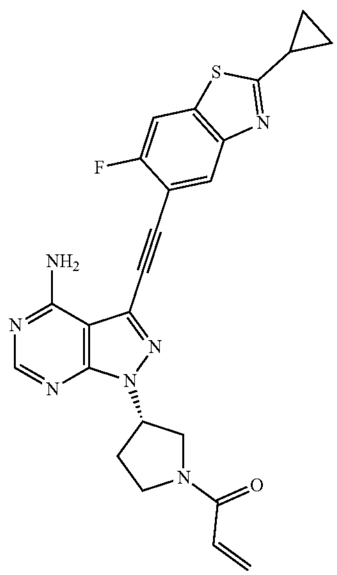 [SMILES: C=CC(=O)N1CC[C@H](n2nc(C#Cc3cc4nc(C5CC5)sc4cc3F)c3c(N)ncnc32)C1] | (S)-1-(3-(4-amino-3-((2-cyclopropyl-6-fluorobenzo[d]thiazol-5-yl)ethynyl)-1H-pyrazolo[3,4-d]pyrimidin-1-yl)pyrrolidin-1-yl)prop-2-en-1-one | 474 |
| 60 | 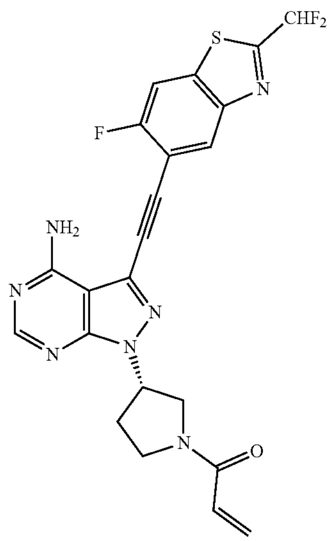 [SMILES: C=CC(=O)N1CC[C@H](n2nc(C#Cc3cc4nc(C(F)F)sc4cc3F)c3c(N)ncnc32)C1] | (S)-1-(3-(4-amino-3-((2-(difluoromethyl)-6-fluoro-benzo[d]thiazol-5-yl)ethynyl)-1H-pyrazolo[3,4-d]pyrimidin-1-yl)pyrrolidin-1-yl)prop-2-en-1-one | 484 |

-continued
| Example No. | Structural formula | Chemical name | [M + H]+ |
|---|---|---|---|
| 61 | 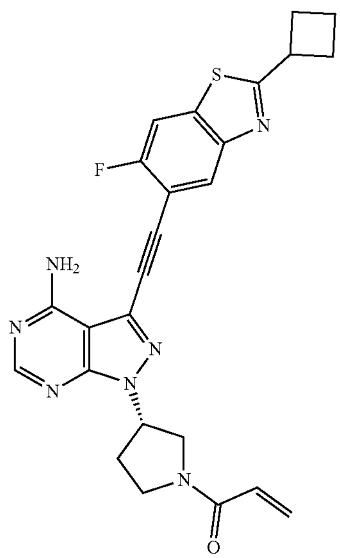 [SMILES: C=CC(=O)N1CC[C@H](n2nc(C#Cc3cc4nc(C5CCC5)sc4cc3F)c3c(N)ncnc32)C1] | (S)-1-(3-(4-amino-3-((2-cyclobutyl-6-fluorobenzo[d]thiazol-5-yl)ethynyl)-1H-pyrazolo[3,4-d]pyrimidin-1-yl)pyrrolidin-1-yl)prop-2-en-1-one | 488 |
| 62 | 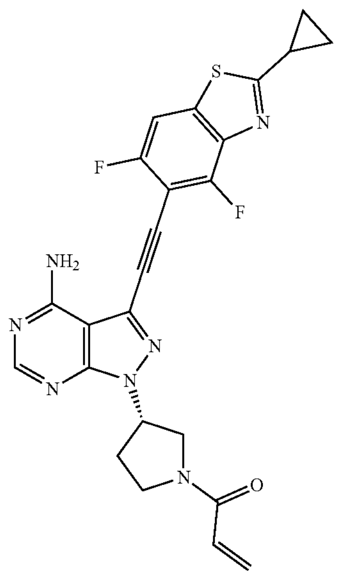 [SMILES: C=CC(=O)N1CC[C@H](n2nc(C#Cc3c(F)cc4sc(C5CC5)nc4c3F)c3c(N)ncnc32)C1] | (S)-1-(3-(4-amino-3-((2-cyclopropyl-4,6-difluoro-benzo[d]thiazol-5-yl)ethynyl)-1H-pyrazolo[3,4-d]pyrimidin-1-yl)pyrrolidin-1-yl)prop-2-en-1-one | 492 |

-continued
| Example No. | Structural formula | Chemical name | [M + H]+ |
|---|---|---|---|
| 63 | 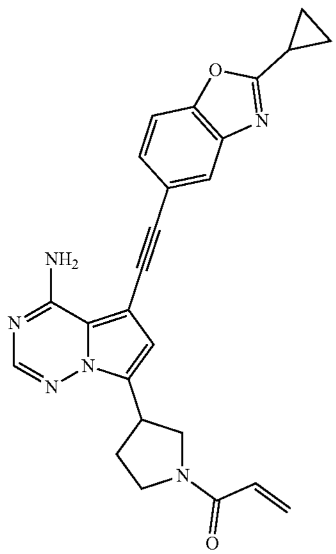 [SMILES: C=CC(=O)N1CCC(c2cc(C#Cc3ccc4oc(C5CC5)nc4c3)c3c(N)ncnn23)C1] | 1-(3-(4-amino-5-((2-cyclopropylbenzo[d]oxazol-5-yl)ethynyl)pyrrolo[2,1-f][1,2,4]triazin-7-yl)pyrrolidin-1-yl)prop-2-en-1-one | 439 |
| 64 | 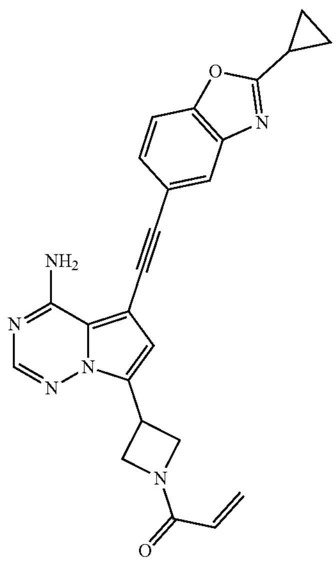 [SMILES: C=CC(=O)N1CC(c2cc(C#Cc3ccc4oc(C5CC5)nc4c3)c3c(N)ncnn23)C1] | 1-(3-(4-amino-5-((2-cyclopropylbenzo[d]oxazol-5-yl)ethynyl)pyrrolo[2,1-f][1,2,4]triazin-7-yl)azetidin-1-yl)prop-2-en-1-one | 425 |

-continued
| Example No. | Structural formula | Chemical name | [M + H]+ |
|---|---|---|---|
| 65 | 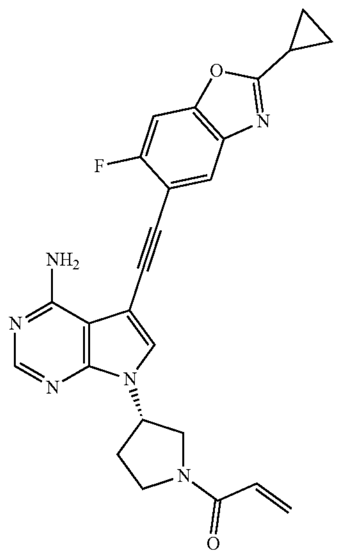 [SMILES: C=CC(=O)N1CC[C@H](n2cc(C#Cc3cc4nc(C5CC5)oc4cc3F)c3c(N)ncnc32)C1] | (S)-1-(3-(4-amino-5-((2-cyclopropyl-6-fluorobenzo[d]oxazol-5-yl)ethynyl)-7H-pyrrolo[2,3-d]pyrimidin-7-yl)pyrrolidin-1-yl)prop-2-en-1-one | 457 |
| 67 | 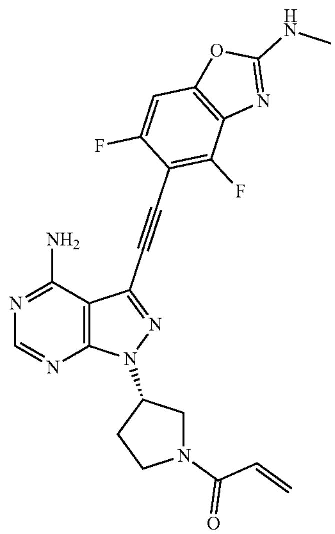 [SMILES: C=CC(=O)N1CC[C@H](n2nc(C#Cc3c(F)cc4oc(NC)nc4c3F)c3c(N)ncnc32)C1] | (S)-1-(3-(4-amino-3-((4,6-difluoro-2-(methylamino)benzo[d]oxazol-5-yl)ethynyl)-1H-pyrazolo[3,4-d]pyrimidin-1-yl)pyrrolidin-1-yl)prop-2-en-1-one | 465 |

-continued
| Example No. | Structural formula | Chemical name | [M + H]$^+$ |
|---|---|---|---|
| 68 | 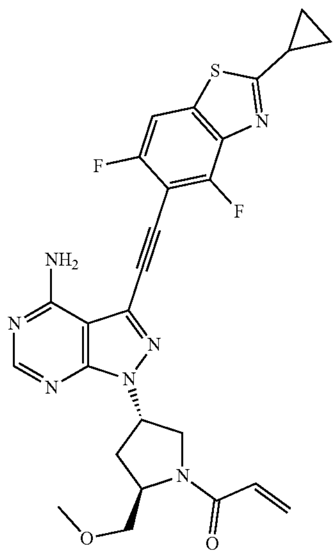 [SMILES: C=CC(=O)N1C[C@@H](n2nc(C#Cc3c(F)cc4sc(C5CC5)nc4c3F)c3c(N)ncnc32)C[C@@H]1COC] | 1-((2R,4S)-4-(4-amino-3-((2-cyclopropyl-4,6-difluoro-benzo[d]thiazol-5-yl)ethynyl)-1H-pyrazolo[3,4-d]pyrimidin-1-yl)-2-(methoxy-methyl)pyrrolidin-1-yl)prop-2-en-1-one | 536 |
| 69 | 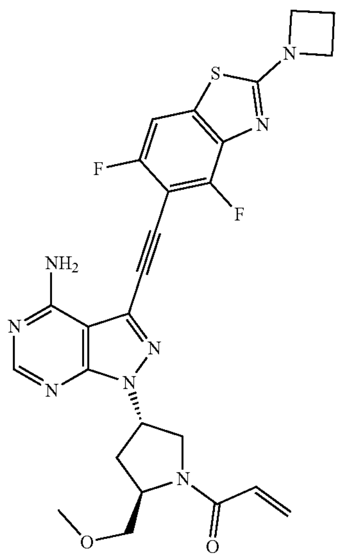 [SMILES: C=CC(=O)N1C[C@@H](n2nc(C#Cc3c(F)cc4sc(N5CCC5)nc4c3F)c3c(N)ncnc32)C[C@@H]1COC] | 1-((2R,4S)-4-(4-amino-3-((2-(azetidin-1-yl)-4,6-difluorobenzo[d]thiazol-5-yl)ethynyl)-1H-pyrazolo[3,4-d]pyrimidin-1-yl)-2-(methoxy-methyl)pyrrolidin-1-yl)prop-2-en-1-one | 551 |

-continued
| Example No. | Structural formula | Chemical name | $[M + H]^+$ |
|---|---|---|---|
| 70 | 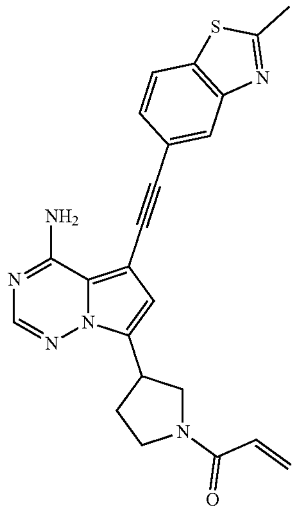 [SMILES: C=CC(=O)N1CCC(c2cc(C#Cc3ccc4sc(C)nc4c3)c3c(N)ncnn23)C1] | 1-(3-(4-amino-5-((2-methyl-benzo[d]thiazol-5-yl)ethynyl) pyrrolo[2,1-f][1,2,4] triazin-7-yl)pyrrolidin-1-yl) prop-2-en-1-one | 429 |
| 71 | 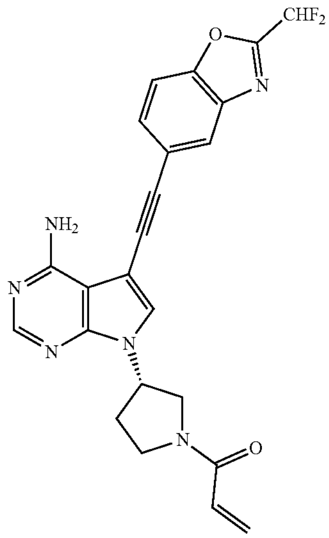 [SMILES: C=CC(=O)N1CC[C@H](n2cc(C#Cc3ccc4oc(C(F)F)nc4c3)c3c(N)ncnc32)C1] | (S)-1-(3-(4-amino-5-((2-(difluoromethyl)benzo[d] oxazol-5-yl)ethynyl)-7H-pyrrolo[2,3-d]pyrimidin-7-yl)pyrrolidin-1-yl)prop-2-en-1-one | 449 |
| 72 | 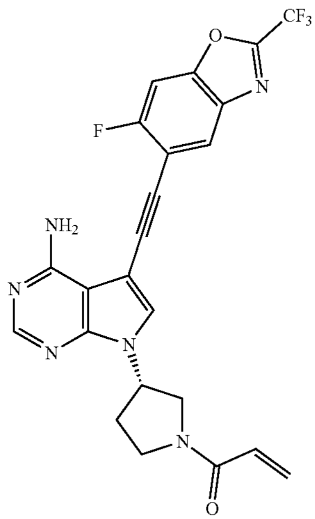 [SMILES: C=CC(=O)N1CC[C@H](n2cc(C#Cc3cc4nc(C(F)(F)F)oc4cc3F)c3c(N)ncnc32)C1] | (S)-1-(3-(4-amino-5-((6-fluoro-2-(trifluoromethyl) benzo[d]oxazol-5-yl)ethynyl)-7H-pyrrolo[2,3-d]pyrimidin-7-yl)pyrrolidin-1-yl) prop-2-en-1-one | 485 |

-continued
| Example No. | Structural formula | Chemical name | [M + H]+ |
|---|---|---|---|
| 73 | 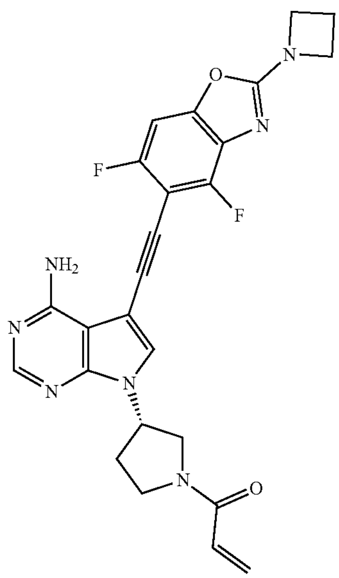 [SMILES: C=CC(=O)N1CC[C@H](n2cc(C#Cc3c(F)cc4oc(N5CCC5)nc4c3F)c3c(N)ncnc32)C1] | (S)-1-(3-(4-amino-5-((2-(azetidin-1-yl)-4,6-difluoro-benzo[d]oxazol-5-yl)ethynyl)-7H-pyrrolo[2,3-d]pyrimidin-7-yl)pyrrolidin-1-yl) prop-2-en-1-one | 490 |
| 74 | 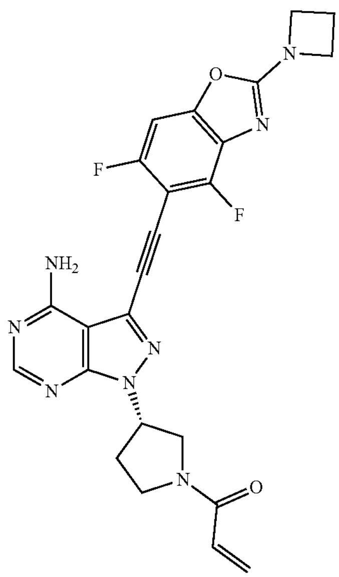 [SMILES: C=CC(=O)N1CC[C@H](n2nc(C#Cc3c(F)cc4oc(N5CCC5)nc4c3F)c3c(N)ncnc32)C1] | (S)-1-(3-(4-amino-3-((2-(azetidin-1-yl)-4.6-difluoro-benzo[d]oxazol-5-yl)ethynyl)-1H-pyrazolo[3,4-d] pyrimidin-1-yl)pyrrolidin-1-yl)prop-2-en-1-one | 491 |

-continued

| Example No. | Structural formula | Chemical name | [M + H]+ |
|---|---|---|---|
| 75 | 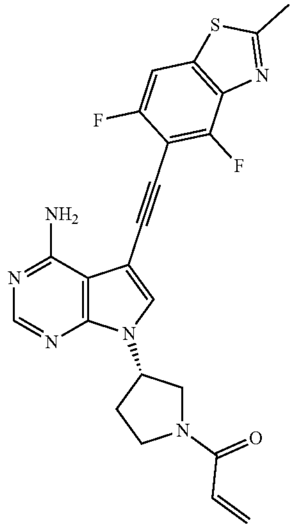 [SMILES: C=CC(=O)N1CC[C@H](n2cc(C#Cc3c(F)cc4sc(C)nc4c3F)c3c(N)ncnc32)C1] | (S)-1-(3-(4-amino-5-((4,6-difluoro-2-methylbenzo[d]thiazol-5-yl)ethynyl)-7H-pyrrolo[2,3-d]pyrimidin-7-yl)pyrrolidin-1-yl)prop-2-en-1-one | 465 |

$^1H$ NMR Data of the Compounds Prepared in the Above Examples are as Follows:

| Example No. | $^1H$ NMR |
|---|---|
| 2 | (400 MHz, MeOH-$d_4$): δ 8.07 (s, 1H), 7.66 (d, J = 1.5 Hz, 1H), 7.51-7.33 (m, 3H), 6.69-6.41 (m, 1H), 6.32-6.14 (m, 1H), 5.76-5.59 (m, 1H), 5.38-5.16 (m, 1H), 4.17-3.92 (m, 1H), 3.91-3.55 (m, 3H), 2.55 (s, 3H), 2.50-2.33 (m, 2H). |
| 3 | (400 MHz, DMSO-$d_6$): δ 8.11 (s, 1H), 7.86-7.85 (d, J = 4.0 Hz, 1H), 7.70-7.63 (t, J = 12 Hz, 2H), 7.51-7.48 (d, J = 12 Hz, 1H), 6.78-6.48 (m, 3H), 6.14-6.07 (m, 1H), 5.67-5.59 (m, 1H), 5.33-5.19 (m, 1H), 4.06-3.79 (m, 2H), 3.71-3.43 (m, 2H), 2.94-2.88 (q, J = 8 Hz, 2H), 2.40-2.35 (m, 1H), 2.33-2.27 (m, 1H), 1.30-1.27 (t, J = 8 Hz, 3H). |
| 4 | (400 MHz, DMSO-$d_6$): δ 8.16 (s, 1H), 7.87 (s, 1H), 7.73-7.65 (t, J = 16 Hz, 2H), 7.52-7.49 (d, J = 8 Hz, 1H), 7.02-6.48 (m, 3H), 6.14-6.07 (m, 1H), 5.67-5.59 (m, 1H), 5.34-5.21 (m, 1H), 4.07-3.79 (m, 2H), 3.71-3.41 (m, 2H), 3.24-3.18 (t, J = 8 Hz, 1H), 2.41-2.28 (m, 2H), 1.33-1.31 (d, J = 8 Hz, 6H). |
| 5 | (400 MHz, DMSO-$d_6$): δ 8.11 (s, 1H), 7.87-7.86 (m, 1H), 7.70-7.64 (m, 2H), 7.51-7.49 (m, 1H), 6.79-6.48 (m, 3H), 6.14-6.07 (m, 1H), 5.67-5.59 (m, 1H), 5.33-5.19 (m, 1H), 4.06-3.44 (m, 5H), 2.40-2.28 (m, 6H), 2.09-1.86 (m, 2H). |
| 6 | (400 MHz, DMSO-$d_6$): δ 8.82 (s, 1H), 8.18 (d, J = 1.4 Hz, 1H), 8.07 (d, J = 1.7 Hz, 1H), 7.83 (d, J = 8.5 Hz, 1H), 7.75 (d, J = 16.0 Hz, 1H), 7.65 (dd, J = 8.2, 1.5 Hz, 1H), 6.71 (br s, 1H), 6.69-6.55 (m, 1H), 6.21-6.14 (m, 1H), 5.74-5.66 (m, 1H), 5.40-5.30 (m, 1H), 4.13-3.52 (m, 4H), 2.46-2.42 (m, 1H), 2.39-2.32 (m, 1H). |
| 7 | (400 MHz, DMSO-$d_6$): δ 8.11 (s, 1H), 7.90-7.86 (m, 1H), 7.66-7.62 (d, J = 16 Hz, 1H), 7.36-7.30 (m, 2H), 7.14-7.12 (m, 1H), 6.78-6.48 (m, 3H), 6.14-6.07 (m, 1H), 5.67-5.59 (m, 1H), 5.32-5.18 (m, 1H), 4.06-3.79 (m, 2H), 3.70-3.43 (m, 2H), 2.85-2.84 (d, J = 4 Hz, 3H), 2.40-2.28 (m, 2H). |
| 20 | (400 MHz, DMSO-$d_6$): δ 8.29 (s, 1H), 8.03 (s, 1H), 7.80-7.49 (m, 3H), 6.73-6.51 (m, 1H), 6.24-6.10 (m, 1H), 5.78-5.64 (m, 1H), 5.57-5.42 (m, 1H), 4.12-3.63 (m, 4H), 2.99-2.83 (m, 1H), 2.39-2.16 m, 3H), 1.32-1.11 (m, 4H). |
| 29 | (400 MHz, DMSO-$d_6$): δ 8.29 (s, 1H), 8.05 (q, J = 4.4 Hz, 1H), 7.62 (dd, J = 6.4, 2.4 Hz, 1H), 7.58 (d, J = 9.1 Hz, 1H), 6.70-6.50 (m, 1H), 6.20-6.14 (m, 1H), 5.73-5.65 (m, 1H), 5.60-5.41 (m, 1H), 4.12-3.78 (m, 3H), 3.75-3.56 (m, 1H), 2.91 (d, J = 4.7 Hz, 3H), 2.47-2.30 (m, 2H). |
| 30 | (400 MHz, DMSO-$d_6$): δ 8.29 (s, 1H), 8.16 (t, J = 5.5 Hz, 1H), 7.61 (dd, J = 6.4, 2.4 Hz, 1H), 7.58 (d, J = 9.1 Hz, 1H), 6.72-6.53 (m, 1H), 6.22-6.12 (m, 1H), 5.75-5.64 (m, 1H), 5.58-5.42 (m, 1H), 4.16-3.56 (m, 4H), 3.38-3.31 (m, 2H), 2.48-2.30 (m, 2H), 1.19 (t, J = 7.2 Hz, 3H). |
| 31 | (400 MHz, DMSO-$d_6$): δ 8.29 (s, 1H), 7.67-7.59 (m, 2H), 6.70-6.50 (m, 1H), 6.20-6.14 (m, 1H), 5.73-5.65 (m, 1H), 5.60-5.41 (m, 1H), 4.12-3.79 (m, 3H), 3.74-3.56 (m, 1H), 3.14 (s, 6H), 2.46-2.30 (m, 2H). |

-continued

| Example No. | $^1$H NMR |
|---|---|
| 33 | (400 MHz, DMSO-$d_6$): δ 8.41 (s, 1H), 8.29 (s, 1H), 7.66 (dd, J = 6.3, 2.2 Hz, 1H), 7.61 (d, J = 9.0 Hz, 1H), 6.70-6.55 (m, 1H), 6.20-6.14 (m, 1H), 5.73-5.65 (m, 1H), 5.60-5.41 (m, 1H), 4.12-3.79 (m, 3H), 3.73-3.58 (m, 1H), 2.77-2.72 (m, 1H), 2.45-2.33 (m, 2H), 0.77-0.71 (m, 2H), 0.60-0.56 (m, 2H). |
| 34 | (400 MHz, DMSO-$d_6$): δ 8.29 (s, 1H), 7.66 (dd, J = 13.8, 7.6 Hz, 2H), 6.70-6.55 (m, 1H), 6.20-6.14 (m, 1H), 5.73-5.65 (m, 1H), 5.60-5.41 (m, 1H), 4.22 (t, J = 7.6 Hz, 4H), 4.12-3.76 (m, 3H), 3.71-3.58 (m, 1H), 2.45-2.34 (m, 4H). |
| 35 | (400 MHz, DMSO-$d_6$): δ 8.29 (s, 1H), 8.11 (dd, J = 6.5, 2.4 Hz, 1H), 7.86 (d, J = 9.0 Hz, 1H), 6.72-6.53 (m, 1H), 6.22-6.12 (m, 1H), 5.75-5.64 (m, 1H), 5.59-5.43 (m, 1H), 4.17-3.56 (m, 4H), 2.47-2.26 (m, 3H), 1.28-1.12 (m, 4H). |
| 36 | (400 MHz, DMSO-$d_6$): δ 8.28-8.17 (m, 2H), 7.94 (d, J = 8.9 Hz, 1H), 6.67-6.46 (m, 1H), 6.16-6.06 (m, 1H), 5.69-5.56 (m, 1H), 5.54-5.34 (m, 1H), 4.14-3.48 (m, 4H), 2.40-2.21 (m, 2H), 1.81-1.64 (m, 2H), 1.54-1.43 (m, 2H). |
| 38 | (400 MHz, DMSO-$d_6$): δ 8.30 (s, 1H), 8.21 (dd, J = 6.5, 2.4 Hz, 1H), 7.90 (d, J = 9.0 Hz, 1H), 6.76-6.49 (m, 1H), 6.22-6.10 (m, 1H), 5.78-5.62 (m, 1H), 5.60-5.41 (m, 1H), 4.16-3.56 (m, 5H), 3.02-2.78 (m, 1H), 2.48-2.34 (m, 6H), 2.19-1.92 (m, 2H). |
| 39 | (400 MHz, DMSO-$d_6$): δ 8.28 (d, J = 1.0 Hz, 1H), 8.05 (s, 1H), 7.73-7.67 (m, 2H), 6.71-6.55 (m, 1H), 6.21-6.14 (m, 1H), 5.74-5.66 (m, 1H), 5.58-5.45 (m, 1H), 4.15-4.10 (m, 0.5H), 3.99-3.71 (m, 3H), 3.70-3.61 (m, 0.5H), 2.48-2.33 (m, 2H), 1.58 (s, 3H), 1.41-1.34 (m, 2H), 1.11-1.08 (m, 2H). |
| 41 | (400 MHz, DMSO-$d_6$): δ 8.89 (s, 1H), 8.72 (s, 1H), 8.29 (s, 1H), 6.76-6.51 (m, 1H), 6.26-6.10 (m, 1H), 5.78-5.62 (m, 1H), 5.62-5.42 (m, 1H), 4.20-3.58 (m, 4H), 2.87 (s, 3H), 2.48-2.30 (m, 2H). |
| 42 | (400 MHz, DMSO-$d_6$): δ 8.18 (s, 1H), 8.13 (s, 1H), 8.08 (d, J = 8.3 Hz, 1H), 7.77 (d, J = 16.2 Hz, 1H), 7.58 (d, J = 8.3 Hz, 1H), 6.94-6.61 (m, 2H), 6.65-6.54 (m, 1H), 6.23-6.12 (m, 1H), 5.76-5.63 (m, 1H), 5.43-5.23 (m, 1H), 4.16-3.86 (m, 2H), 3.78-3.51 (m, 2H), 2.82 (s, 3H), 2.50-2.32 (m, 2H). |
| 43 | (400 MHz, MeOH-$d_4$): δ 8.17 (s, 1H), 7.99 (s, 1H), 7.85 (d, J = 8.3 Hz, 1H), 7.51 (d, J = 8.4 Hz, 1H), 7.42 (d, J = 4.0 Hz, 1H), 6.63-6.48 (m, 1H), 6.27-6.20 (m, 1H), 5.73-5.66 (m, 1H), 5.36-5.24 (m, 1H), 4.15-3.96 (m, 1H), 3.89-3.57 (m, 3H), 2.55-2.34 (m, 3H), 1.27-1.08 (m, 4H). |
| 44 | (400 MHz, MeOH-$d_4$): δ 8.10 (s, 1H), 7.94 (dd, J = 3.9, 1.5 Hz, 1H), 7.85 (dd, J = 8.3, 3.8 Hz, 1H), 7.59-7.37 (m, 2H), 6.67-6.44 (m, 1H), 6.27-6.20 (m, 1H), 5.73-5.05 (m, 1H), 5.37-5.20 (m, 1H), 4.15-3.96 (m, 1H), 3.93-3.57 (m, 3H), 3.11-3.05 (m, 2H), 2.55-2.31 (m, 2H), 1.37 (t, J = 7.5 Hz, 3H). |
| 45 | (400 MHz, MeOH-$d_4$): δ 8.18 (d, J = 4.6 Hz, 1H), 8.09 (d, J = 2.0 Hz, 1H), 8.04 (dd, J = 8.6, 3.6 Hz, 1H), 7.61 (dd, J = 8.8, 3.6 Hz, 1H), 7.51 (dd, J = 13.6, 3.1 Hz, 1H), 7.06 (t, J = 54.2 Hz, 1H), 6.62-6.48 (m, 1H), 6.26-6.20 (m, 1H), 5.72-5.65 (m, 1H), 5.35-5.26 (m, 1H), 4.15-3.96 (m, 1H), 3.90-3.57 (m, 3H), 2.51-2.38 (m, 2H). |
| 47 | (400 MHz, DMSO-$d_6$): δ 8.23-8.15 (m, 2H), 8.11 (d, J = 9.3 Hz, 1H), 7.82 (d, J = 16.7 Hz, 1H), 6.71-6.54 (m, 1H), 6.23-6.12 (m, 1H), 5.76-5.65 (m, 1H), 5.43-5.24 (m, 1H), 4.16-3.48 (m, 4H), 2.81 (s, 3H), 2.47-2.30 (m, 2H). |
| 48 | (400 MHz, DMSO-$d_6$): δ 8.21 (s, 1H), 8.15-8.01 (m, 2H), 7.81 (d, J = 16.8 Hz, 1H), 6.80 (brs, 2H), 6.73-6.52 (m, 1H), 6.27-6.14 (m, 1H), 5.81-5.66 (m, 1H), 5.42-5.22 (m, 1H), 4.18-3.86 (m, 2H), 3.79-3.49 (m, 2H), 2.65-2.51 (m, 1H), 2.49-2.29 (m, 2H), 1.27-1.09 (m, 4H). |
| 50 | (400 MHz, DMSO-$d_6$): δ 8.50 (dd, J = 6.4, 3.6 Hz, 1H), 8.32 (d, J = 6.4 Hz, 1H), 8.20 (s, 1H), 7.84 (d, J = 16.8 Hz, 1H), 7.50 (t, J = 53.6 Hz, 1H), 7.00-6.68 (m, 2H), 6.65-6.59 (m, 1H), 6.20-6.14 (m, 1H), 5.73-5.67 (m, 1H), 5.39-5.27 (m, 1H), 4.12-3.88 (m, 2H), 3.72-3.52 (m, 2H), 2.45-2.32 (m, 2H). |
| 51 | (400 MHz, DMSO-$d_6$): δ 8.20 (s, 1H), 7.90 (d, J = 17.8 Hz, 1H), 6.78 (brs, 2H), 6.71-6.52 (m, 1H), 6.25-6.11 (m, 1H), 5.73-5.66 (m, 2H), 5.43-5.23 (m, 1H), 4.19-3.84 (m, 2H), 3.80-3.49 (m, 2H), 2.65-2.53 (m, 1H), 2.49-2.33 (m, 2H), 1.33-1.13 (m, 4H). |
| 52 | (400 MHz, DMSO-$d_6$): δ 8.32 (s, 1H), 8.28 (s, 1H), 8.12 (d, J = 8.3 Hz, 1H), 7.72 (d, J = 8.3 Hz, 1H), 6.74-6.53 (m, 1H), 6.24-6.11 (m, 1H), 5.75-5.63 (m, 1H), 5.60-5.42 (m, 1H), 4.18-3.57 (m, 4H), 2.83 (s, 3H), 2.47-2.30 (m, 2H). |
| 53 | (400 MHz, MeOH-$d_4$): δ 8.18 (s, 1H), 8.09 (s, 1H), 7.91 (d, J = 8.4 Hz, 1H), 7.56 (d, J = 8.3 Hz, 1H), 6.64-6.49 (m, 1H), 6.25-6.21 (m, 1H), 5.76-5.63 (m, 1H), 5.50-5.45 (m, 1H), 4.12-3.66 (m, 4H), 3.12-3.07 (q, J = 7.5 Hz, 2H), 2.50-2.41 (m, 2H), 1.39 (t, J = 7.5 Hz, 3H). |
| 54 | (400 MHz, MeOH-$d_4$): δ 8.17 (s, 1H), 7.99 (s, 1H), 7.85 (d, J = 8.3 Hz, 1H), 7.51 (d, J = 8.4 Hz, 1H), 6.64-6.48 (m, 1H), 6.29-6.18 (m, 1H), 5.71-5.65 (m, 1H), 5.51-5.44 (m, 1H), 4.12-3.65 (m, 4H), 2.55-2.34 (m, 3H), 1.27-1.08 (m, 4H). |

-continued

| Example No. | $^1$H NMR |
|---|---|
| 55 | (400 MHz, MeOH-$d_4$): δ 8.32 (s, 1H), 8.17 (s, 1H), 8.09 (d, J = 8.4 Hz, 1H), 7.72 (d, J = 8.4 Hz, 1H), 7.07 (t, J = 54.2 Hz, 1H), 6.64-6.48 (m, 1H), 6.33-6.13 (m, 1H), 5.71-6.65 (m, 1H), 5.60-5.40 (m, 1H), 4.15-4.00 (m, 1H), 4.00-3.63 (m, 3H), 2.52-2.39 (m, 2H). |
| 57 | (400 MHz, DMSO-$d_6$): δ 8.40 (dd, J = 6.5, 2.5 Hz, 1H), 8.30 (s, 1H), 8.16 (d, J = 9.3 Hz, 1H), 6.73-6.54 (m, 1H), 6.23-6.12 (m, 1H), 5.76-5.64 (m, 1H), 5.60-5.44 (m, 1H), 4.17-3.57 (m, 4H), 2.82 (s, 3H), 2.48-2.31 (m, 2H). |
| 59 | (400 MHz, DMSO-$d_6$): δ 8.47-8.25 (m, 2H), 8.12 (d, J = 9.3 Hz, 1H), 6.76-6.51 (m, 1H), 6.29-6.07 (m, 1H), 5.79-5.61 (m, 1H), 5.62-5.43 (m, 1H), 4.15-3.62 (m, 4H), 2.69-2.55 (m, 1H), 2.48-2.30 (m, 2H), 1.38-1.02 (m, 4H). |
| 60 | (400 MHz, DMSO-$d_6$): δ 8.73 (dd, J = 6.4, 3.6 Hz, 1H), 8.37 (d, J = 9.2 Hz, 1H), 8.30 (s, 1H), 7.68-7.38 (m, 1H), 7.52 (t, J = 53.6 Hz, 1H), 7.00-6.70 (m, 1H), 6.66-6.60 (m, 1H), 6.20-6.14 (m, 1H), 5.72-5.66 (m, 1H), 5.57-5.47 (m, 1H), 4.12-3.92 (m, 1H), 3.92-3.80 (m, 2H), 3.72-3.61 (m, 1H), 2.53-2.32 (m, 2H). |
| 62 | (400 MHz, DMSO-$d_6$): δ 8.31 (s, 1H), 8.04 (d, J = 8.7 Hz, 1H), 6.91-6.54 (brs, 2H), 6.73-6.55 (m, 1H), 6.25-6.11 (m, 1H), 5.76-5.63 (m, 1H), 5.61-5.44 (m, 1H), 4.22-3.88 (m, 4H), 2.69-2.56 (m, 2H), 2.47-2.30 (m, 1H), 1.43-1.05 (m, 4H). |
| 63 | (400 MHz, DMSO-$d_6$): δ 7.99 (s, 1H), 7.87 (s, 1H), 7.68 (d, J = 8.4 Hz, 1H), 7.54 (dd, J = 8.4, 1.7 Hz, 1H), 6.84 (d, J = 12.5 Hz, 1H), 6.68-6.56 (m, 1H), 6.23-6.13 (m, 1H), 5.83-5.60 (m, 1H), 4.12-3.58 (m, 4H), 3.54-2.03 (m, 2H), 2.37-2.25 (m, 2H), 1.29-1.12 (m, 4H). |
| 64 | (400 MHz, DMSO-$d_6$): δ 8.19 (s, 1H), 7.90-7.8 (m, 1H), 7.82-7.7 (m, 2H), 6.85-6.5 (m, 3H), 6.21-6.10 (m, 1H), 5.74-5.6 (m, 1H), 5.38-5.21 (m, 1H), 4.13-3.86 (m, 2H), 3.77-3.50 (m, 2H), 2.47-2.26 (m, 3H), 1.24-1.13 (m, 3H). |
| 65 | (400 MHz, DMSO-$d_6$): δ 8.19 (s, 1H), 7.90-7.88 (m, 1H), 7.83-.74 (m, 2H), 6.68-6.55 (m, 3H), 6.21-6.14 (m, 1H), 5.74-5.66 (m, 1H), 5.38-5.27 (m, 1H), 4.13-4.09 (m, 0.5H), 3.96-3.87 (m, 1.5H), 3.77-3.67 (m, 1.5H), 3.57-3.50 (m, 0.5H), 2.46-2.42 (m, 1H), 2.39-2.36 (m, 1H), 2.31-2.26 (m, 1H), 1.24-1.19 (m, 2H), 1.17-1.13 (m, 2H). |
| 67 | (400 MHz, DMSO-$d_6$): δ 8.29 (s, 1H), 8.31-8.26(m, 1H), 7.56 (d, J = 8.4 Hz, 1H), 6.71-6.55 (m, 1H), 6.71(brs, 2H), 6.24-6.12 (m, 1H), 6.74-5.64 (m, 1H), 5.61-5.38 (m, 1H), 4.17-3.57 (m, 4H), 2.93 (d, J = 4.7 Hz, 3H), 2.49-2.30 (m, 2H). |
| 68 | (400 MHz, MeOH-$d_4$): δ 8.29 (s, 1H), 7.71 (d, J = 8.5 Hz, 1H), 6.88-6.55 (m, 1H), 6.38-6.27 (m, 1H), 5.83-5.67 (m, 2H), 4.73-4.63 (m, 1H), 4.20-4.11 (m, 1H), 3.97-3.80 (m, 1H), 3.64-3.56 (m, 1H), 3.44 (d, J = 2.3 Hz, 3H), 2.93-2.66 (m, 2H), 2.60-2.47 (m, 2H), 1.37-1.24 (m, 4H). |
| 69 | (400 MHz, MeOH-$d_4$): δ 8.28 (s, 1H), 7.27 (d, J = 8.2 Hz, 1H), 6.90-6.54 (m, 1H), 6.38-6.24 (m, 1H), 5.84-5.67 (m, 2H), 4.72-4.62 (m, 1H), 4.35 (t, J = 7.7 Hz, 4H), 4.19-4.09 (m, 2H), 3.96-3.80 (m, 1H), 3.59 (td, J = 5.9, 5.3, 3.5 Hz, 1H), 3.43 (d, J = 2.2 Hz, 3H), 2.94-2.69 (m, 2H), 2.60-2.54 (m, 2H). |
| 70 | (400 MHz, MeOH-$d_4$): δ 7.94 (s, 1H), 7.83-7.79 (m, 1H), 7.75 (s, 1H), 7.57-7.50 (m, 1H), 7.46-7.44 (m, 1H), 6.68 (d, 1H), 6.57-6.53 (m, 1H), 6.25 (d, 1H), 6.50-6.45 (m, 1H), 4.02-3.54 (m, 4H), 2.75 (s, 3H), 2.48-2.30 (m, 1H), 2.20-2.25 (m, 1H) |
| 71 | (400 MHz, DMSO-$d_6$): δ 8.28-8.15 (m, 2H), 7.95 (d, J = 8.6 Hz, 1H), 7.85-7.71 (m, 2H), 7.44 (t, J = 51.9 Hz, 1H), 6.92-6.51 (m, 3H), 6.24-6.11 (m, 1H), 5.78-5.61 (m, 1H), 5.44-5.22 (m, 1H), 4.18-3.50 (m, 4H), 2.45-2.27 (m, 2H). |
| 72 | (400 MHz, DMSO-$d_6$): δ 8.40-8.37 (m, 1H), 8.22-8.19 (m, 1H), 7.83 (d, J = 16.3 Hz, 1H), 6.81-6.55 (m, 3H), 6.21-6.14 (m, 1H), 5.74-5.66 (m, 1H), 5.39-5.26 (m, 1H), 4.14-4.09 (m, 0.5H), 3.97-3.86 (m, 2H), 3.78-3.68 (m, 2H), 3.58-3.50 (m, 0.5H), 2.48-2.32 (m, 2H). |
| 73 | (400 MHz, DMSO-$d_6$): δ 8.13 (d, J = 1.4 Hz, 1H), 7.78 (d, J = 17.7 Hz, 1H), 7.50 (d, J = 8.4 Hz, 1H), 6.72 (brs, 2H), 6.61-6.47 (m, 1H), 6.19-6.01 (m, 1H), 5.74-5.55 (m, 1H), 5.37-5.15 (m, 1H), 4.17 (t, J = 7.6 Hz, 4H), 4.09-3.78 (m, 2H), 3.69-3.46 (m, 2H), 2.45-2.25 (m, 4H). |
| 74 | (400 MHz, DMSO-$d_6$): δ 8.30 (s, 1H), 7.63 (d, J = 8.7 Hz, 1H), 6.75 (brs, 2H), 6.72-6.52 (m, 1H), 6.22-6.11 (m, 1H), 5.75-5.62 (m, 1H), 5.60-5.42 (m, 1H), 4.25 (t, J = 7.7 Hz, 4H), 4.15-3.86 (m, 2H), 3.87-3.58 (m, 2H), 2.49-2.31 (m, 4H). |
| 75 | (400 MHz, DMSO-$d_6$): δ 8.14 (s, 1H), 7.96 (d, J = 8.8 Hz, 1H), 7.84 (d, J = 17.9 Hz, 1H), 7.06-6.41 (m, 3H), 6.20-6.04 (m, 1H), 5.73-5.53 (m, 1H), 5.39-5.14 (m, 1H), 4.16-3.41 (m, 4H), 2.77 (s, 3H), 2.37-2.24 (m, 2H). |

Example 76: Preparation of (S)-1-(3-(4-amino-5-((2-(trifluoromethyl)benzo[d]oxazol-5-yl)ethynyl)-7H-pyrrolo[2,3-d]pyrimidin-7-yl)pyrrolidin-1-yl)prop-2-en-1-one

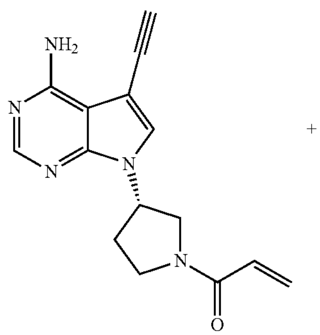

+

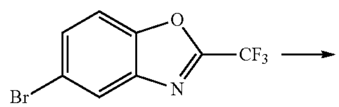

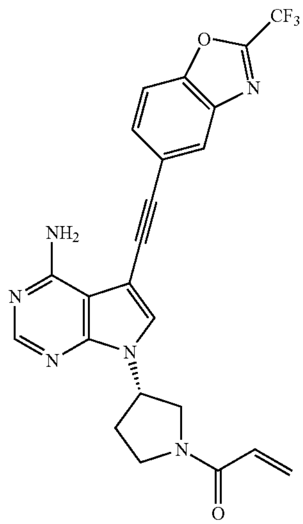

(S)-1-(3-(4-amino-5-ethynyl-7H-pyrrolo[2,3-d]pyrimidin-7-yl)pyrrolidin-1-yl)prop-2-en-1-one (30 mg, 0.1 mmol), 5-bromo-2-(trifluoromethyl)benzo[d]oxazole (28 mg, 0.1 mmol), triethylamine (0.2 mL), cuprous iodide (2 mg, 0.01 mmol) and tetrakis(triphenylphosphine)palladium (12 mg, 0.01 mmol) were added to DMF (1 mL). The reaction mixture was stirred at 80° C. for 12 hrs under nitrogen protection, and then directly separated by the reverse phase column chromatography and lyophilized to obtain (S)-1-(3-(4-amino-5-((2-(trifluoromethyl)benzo[d]oxazol-5-yl)ethynyl)-7H-pyrrolo[2,3-d]pyrimidin-7-yl)pyrrolidin-1-yl)prop-2-en-1-one (3.5 mg, yield: 6%). MS m/z (ESI): 467 $[M+H]^+$.

$^1$HNMR (400 MHZ, DMSO-$d_6$): δ 8.21 (s, 1H), 8.12 (s, 1H), 7.96-7.94 (d, J=8 Hz, 1H), 7.81-7.79 (d, J=8 Hz, 1H), 7.75-7.73 (d, 1H J=8 Hz, 1H), 6.85-6.48 (m, 3H), 6.14-6.07 (m, 1H), 5.67-5.59 (m, 1H), 5.34-5.18 (m, 1H), 4.06-3.43 (m, 4H), 2.40-2.28 (m, 2H).

Example 77: Preparation of (E)-1-(3-(4-amino-3-((2-(azetidin-1-yl)-4,6-difluorobenzo[d]oxazol-5-yl)ethynyl)-1H-pyrazolo[3,4-d]pyrimidin-1-yl)azetidin-1-yl)-4-(dimethylamino)but-2-en-1-one

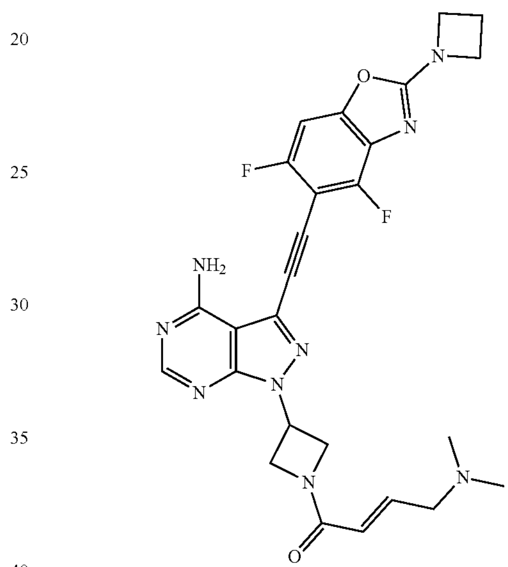

Step 1: Synthesis of 1-(azetidin-3-yl)-3-iodo-1H-pyrazolo[3,4-d]pyrimidin-4-amine

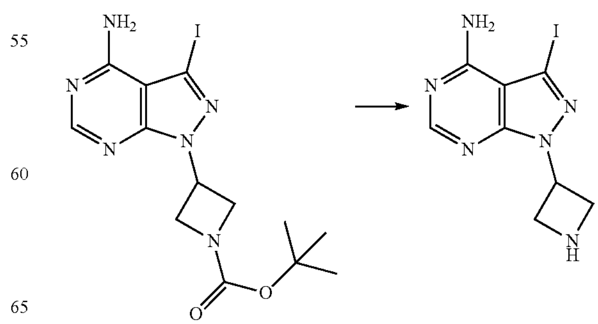

Tert-butyl 3-(4-amino-3-iodo-1H-pyrazolo[3,4-d]pyrimidin-1-yl)azetidine-1-carboxylate (2000 mg, 4.81 mmol) was dissolved in dichloromethane (20 mL), and HCl/dioxane solution (5 mL) was added. The reaction mixture was stirred at room temperature for 2 hrs. After the reaction was completed, the reaction mixture was concentrated to dryness to obtain 1-(azetidin-3-yl)-3-iodo-1H-pyrazolo[3,4-d]pyrimidin-4-amine (1400 mg, yield: 82.64%). MS m/z (ESI): 317 $[M+H]^+$.

Step 2: Synthesis of (E)-1-(3-(4-amino-3-iodo-1H-pyrazolo[3,4-d]pyrimidin-1-yl)azetidin-1-yl)-4-(dimethylamino) but-2-en-1-one

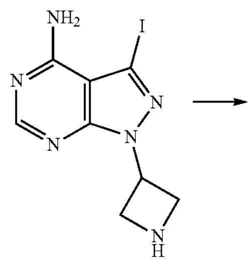

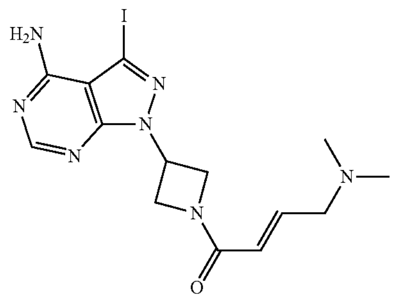

1-(azetidin-3-yl)-3-iodo-1H-pyrazolo[3,4-d]pyrimidin-4-amine (700 mg, 1.99 mmol) was dissolved in N,N-dimethylformamide (5 mL), and (2E)-4-(dimethylamino)but-2-enoic acid (394.59 mg, 2.38 mmol), 2-(7-azabenzotriazol-1-yl)-N,N,N',N'-tetramethyluronium hexafluorophosphate (1132.38 mg, 2.98 mmol) and N,N-diisopropylethylamine (769.79 mg, 5.96 mmol) were added. The reaction mixture was stirred at room temperature for 2 hrs. After the reaction was completed, the reaction mixture was separated by the reverse phase chromatography to obtain (E)-1-(3-(4-amino-3-iodo-1H-pyrazolo[3,4-d]pyrimidin-1-yl)azetidin-1-yl)-4-(dimethylamino)but-2-en-1-one (400 mg, yield: 47%). MS m/z (ESI): 428 $[M+H]^+$.

Step 3: Synthesis of (E)-1-(3-(4-amino-3-((2-(azetidin-1-yl)-4,6-difluorobenzo[d]oxazol-5-yl)ethynyl)-1H-pyrazolo[3,4-d]pyrimidin-1-yl)azetidin-1-yl)-4-(dimethylamino)but-2-en-1-one

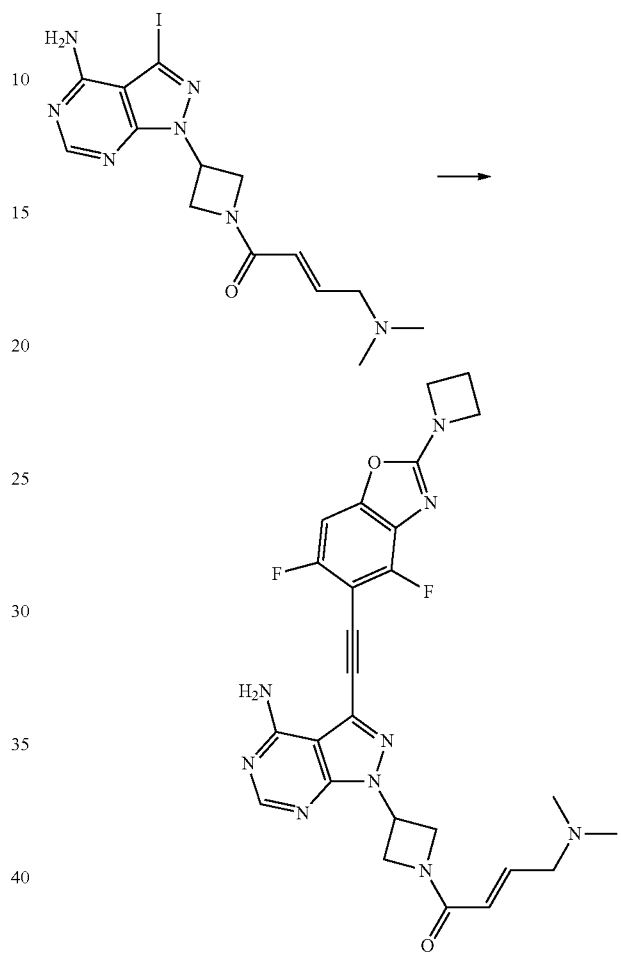

(E)-1-(3-(4-amino-3-iodo-1H-pyrazolo[3,4-d]pyrimidin-1-yl)azetidin-1-yl)-4-(dimethylamino)but-2-en-1-one (100 mg, 0.23 mmol), 2-(azetidin-1-yl)-5-ethynyl-4,6-difluoro-1,3-benzoxazole (65.77 mg, 0.28 mmol), triethylamine (1 mL), cuprous iodide (4.46 mg, 0.02 mmol) an d bis[5-(diphenylphosphinoalkyl)cyclopent-1,3-dien-1-yl]iron palladium dichloride (8.56 mg, 0.01 mmol) were added to DMF (5 mL). The reaction mixture was stirred at 60° C. for 2 hrs under nitrogen protection, and then directly separated by the reverse phase column chromatography to obtain (E)-1-(3-(4-amino-3-((2-(azetidin-1-yl)-4,6-difluorobenzo[d]oxazol-5-yl)ethynyl)-1H-pyrazolo[3,4-d]pyrimidin-1-yl)azetidin-1-yl)-4-(dimethylamino)but-2-en-1-one (30 mg, yield: 24%). MS m/z (ESI): 534 $[M+H]^+$.

$^1$H NMR (400 MHz, DMSO-$d_6$): δ 8.51-7.86 (m, 2H), 7.55 (d, J=8.4 Hz, 1H), 6.77-6.28 (m, 2H), 6.11 (d, J=15.4 Hz, 1H), 5.82-5.52 (m, 1H), 4.67 (t, J=8.6 Hz, 1H), 4.54 (dd, J=9.3, 5.2 Hz, 1H), 4.38 (t, J=9.3 Hz, 1H), 4.24 (dd, J=10.6, 5.2 Hz, 1H), 4.18 (t, J=7.6 Hz, 4H), 2.97 (d, J=6.2 Hz, 2H), 2.40-2.34 (m, 2H), 2.08 (s, 6H).

Examples 78 can be Prepared by Selecting Corresponding Raw Materials According to all or Part of the Synthesis Method in Example 77.

| Example No. | Structural formula | Chemical name | $[M + H]^+$ |
|---|---|---|---|
| 78 | 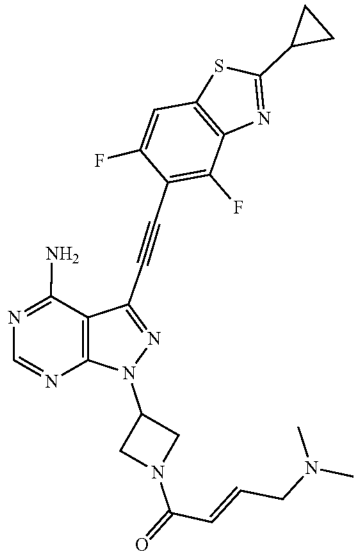 [SMILES: CN(C)C/C=C/C(=O)N1CC(n2nc(C#Cc3c(F)cc4sc(C5CC5)nc4c3F)c3c(N)ncnc32)C1] | (E)-1-(3-(4-amino-3-((2-cyclopropyl-4,6-difluoro-benzo[d]thiazol-5-yl)ethynyl)-1H-pyrazolo[3,4-d]pyrimidin-1-yl)azetidin-1-yl)-4-(dimethylamino)but-2-en-1-one | 535 |

$^1H$ NMR Data of the Compounds Prepared in the Above Examples are as Follows:

| Example No. | $^1H$ NMR |
|---|---|
| 78 | (400 MHz, DMSO-$d_6$): δ 8.51-8.17 (m, 2H), 8.04 (dd, J = 8.8, 1.3 Hz, 1H), 6.89-6.29 (m, 2H), 6.33-6.10 (m, 1H), 5.88-5.54 (m, 1H), 4.76 (t, J = 8.7 Hz, 1H), 4.62 (dd, J = 9.2, 5.2 Hz, 1H), 4.46 (t, J = 9.4 Hz, 1H), 4.32 (dd, J = 10.6, 5.3 Hz, 1H), 3.15-3.08 (m, 2H), 2.65-2.54 (m, 1H), 2.21 (s, 6H), 1.36-1.15 (m, 4H). |

Biological Test Evaluation

I. Cell Proliferation Assay for Tel-FGFR2 WT and Various Mutant FGFR2 in Baf3

By transfection, cell strains of the intracellular kinase domain fusion protein of TEL-FGFR2 WT or the intracellular domain fusion proteins containing FGFR2 V564I, V564F, V564L, N549K and K659M mutations were stably expressed in Baf cells. On day 1, the cell suspension was plated into a 96-well plate containing growth medium (DMEM containing 1% Glutamax, 10% FBS and 1% Pen/Strep) at 2000-4000 cells/90 μL/per well, and then the mixture was incubated overnight at 37° C. and 5% $CO_2$. On day 2, 10 μL of growth medium containing a 10-fold stock solution of test compound was added to the cell culture (9 dose points, 3× serial dilution, starting from 1 μM, finally 0.3% DMSO). After incubation at 37° C. and 5% $CO_2$ for 48 hrs, 50 μL of CellTiter Glo (CTG) reagent was added to the cell-containing 96-well plate on day 3, and the plate was then incubated at room temperature for 10 min. Then relative light units (RLUs) were measured on a microplate reader with a luminescence detection module. RLU values were normalized to % survival, and concentration-response curves were plotted using Prism to calculate $IC_{50}$ (nM).

TABLE 1

Biological Test Results

| | BaF3 $IC_{50}$(nM) | | | | | |
|---|---|---|---|---|---|---|
| Example No. | WT (FGFR2) | V564F (FGFR2) | V564L (FGFR2) | V564I (FGFR2) | N549K (FGFR2) | K659M (FGFR2) |
| 1 | ++++ | ++++ | ++++ | +++++ | ++++ | ++++ |
| 2 | ++++ | +++++ | ++++ | NT | ++++ | NT |
| 3 | ++++ | ++++ | ++++ | NT | ++++ | NT |
| 4 | ++++ | ++++ | NT | NT | NT | NT |
| 5 | ++++ | ++++ | NT | NT | NT | NT |
| 6 | NT | NT | NT | NT | NT | NT |
| 7 | ++++ | ++++ | +++ | NT | +++ | NT |
| 8 | NT | NT | NT | NT | NT | NT |
| 9 | NT | NT | NT | NT | NT | NT |

TABLE 1-continued

| Biological Test Results | | | | | | |
|---|---|---|---|---|---|---|
| | BaF3 $IC_{50}$(nM) | | | | | |
| Example No. | WT (FGFR2) | V564F (FGFR2) | V564L (FGFR2) | V564I (FGFR2) | N549K (FGFR2) | K659M (FGFR2) |
| 10 | NT | NT | NT | NT | NT | NT |
| 11 | NT | NT | NT | NT | NT | NT |
| 12 | NT | NT | NT | NT | NT | NT |
| 13 | NT | NT | NT | NT | NT | NT |
| 14 | NT | NT | NT | NT | NT | NT |
| 15 | NT | NT | NT | NT | NT | NT |
| 16 | NT | NT | NT | NT | NT | NT |
| 17 | NT | NT | NT | NT | NT | NT |
| 18 | ++++ | NT | NT | NT | NT | NT |
| 19 | NT | NT | NT | NT | NT | NT |
| 20 | ++++ | ++++ | ++++ | +++++ | ++++ | +++ |
| 21 | NT | NT | NT | NT | NT | NT |
| 22 | NT | NT | NT | NT | NT | NT |
| 23 | NT | NT | NT | NT | NT | NT |
| 24 | NT | NT | NT | NT | NT | NT |
| 25 | NT | NT | NT | NT | NT | NT |
| 26 | NT | NT | NT | NT | NT | NT |
| 27 | NT | NT | NT | NT | NT | NT |
| 28 | NT | NT | NT | NT | NT | NT |
| 29 | +++ | ++++ | NT | NT | NT | NT |
| 30 | +++ | ++++ | NT | NT | NT | NT |
| 31 | +++ | ++++ | NT | NT | NT | NT |
| 32 | NT | NT | NT | NT | NT | NT |
| 33 | +++ | ++++ | NT | NT | NT | NT |
| 34 | ++++ | ++++ | NT | NT | NT | NT |
| 35 | ++++ | +++++ | NT | NT | NT | NT |
| 36 | +++++ | +++++ | NT | +++++ | NT | ++++ |
| 37 | NT | NT | NT | NT | NT | NT |
| 38 | ++++ | ++++ | NT | NT | NT | NT |
| 39 | ++++ | ++++ | NT | NT | NT | NT |
| 40 | NT | NT | NT | NT | NT | NT |
| 41 | ++ | +++ | ++++ | NT | +++ | NT |
| 42 | ++++ | +++++ | ++++ | NT | ++++ | +++ |
| 43 | +++ | ++++ | NT | NT | NT | NT |
| 44 | ++++ | ++++ | ++++ | +++++ | ++++ | NT |
| 45 | +++ | ++++ | ++++ | NT | ++++ | NT |
| 46 | NT | NT | NT | NT | NT | NT |
| 47 | ++++ | +++++ | NT | NT | NT | NT |
| 48 | ++++ | ++++ | ++++ | +++++ | ++++ | NT |
| 49 | NT | NT | NT | NT | NT | NT |
| 50 | ++++ | ++++ | NT | NT | NT | NT |
| 51 | ++++ | +++++ | ++++ | +++++ | ++++ | NT |
| 52 | ++++ | ++++ | +++ | NT | +++ | NT |
| 53 | ++++ | ++++ | ++++ | +++++ | ++++ | NT |
| 54 | +++ | ++++ | ++++ | NT | ++++ | NT |
| 55 | +++ | +++ | +++ | NT | ++++ | NT |
| 56 | NT | NT | NT | NT | NT | NT |
| 57 | ++++ | +++++ | ++++ | +++++ | ++++ | NT |
| 58 | NT | NT | NT | NT | NT | NT |
| 59 | ++++ | ++++ | ++++ | +++++ | ++++ | NT |
| 60 | +++ | ++++ | NT | NT | NT | NT |
| 61 | NT | NT | NT | NT | NT | NT |
| 62 | ++++ | +++++ | ++++ | +++++ | ++++ | +++ |
| 63 | +++ | ++++ | NT | NT | NT | NT |
| 64 | NT | NT | NT | NT | NT | NT |
| 65 | +++++ | +++++ | NT | NT | NT | NT |
| 67 | +++ | ++++ | NT | NT | NT | NT |
| 68 | +++++ | +++++ | +++++ | NT | +++++ | ++++ |
| 69 | ++++ | +++++ | ++++ | NT | ++++ | +++ |
| 70 | +++ | ++++ | NT | NT | NT | NT |
| 71 | ++++ | ++++ | +++ | NT | ++++ | NT |
| 72 | +++ | +++ | NT | NT | NT | NT |
| 73 | +++++ | +++++ | NT | NT | NT | NT |
| 74 | ++++ | +++++ | ++++ | +++++ | ++++ | +++ |
| 75 | ++++ | ++++ | NT | +++++ | NT | ++++ |
| 76 | NT | NT | NT | NT | NT | NT |

TABLE 1-continued

| Biological Test Results | | | | | | |
|---|---|---|---|---|---|---|
| | BaF3 $IC_{50}$(nM) | | | | | |
| Example No. | WT (FGFR2) | V564F (FGFR2) | V564L (FGFR2) | V564I (FGFR2) | N549K (FGFR2) | K659M (FGFR2) |
| 77 | ++++ | +++++ | ++++ | NT | ++++ | +++ |
| 78 | ++++ | +++++ | ++++ | NT | ++++ | +++ |

Notes

1. "NT" is an abbreviation of "Not Tested", and means that an object has not been detected yet.

2. "+++++" indicates that the $IC_{50}$ value ≤0.5 nM; "++++" indicates that 0.5 nM < $IC_{50}$ value ≤5.0 nM; "+++" indicates that 5.0 nM < $IC_{50}$ value ≤50.0 nM; "++" indicates that 50.0 nM < $IC_{50}$ value ≤500.0 nM; "+" indicates that 500.0 nM is < $IC_{50}$ value.

II. Cell Proliferation Assay for Tel-FGFR3 WT and FGFR3 V555M in BaF3

For the compounds of the Examples of the present invention, cell strains of TEL-FGFR3 WT intracellular kinase domain fusion protein or intracellular domain fusion protein containing FGFR3 V555M or FGFR3 N540K mutation were stably expressed in Baf cells by transfection and were used to determine the cell proliferation effect of BaF3-Tel-FGFR3 WT. FGFR3 V555M or FGFR3 N540K. The specific test process was as follows:

1) The cell suspension was plated into a 96-well plate containing growth medium (DMEM containing 1% Glutamax, 10% FBS and 1% Pen/Strep) at 2000-4000 cells/90 µL/per well, and then the mixture was incubated overnight at 37° C. and 5% $CO_2$.
2) 10 µL of growth medium containing a 10-fold stock solution of test compound was added to the cell culture (9 dose points, 3× serial dilution, starting from 1 µM, finally 0.3% DMSO).
3) The mixture was incubated at 37° C. and 5% $CO_2$ for 48 hrs.
4) 50 µL of CellTiter Glo (CTG) reagent was added to the cell-containing 96-well plate, and the plate was then incubated at room temperature for 10 min.
5) Relative light units (RLUs) were measured on a microplate reader with a luminescence detection module. RLU values were normalized to % survival, and concentration-response curves were plotted using Prism to calculate $IC_{50}$ (nM). The test results are shown in the table below.

TABLE 2

| Biological Test Results | | | |
|---|---|---|---|
| Example | BaF3 $IC_{50}$(nM) | | |
| No. | WT(FGFR3) | V555M(FGFR3) | N540K(FGFR3) |
| 1 | ++++ | ++++ | ++++ |
| 2 | ++++ | +++ | NT |
| 3 | ++++ | +++ | NT |
| 4 | NT | NT | NT |
| 5 | NT | NT | NT |
| 6 | NT | NT | NT |
| 7 | +++ | +++ | NT |
| 8 | NT | NT | NT |
| 9 | NT | NT | NT |
| 10 | NT | NT | NT |
| 11 | NT | NT | NT |
| 12 | NT | NT | NT |
| 13 | NT | NT | NT |
| 14 | NT | NT | NT |
| 15 | NT | NT | NT |
| 16 | NT | NT | NT |
| 17 | NT | NT | NT |
| 18 | NT | NT | NT |
| 19 | NT | NT | NT |
| 20 | ++++ | ++++ | ++++ |
| 21 | NT | NT | NT |
| 22 | NT | NT | NT |
| 23 | NT | NT | NT |
| 24 | NT | NT | NT |
| 25 | NT | NT | NT |
| 26 | NT | NT | NT |
| 27 | NT | NT | NT |
| 28 | NT | NT | NT |
| 29 | +++ | +++ | NT |
| 30 | +++ | +++ | NT |
| 31 | +++ | +++ | NT |
| 32 | NT | NT | NT |
| 33 | +++ | ++ | NT |
| 34 | +++ | ++++ | NT |
| 35 | ++++ | ++++ | NT |
| 36 | +++++ | ++++ | NT |
| 37 | NT | NT | NT |
| 38 | ++++ | +++ | NT |
| 39 | NT | NT | NT |
| 40 | NT | NT | NT |
| 41 | ++ | ++ | NT |
| 42 | ++++ | +++ | NT |
| 43 | NT | NT | NT |
| 44 | +++ | +++ | NT |
| 45 | +++ | +++ | NT |
| 46 | NT | NT | NT |
| 47 | ++++ | +++ | NT |
| 48 | ++++ | ++++ | NT |
| 49 | NT | NT | NT |
| 50 | +++ | +++ | NT |
| 51 | ++++ | ++++ | NT |
| 52 | ++++ | +++ | NT |
| 53 | +++ | +++ | NT |
| 54 | +++ | +++ | NT |
| 55 | +++ | +++ | NT |
| 56 | NT | NT | NT |
| 57 | ++++ | +++ | NT |
| 58 | NT | NT | NT |
| 59 | ++++ | ++++ | NT |
| 60 | NT | NT | NT |
| 61 | NT | NT | NT |
| 62 | ++++ | ++++ | ++++ |
| 63 | +++ | +++ | NT |
| 64 | NT | NT | NT |
| 65 | ++++ | ++++ | NT |
| 67 | ++++ | ++++ | +++ |
| 68 | +++++ | +++++ | ++++ |
| 69 | ++++ | +++++ | NT |
| 70 | NT | NT | NT |
| 71 | ++++ | +++ | NT |
| 72 | +++ | ++ | NT |
| 73 | ++++ | ++++ | NT |

TABLE 2-continued

Biological Test Results

| Example | BaF3 $IC_{50}$(nM) | | |
|---|---|---|---|
| No. | WT(FGFR3) | V555M(FGFR3) | N540K(FGFR3) |
| 74 | ++++ | +++++ | ++++ |
| 75 | +++++ | ++++ | NT |
| 76 | ++ | ++ | NT |
| 77 | ++++ | ++++ | +++ |
| 78 | +++++ | +++++ | +++ |

Notes

1. "NT" is an abbreviation of "Not Tested", and means that an object has not been detected yet.
2. "+++++" indicates that the $IC_{50}$ value ≤ 0.5 nM; "++++" indicates that 0.5 nM < $IC_{50}$ value ≤ 5.0 nM; "+++" indicates that 5.0 nM < $IC_{50}$ value ≤ 50.0 nM; "++" indicates that 50.0 nM < $IC_{50}$ value ≤ 500.0 nM; "+" indicates that 500.0 nM is < $IC_{50}$ value.

From the biological activity data of the compounds of specific Examples, the series of compounds of the present invention have strong inhibition effect on wild-type FGFRs and mutant FGFRs at cellular level, and the inhibition effect for the mutations is not weakened.

All documents mentioned in the present invention are incorporated as references, just as each document is individually cited as a reference. In addition, it should be understood that various modifications or changes may be made by those skilled in the art after reading the above disclosure of the present invention, and these equivalent forms also fall within the scope defined by the claims appended hereto.

We claim:

1. A compound of formula (II), a stereoisomer or pharmaceutically acceptable salt thereof:

(I)

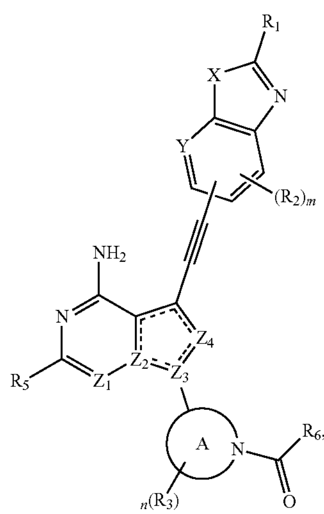

wherein, "---" is a double bond or a single bond;

X is O or S; Y is $CR_4$ or N;

$Z_1$ and $Z_4$ are each independently N or $CR_7$;

$Z_2$ and $Z_3$ are each independently N or C;

ring A is 3-8 membered nitrogen-containing heterocyclyl, wherein, the nitrogen atom is connected to carbonyl;

$R_1$ is selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, —$SF_5$, —$S(O)_rR_8$, —O—$R_9$, —C(O)$OR_9$, —C(O)$R_{10}$, —O—C(O)$R_{10}$, —$NR_{11}R_{12}$, —C(=$NR_{11}$)$R_{10}$, —N($R_{11}$)—C(=$NR_{12}$)$R_{10}$, —C(O)$NR_{11}R_{12}$ and —N($R_{11}$)—C(O)$R_{10}$, the above groups are optionally further substituted with one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{5-8}$ aryl, 5-8 membered heteroaryl, =O, —$SF_5$, —$S(O)_rR_8$, —O—$R_9$, —C(O) $OR_9$, —C(O)$R_{10}$, —O—C(O)$R_{10}$, —$NR_{11}R_{12}$, —C(=$NR_{11}$) $R_{10}$, —N($R_{11}$)—C(=$NR_{12}$)$R_{10}$, —C(O)$NR_{11}R_{12}$ and —N($R_{11}$)—C(O)$R_{10}$;

each $R_2$ is independently selected from the group consisting of hydrogen, deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, —$SF_5$, —$S(O)_rR_8$, —O—$R_9$, —C(O)$OR_9$, —C(O)$R_{10}$, —O—C(O)$R_{10}$, —$NR_{11}R_{12}$, —C(=$NR_{11}$)$R_{10}$, —N($R_{11}$)—C(=$NR_{12}$)$R_{10}$, —C(O) $NR_{11}R_{12}$ and—N($R_{11}$)—C(O)$R_{10}$;

each $R_3$ is independently selected from the group consisting of hydrogen, deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, —$SF_5$, —$S(O)_rR_8$, —$CH_2$—O—$R_9$, —C(O) $OR_9$, —C(O)$R_{10}$, —O—C(O)$R_{10}$, —$NR_{11}R_{12}$, —C(=$NR_{11}$)$R_{10}$, —N($R_{11}$)—C(=$NR_{12}$)$R_{10}$, —C(O) $NR_{11}R_{12}$ and—N($R_{11}$)—C(O)$R_{10}$;

$R_4$ is selected from the group consisting of hydrogen, deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, —$SF_5$, —$S(O)_rR_8$, —O—$R_9$, —C(O)$OR_9$, —C(O)$R_{10}$, —O—C(O)$R_{10}$, —$NR_{11}R_{12}$, —C(=$NR_{11}$)$R_{10}$, —N($R_{11}$)—C(=$NR_{12}$) $R_{10}$, —C(O) $NR_{11}R_{12}$ and —N($R_{11}$)—C(O)$R_{10}$;

$R_6$ is selected from the group consisting of $C_{1-4}$ alkyl, $C_{2-4}$ alkenyl, $C_{2-4}$ alkynyl, $C_{3-6}$ cycloalkyl, 3-6 membered heterocyclyl, —C(O)$R_{10}$, —$NR_{11}R_{12}$, —C(=$NR_{11}$)$R_{10}$ and—N($R_{11}$)—C(=$NR_{12}$)$R_{10}$, the above groups are optionally further substituted with one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, =O, —$SF_5$, —$S(O)_rR_8$, —O—$R_9$, —C(O) $OR_9$, —C(O)$R_{10}$, —O—C(O)$R_{10}$, —$CH_2$—$NR_{11}R_{12}$, —C(=$NR_{11}$) $R_{10}$, —N($R_{11}$)—C(=$NR_{12}$) $R_{10}$, —C(O) $NR_{11}R_{12}$ and —N($R_{11}$)—C(O)$R_{10}$;

each $R_7$ is independently selected from the group consisting of hydrogen, deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, —$SF_5$, —$S(O)_rR_8$, —O—$R_9$, —C(O)$OR_9$, —C(O)$R_{10}$, —O—C(O)$R_{10}$, —$NR_{11}R_{12}$, —C(=$NR_{11}$)$R_{10}$, —N($R_{11}$)—C(=$NR_{12}$)$R_{10}$, —C(O) $NR_{11}R_{12}$ and —N($R_{11}$)—C(O)$R_{10}$;

each $R_8$ is independently selected from the group consisting of hydrogen, deuterium, hydroxy, $C_{1-10}$ alkyl, $C_{2-10}$ alkenyl, $C_{3-12}$ cycloalkyl, 3-12 membered heterocyclyl, $C_{5-10}$ aryl, 5-10 membered heteroaryl and —$NR_{11}R_{12}$, the above groups are optionally further substituted with one or more substituents selected from the group consisting of deuterium, halogen, hydroxy, oxo, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{5-10}$ aryl, $C_{5-10}$ aryloxy, 5-10 membered heteroaryl, 5-10 membered heteroaryloxy and —$NR_{11}R_{12}$;

each $R_9$ is independently selected from the group consisting of hydrogen, deuterium, $C_{1-10}$ alkyl, $C_{2-10}$ alkenyl, $C_{3-12}$ cycloalkyl, 3-12 membered heterocyclyl, $C_{5-10}$ aryl and 5-10 membered heteroaryl, the above groups are optionally further substituted with one or more substituents selected from the group consisting of deuterium, halogen, hydroxy, oxo, cyano, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{5-10}$ aryl, $C_{5-10}$ aryloxy, 5-10 membered heteroaryl, 5-10 membered heteroaryloxy and —$NR_{11}R_{12}$;

each $R_{10}$ is independently selected from the group consisting of hydrogen, deuterium, hydroxy, $C_{1-10}$ alkyl, $C_{1-10}$ alkoxy, $C_{2-10}$ alkenyl, $C_{2-10}$ alkynyl, $C_{3-12}$ cycloalkyl, $C_{3-12}$ cycloalkyloxy, 3-12 membered heterocyclyl, 3-12 membered heterocyclyloxy, $C_{5-10}$ aryl, $C_{5-10}$ aryloxy, 5-10 membered heteroaryl, 5-10 membered heteroaryloxy and —$NR_{11}R_{12}$, the above groups are optionally further substituted with one or more substituents selected from the group consisting of deuterium, halogen, hydroxy, cyano, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{5-10}$ aryl, $C_{5-10}$ aryloxy, 5-10 membered heteroaryl, 5-10 membered heteroaryloxy and —$NR_{11}R_{12}$;

each of $R_{11}$ and $R_{12}$ is independently selected from the group consisting of hydrogen, deuterium, hydroxy, $C_{1-10}$ alkoxy, $C_{1-10}$ alkyl, $C_{2-10}$ alkenyl, $C_{2-10}$ alkynyl, $C_{3-12}$ cycloalkyl, 3-12 membered heterocyclyl, $C_{5-10}$ aryl, 5-10 membered heteroaryl, sulfinyl, sulfonyl, methylsulfonyl, isopropylsulfonyl, cyclopropylsulfonyl, p-toluenesulfonyl, aminosulfonyl, dimethylaminosulfonyl, amino, monoalkylamino, dialkylamino and $C_{1-10}$ alkanoyl, the above groups are optionally further substituted with one or more substituents selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-10}$ alkanoyl;

or, $R_{11}$ and $R_{12}$, together with a nitrogen atom directly connected thereto, form 4-10 membered heterocyclyl, the above group is optionally further substituted with one or more substituents selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuteroalkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-10}$ alkanoyl;

m is 0, 1 or 2;

n is 0, 1, 2, 3 or 4; and each r is independently 0, 1 or 2.

2. The compound of formula (II), the stereoisomer or pharmaceutically acceptable salt thereof of claim 1, wherein, the compound of formula (II) is a compound having formula (IIIa) or formula (IIIb):

(IIIa)

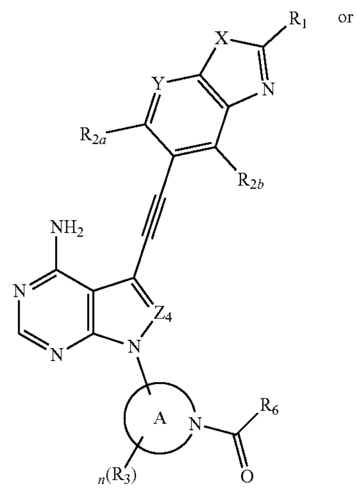

or (IIIb)

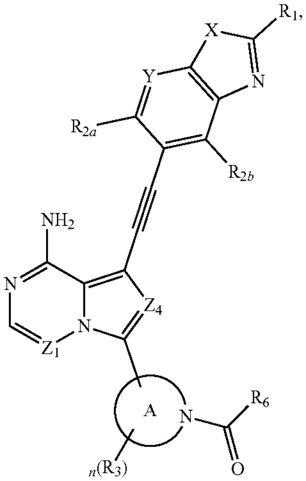

wherein, each Y is independently CH or N;

each ring A is independently 4-6 membered nitrogen-containing heterocyclyl, wherein, the nitrogen atom is connected to carbonyl;

each $R_1$ is independently selected from the group consisting of hydrogen, deuterium, halogen, cyano, $C_{1-4}$ alkyl, $C_{3-6}$ cycloalkyl, 3-6 membered heterocyclyl, —$SF_5$, —O—$R_9$, —C(O) $OR_9$, —C(O)$R_{10}$, —O—C(O)$R_{10}$ and —$NR_{11}R_{12}$, the above groups are optionally further substituted with one or more substituents selected from the group consisting of deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, =O, —$SF_5$, —O—$R_9$, —C(O)$OR_9$, —C(O)$R_{10}$, —O—C(O)$R_{10}$ and —$NR_{11}R_{12}$;

each of $R_{2a}$ and $R_{2b}$ is independently selected from the group consisting of hydrogen, deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, —$SF_5$, —O—$R_9$, —C(O) $OR_9$, —C(O)$R_{10}$, —O—C(O) $R_{10}$ and —$NR_{11}R_{12}$;

each $R_3$ is independently selected from the group consisting of hydrogen, deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, —$SF_5$, —$CH_2$—O—$R_9$, —C(O) $OR_9$, —C(O)$R_{10}$, —O—C(O)$R_{10}$ and —$NR_{11}R_{12}$;

each $R_6$ is independently vinyl, the above group is optionally further substituted with one or more substituents selected from the group consisting of deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, —O, —$SF_5$, —O—$R_9$, —C(O)O$R_9$, —C(O)$R_{10}$, —O—C(O)$R_{10}$ and —$CH_2$—N$R_{11}R_{12}$; and each $R_7$ is independently selected from the group consisting of hydrogen, deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, —$SF_5$, —O—$R_9$, —C(O)O$R_9$, —C(O)$R_{10}$, —O—C(O) $R_{10}$ and —N$R_{11}R_{12}$.

3. The compound of formula (II), the stereoisomer or pharmaceutically acceptable salt thereof of claim 2, wherein, ring A, together with—$(R_3)_n$, forms the following structure:

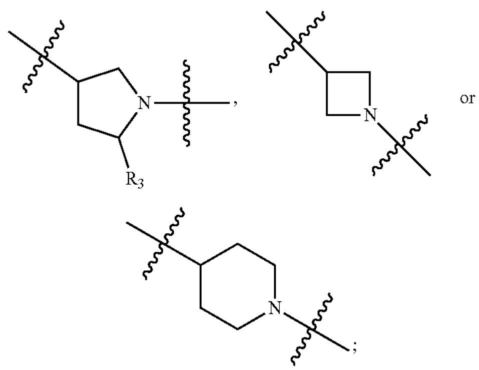

$R_3$ is selected from the group consisting of hydrogen, deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, —$SF_5$, —$CH_2$—O—$R_9$, —C(O)O$R_9$, —C(O)$R_{10}$, —O—C(O)$R_{10}$ and —N$R_{11}R_{12}$.

4. The compound of formula (II), the stereoisomer or pharmaceutically acceptable salt thereof of claim 1, wherein, the compound of formula (II) is a compound having formula ($IVa_1$) or formula ($IVa_2$):

($IVa_1$)

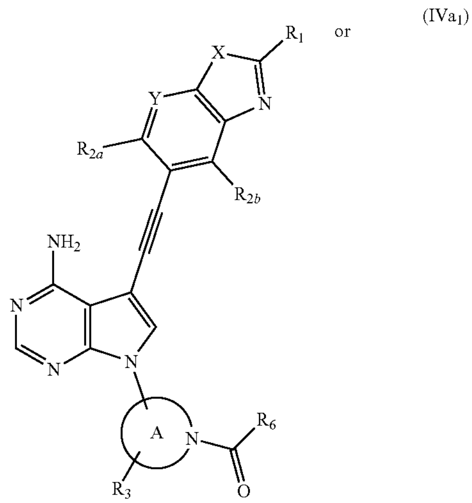

or

-continued ($IVa_2$)

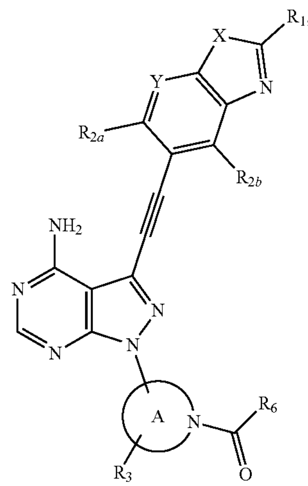

wherein, each Y is independently CH or N;

ring A, together with—$R_3$, forms the following structure:

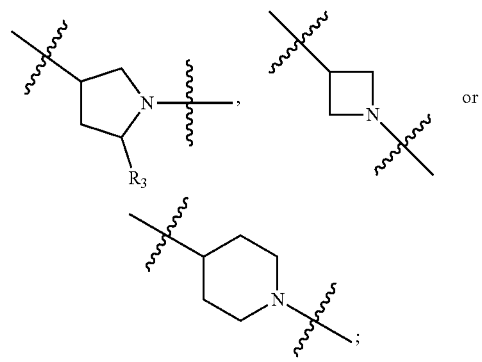

$R_3$ is selected from the group consisting of hydrogen, deuterium, halogen, $C_{1-4}$ alkyl, $C_{1-4}$ haloalkyl, $C_{1-4}$ deuterioalkyl and —$CH_2$—O—$R_9$;

each $R_1$ is independently selected from the group consisting of hydrogen, deuterium, fluorine, chlorine, cyano, $C_{1-4}$ alkyl, $C_{3-6}$ cycloalkyl, 3-6 membered heterocyclyl, —$SF_5$, —O—$R_9$, —C(O)O$R_9$, —C(O)$R_{10}$, —O—C(O)$R_{10}$ and —N$R_{11}R_{12}$, the above groups are optionally further substituted with one or more substituents selected from the group consisting of deuterium, fluorine, chlorine, cyano, $C_{1-4}$ alkyl, $C_{1-4}$ haloalkyl, $C_{1-4}$ deuterioalkyl, $C_{3-6}$ cycloalkyl, 3-6 membered heterocyclyl, —O, —$SF_5$, —O—$R_9$, —C(O) O$R_9$, —C(O) $R_{10}$, —O—C(O) $R_{10}$ and —N$R_{11}R_{12}$;

each of $R_{2a}$ and $R_{2b}$ is independently selected from the group consisting of hydrogen, deuterium, fluorine, chlorine, cyano, $C_{1-4}$ alkyl, $C_{1-4}$ haloalkyl, $C_{1-4}$ deuterioalkyl, $C_{3-6}$ cycloalkyl, —$SF_5$, —O—$R_9$, —C(O) O$R_9$, —C(O)$R_{10}$, —O—C(O) $R_{10}$ and —N$R_{11}R_{12}$; and each $R_6$ is independently vinyl, the above group is optionally further substituted with one or more substituents selected from the group consisting of deuterium, fluorine, cyano, methyl, ethyl, n-propyl and —$CH_2$—N$R_{11}R_{12}$.

5. The compound of formula (II), the stereoisomer or pharmaceutically acceptable salt thereof of claim 1, wherein, the compound of formula (II) is a compound having formula ($IVb_1$) or formula ($IVb_2$):

(IVb$_1$)

or

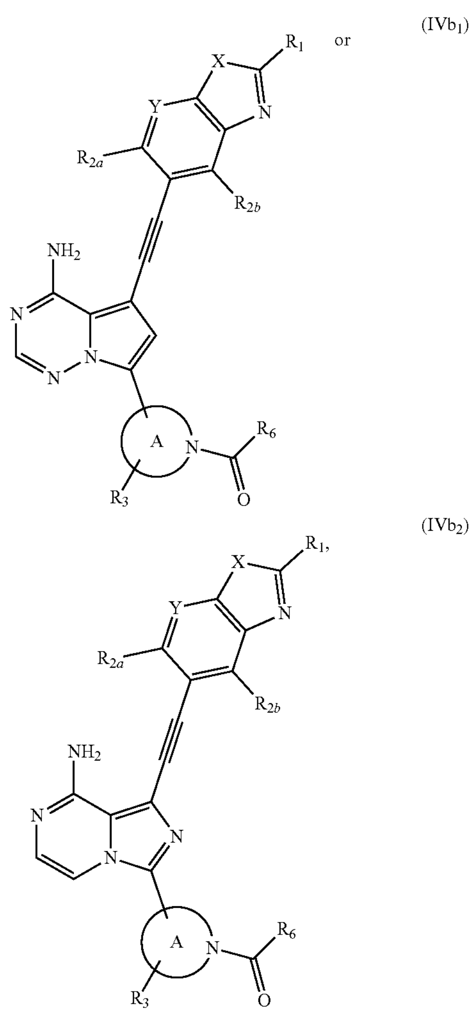

(IVb$_2$)

wherein, each Y is independently CH or N;

ring A, together with —$R_3$, forms the following structure:

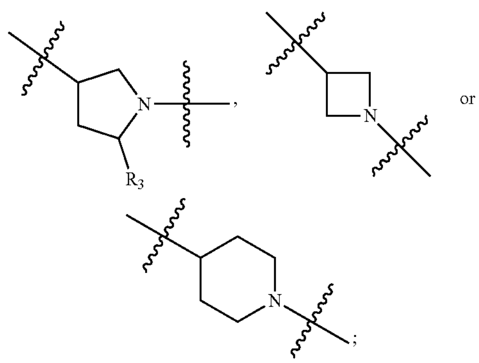

$R_3$ is selected from the group consisting of hydrogen, deuterium, halogen, $C_{1-4}$ alkyl, $C_{1-4}$ haloalkyl, $C_{1-4}$ deuterioalkyl and —$CH_2$—O—$R_9$;

each $R_1$ is independently selected from the group consisting of hydrogen, deuterium, fluorine, chlorine, cyano, $C_{1-4}$ alkyl, $C_{3-6}$ cycloalkyl, 3-6 membered heterocyclyl, —$SF_5$, —O—$R_9$, —C(O)O$R_9$, —C(O)$R_{10}$, —O—C(O)$R_{10}$ and —$NR_{11}R_{12}$, the above groups are optionally further substituted with one or more substituents selected from the group consisting of deuterium, fluorine, chlorine, cyano, $C_{1-4}$ alkyl, $C_{1-4}$ haloalkyl, $C_{1-4}$ deuterioalkyl, $C_{3-6}$ cycloalkyl, 3-6 membered heterocyclyl, =O, —$SF_5$, —O—$R_9$, —C(O) O$R_9$, —C(O) $R_{10}$, —O—C(O)$R_{10}$ and —$NR_{11}R_{12}$;

each of $R_{2a}$ and $R_{2b}$ is independently selected from the group consisting of hydrogen, deuterium, fluorine, chlorine, cyano, $C_{1-4}$ alkyl, $C_{1-4}$ haloalkyl, $C_{1-4}$ deuterioalkyl, $C_{3-6}$ cycloalkyl, —$SF_5$, —O—$R_9$, —C(O) O$R_9$, —C(O)$R_{10}$, —O—C(O) $R_{10}$ and —$NR_{11}R_{12}$; and each $R_6$ is independently vinyl, the above group is optionally further substituted with one or more substituents selected from the group consisting of deuterium, fluorine, cyano, methyl, ethyl, n-propyl and —$CH_2$—$NR_{11}R_{12}$.

6. The compound of formula (II), the stereoisomer or pharmaceutically acceptable salt thereof of claim 1, wherein, each $R_8$ is independently selected from the group consisting of hydrogen, deuterium, hydroxy, $C_{1-4}$ alkyl, $C_{2-4}$ alkenyl, $C_{3-6}$ cycloalkyl, 3-6 membered heterocyclyl, $C_{5-8}$ aryl, 5-8 membered heteroaryl and —$NR_{11}R_{12}$, the above groups are optionally further substituted with one or more substituents selected from the group consisting of deuterium, halogen, hydroxy, oxo, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy and —$NR_{11}R_{12}$;

each $R_9$ is independently selected from the group consisting of hydrogen, deuterium, $C_{1-4}$ alkyl, $C_{2-4}$ alkenyl, $C_{3-6}$ cycloalkyl, 3-6 membered heterocyclyl, $C_{5-8}$ aryl and 5-8 membered heteroaryl, the above groups are optionally further substituted with one or more substituents selected from the group consisting of deuterium, halogen, hydroxy, oxo, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy and —$NR_{11}R_{12}$;

each $R_{10}$ is independently selected from the group consisting of hydrogen, deuterium, hydroxy, $C_{1-4}$ alkyl, $C_{1-4}$ alkoxy, $C_{2-4}$ alkenyl, $C_{2-4}$ alkynyl, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy and —$NR_{11}R_{12}$, the above groups are optionally further substituted with one or more substituents selected from the group consisting of deuterium, halogen, hydroxy, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy and —$NR_{11}R_{12}$;

each of $R_{11}$ and $R_{12}$ is independently selected from the group consisting of hydrogen, deuterium, hydroxy, $C_{1-4}$ alkoxy, $C_{1-4}$ alkyl, $C_{2-4}$ alkenyl, $C_{2-4}$ alkynyl, $C_{3-6}$ cycloalkyl, 3-6 membered heterocyclyl, $C_{5-8}$ aryl, 5-8 membered heteroaryl, sulfinyl, sulfonyl, methylsulfonyl, isopropylsulfonyl, cyclopropylsulfonyl, p-toluenesulfonyl, aminosulfonyl, dimethylaminosulfonyl, amino, monoalkylamino, dialkylamino and $C_{1-4}$ alkanoyl, the above groups are optionally further substituted with one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy, amino, monoalkylamino, dialkylamino and $C_{1-4}$ alkanoyl;

or, $R_{11}$ and $R_{12}$, together with a nitrogen atom directly connected thereto, form 4-6 membered heterocyclyl, the above group is optionally further substituted with one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy, amino, monoalkylamino, dialkylamino and $C_{1-4}$ alkanoyl.

7. The compound of formula (II), the stereoisomer or pharmaceutically acceptable salt thereof of claim 1, wherein the compound is selected from the group consisting of:

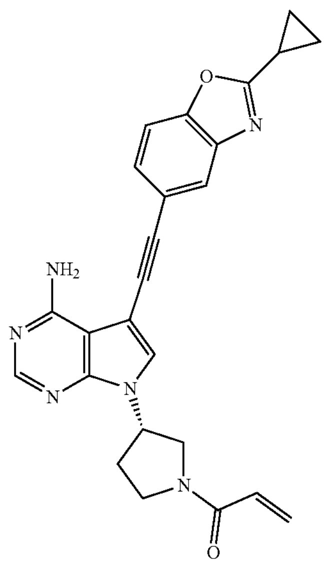

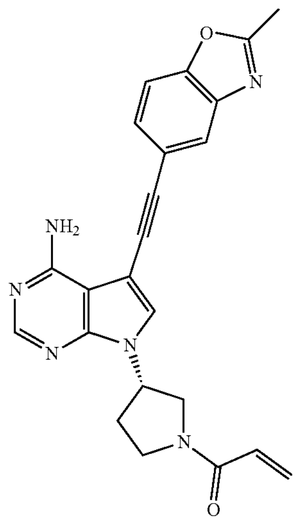

-continued

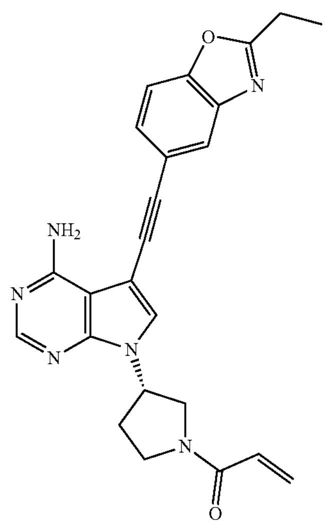

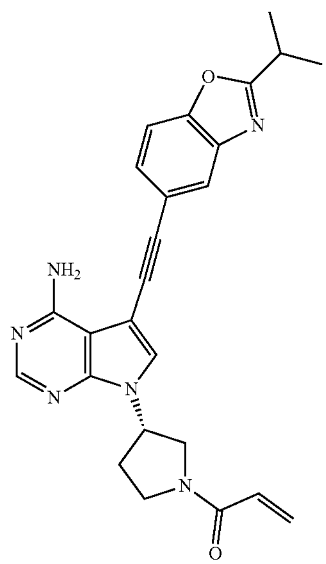

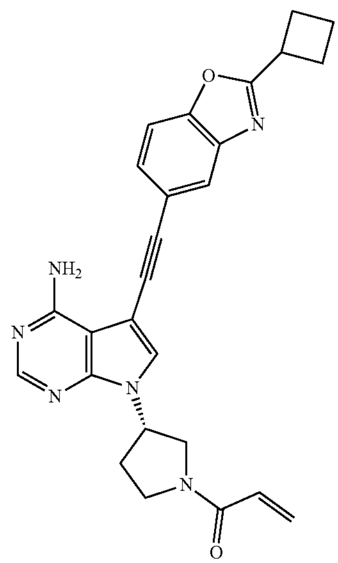

-continued
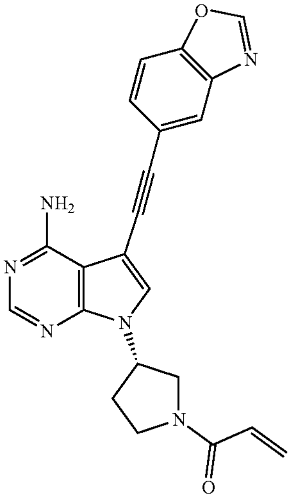
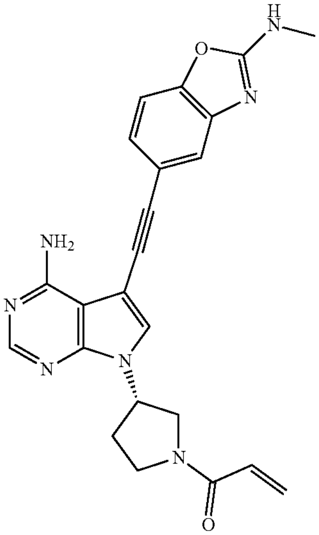 [SMILES: C=CC(=O)N1CC[C@H](n2cc(C#Cc3ccc4oc(NC)nc4c3)c3c(N)ncnc32)C1]
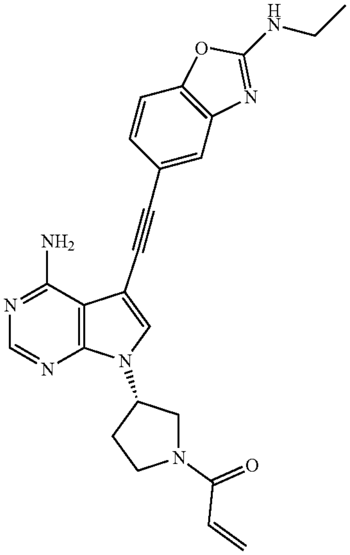
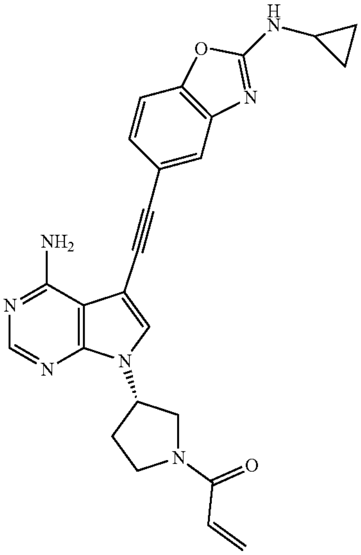
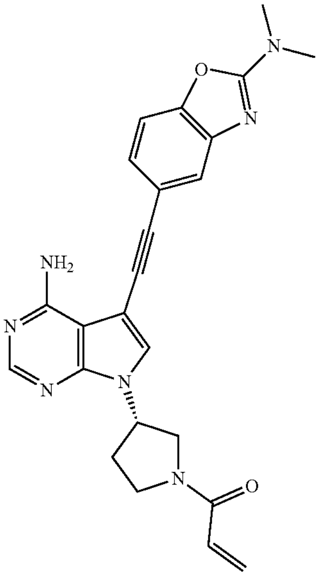
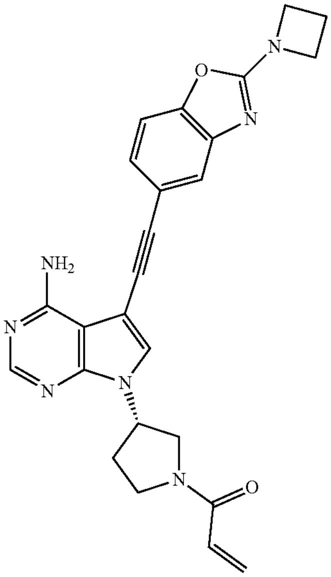
-continued -continued
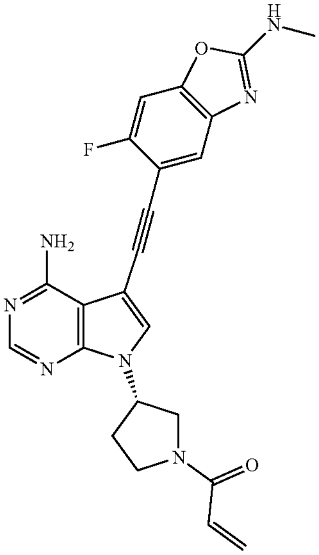
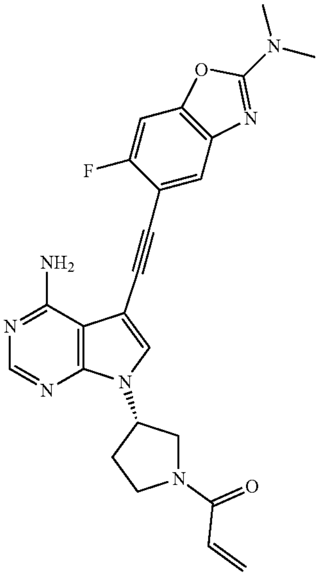
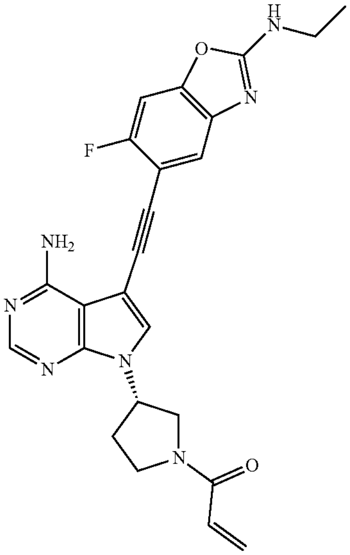
-continued
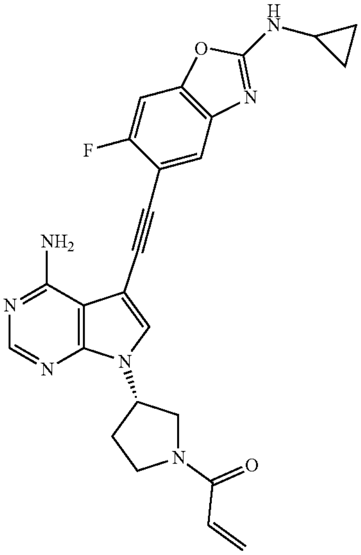
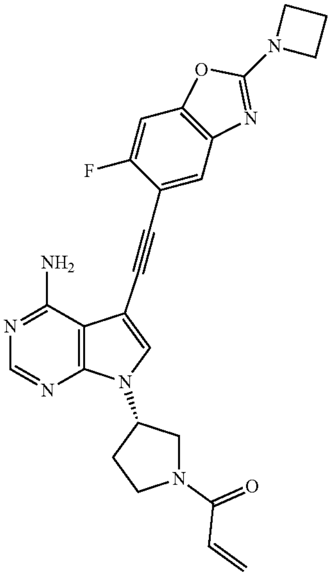
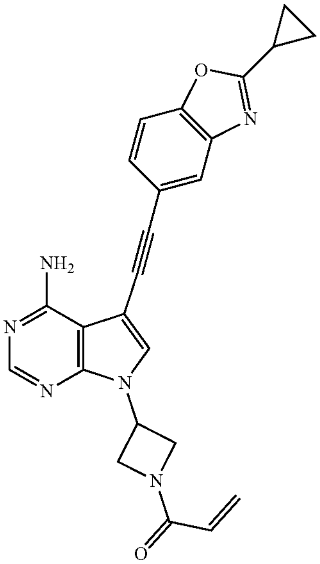

-continued
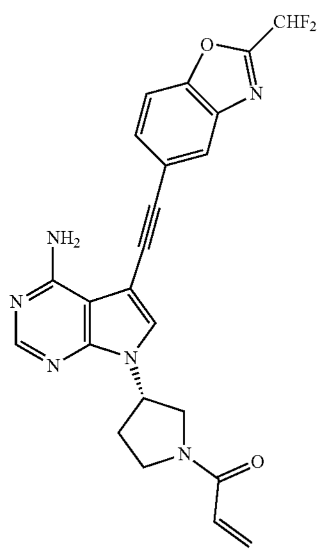
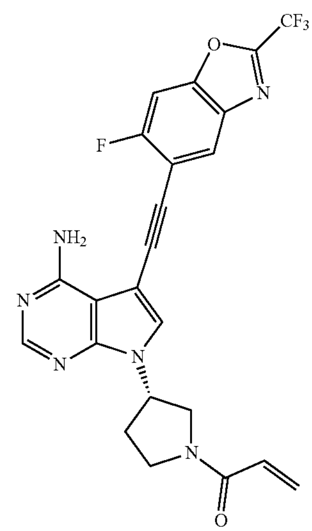
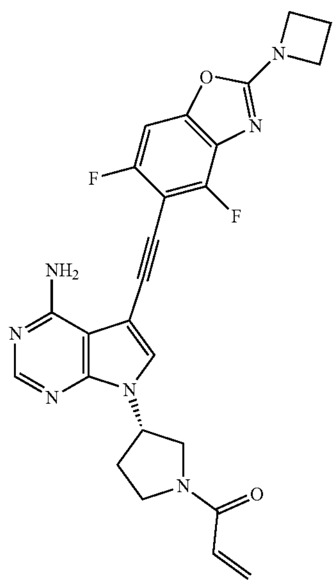
-continued
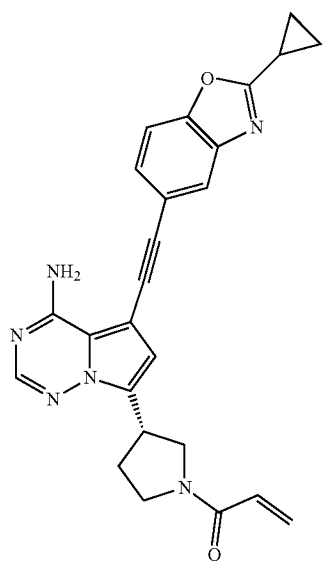
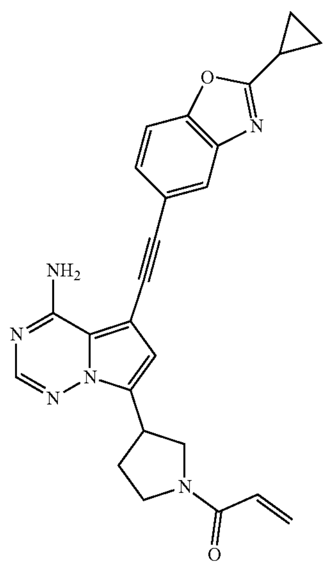
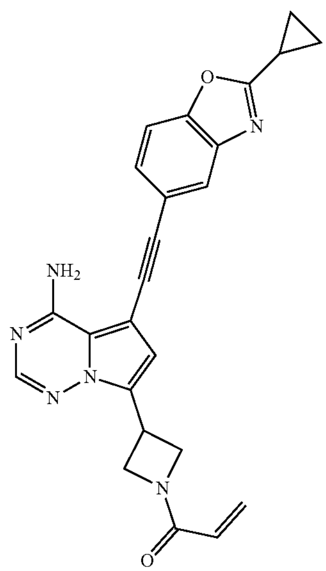

-continued
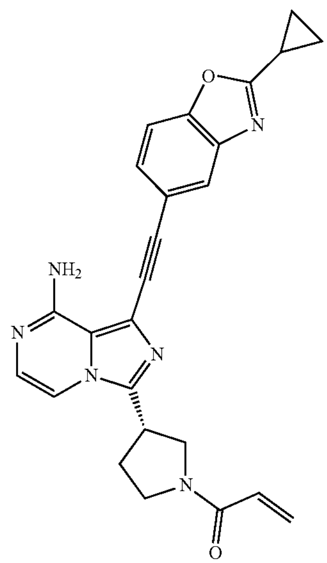
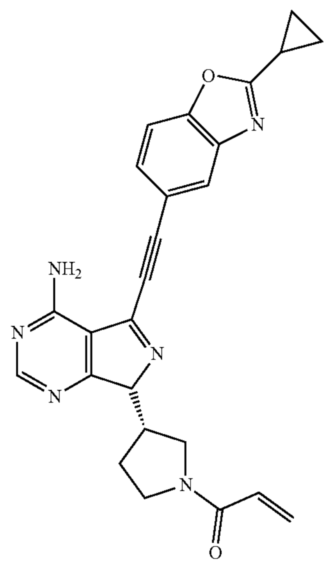
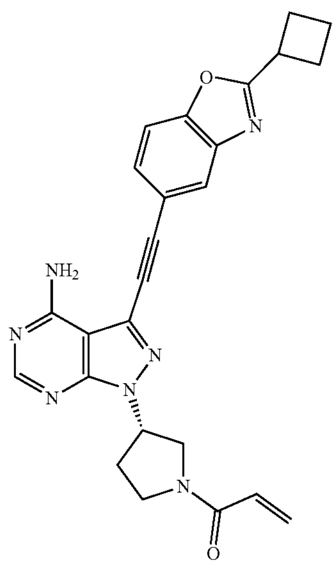
-continued
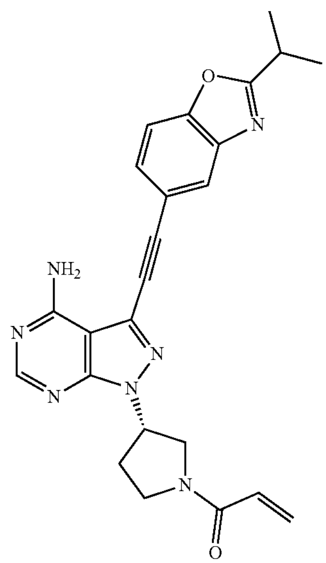
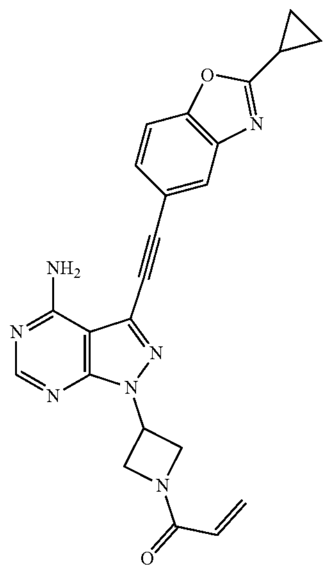
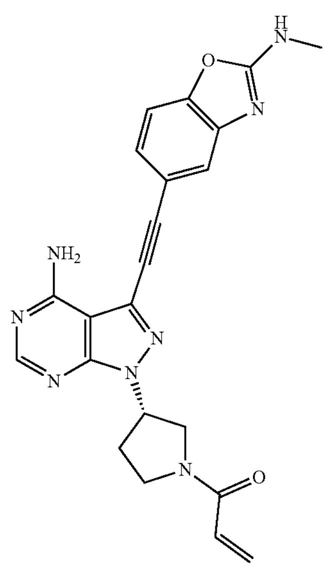

-continued
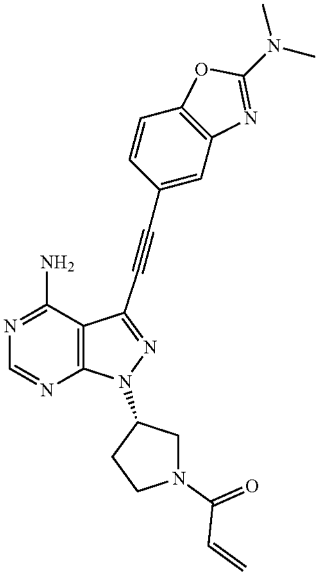
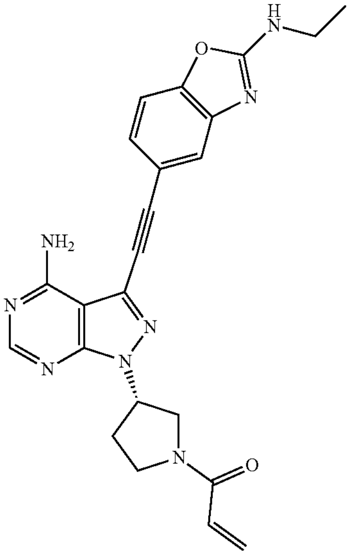
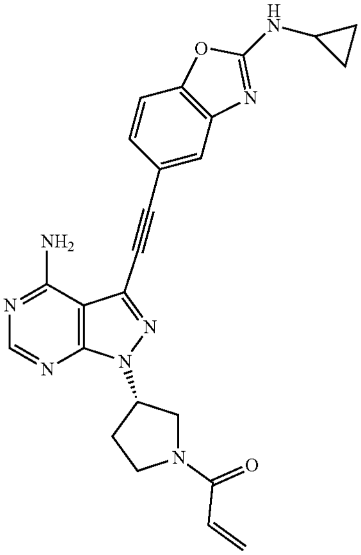
-continued
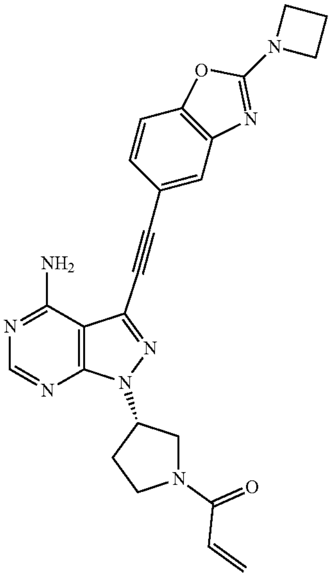
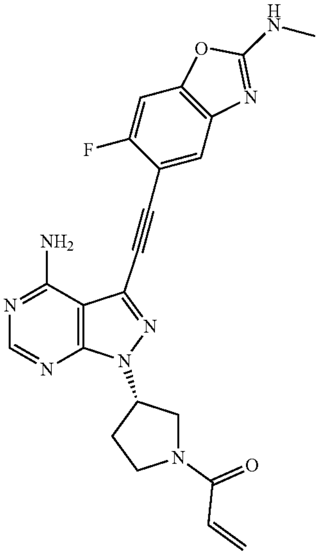
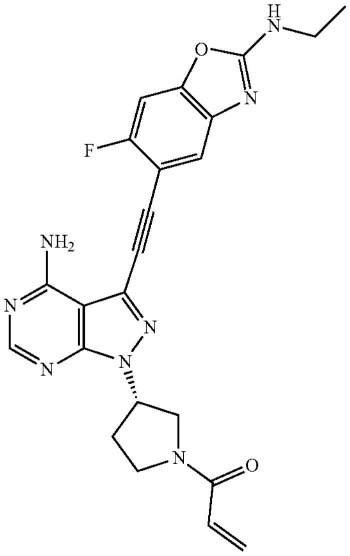

-continued
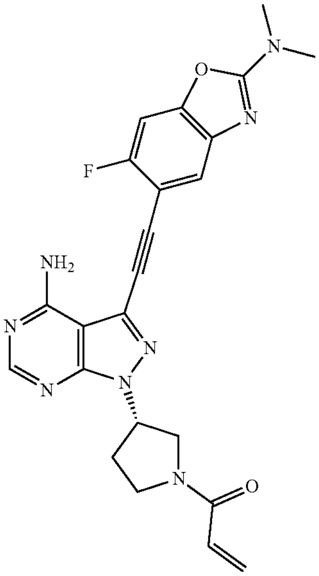
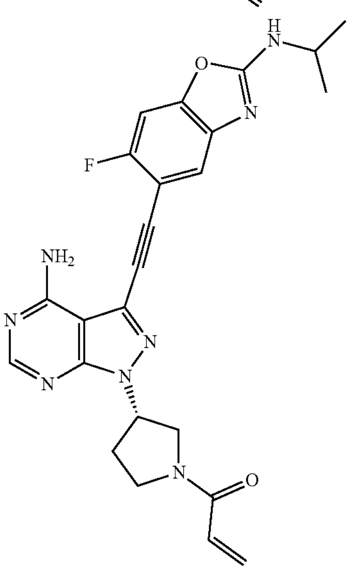
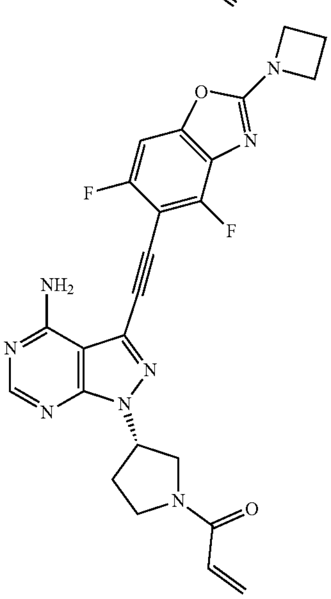
-continued
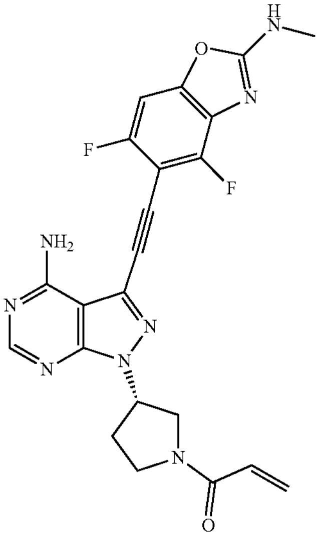
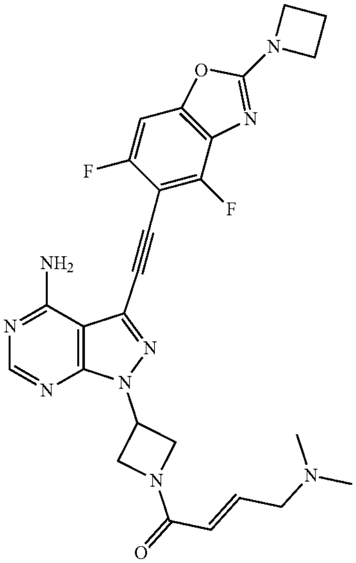
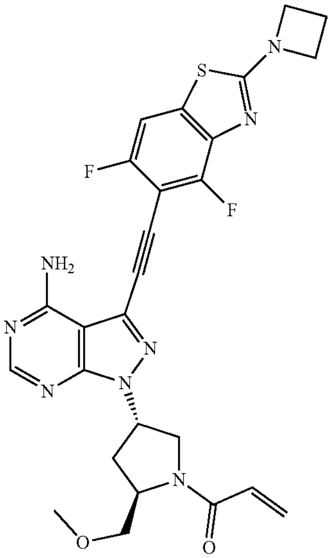

-continued
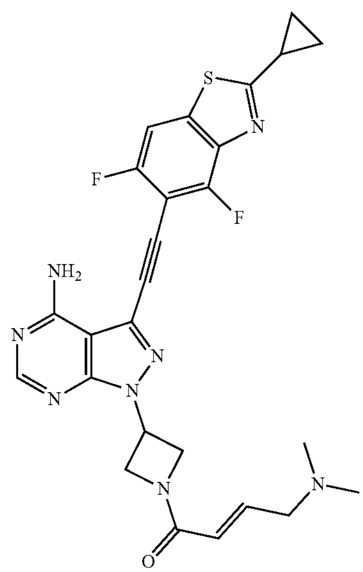
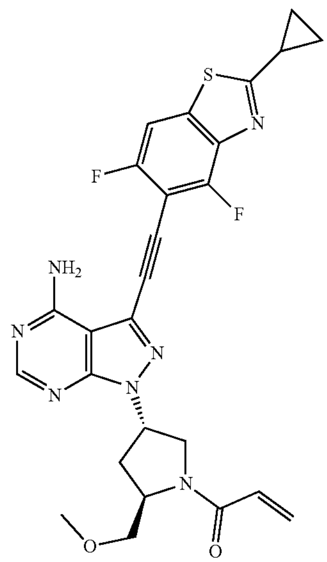
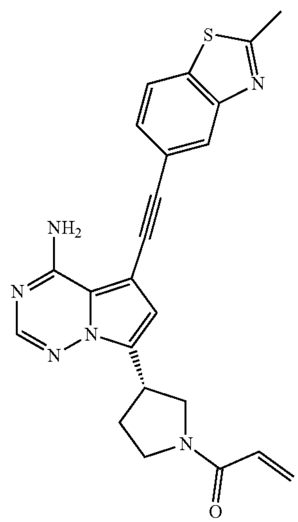
-continued
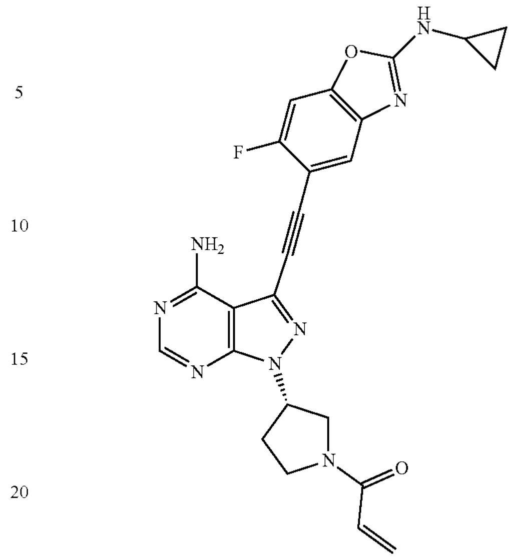
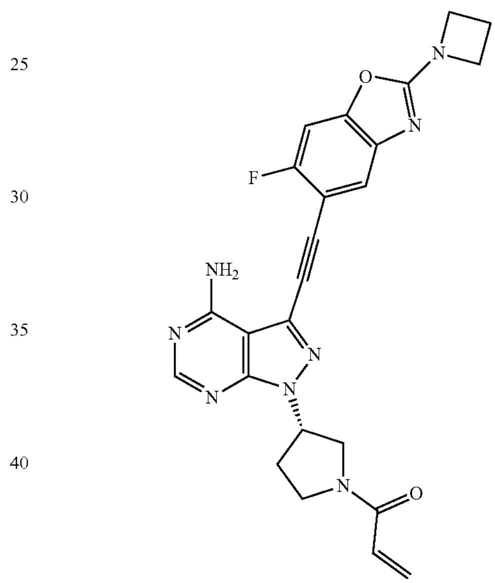
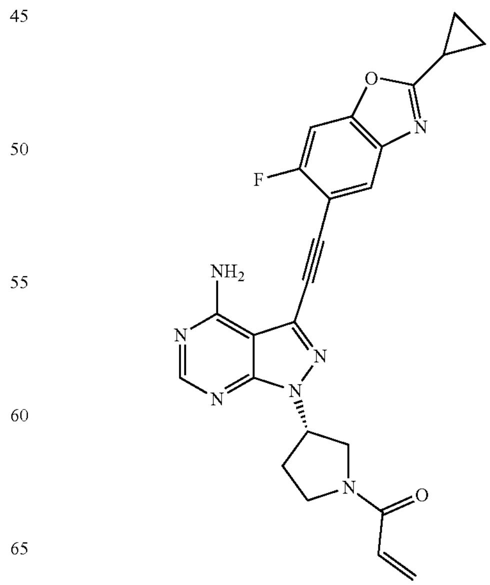

-continued
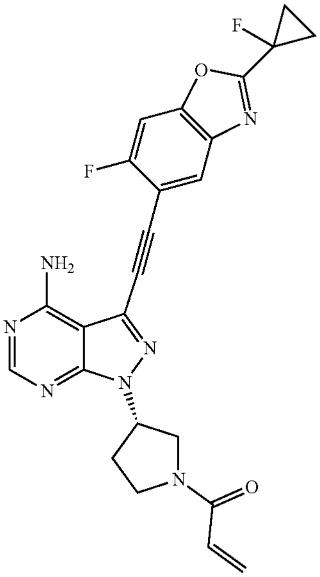
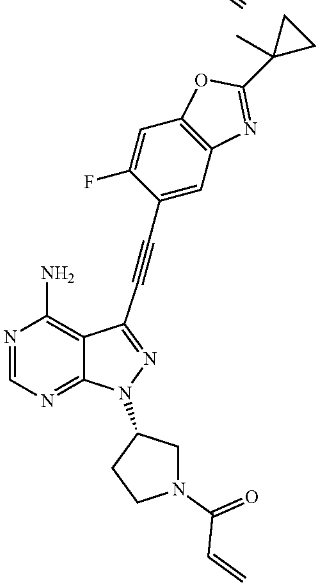
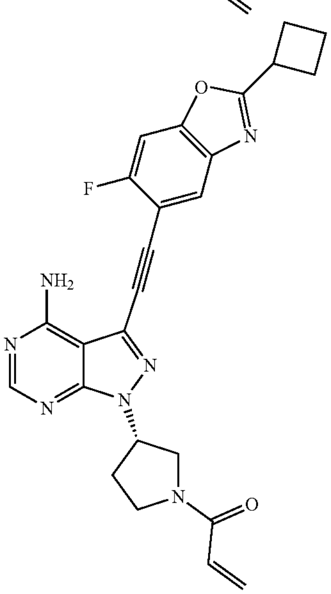
-continued
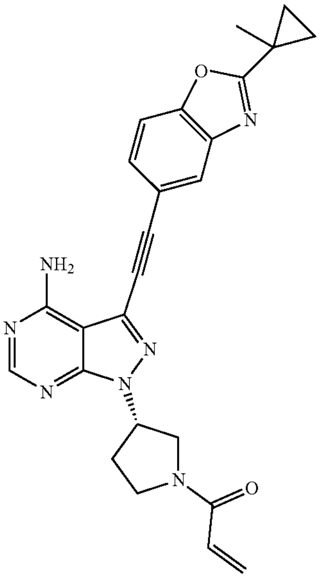
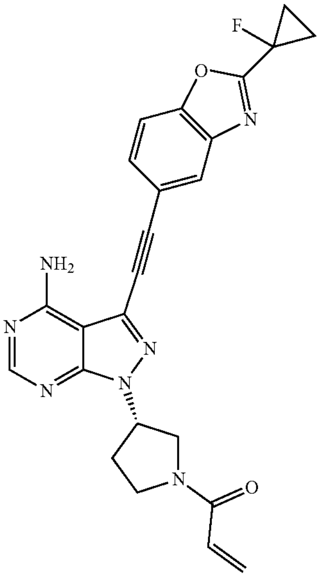
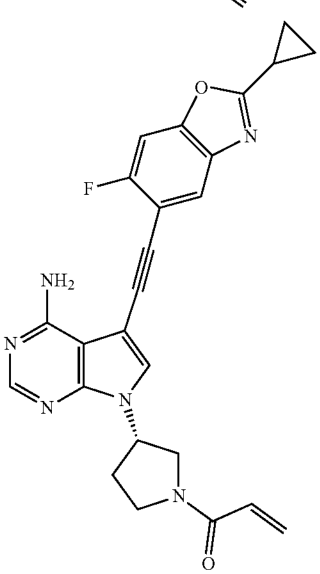

-continued
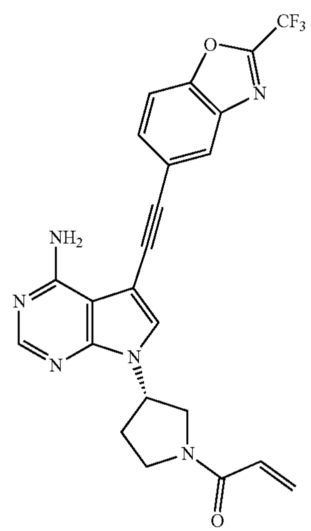
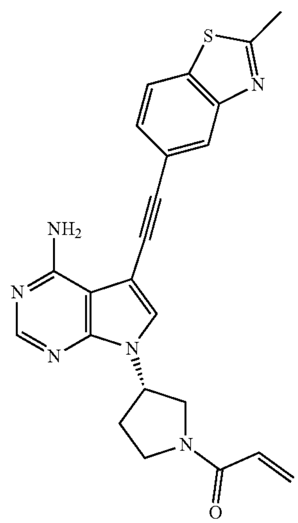
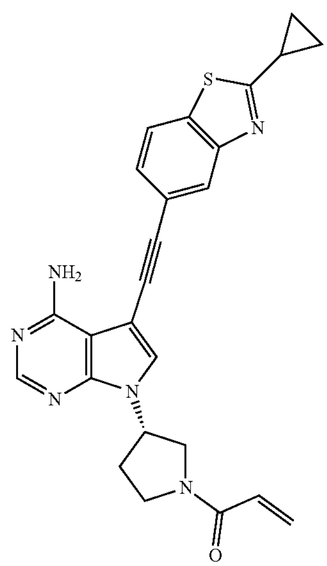
-continued
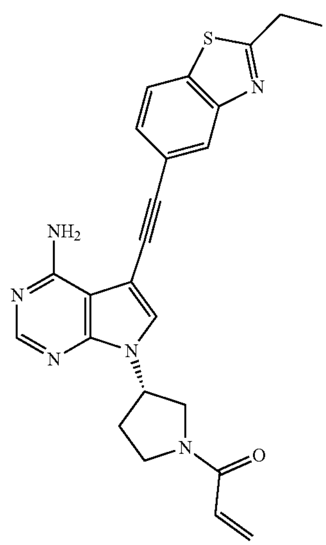
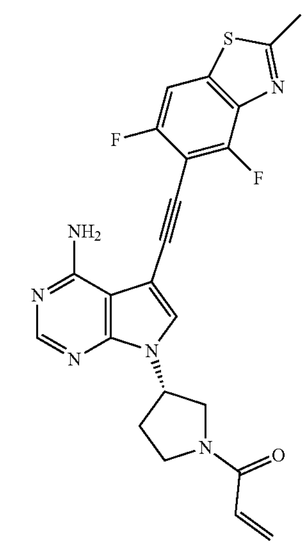
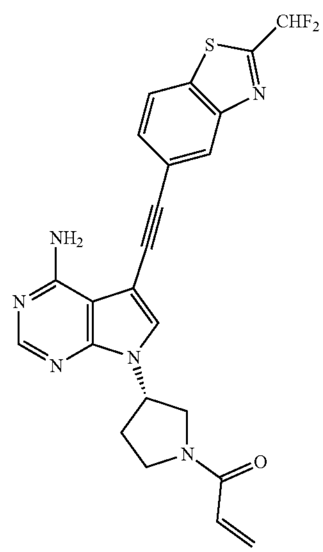

-continued
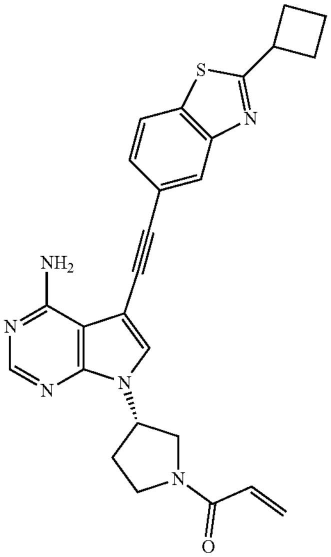
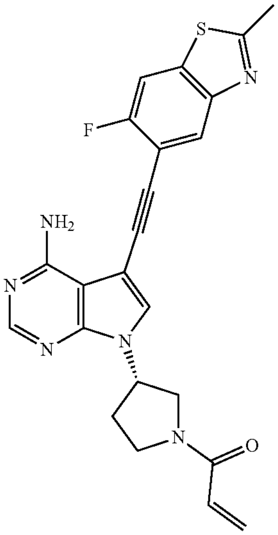
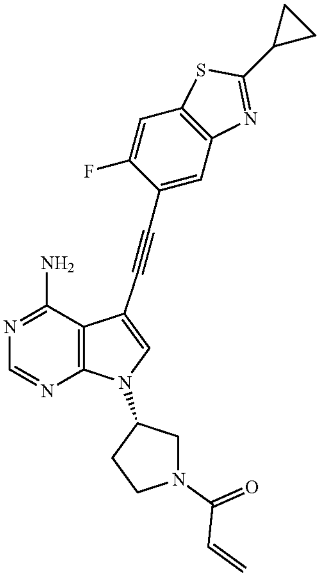
-continued
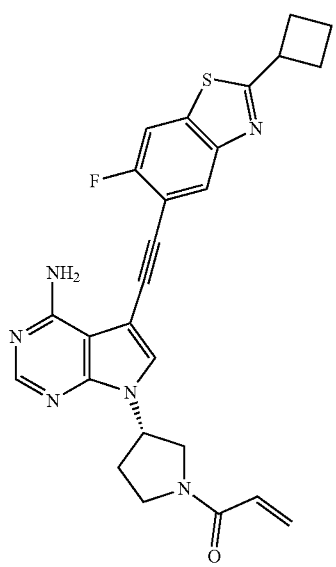
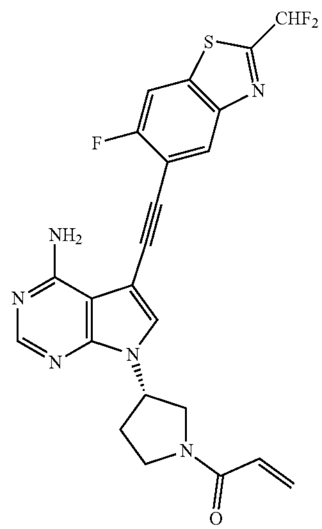
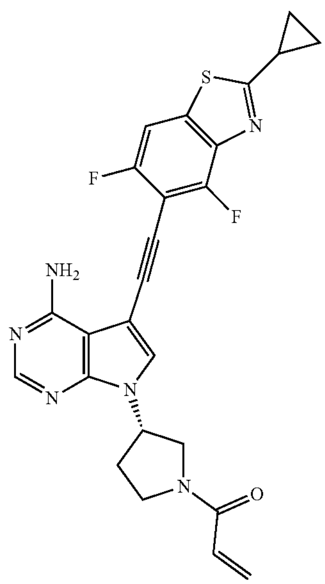

-continued
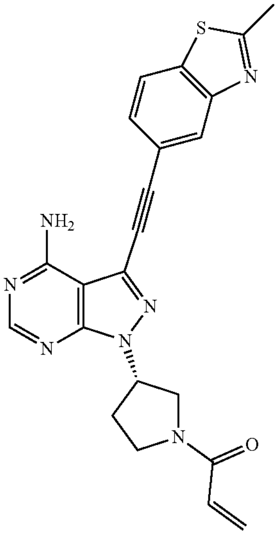
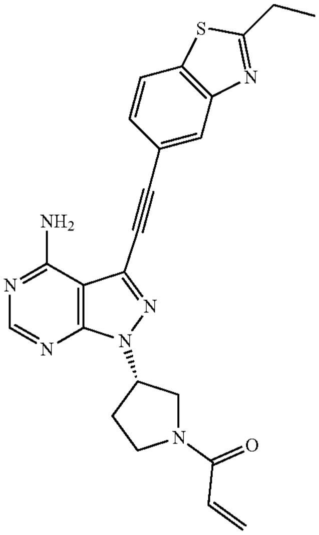
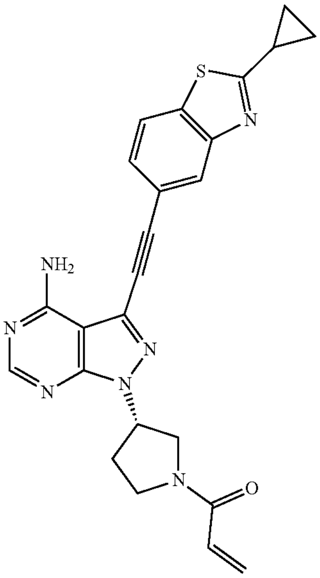
-continued
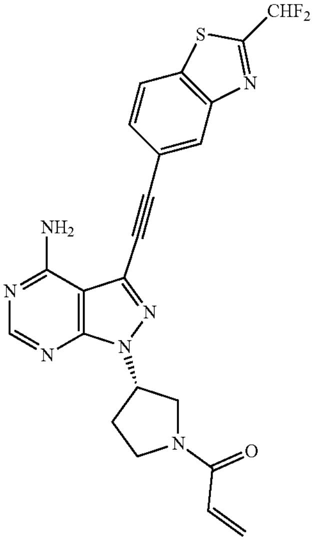
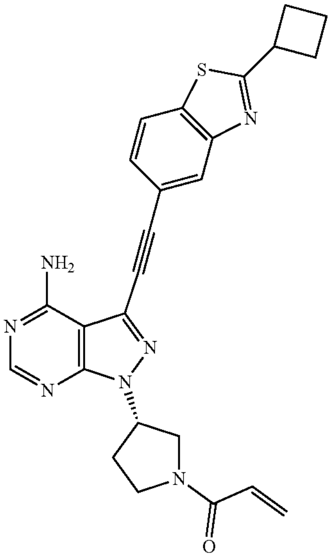
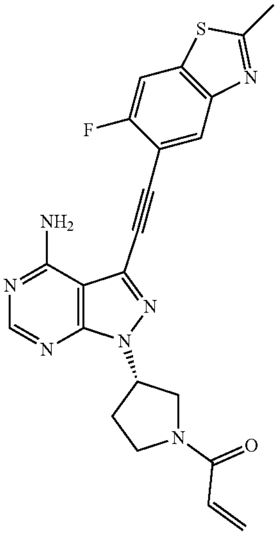

-continued
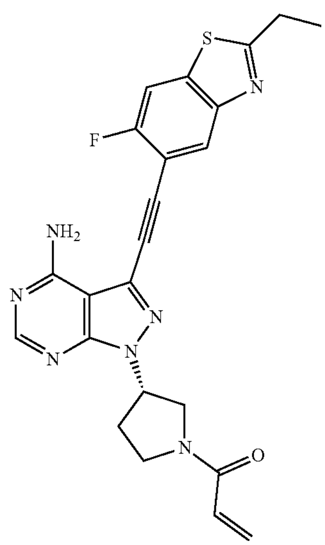
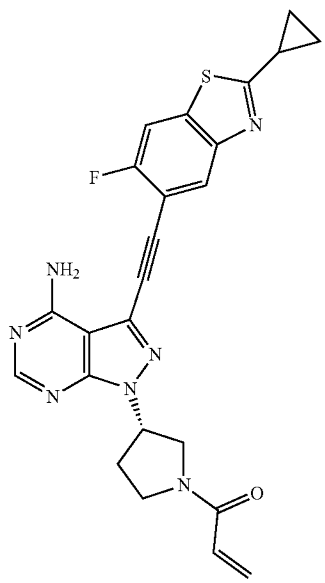
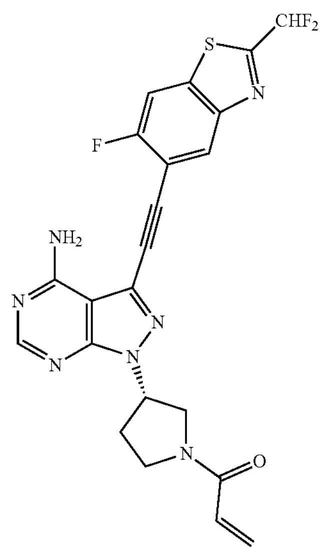
-continued
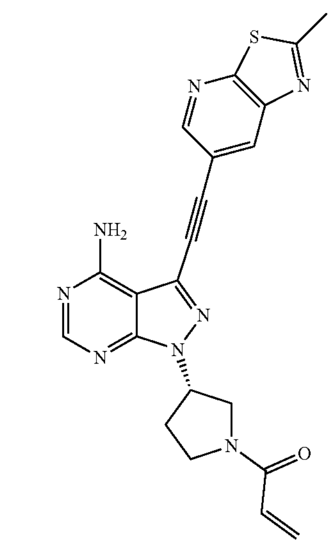
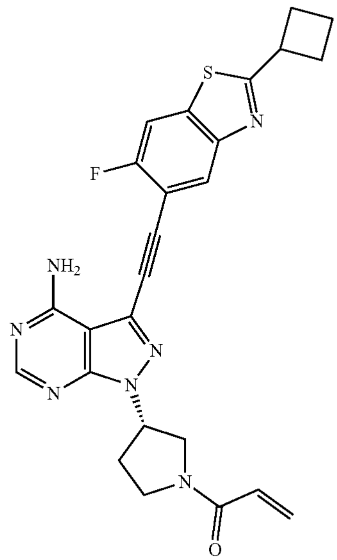
and
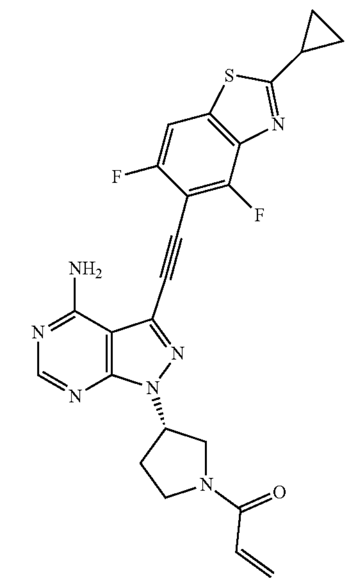
.

8. A method for preparing the compound of formula (II), the stereoisomer or pharmaceutically acceptable salt thereof of claim 1, comprising the following step:

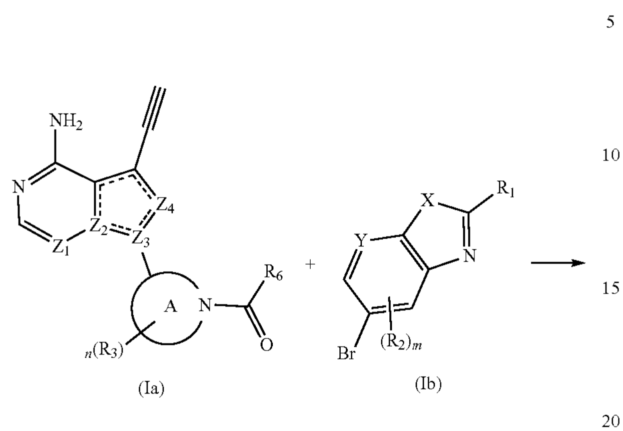

(Ia) (Ib)

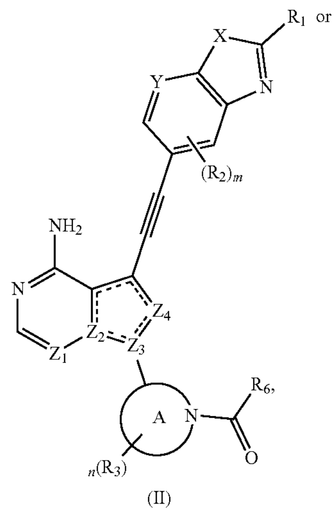

or (II)

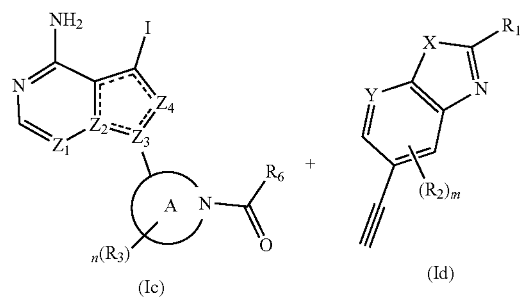

(Ic) (Id)

-continued

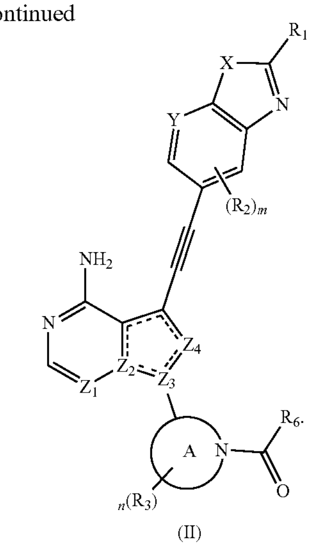

(II)

9. A pharmaceutical composition, comprising the compound of formula (II), the stereoisomer or pharmaceutically acceptable salt thereof of claim 1 and a pharmaceutically acceptable carrier.

10. A method for treating a tumor patient resistant to an FGFR inhibitor comprising administering the compound of formula (II), the stereoisomer or pharmaceutically acceptable salt thereof of claim 1 to a subject in need thereof.

11. The method of claim 10, wherein, the tumor patient is one having mutations at FGFR V561, V565, N550, N540, V555, E566, K660 and/or V550.

12. A method for treating an FGFR kinase-mediated disease state or condition comprising administering the compound of formula (II), the stereoisomer or pharmaceutically acceptable salt thereof of claim 1 to a subject in need thereof.

13. The method of claim 12, wherein the FGFR kinase-mediated disease state or condition is an FGFR kinase-mediated tumor or cancer.

14. The method of claim 13, wherein, the tumor or cancer is bladder cancer, breast cancer, cervical cancer, colorectal cancer, endometrial cancer, gastric cancer, head and neck cancer, renal carcinoma, liver cancer, lung cancer, ovarian cancer, prostate cancer, esophageal cancer, gallbladder cancer, pancreatic cancer, thyroid cancer, skin cancer, leukemia, multiple myeloma, chronic lymphocytic lymphoma, adult T-cell leukemia, B-cell lymphoma, acute myelocytic leukemia, Hodgkin lymphoma or non-Hodgkin lymphoma, Waldenstrom macroglobulinemia, hairy cell lymphoma, cell lymphoma, Burkitt lymphoma, glioblastoma, melanoma or rhabdomyosarcoma.

15. A method for treating myeloproliferative disease, skeleton or cartilage cell disorder, or hypophosphatemia comprising administering the compound of formula (II), the stereoisomer or pharmaceutically acceptable salt thereof of claim 1 to a subject in need thereof.

16. The method of claim 15, wherein, the myeloproliferative disease is erythrocytosis, primary thrombocytosis or primary myelofibrosis; the skeleton or cartilage cell disorder is dysplasia, achondroplasia, dwarfism, thanatophoric dysplasia (TD), Alpert's syndrome, Crouzon syndrome, Jackson-Weiss syndrome, Beare-Stevenson cutis gyrata syndrome, Pfeiffer syndrome or cranial muscular atrophy syndrome; the hypophosphatemia is X-linked hypophosphatemic rickets, autosomal recessive hypophosphatemic rickets, autosomal dominant hypophosphatemic rickets or tumor-induced oothecomalacia.

17. A method for treating diseases associated with aberrant expression and mutation of FGFR2 and/or FGFR3 receptor or aberrant expression and activity of a corresponding ligand as a selective FGFR2 and/or FGFR3 inhibitor comprising administering the compound of formula (II), the stereoisomer or pharmaceutically acceptable salt thereof of claim 1 to a subject in need thereof.

18. The method of claim 11, wherein the tumor patient is one having FGFR2 V565F, V565I, V565L, V565M, N550K, N550H, E566A, E566G, K660M and/or K660Q mutations.

19. The method of claim 11, wherein the tumor patient is one having FGFR3 V555M, V555L and/or N540K mutations.

* * * * *